US012012605B2

(12) United States Patent
Gao et al.

(10) Patent No.: US 12,012,605 B2
(45) Date of Patent: *Jun. 18, 2024

(54) GENERATING NORTHERN LEAF BLIGHT RESISTANT MAIZE

(71) Applicant: PIONEER HI-BRED INTERNATIONAL, INC., Johnston, IA (US)

(72) Inventors: Huirong Gao, Johnston, IA (US); Bailin Li, Johnston, IA (US); Robert B Meeley, Des Moines, IA (US); Leandro Daniel Perugini, Urbandale, IA (US); Girma M Tabor, Johnston, IA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 432 days.

This patent is subject to a terminal disclaimer.

(21) Appl. No.: 16/341,531

(22) PCT Filed: Oct. 10, 2017

(86) PCT No.: PCT/US2017/055835
§ 371 (c)(1),
(2) Date: Apr. 12, 2019

(87) PCT Pub. No.: WO2018/071362
PCT Pub. Date: Apr. 19, 2018

(65) Prior Publication Data
US 2022/0275392 A1      Sep. 1, 2022

Related U.S. Application Data

(60) Provisional application No. 62/407,867, filed on Oct. 13, 2016.

(51) Int. Cl.
C12N 15/82     (2006.01)

(52) U.S. Cl.
CPC ......... *C12N 15/82* (2013.01); *C12N 15/8213* (2013.01); *C12N 15/8282* (2013.01)

(58) Field of Classification Search
None
See application file for complete search history.

(56) References Cited

U.S. PATENT DOCUMENTS

| | | |
|---|---|---|
| 5,844,116 A | 12/1998 | Piper |
| 6,504,084 B1 | 1/2003 | Crane, III et al. |
| 6,720,487 B1 | 4/2004 | Hoffbeck |
| 6,765,132 B1 | 7/2004 | Brenner et al. |
| 8,062,847 B2 | 11/2011 | Broglie et al. |
| 8,921,646 B2 | 12/2014 | Wilson et al. |
| 9,040,772 B2 | 5/2015 | Li et al. |
| 11,447,793 B2 | 9/2022 | Li et al. |
| 11,560,568 B2 | 1/2023 | Cigan et al. |
| 11,653,609 B2 * | 5/2023 | Hou .................. C07K 14/415 800/279 |

| | | |
|---|---|---|
| 2008/0083042 A1 | 4/2008 | Butruille et al. |
| 2010/0095395 A1 | 4/2010 | Wilson et al. |
| 2011/0008793 A1 | 1/2011 | Butruille et al. |
| 2015/0218660 A1 | 8/2015 | Li et al. |
| 2015/0240253 A1 | 8/2015 | McGonigle et al. |
| 2015/0315605 A1 | 11/2015 | Li et al. |
| 2015/0376644 A1 | 12/2015 | Li et al. |
| 2019/0075749 A1 | 3/2019 | Hou et al. |
| 2019/0177744 A1 | 6/2019 | Li et al. |
| 2021/0137040 A1 | 5/2021 | Ouzunova et al. |
| 2021/0274739 A1 | 9/2021 | Hou et al. |
| 2022/0064662 A1 | 3/2022 | Abbitt et al. |
| 2022/0408678 A1 | 12/2022 | Hou et al. |
| 2023/0203525 A1 | 6/2023 | Li et al. |
| 2023/0210080 A1 | 7/2023 | Hou et al. |

FOREIGN PATENT DOCUMENTS

| | | |
|---|---|---|
| WO | WO-2008021225 A2 | 2/2008 |
| WO | WO-2009091518 A2 | 7/2009 |
| WO | 2010/045211 A2 | 4/2010 |
| WO | WO-2011163590 A1 | 12/2011 |
| WO | WO-2014036048 A1 | 3/2014 |
| WO | 2015026883 A1 | 2/2015 |
| WO | 2015026885 A1 | 2/2015 |
| WO | 2015026886 A1 | 2/2015 |
| WO | 2015026887 A1 | 2/2015 |

(Continued)

OTHER PUBLICATIONS

Welz et al 2000 (Plant Breeding 119: p. 1-14) (Year: 2000).*
Thatcher et al 2022 Molecular Plant Pathology 00: p. 1-10 (Year: 2022).*
Hurni, Severine, et al.: "The maize disease resistance gene Htn1 against northern corn leaf blight encodes a wall-associated receptor-like kinase", PNAS Proceedings of the National Academy of Sciences, Jul. 14, 2015 (Jul. 14, 2015), vol. 112, No. 28, pp. 8780-8785.
Shi, Jinrui, et al.: "ARGOS8 variants generated by CRISPR-Cas9 improve maize grain yield under field drought stress conditions", Plant Biotechnology Journal, Aug. 17, 2016 (Aug. 17, 2016), vol. 15, No. 2, pp. 207-216.
International Search Report and Written Opinion, International Application No. PCT/US2017/055835 dated Mar. 13, 2018.

(Continued)

*Primary Examiner* — Matthew R Keogh

(57) ABSTRACT

Compositions and methods for obtaining plant cells with modified Ht1 nucleotide sequences, modified NLB18 sequences, or both, are provided herein. The methods involve introducing double-strand breaks into the maize genome in an endogenous Ht1 encoding sequence, an endogenous NLB18 encoding sequence, or both, to modify the genomic sequence in order to enhance northern leaf blight resistance of a plant produced from the plant cell. Further provided are methods that introduce resistant alleles of Ht1 and/or NLB18 into specific sites in the genome. Plants produced by the plant cells, and seeds produced from the plants are also included. Guide polynucleotides are also provided for the use of the CRISPR-Cas system in inducing double strand breaks.

18 Claims, 11 Drawing Sheets

Specification includes a Sequence Listing.

(56) References Cited

FOREIGN PATENT DOCUMENTS

| WO | WO-2016040030 A1 | 3/2016 |
|---|---|---|
| WO | 2017/066597 A1 | 4/2017 |
| WO | WO-2018071362 A1 | 4/2018 |
| WO | WO-2021257206 A1 | 12/2021 |

OTHER PUBLICATIONS

International Search Report and Written Opinion, International Application No. PCT/US2016/057081 dated Feb. 8, 2017.
Non-Final Office Action for U.S. Appl. No. 17/319,319, dated Sep. 22, 2022.
Li, L. J.; et al.: "The physical location of the gene ht1 (Helminthosporium turcium resistance1) in maize (Zea mays L.)", Hereditas, 1998, vol. 129, pp. 101-106.
Schnable, P. S., et al.: "The B73 Maize Genome: Complexity, Diversity, and Dynamics", Science Magazine (2009) vol. 326, No. 5956, pp. 1112-1115.
UniProt Database Accession No. UPI000220E9DC dated Mar. 19, 2013.
Yang, et al.: "Quantitative Disease Resistance: Dissection and Adoption in Maize," Molecular Plant, Mar. 2017, vol. 10, pp. 402-413.
Extended European Search Report for European Application No. 23158586.0, dated Oct. 23, 2023, 8 Pages.
Asea G., et al., "Validation of Consensus Quantitative Trait Loci Associated with Resistance to Multiple Foliar Pathogens of Maize," Phytopathology, 2009, vol. 99, No. 5, pp. 540-547.
Balint-Kurti P.J., et al., "Use of a Maize Advanced Intercross Line for Mapping of QTL for Northern Leaf Blight Resistance and Multiple Disease Resistance," Crop Science, Mar.-Apr. 2010, vol. 50, pp. 458-466.
Bentolila S., et al., "Identification of an RFLP Marker Tightly Linked to the Ht1 Gene in Maize," Theoretical and Applied Genetics, 1991, vol. 82, pp. 393-398.
Chung C-L., et al., "Characterization and Fine-Mapping of a Resistance Locus for Northern Leaf Blight in Maize Bin 8.06," Theoretical and Applied Genetics, International Journal of Plant Breeding Research, Springer, Berlin, DE, Mar. 9, 2010, vol. 121, No. 2, pp. 205-227, ISSN 1432-2242, XP019836046.
David Z., et al., "Linkage of a Second Gene for NCLB Resistance to Molecular Markers in Maize," Maize Genetics Cooperation Newsletter, vol. 66, pp. 69-70.
Extended European Search Report for European Application No. 18167377.3, dated May 29, 2018, 8 Pages.
International Preliminary Report on Patentability for International Application No. PCT/US2011/041822, dated Jan. 10, 2013, 7 Pages.
International Preliminary Report on Patentability for International Application No. PCT/US2016/057081, dated Apr. 26, 2018, 7 Pages.
International Preliminary Report on Patentability for International Application No. PCT/US2017/055835, dated Apr. 25, 2019, 12 Pages.
International Preliminary Report on Patentability for International Application No. PCT/US2021/031741, dated Dec. 29, 2022, 8 Pages.
International Preliminary Report on Patentability for International Application No. PCT/US2021/044479, dated Feb. 23, 2023, 9 Pages.
International Search Report and Written Opinion for International Application No. PCT/US2011/041822, dated Oct. 6, 2011, 10 Pages.
International Search Report and Written Opinion for International Application No. PCT/US2021/031741, dated Aug. 5, 2021, 13 Pages.
International Search Report and Written Opinion for International Application No. PCT/US2021/044479, dated Feb. 18, 2022, 13 Pages.
Kevin S.D., et al., "Mapping the HtN Resistance Gene to the Long Arm of Chromosome 8," Maize Genetics Cooperation Newsletter, 1993, vol. 67.
Kevin S.D., et al., "The Use of Molecular Markers to Study Setosphaeria Turcica Resistance in Maize," Phytopathology, 1993, vol. 82, No. 12, pp. 1326-1330.
Lehti-Shiu M.D., et al., "Diversity, Classification and Function of the Plant Protein Kinase Superfamily," Philosophical Transactions of the Royal Society B, 2012, vol. 367, pp. 2619-2639.
Manju G., et al., "Identification of RFLP Markers for the Ht1 Gene by Comparison of Inbreds and their HT1-Inversions," Maize Genetics Cooperation Newsletter, 1989.
Paterson A.H., et al., "The Sorghum Bicolor Genome and the Diversification of Grasses," Nature, Jan. 29, 2009, vol. 457, No. 29, DOI: 10.1038/nature07723, pp. 551-556, XP009145526.
Romeis T., "Protein Kinases in the Plant Defence Response," Current Opinion in Plant Biology, 2001, vol. 4, pp. 407-414.
Schnable, "A0A096THR4," Nov. 26, 2014, [Retrieved on Jan. 16, 2017] XP055335643, Retrieved from URL: http://www.uniprot.org/uniprot/A0A096THR4.txt?version=1.
Soderlund C., et al., "Sequencing, Mapping, and Analysis of 27,455 Maize Full-Length cDNAs," PLOS Genetics, Nov. 2009, vol. 5, No. 11, e1000740, 13 Pages.
UNIPROT: "SubName: Full=Putative Disease Resistance RPP13-Like Protein 3 {ECO:0000313|EMBL:PWZ41471.1}," UniProt, Apr. 22, 2020, Database Accession No. A0A3L6G3T9, 2 Pages, Retrieved from URL: EBI, XP002803769.
UNIPROT: "SubName: Full=Uncharacterized protein {ECO:0000313|EMBL:EES01295.1}," UniProt, Database Accession No. C5XGV9, Sep. 1, 2009, XP002781139, Retrieved from URL: EBI.
UNIPROT: "Subname: Full=Uncharacterized protein," Database UniProt [Online], Accession No. ROJM84_SETT2, Database Accession No. ROJM84, XP55887658, Retrieved from URL: https://www.uniprot.org/uniprot/ROJM84.txt.
Webb C.A., et al., "Genetic and Molecular Characterization of the Maize rp3 Rust Resistance Locus," Genetics, Sep. 2002, vol. 162, pp. 381-394.
Wilson R.K., et al., "Zea mays Chromosome 8 Clone CH201-117L11, ZMMBBc0117L01, * Sequencing in Progress *, 14 Unordered Pieces," Nucleotide, GenBank Accession No. AC197148.2, Jun. 27, 2008, pp. 1-44.
Wisser R.J., et al., "Selection Mapping of Loci for Quantitative Disease Resistance in a Diverse Maize Population Genetics," Sep. 2008, vol. 180, pp. 583-599.
Wisser R.J., et al., "The Genetic Architecture of Disease Resistance in Maize: A Synthesis of Published Studies," Phytopathology, 2006, vol. 96, No. 2, pp. 120-129, DOI:10.1094/PHYTO-96-0120, XP009100368.
Yang E., et al., "Organisms with Candidate Sequences in the Localization Region of Maize Leaf Spot Resistance Gene Ht1," Hereditas.
Zheng P., et al., "A Phenylalanine in DGAT is a Key Determinant of Oil Content and Composition in Maize," Nature Genetics, Mar. 2008, vol. 40, No. 3, pp. 367-372.
Zuo W., et al., "A Maize Wall-Associated Kinase Confers Quantitative Resistance to Head Smut," Nature Genetics, Feb. 2015, vol. 47, No. 2, pp. 151-158, 9 Pages.

* cited by examiner

SEQUENCE LISTING

```
<160> NUMBER OF SEQ ID NOS: 95

<210> SEQ ID NO 1
<211> LENGTH: 21
<212> TYPE: DNA
<213> ORGANISM: Zea mays

<400> SEQUENCE: 1
gatgggtcct gcgctcgatg t                                               21

<210> SEQ ID NO 2
<211> LENGTH: 20
<212> TYPE: DNA
<213> ORGANISM: Zea mays

<400> SEQUENCE: 2
gctcggtgta cttgtcaacg                                                 20

<210> SEQ ID NO 3
<211> LENGTH: 20
<212> TYPE: DNA
<213> ORGANISM: Zea mays

<400> SEQUENCE: 3
gctagcgagc ttgtcgagtg                                                 20

<210> SEQ ID NO 4
```

<211> LENGTH: 4296
<212> TYPE: DNA
<213> ORGANISM: Streptococcus pyogenes

<400> SEQUENCE: 4

| | | | | | |
|---|---|---|---|---|---|
| atggataaga | agtacagcat | cggcctcgac | atcgggacca | acagcgtcgg | ctgggccgtc | 60 |
| atcaccgacg | aatataaggt | gccccagcaag | aagttcaagg | tgctcgggaa | tacagaccgc | 120 |
| cacagcatca | agaagaacct | gatcggcgcc | ctcctgttcg | actcgggcga | gaccgctgag | 180 |
| gccaccagac | taaagaggac | cgctcgccgc | cgctacaccc | gccgcaagaa | ccgcatatgc | 240 |
| tacctccagg | agatcttcag | caacgagatg | gccaaggtgg | acgacagctt | cttccaccgc | 300 |
| cttgaggagt | cgttcctcgt | ggaggaggac | aagaagcatg | agaggcaccc | gatcttcggg | 360 |
| aacatcgtgg | acgaggtaag | tttctgcttc | tacctttgat | atatatataa | taattatcat | 420 |
| taattagtag | taatataata | tttcaaatat | tttttcaaa | ataaaagaat | gtagtatata | 480 |
| gcaattgctt | ttctgtagtt | tataagtgtg | tatattttaa | tttataactt | ttctaatata | 540 |
| tgaccaaaac | atggtgatgt | gcaggtggcg | taccacgaga | agtacccgac | gatctaccac | 600 |
| ctccgcaaga | agctggtcga | ctccacagac | aaggccgacc | tcagactgat | ctacctggcc | 660 |
| ctcgcgcaca | tgatcaagtt | ccgcgggcac | ttcctcatcg | agggcgacct | gaacccggac | 720 |
| aactccgacg | tcgacaagct | cttcatccag | ctggtccaga | cctacaatca | actgttcgag | 780 |
| gagaacccga | tcaacgcgtc | cggcgtggac | gcgaaggcca | tcctcagcgc | gaggctcagc | 840 |
| aaatcaagac | ggctggagaa | cctgatcgcc | cagctcccag | gcgagaagaa | aaacggcttg | 900 |
| ttcggcaacc | tgatcgcgct | ctcgctcggc | ctcacgccca | acttcaaatc | aaacttcgac | 960 |
| ctggccgagg | acgcgaaact | gcagctgtcc | aaggacactt | acgacgacga | cctcgacaac | 1020 |
| ctgctggcgc | aaatcggtga | ccagtacgca | gacctcttcc | tggccgccaa | gaacctctcg | 1080 |
| gacgccatcc | tgctgtccga | tatcctgaga | gtgaatacgg | agatcaccaa | ggcgccgctc | 1140 |
| agcgcctcca | tgattaaaag | gtacgacgag | caccaccagg | acctgacgct | gctcaaggcc | 1200 |
| ctggtgcgcc | agcagctccc | cgagaagtac | aaggagatct | tcttcgacca | atcaaaaaac | 1260 |
| ggctacgccg | gctacatcga | cgggggcgcc | tcccaggagg | agttctacaa | gttcatcaaa | 1320 |
| ccaattctcg | agaagatgga | cggcacggag | gagcttctcg | tgaagctcaa | ccgggaggac | 1380 |
| ctcctgagga | agcagaggac | gttcgacaac | ggctcgatac | cgcatcagat | ccacctgggc | 1440 |
| gagctccacg | ccatcctgcg | ccggcaggag | gatttctatc | cgttcctcaa | ggacaacagg | 1500 |
| gagaagatcg | agaaaattct | gacgttccgc | atcccgtact | acgtgggccc | tctcgcgcgc | 1560 |
| gggaacagcc | ggttcgcctg | gatgactcgg | aagtcggagg | agacgatcac | gccgtggaac | 1620 |
| ttcgaggagg | tggtggacaa | gggcgcctcc | gcccagtcgt | tcatcgagcg | catgacgaac | 1680 |
| ttcgataaaa | atctgcccaa | tgaaaaagtg | ctcccgaagc | acagcctcct | ctacgagtac | 1740 |
| ttcacggtgt | acaacgagct | cacgaaggtg | aagtacgtga | ccgagggtat | gcggaagccg | 1800 |
| gcgttcctga | gcggcgagca | gaagaaggcc | atcgtggacc | tcctcttcaa | gacgaaccgg | 1860 |
| aaagtcaccg | tgaagcaatt | aaaggaggac | tacttcaaga | aaatagagtg | cttcgacagc | 1920 |
| gtcgagatct | cggcgtcga | ggacaggttc | aacgcgtcgc | tgggcacata | ccacgacctc | 1980 |
| ctcaagatca | ttaaagacaa | ggacttcctg | gacaacgagg | agaacgagga | catcctcgag | 2040 |
| gacatcgtgc | tgaccctcac | cctgtttgag | gaccggggaga | tgatcgagga | gcgcctcaag | 2100 |
| acgtacgctc | accttttcga | cgacaaggtg | atgaaacagc | tgaagcggcg | ccgctacacc | 2160 |
| ggatggggcc | ggctctcccg | caagctcatt | aatgggatca | gggacaagca | gtccggcaag | 2220 |

```
accatactcg atttcctgaa gagcgacggc ttcgccaacc ggaacttcat gcagctcatc    2280
cacgacgact ccctcacttt caaggaggac atccagaagg cccaggtcag cggacagggc    2340
gactcgctcc acgaacacat cgccaacctg gccgggtcgc ctgcgattaa aaagggaatc    2400
cttcagaccg tcaaggtcgt ggacgagctg gtgaaggtga tgggcaggca caagcccgaa    2460
aatatcgtca ttgagatggc ccgggagaac cagaccacgc agaaaggcca agaacagc      2520 cgggagcgca tgaaacggat cgaggagggt atcaaggagc tgggctcgca gatcctcaag    2580
gagcaccctg tggaaaatac ccagctgcag aatgaaaagc tctacctcta ctacctccag    2640 aacgccgcg acatgtacgt ggaccaggag ctggacatta atcgcctctc ggactacgac     2700
gtcgaccaca tcgtcccgca gtccttcctg aaggacgaca gcatcgacaa caaggtcttg    2760
acccgctccg ataaaaatcg cgggaagtcc gacaacgtgc cgtcggagga ggtggtcaag    2820
aagatgaaaa actactggcg ccagctgctc aacgccaagc taatcacgca gcgcaagttc    2880
gacaacctca ccaaggccga acgcggcggt ctctccgagc ttgataaggc tgggttcatc    2940
aagagacagc tggtggagac ccggcagatc accaagcatg tcgcccagat cctggactcg    3000
cgcatgaata ctaagtacga tgaaaacgac aagctcatcc gcgaggtgaa ggtgatcacc    3060
ctgaagagca agctggtctc ggacttccgg aaggacttcc agttctacaa ggtccgggag    3120
atcaacaact accaccacgc gcacgacgcc tacctgaacg cggtggtggg cacagccctt    3180
ataaagaagt accctaagct cgagtccgag ttcgtgtacg gcgactacaa ggtgtacgac    3240
gtccgcaaga tgatcgcgaa gagcgagcag gagatcggga aggccaccgc aaaatacttc    3300
ttctactcca acatcatgaa cttcttcaag accgagatca ccctggccaa cggggagatc    3360
cgcaagcgcc cgctgattga cgaacggga gagacaggcg agatagtctg ggacaagggc     3420
agggacttcg ccaccgtgcg caaggttctg tccatgccgc aggtgaacat cgtgaagaag    3480
actgaggtgc agacaggcgg cttctcgaag gagtccatcc tgcccaagcg aacagcgac     3540 aagctcatcg cgcggaagaa ggactgggac cctaaaaaat atggcgggtt cgactcgccc    3600
accgtggctt actcggtcct cgtggtggcc aaggtcgaga agggcaaaag caagaagctg    3660
aagagcgtca aggagctcct cggcatcacc atcatggagc ggtccagctt cgagaagaac    3720
ccgatcgact cctcgaggc gaagggatat aaggaggtga agaaggacct catcattaaa      3780
ctgccgaagt actcgctatt cgaactggag aatggtcgca agaggatgct cgcgagcgct    3840
ggcgagctgc agaaagggaa cgagctggct ctcccgagca gtacgtcaa cttcctctac      3900 ctggcctccc actatgaaaa gctcaaggcc tcgccgagg acaacgagca gaagcagctg      3960
ttcgtcgagc agcacaagca ttacctcgac gagatcatcg agcagatctc ggagttcagc    4020
aagcgcgtga tcctggccga cgccaacctc gacaaggtgc tgtccgcata taacaagcac    4080
cgcgacaaac caatacggga gcaggccgaa aatatcatcc acctgttcac cctcacgaac    4140
ctgggcgccc ccgccgcgtt caagtacttc gacacaacca tcgaccgcaa gcggtacacg    4200
agcacgaagg aggtgctgga cgccacgttg attcaccagt ccatcacggg cctgtatgaa    4260
acaaggatcg atctcagcca gctcggcggc gactag                              4296
```

<210> SEQ ID NO 5
<211> LENGTH: 9
<212> TYPE: PRT
<213> ORGANISM: Simian virus 40

<400> SEQUENCE: 5

Met Ala Pro Lys Lys Arg Lys Val
1               5

<210> SEQ ID NO 6
<211> LENGTH: 1000
<212> TYPE: DNA
<213> ORGANISM: Zea mays

<400> SEQUENCE: 6
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgttttca gctgttttg ttagccccat cgaatccttg acataatgat      540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta tttttttata tacctttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt                          1000

<210> SEQ ID NO 7
<211> LENGTH: 21
<212> TYPE: DNA
<213> ORGANISM: Artificial
<220> FEATURE:
<223> OTHER INFORMATION: Ht1-CR2 DNA version of guide RNA

<400> SEQUENCE: 7
gatgggtcct gcgctcgatg t                                                21

<210> SEQ ID NO 8
<211> LENGTH: 20
<212> TYPE: DNA
<213> ORGANISM: Artificial
<220> FEATURE:
<223> OTHER INFORMATION: Ht1-CR4 DNA version of guide RNA

<400> SEQUENCE: 8
gctcggtgta cttgtcaacg                                                  20

<210> SEQ ID NO 9
<211> LENGTH: 20
<212> TYPE: DNA
<213> ORGANISM: Artificial
<220> FEATURE:
<223> OTHER INFORMATION: Ht1-STH1-CR1 DNA version of guide RNA -continued

```
<400> SEQUENCE: 9
gctagcgagc ttgtcgagtg                                              20

<210> SEQ ID NO 10
<211> LENGTH: 37
<212> TYPE: DNA
<213> ORGANISM: Artificial
<220> FEATURE:
<223> OTHER INFORMATION: Ht1f3 forward primer

<400> SEQUENCE: 10
atcgggaagc tgaagaggaa gaatcgcctg tgaagga                           37

<210> SEQ ID NO 11
<211> LENGTH: 38
<212> TYPE: DNA
<213> ORGANISM: Artificial
<220> FEATURE:
<223> OTHER INFORMATION: Ht1r4v2 reverse primer

<400> SEQUENCE: 11
atccgacggt agtgtttgat ggcaatcagc tccttcct                          38

<210> SEQ ID NO 12
<211> LENGTH: 58
<212> TYPE: DNA
<213> ORGANISM: Artificial
<220> FEATURE:
<223> OTHER INFORMATION: Forward primer secondary PCR Rxn

<400> SEQUENCE: 12
aatgatacgg cgaccaccga gatctacaca tacgagatcc gtaatcggga agctgaag    58

<210> SEQ ID NO 13
<211> LENGTH: 56
<212> TYPE: DNA
<213> ORGANISM: Artificial
<220> FEATURE:
<223> OTHER INFORMATION: Reverse primer secondary PCR Rxn
<220> FEATURE:
<221> NAME/KEY: misc_feature
<222> LOCATION: (25)..(32)
<223> OTHER INFORMATION: n is a, c, g, or t

<400> SEQUENCE: 13
caagcagaag acggcatacg agatnnnnnn nnacacgcac gatccgacgg tagtgt      56

<210> SEQ ID NO 14
<211> LENGTH: 21
<212> TYPE: DNA
<213> ORGANISM: Zea mays

<400> SEQUENCE: 14
gtttggatgt cacatgattg g                                            21

<210> SEQ ID NO 15
<211> LENGTH: 23
<212> TYPE: DNA
<213> ORGANISM: Zea mays

<400> SEQUENCE: 15
gttgtttggt atatgcagag cgg                                          23

<210> SEQ ID NO 16
```

```
<211> LENGTH: 23
<212> TYPE: DNA
<213> ORGANISM: Zea mays

<400> SEQUENCE: 16
gctgctcacg tgatcagcca agg                                              23

<210> SEQ ID NO 17
<211> LENGTH: 22
<212> TYPE: DNA
<213> ORGANISM: Zea mays

<400> SEQUENCE: 17
gttggttaga atgaaaacta gg                                               22

<210> SEQ ID NO 18
<211> LENGTH: 18
<212> TYPE: DNA
<213> ORGANISM: Artificial
<220> FEATURE:
<223> OTHER INFORMATION: HT1-CR6 DNA version of guide RNA

<400> SEQUENCE: 18
gtttggatgt cacatgat                                                    18

<210> SEQ ID NO 19
<211> LENGTH: 20
<212> TYPE: DNA
<213> ORGANISM: Artificial
<220> FEATURE:
<223> OTHER INFORMATION: HT1-CR9 DNA version of guide RNA

<400> SEQUENCE: 19
gctgctcacg tgatcagcca                                                  20

<210> SEQ ID NO 20
<211> LENGTH: 20
<212> TYPE: DNA
<213> ORGANISM: Artificial
<220> FEATURE:
<223> OTHER INFORMATION: HT1-CR7 DNA version of guide RNA

<400> SEQUENCE: 20
gttgtttggt atatgcagag                                                  20

<210> SEQ ID NO 21
<211> LENGTH: 19
<212> TYPE: DNA
<213> ORGANISM: Artificial
<220> FEATURE:
<223> OTHER INFORMATION: HT1-CR10 DNA version of guide RNA

<400> SEQUENCE: 21
gttggttaga atgaaaact                                                   19

<210> SEQ ID NO 22
<211> LENGTH: 25
<212> TYPE: DNA
<213> ORGANISM: Artificial
<220> FEATURE:
<223> OTHER INFORMATION: Ht1HR1f1 forward primer

<400> SEQUENCE: 22
attatgtttt caaatggttg gcact                                            25
```

```
<210> SEQ ID NO 23
<211> LENGTH: 29
<212> TYPE: DNA
<213> ORGANISM: Artificial
<220> FEATURE:
<223> OTHER INFORMATION: Ht1HR1r1 reverse primer

<400> SEQUENCE: 23
cgattttgga ggttatagaa ttgaattgg                                        29

<210> SEQ ID NO 24
<211> LENGTH: 28
<212> TYPE: DNA
<213> ORGANISM: Artificial
<220> FEATURE:
<223> OTHER INFORMATION: Ht1HR2f1 forward primer

<400> SEQUENCE: 24
tagacttacc tgtccttcga gtgttaga                                         28

<210> SEQ ID NO 25
<211> LENGTH: 29
<212> TYPE: DNA
<213> ORGANISM: Artificial
<220> FEATURE:
<223> OTHER INFORMATION: Ht1HR2r1 reverse primer

<400> SEQUENCE: 25
gaatgagaat cccaataata tccaaaggt                                        29

<210> SEQ ID NO 26
<211> LENGTH: 22
<212> TYPE: DNA
<213> ORGANISM: Artificial
<220> FEATURE:
<223> OTHER INFORMATION: hdr2b_f forward primer

<400> SEQUENCE: 26
gatctagagg gatgccgtga tc                                               22

<210> SEQ ID NO 27
<211> LENGTH: 24
<212> TYPE: DNA
<213> ORGANISM: Artificial
<220> FEATURE:
<223> OTHER INFORMATION: hdr2b_r reverse primer

<400> SEQUENCE: 27
ccaggtatct cagatgaaac aagc                                             24

<210> SEQ ID NO 28
<211> LENGTH: 17
<212> TYPE: DNA
<213> ORGANISM: Artificial
<220> FEATURE:
<223> OTHER INFORMATION: hdr2b_PV probe

<400> SEQUENCE: 28
cagtcaggtt cgtcgat                                                     17

<210> SEQ ID NO 29
<211> LENGTH: 17
<212> TYPE: DNA
<213> ORGANISM: Artificial
<220> FEATURE:
<223> OTHER INFORMATION: hdr2b_PG probe
```

```
<400> SEQUENCE: 29
cagtcagggt cgacgat                                                    17

<210> SEQ ID NO 30
<211> LENGTH: 18
<212> TYPE: DNA
<213> ORGANISM: Zea mays

<400> SEQUENCE: 30
gaagatagaa gtaggccg                                                   18

<210> SEQ ID NO 31
<211> LENGTH: 17
<212> TYPE: DNA
<213> ORGANISM: Zea mays

<400> SEQUENCE: 31
gttaacgatg tcaacgt                                                    17

<210> SEQ ID NO 32
<211> LENGTH: 21
<212> TYPE: DNA
<213> ORGANISM: Zea mays

<400> SEQUENCE: 32
gttcgcatta gtctaggatt a                                               21

<210> SEQ ID NO 33
<211> LENGTH: 18
<212> TYPE: DNA
<213> ORGANISM: Artificial
<220> FEATURE:
<223> OTHER INFORMATION: NLB18-CR1 DNA version of guide RNA

<400> SEQUENCE: 33
gaagatagaa gtaggccg                                                   18

<210> SEQ ID NO 34
<211> LENGTH: 17
<212> TYPE: DNA
<213> ORGANISM: Artificial
<220> FEATURE:
<223> OTHER INFORMATION: NLB18-CR8 DNA version of guide RNA

<400> SEQUENCE: 34
gttaacgatg tcaacgt                                                    17

<210> SEQ ID NO 35
<211> LENGTH: 21
<212> TYPE: DNA
<213> ORGANISM: Artificial
<220> FEATURE:
<223> OTHER INFORMATION: NLB18-CR4 DNA version of guide RNA

<400> SEQUENCE: 35
gttcgcatta gtctaggatt a                                               21

<210> SEQ ID NO 36
<211> LENGTH: 21
<212> TYPE: DNA
<213> ORGANISM: Zea mays

<400> SEQUENCE: 36
gtacgtaacg tgcagtactg g                                               21
```

```
<210> SEQ ID NO 37
<211> LENGTH: 24
<212> TYPE: DNA
<213> ORGANISM: Zea mays

<400> SEQUENCE: 37
gcataatgag gatcgaggat gagg                                              24

<210> SEQ ID NO 38
<211> LENGTH: 21
<212> TYPE: DNA
<213> ORGANISM: Zea mays

<400> SEQUENCE: 38
gctcgtgttg gagatacagg g                                                 21

<210> SEQ ID NO 39
<211> LENGTH: 21
<212> TYPE: DNA
<213> ORGANISM: Artificial
<220> FEATURE:
<223> OTHER INFORMATION: 8HR1f1 forward primer

<400> SEQUENCE: 39
cagtccgtgg attgaagcca t                                                 21

<210> SEQ ID NO 40
<211> LENGTH: 22
<212> TYPE: DNA
<213> ORGANISM: Artificial
<220> FEATURE:
<223> OTHER INFORMATION: PH26NPr reverse primer

<400> SEQUENCE: 40
acccactcag ttccatgaca ga                                                22

<210> SEQ ID NO 41
<211> LENGTH: 20
<212> TYPE: DNA
<213> ORGANISM: Artificial
<220> FEATURE:
<223> OTHER INFORMATION: PH26NTf forward primer

<400> SEQUENCE: 41
aacgagccga gtcgagtcaa                                                   20

<210> SEQ ID NO 42
<211> LENGTH: 23
<212> TYPE: DNA
<213> ORGANISM: Artificial
<220> FEATURE:
<223> OTHER INFORMATION: 8HR2r1 reverse primer

<400> SEQUENCE: 42
ctggtagctc tgtctccgag acg                                               23

<210> SEQ ID NO 43
<211> LENGTH: 21
<212> TYPE: DNA
<213> ORGANISM: Artificial
<220> FEATURE:
<223> OTHER INFORMATION: 10HR1f forward primer
```

-continued

<400> SEQUENCE: 43
tggcttgtct atgcgcatct c                                        21

<210> SEQ ID NO 44
<211> LENGTH: 24
<212> TYPE: DNA
<213> ORGANISM: Artificial
<220> FEATURE:
<223> OTHER INFORMATION: Ht1Pr reverse primer

<400> SEQUENCE: 44
tgacagttga taaagaccgg atga                                     24

<210> SEQ ID NO 45
<211> LENGTH: 24
<212> TYPE: DNA
<213> ORGANISM: Artificial
<220> FEATURE:
<223> OTHER INFORMATION: Ht1Tf forward primer

<400> SEQUENCE: 45
tgaaccggct aggaaagttt agtt                                     24

<210> SEQ ID NO 46
<211> LENGTH: 25
<212> TYPE: DNA
<213> ORGANISM: Artificial
<220> FEATURE:
<223> OTHER INFORMATION: 10HR2r reverse primer

<400> SEQUENCE: 46
ggacatctat acttgagggc ttcac                                    25

<210> SEQ ID NO 47
<211> LENGTH: 20
<212> TYPE: DNA
<213> ORGANISM: Artificial
<220> FEATURE:
<223> OTHER INFORMATION: 45hr1f1 forward primer

<400> SEQUENCE: 47
gcgtgcgtgc ttacatgatg                                          20

<210> SEQ ID NO 48
<211> LENGTH: 22
<212> TYPE: DNA
<213> ORGANISM: Artificial
<220> FEATURE:
<223> OTHER INFORMATION: PH26NPr reverse primer

<400> SEQUENCE: 48
acccactcag ttccatgaca ga                                       22

<210> SEQ ID NO 49
<211> LENGTH: 20
<212> TYPE: DNA
<213> ORGANISM: Artificial
<220> FEATURE:
<223> OTHER INFORMATION: PH26NTf forward primer

<400> SEQUENCE: 49
aacgagccga gtcgagtcaa                                          20

<210> SEQ ID NO 50

```
<211> LENGTH: 30
<212> TYPE: DNA
<213> ORGANISM: Artificial
<220> FEATURE:
<223> OTHER INFORMATION: 45hr2r1 reverse primer

<400> SEQUENCE: 50
agtcgacatt aaacaatgtt agttgtagcc                                        30

<210> SEQ ID NO 51
<211> LENGTH: 2658
<212> TYPE: DNA
<213> ORGANISM: Zea mays

<400> SEQUENCE: 51
atggagaacc cagacgcgca ggcgaaggcg tgggcggcgg agatgcgcga gctggcctac       60
gacatggagg acagcatcga tctcttcacc caccacgtcg accacgaacc ggccgacacc      120
gccaccaccg gcgtcaagag gttcttcctc cggatcatcc ggaagcttaa gaaactccac      180
taccgccaca ggtttgttca ggagatcaaa caactccacg accttgccaa cgaatcgtac      240
cggcgtagga agaggtacag gattgaggag ggcggttcaa gcctctcgca cgcggagatc      300
gatcctcggt tagaggcgct ctacgtggag gtggagaaac tcgtgggcat ccagggccca      360
agccaggaga tcattggaca gctcgtcggc gagaacgcag cggagcgacg gagggttgtc      420
gccgttgttg gatctggagg ttcaggcaag accacacttg ccaaacaggt gtacgagaaa      480
atcaggtgcc aattctcttg tgcagccttt gtgtctgtgt cgcaaaagcc aacatgaat       540 agcctcctgt gggagttgct atctcaaatc gggaaccatg gtggagattt aggaatgatg      600
gcagtaggat attgcagtga caaacaactg atcgacagac taagatcaca tcttgaaaag      660
cagaggtatc tcgttgtgat agatgatgtt tggacaaact cagcgtggga gaccatacaa      720
tgtgcgctcc ctaaaaatgc ccatgcaagt aaaataattc tgacaacacg aatcaacagt      780
gtaggccagt tctcctgcac tccagatgag ggttttatct atcagatgaa gcctcttgc      840 agaaacgatt ctgaaaatct gtttctgaaa aggacactat gtgataaaga taagtttcct      900
gctcagctgg aggggattaa aaacgagata atcgagaaat gcgatggttt gccactggct      960
attgttactc tagctagcat gttagctact aaacagagaa caagggaaga atgggagagg     1020
gcacttgatt caatccattc tatgcacaag aaagatagtg gcctgaagt gatggacaag      1080 atactgtctc tgagttacag ggatctacct cacaacatga aaattgctt gctgtatctc      1140 agtacatttc cagaggacca cacgatttac aaagatgccc tagtatggag atggatggct     1200
gaagggttta tcgctgaaac acaaggcttt actttggagc aggttgccga gggctacttc     1260
tacgagtttg tgaacaggag tttggttcag cccataacct tgcgttcaag atatgaaatg     1320
cgtggagaag gaggttgccg agtccatgac attgtactga acttcctcat ctctcgtgca     1380
gctgaagaga cttttttaac tacgctgtat ggcgcccagg gggttccatc ttcagaccga     1440
aggattcgcc ggctctctgt ctgggacagt ccagaacacg cactgcagt ctctagagcg      1500 accatgaatc tgtcccatct ccggtcagtt agaatatgca acgttggaga ctggcccgtg     1560
cctgctgttc tagacttacc tgtccttcga gtgttagatc tagagggatg ccgtgatctg     1620
aggatcgacg aacctgactg cattctaagc ttgtttcatc tgagatacct gggtttccgc     1680
agcgcaagtg tgtcgtgct accggctcaa atcggaaatt tacaccatct gcagaccatc      1740
gatttaagcg ggactggagt gacacagctg ccagaaagca ttgtccagct caagcgactg     1800
atgcatcttg ttgggcaacg gctcatcatg ccagacgggt ttggtagcat ggaatccctt     1860
```

```
gaggagttag gtactatcga ctgctgcaag tgccccgtca gttttgggga agacctagca    1920
cttctgagca ggctgagggt gctccgagtg gctttcatcg gggtcgaaac aagtgacatg    1980
gaaaccagaa ggaaatcttt gatgtcatcc ctctgcaaac tcggaggaga caaccttcgg    2040
cgtgtcacta ttatcgacct cgctggcggt ggagattgct tgtggagtc gtggcaccct     2100 cctcctcgtc tcctccagaa gttcatccat atcagtcagc aacagcactt ctccaggttt    2160
ccagaatgga tcagttcctg cctatgtgat ctcacccacc tggatataaa ggccgaaaag    2220
atggaagggg agcatctaag tgttcttgaa cacctgcccg ccatccgttg cctataccct    2280
ttcgtgaagc gagtctccga agacgggctc gccatcagcc acggcgcgtt ccgatgtcta    2340
cggcgtctcg agttctgcaa cgtagatgga cctggtttga tgtttgcagg aggcgttcca    2400
atgttggaat ggctgaggct cgggttcgac gcggatagag cgcaatcgac atacggcggt    2460
ctggaggttg gcatccagcg cctctcgtct ctcaaacatg tcgtgctcat tgtatggatg    2520
gtttctgaag gcggtgatga tccagcggag caagccgtct ggtctgccat caatggccaa    2580
gtagagatgc tccccaactc tccgacggtt gatatccggt ttcgtagacg gagtcagctg    2640
caggcaagct cagaataa                                                  2658

<210> SEQ ID NO 52
<211> LENGTH: 885
<212> TYPE: PRT
<213> ORGANISM: Zea mays

<400> SEQUENCE: 52

Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Val Gln Glu Ile Lys Gln Leu His Asp Leu Ala Asn Glu Ser Tyr
65                  70                  75                  80

Arg Arg Arg Lys Arg Tyr Arg Ile Glu Glu Gly Gly Ser Ser Leu Ser
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
        115                 120                 125

Val Gly Glu Asn Ala Ala Glu Arg Arg Arg Val Val Ala Val Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
        195                 200                 205

Gln Leu Ile Asp Arg Leu Arg Ser His Leu Glu Lys Gln Arg Tyr Leu
    210                 215                 220
```

```
Val Val Ile Asp Asp Val Trp Thr Asn Ser Ala Trp Glu Thr Ile Gln
225                 230                 235                 240

Cys Ala Leu Pro Lys Asn Ala His Ala Ser Lys Ile Ile Leu Thr Thr
            245                 250                 255

Arg Ile Asn Ser Val Gly Gln Phe Ser Cys Thr Pro Asp Glu Gly Phe
        260                 265                 270

Ile Tyr Gln Met Lys Pro Leu Cys Arg Asn Asp Ser Glu Asn Leu Phe
    275                 280                 285

Leu Lys Arg Thr Leu Cys Asp Lys Asp Lys Phe Pro Ala Gln Leu Glu
290                 295                 300

Gly Ile Lys Asn Glu Ile Ile Glu Lys Cys Asp Gly Leu Pro Leu Ala
305                 310                 315                 320

Ile Val Thr Leu Ala Ser Met Leu Ala Thr Lys Gln Arg Thr Arg Glu
            325                 330                 335

Glu Trp Glu Arg Ala Leu Asp Ser Ile His Ser Met His Lys Lys Asp
        340                 345                 350

Ser Gly Leu Glu Val Met Asp Lys Ile Leu Ser Leu Ser Tyr Arg Asp
    355                 360                 365

Leu Pro His Asn Met Arg Asn Cys Leu Leu Tyr Leu Ser Thr Phe Pro
370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
            405                 410                 415

Glu Gly Tyr Phe Tyr Glu Phe Val Asn Arg Ser Leu Val Gln Pro Ile
        420                 425                 430

Thr Leu Arg Ser Arg Tyr Glu Met Arg Gly Glu Gly Cys Arg Val
    435                 440                 445

His Asp Ile Val Leu Asn Phe Leu Ile Ser Arg Ala Ala Glu Glu Asn
450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
            485                 490                 495

Val Ser Arg Ala Thr Met Asn Leu Ser His Leu Arg Ser Val Arg Ile
        500                 505                 510

Cys Asn Val Gly Asp Trp Pro Val Pro Ala Val Leu Asp Leu Pro Val
    515                 520                 525

Leu Arg Val Leu Asp Leu Glu Gly Cys Arg Asp Leu Arg Ile Asp Glu
530                 535                 540

Pro Asp Cys Ile Leu Ser Leu Phe His Leu Arg Tyr Leu Gly Phe Arg
545                 550                 555                 560

Ser Ala Ser Gly Val Val Leu Pro Ala Gln Ile Gly Asn Leu His His
            565                 570                 575

Leu Gln Thr Ile Asp Leu Ser Gly Thr Gly Val Thr Gln Leu Pro Glu
        580                 585                 590

Ser Ile Val Gln Leu Lys Arg Leu Met His Leu Val Gly Gln Arg Leu
    595                 600                 605

Ile Met Pro Asp Gly Phe Gly Ser Met Glu Ser Leu Glu Glu Leu Gly
610                 615                 620

Thr Ile Asp Cys Cys Lys Cys Pro Val Ser Phe Gly Glu Asp Leu Ala
625                 630                 635                 640
```

Leu Leu Ser Arg Leu Arg Val Leu Arg Val Ala Phe Ile Gly Val Glu
            645                 650                 655

Thr Ser Asp Met Glu Thr Arg Arg Lys Ser Leu Met Ser Ser Leu Cys
            660                 665                 670

Lys Leu Gly Gly Asp Asn Leu Arg Arg Val Thr Ile Ile Asp Leu Ala
            675                 680                 685

Gly Gly Gly Asp Cys Phe Val Glu Ser Trp His Pro Pro Arg Leu
            690                 695                 700

Leu Gln Lys Phe Ile His Ile Ser Gln Gln Gln His Phe Ser Arg Phe
705                 710                 715                 720

Pro Glu Trp Ile Ser Ser Cys Leu Cys Asp Leu Thr His Leu Asp Ile
            725                 730                 735

Lys Ala Glu Lys Met Glu Arg Glu His Leu Ser Val Leu Glu His Leu
            740                 745                 750

Pro Ala Ile Arg Cys Leu Tyr Leu Phe Val Lys Arg Val Ser Glu Asp
            755                 760                 765

Gly Leu Ala Ile Ser His Gly Ala Phe Arg Cys Leu Arg Arg Leu Glu
            770                 775                 780

Phe Cys Asn Val Asp Gly Pro Gly Leu Met Phe Ala Gly Gly Val Pro
785                 790                 795                 800

Met Leu Glu Trp Leu Arg Leu Gly Phe Asp Ala Asp Arg Ala Gln Ser
            805                 810                 815

Thr Tyr Gly Gly Leu Glu Val Gly Ile Gln Arg Leu Ser Ser Leu Lys
            820                 825                 830

His Val Val Leu Ile Val Trp Met Val Ser Glu Gly Gly Asp Asp Pro
            835                 840                 845

Ala Glu Gln Ala Val Trp Ser Ala Ile Asn Gly Gln Val Glu Met Leu
            850                 855                 860

Pro Asn Ser Pro Thr Val Asp Ile Arg Phe Arg Arg Arg Ser Gln Leu
865                 870                 875                 880

Gln Ala Ser Ser Glu
            885

<210> SEQ ID NO 53
<211> LENGTH: 2652
<212> TYPE: DNA
<213> ORGANISM: Zea mays

<400> SEQUENCE: 53
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg cgtcaagag gttcttcctc cggatcatcc ggaagcttaa gaaactccac     180
taccgccaca ggtttgttca ggagatcaaa caactccacg accttgccaa cgaatcgtac     240
cggcgtagga gaggtacag gattgaggag gcggttcaa gcctctcgca cgcggagatc     300
gatcctcggt tagaggcgct ctacgtggag gtggagaaac tcgtgggcat ccagggccca     360
agccaggaga tcattggaca gctcgtcggc gagaacgcag cggagcgacg gagggttgtc     420
gccgttgttg atctggagg ttcaggcaag accacacttg ccaaacaggt gtacgagaaa     480
atcaggtgcc aattctcttg tgcagccttt gtgtctgtgt cgcaaaagcc aacatgaat     540 agcctcctgt gggagttgct atctcaaatc gggaaccatg gtggagattt aggaatgatg     600
gcagtaggat attgcagtga caacaactg atcgacagac taagatcaca tcttgaaaag     660

```
cagaggtatc tcgttgtgat agatgatgtt tggacaaact cagcgtggga gaccatacaa    720
tgtgcgctcc ctaaaaatgc ccatgcaagt aaaataattc tgacaacacg aatcaacagt    780
gtaggccagt tctcctgcac tccagatgag ggttttatct atcagatgaa gcctctttgc    840
agaaacgatt ctgaaaatct gtttctgaaa aggacactat gtgataaaga taagtttcct    900
gctcagctgg aggggattaa aaacgagata atcgagaaat gcgatggttt gccactggct    960
attgttactc tagctagcat gttagctact aaacagagaa caaggaaaga atgggagagg   1020
gcacttgatt caatccattc tatgcacaag aaagatagtg gcctggaagt gatggacaag   1080
atactgtctc tgagttacag ggatctacct cacaacatga gaaattgctt gctgtatctc   1140
agtacatttc cagaggacca cacgatttac aaagatgccc tagtatggag atggatggct   1200
gaagggttta tcgctgaaac acaaggcttt actttggagc aggttgccga gggctacttc   1260
tacgagtttg tgaacaggag tttggttcag cccataacct tgcgttcaag atatgaaatg   1320
cgtggagaag gaggttgccg agtccatgac attgtactga acttcctcat ctctcgtgca   1380
gctgaagaga acttttttaac tacgctgtat ggcgcccagg gggttccatc ttcagaccga   1440
aggattcgcc ggctctctgt ctgggacagt ccagaacacg cactggcagt ctctagagcg   1500
accatgaatc tgtcccatct ccggtcagtt agaaatatgca acgttggaga ctggcccgtg   1560
cctgctgttc tagacttacc tgtccttcga gtgttagatc tagagggatg ccgtgatctg   1620
aggatcgacg aacctgactg cattctaagc ttgtttcatc tgagatacct gggtttccgc   1680
agcgcaagtg gtgtcgtgct accggctcaa atcggaaatt tacaccatct gcagaccatc   1740
gatttaagcg ggactggagt gacacagctg ccagaaagca ttgtccagct caagcgactg   1800
atgcatcttg ttgggcaacg gctcatcatg ccagacgggt ttggtagcat ggaatccctt   1860
gaggagttag gtactatcga ctgctgcaag tgccccgtca gttttgggga agacctagca   1920
cttctgagca ggctgagggt gctccgagtg gctttcatcg gggtcgaaac aagtgacatg   1980
gaaaccagaa ggaaatcttt gatgtcatcc ctctgcaaac tcggaggaga caaccttcgg   2040
cgtgtcacta ttatcgacct cgctggcggt ggagattgct ttgtggagtc gtggcaccct   2100
cctcctcgtc tcctccagaa gttcatccat atcagtcagc acttctccag gtttccagaa   2160
tggatcagtt cctgcctatg tgatctcacc cacctggata taaaggccga aaagatggaa   2220
agggagcatc taagtgttct tgaacacctg cccgccatcc gttgcctata ccttttcgtg   2280
aagcgagtct ccgaagacgg gctcgtcatc agccacggcg cgttccgatg tctacggcgt   2340
ctcgagttct gtaacgtaga tggacctggt ttgatgtttg caggaggcgt tccaatgttg   2400
gaatggctga ggctcgggtt cgacgcggat agagcgcaat cgacatacgg cggtctggag   2460
gttggcatcc agcgcctctc gtctctcaaa catgtcgtgc tcattgtatg gatggtttct   2520
gaaggcggtg atgatccagc ggagcaagcc gtctggtctg ccatcaatgg ccaagtagag   2580
atgctcccca actctccgac ggttgatatc cggtttcgta gacggagtca gctgcaggca   2640
agctcagaat aa                                                        2652
```

<210> SEQ ID NO 54
<211> LENGTH: 883
<212> TYPE: PRT
<213> ORGANISM: Zea mays

<400> SEQUENCE: 54

Met Glu Asn Pro Asp Ala Gln Ala Lys Ala Trp Ala Ala Glu Met Arg
1               5                   10                  15

```
Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
            35                  40                  45

Phe Leu Arg Ile Ile Arg Lys Leu Lys Lys Leu His Tyr Arg His Arg
 50                  55                  60

Phe Val Gln Glu Ile Lys Gln Leu His Asp Leu Ala Asn Glu Ser Tyr
 65                  70                  75                  80

Arg Arg Arg Lys Arg Tyr Arg Ile Glu Glu Gly Gly Ser Ser Leu Ser
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
            115                 120                 125

Val Gly Glu Asn Ala Ala Glu Arg Arg Val Val Ala Val Val Gly
            130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
            195                 200                 205

Gln Leu Ile Asp Arg Leu Arg Ser His Leu Glu Lys Gln Arg Tyr Leu
            210                 215                 220

Val Val Ile Asp Asp Val Trp Thr Asn Ser Ala Trp Glu Thr Ile Gln
225                 230                 235                 240

Cys Ala Leu Pro Lys Asn Ala His Ala Ser Lys Ile Ile Leu Thr Thr
                245                 250                 255

Arg Ile Asn Ser Val Gly Gln Phe Ser Cys Thr Pro Asp Glu Gly Phe
            260                 265                 270

Ile Tyr Gln Met Lys Pro Leu Cys Arg Asn Asp Ser Glu Asn Leu Phe
            275                 280                 285

Leu Lys Arg Thr Leu Cys Asp Lys Asp Lys Phe Pro Ala Gln Leu Glu
            290                 295                 300

Gly Ile Lys Asn Glu Ile Ile Glu Lys Cys Asp Gly Leu Pro Leu Ala
305                 310                 315                 320

Ile Val Thr Leu Ala Ser Met Leu Ala Thr Lys Gln Arg Thr Arg Glu
            325                 330                 335

Glu Trp Glu Arg Ala Leu Asp Ser Ile His Ser Met His Lys Lys Asp
            340                 345                 350

Ser Gly Leu Glu Val Met Asp Lys Ile Leu Ser Leu Ser Tyr Arg Asp
            355                 360                 365

Leu Pro His Asn Met Arg Asn Cys Leu Leu Tyr Leu Ser Thr Phe Pro
            370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
                405                 410                 415

Glu Gly Tyr Phe Tyr Glu Phe Val Asn Arg Ser Leu Val Gln Pro Ile
            420                 425                 430
```

-continued

```
Thr Leu Arg Ser Arg Tyr Glu Met Arg Gly Glu Gly Cys Arg Val
            435                 440                 445

His Asp Ile Val Leu Asn Phe Leu Ile Ser Arg Ala Ala Glu Glu Asn
450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
                485                 490                 495

Val Ser Arg Ala Thr Met Asn Leu Ser His Leu Arg Ser Val Arg Ile
            500                 505                 510

Cys Asn Val Gly Asp Trp Pro Val Pro Ala Val Leu Asp Leu Pro Val
            515                 520                 525

Leu Arg Val Leu Asp Leu Glu Gly Cys Arg Asp Leu Arg Ile Asp Glu
            530                 535                 540

Pro Asp Cys Ile Leu Ser Leu Phe His Leu Arg Tyr Leu Gly Phe Arg
545                 550                 555                 560

Ser Ala Ser Gly Val Val Leu Pro Ala Gln Ile Gly Asn Leu His His
                565                 570                 575

Leu Gln Thr Ile Asp Leu Ser Gly Thr Gly Val Thr Gln Leu Pro Glu
            580                 585                 590

Ser Ile Val Gln Leu Lys Arg Leu Met His Leu Val Gly Gln Arg Leu
            595                 600                 605

Ile Met Pro Asp Gly Phe Gly Ser Met Glu Ser Leu Glu Glu Leu Gly
            610                 615                 620

Thr Ile Asp Cys Cys Lys Cys Pro Val Ser Phe Gly Glu Asp Leu Ala
625                 630                 635                 640

Leu Leu Ser Arg Leu Arg Val Leu Arg Val Ala Phe Ile Gly Val Glu
                645                 650                 655

Thr Ser Asp Met Glu Thr Arg Arg Lys Ser Leu Met Ser Ser Leu Cys
            660                 665                 670

Lys Leu Gly Gly Asp Asn Leu Arg Arg Val Thr Ile Ile Asp Leu Ala
            675                 680                 685

Gly Gly Gly Asp Cys Phe Val Glu Ser Trp His Pro Pro Arg Leu
            690                 695                 700

Leu Gln Lys Phe Ile His Ile Ser Gln His Phe Ser Arg Phe Pro Glu
705                 710                 715                 720

Trp Ile Ser Ser Cys Leu Cys Asp Leu Thr His Leu Asp Ile Lys Ala
                725                 730                 735

Glu Lys Met Glu Arg Glu His Leu Ser Val Leu Glu His Leu Pro Ala
            740                 745                 750

Ile Arg Cys Leu Tyr Leu Phe Val Lys Arg Val Ser Glu Asp Gly Leu
            755                 760                 765

Val Ile Ser His Gly Ala Phe Arg Cys Leu Arg Arg Leu Glu Phe Cys
            770                 775                 780

Asn Val Asp Gly Pro Gly Leu Met Phe Ala Gly Val Pro Met Leu
785                 790                 795                 800

Glu Trp Leu Arg Leu Gly Phe Asp Ala Asp Arg Ala Gln Ser Thr Tyr
                805                 810                 815

Gly Gly Leu Glu Val Gly Ile Gln Arg Leu Ser Ser Leu Lys His Val
            820                 825                 830

Val Leu Ile Val Trp Met Val Ser Glu Gly Gly Asp Pro Ala Glu
            835                 840                 845
```

Gln Ala Val Trp Ser Ala Ile Asn Gly Gln Val Glu Met Leu Pro Asn
    850                 855                 860

Ser Pro Thr Val Asp Ile Arg Phe Arg Arg Ser Gln Leu Gln Ala
865             870                 875                 880

Ser Ser Glu

<210> SEQ ID NO 55
<211> LENGTH: 2631
<212> TYPE: DNA
<213> ORGANISM: Zea mays

<400> SEQUENCE: 55

| | | | | | |
|---|---|---|---|---|---|
| atggagaacc | cagacgcgca | ggcgaaggcg | tgggcggcgg | agatgcgcga | gctggcctac | 60 |
| gacatggagg | acagcatcga | tctcttcacc | caccacgtcg | accacgaacc | ggccgacacc | 120 |
| gccaccaccg | gcgtcaagag | gttcttcctc | cggatcatcc | ggaagcttaa | gaaactccac | 180 |
| taccgccaca | ggtttgctca | ggagatcaaa | caactccacg | accttgccaa | cgaatcgtac | 240 |
| cggcgtagga | agaggtacag | gattgaggag | ggcggttcaa | gcctcccgca | cgcggagatc | 300 |
| gatcctcggt | tagaggcgct | ctacgtggag | gtggagaaac | tcgtgggcat | ccagggccca | 360 |
| agccaggaga | tcattggaca | gctcgtcggc | gagaacgcag | cggagcggcg | gagggttgtc | 420 |
| gccgttgttg | gatctggagg | ttcaggcaag | accacacttg | ccaaacaggt | gtacgagaaa | 480 |
| atcaggtgcc | aattctcttg | tgcagccttt | gtgtccgtgt | cgcaaaagcc | caacatgaat | 540 |
| agcctcctgt | gggagttgtt | atctcaaatc | gggaaccatg | gtggagattt | aggaatgatg | 600 |
| gcagtaggat | attgcagtga | caaacaactg | atcgacagac | taagatcaca | tcttgaaaag | 660 |
| cagaggtatc | tcgttgtgat | agatgatgtt | tggacaaact | cagcgtggga | gaccatacaa | 720 |
| tgtgcgctcc | ctaaaaatgc | ccatgcaagt | aaaataattc | tgacaacacg | aatcaacagt | 780 |
| gtaggccagt | tctcctgcac | tccagatgag | ggttttatct | atcagatgaa | gcctcttgc | 840 |
| agaaacgatt | ctgaaaatct | gtttctgaaa | aggacactat | gtgataaaga | taagtttcct | 900 |
| gctcagctgg | agggattaa | aaacgagata | tcgagaaat | gcgatggttt | gccactggct | 960 |
| attgttactc | tagctagcat | gttagctact | aaacagagaa | caaggaaga | atgggagagg | 1020 |
| gcacttgatt | caatccattc | tacgcacaag | aaagatagta | gcctggaagt | gatggacaag | 1080 |
| atactgtctc | tgagttacag | ggatctacct | cacaacatga | aaattgctt | gctgtatatc | 1140 |
| agtacatttc | cagaggacca | cacgatttac | aaagatgctc | tagtatggag | atggatggct | 1200 |
| gaagggttta | tcgctgaaac | acaaggcttt | acttggagc | aggttgccga | gggctacttc | 1260 |
| tacgagtttg | tgaacaggag | tttggttcag | cccataacct | tgcgttcaag | atatgaaatg | 1320 |
| cgtggagaag | gaggttgccg | agtccatgac | attgtactga | acttcctcat | ctctcgtgca | 1380 |
| gctgaagaga | actttttaac | tacgctgtat | ggcgcccagg | gggttccatc | ttcagaccga | 1440 |
| aggattcgcc | ggctctctgt | ctgggacagt | ccagaacacg | cactggcagt | ctctagagcg | 1500 |
| accatgaatc | tgtcccatct | ccggtcagtt | agaatatgca | acgttggaga | ctggcccgtg | 1560 |
| cctgctgttc | tagacttacc | tgtccttcga | gtgttagatc | tagagggatg | ccgtgatctg | 1620 |
| aggatcgtcg | accctgactg | cattctaagc | ttgtttcatc | tgaggtacct | gggtttccgc | 1680 |
| agcgcaagtg | gtgtcgtgct | accggctcaa | ataggaaatt | tacaccatct | gcagaccatc | 1740 |
| gatttaagcg | ggactggagt | gacacagctg | ccagaaagca | ttgtccagct | caagcgactg | 1800 |
| atgcatcttg | ttgggcaacg | gctcatcatg | ccagacgggt | ttggtagcat | ggaatcccctt | 1860 |
| gaggagttag | gtactatcga | ctgctgcaag | tgccccgctg | agggtgctcc | gagtgaccga | 1920 |

```
gtggctttcg tcggggtcga acaagtgac atggaaacca gaaggaaatc tttgatgtca   1980
tccctctgca aactcggagg agacaacctt cggcgtgtca ctattatcga cctcgctggc   2040
ggtggagatt gctttgtgga gtcgtggcac cctcctcctc gtctcctcca gaagttcatc   2100
catatcagtc agcaacagca cttctccagg tttccagaat ggatcagttc ctgcctatgt   2160
gatctcaccc acctggatat aaaggccgaa aagatggaaa gggagcatct aagtgttctt   2220
gaacacctgc ccgccatccg ttatctatac cttttcgtga agcgagtctc cgaagacggg   2280
ctcgtcatca gccacagcgc gttccgatgt ctacggcgtc tcgagttctg taacttagat   2340
ggacctggtt tgatgtttgc aggaggcgtt ccaatgctgg aatggctgag gctcgggttc   2400
gacgcggata gagcgcaatc gacatacggc ggtctggagg ttggcatcca gcgcctctcg   2460
tctctcaaac atgtcgtgct cattgtctgt atggtttctg aaggcggtga tgatccagcg   2520
gagcaagccg tctggtctgc catcaatggc caagtagaga tgctccccaa ttctccgacg   2580
gttgatatcc ggtttcgtag acggagtcag ctgcaggcaa gctcagaata a            2631
```

<210> SEQ ID NO 56
<211> LENGTH: 876
<212> TYPE: PRT
<213> ORGANISM: Zea mays

<400> SEQUENCE: 56

```
Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Ala Gln Glu Ile Lys Gln Leu His Asp Leu Ala Asn Glu Ser Tyr
65                  70                  75                  80

Arg Arg Arg Lys Arg Tyr Arg Ile Glu Glu Gly Gly Ser Ser Leu Pro
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
        115                 120                 125

Val Gly Glu Asn Ala Ala Glu Arg Arg Arg Val Val Ala Val Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
        195                 200                 205

Gln Leu Ile Asp Arg Leu Arg Ser His Leu Glu Lys Gln Arg Tyr Leu
    210                 215                 220

Val Val Ile Asp Asp Val Trp Thr Asn Ser Ala Trp Glu Thr Ile Gln
225                 230                 235                 240
```

```
Cys Ala Leu Pro Lys Asn Ala His Ala Ser Lys Ile Ile Leu Thr Thr
            245                 250                 255

Arg Ile Asn Ser Val Gly Gln Phe Ser Cys Thr Pro Asp Glu Gly Phe
            260                 265                 270

Ile Tyr Gln Met Lys Pro Leu Cys Arg Asn Asp Ser Glu Asn Leu Phe
            275                 280                 285

Leu Lys Arg Thr Leu Cys Asp Lys Asp Lys Phe Pro Ala Gln Leu Glu
            290                 295                 300

Gly Ile Lys Asn Glu Ile Ile Glu Lys Cys Asp Gly Leu Pro Leu Ala
305                 310                 315                 320

Ile Val Thr Leu Ala Ser Met Leu Ala Thr Lys Gln Arg Thr Arg Glu
            325                 330                 335

Glu Trp Glu Arg Ala Leu Asp Ser Ile His Ser Thr His Lys Lys Asp
            340                 345                 350

Ser Ser Leu Glu Val Met Asp Lys Ile Leu Ser Leu Ser Tyr Arg Asp
            355                 360                 365

Leu Pro His His Asn Met Arg Asn Cys Leu Leu Tyr Ile Ser Thr Phe Pro
            370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
            405                 410                 415

Glu Gly Tyr Phe Tyr Glu Phe Val Asn Arg Ser Leu Val Gln Pro Ile
            420                 425                 430

Thr Leu Arg Ser Arg Tyr Glu Met Arg Gly Gly Gly Cys Arg Val
            435                 440                 445

His Asp Ile Val Leu Asn Phe Leu Ile Ser Arg Ala Ala Glu Glu Asn
            450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
            485                 490                 495

Val Ser Arg Ala Thr Met Asn Leu Ser His Leu Arg Ser Val Arg Ile
            500                 505                 510

Cys Asn Val Gly Asp Trp Pro Val Pro Ala Val Leu Asp Leu Pro Val
            515                 520                 525

Leu Arg Val Leu Asp Leu Glu Gly Cys Arg Asp Leu Arg Ile Val Asp
530                 535                 540

Pro Asp Cys Ile Leu Ser Leu Phe His Leu Arg Tyr Leu Gly Phe Arg
545                 550                 555                 560

Ser Ala Ser Gly Val Val Leu Pro Ala Gln Ile Gly Asn Leu His His
            565                 570                 575

Leu Gln Thr Ile Asp Leu Ser Gly Thr Gly Val Thr Gln Leu Pro Glu
            580                 585                 590

Ser Ile Val Gln Leu Lys Arg Leu Met His Leu Val Gly Gln Arg Leu
            595                 600                 605

Ile Met Pro Asp Gly Phe Gly Ser Met Glu Ser Leu Glu Glu Leu Gly
            610                 615                 620

Thr Ile Asp Cys Cys Lys Cys Pro Ala Glu Gly Ala Pro Ser Asp Arg
625                 630                 635                 640

Val Ala Phe Val Gly Val Glu Thr Ser Asp Met Glu Thr Arg Arg Lys
            645                 650                 655
```

```
Ser Leu Met Ser Ser Leu Cys Lys Leu Gly Gly Asp Asn Leu Arg Arg
            660                 665                 670

Val Thr Ile Ile Asp Leu Ala Gly Gly Gly Asp Cys Phe Val Glu Ser
        675                 680                 685

Trp His Pro Pro Arg Leu Leu Gln Lys Phe Ile His Ile Ser Gln
    690                 695                 700

Gln Gln His Phe Ser Arg Phe Pro Glu Trp Ile Ser Ser Cys Leu Cys
705                 710                 715                 720

Asp Leu Thr His Leu Asp Ile Lys Ala Glu Lys Met Glu Arg Glu His
                725                 730                 735

Leu Ser Val Leu Glu His Leu Pro Ala Ile Arg Tyr Leu Tyr Leu Phe
            740                 745                 750

Val Lys Arg Val Ser Glu Asp Gly Leu Val Ile Ser His Ser Ala Phe
        755                 760                 765

Arg Cys Leu Arg Arg Leu Glu Phe Cys Asn Leu Asp Gly Pro Gly Leu
    770                 775                 780

Met Phe Ala Gly Gly Val Pro Met Leu Glu Trp Leu Arg Leu Gly Phe
785                 790                 795                 800

Asp Ala Asp Arg Ala Gln Ser Thr Tyr Gly Gly Leu Glu Val Gly Ile
                805                 810                 815

Gln Arg Leu Ser Ser Leu Lys His Val Val Leu Ile Val Cys Met Val
            820                 825                 830

Ser Glu Gly Gly Asp Asp Pro Ala Glu Gln Ala Val Trp Ser Ala Ile
        835                 840                 845

Asn Gly Gln Val Glu Met Leu Pro Asn Ser Pro Thr Val Asp Ile Arg
    850                 855                 860

Phe Arg Arg Arg Ser Gln Leu Gln Ala Ser Ser Glu
865                 870                 875

<210> SEQ ID NO 57
<211> LENGTH: 2667
<212> TYPE: DNA
<213> ORGANISM: Zea mays

<400> SEQUENCE: 57
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg gcgtcaagag gttcttcctc cggatcatcc ggaagcttaa gaaactccac     180
taccgccaca ggtttgctca ggagatcaaa caactccacg accttgccaa cgaatcgtac     240
cggcgtagga agaggtacag gattgaggag ggcggttcaa gcctcccgca cgcggagatc     300
gatcctcggt tagaggcgct ctacgtggag gtggagaaac tcgtgggcat ccagggccca     360
agccaggaga tcattggaca gctcgtcggc gagaacgcag cggagcggcg gagggttgtc     420
gccgttgttg gatctggagg ttcaggcaag accacacttg ccaaacaggt gtacgagaaa     480
atcaggtgcc aattctcttg tgcagccttt gtgtccgtgt cgcaaaagcc aacatgaat      540 agcctcctgt gggagttgtt atctcaaatc gggaaccatg gtggagattt aggaatgatg     600
gcagtaggat attgcagtga caacaactg atcgacagac taagatcaca tcttgaaaag      660
cagagaactg attttcaac tgcttcacaa tctgctctta ggtatctcgt tgtgatagat      720
gatgtttgga caactcagc gtgggagacc atacaatgtg cgctccctaa aaatgcccat      780
gcaagtaaaa taattctgac aacacgaatc aacagtgtag ccagttctc ctgcactcca      840 gatgagggtt ttatctatca gatgaagcct ctttgcagaa acgattctga aaatctgttt      900
```

```
ctgaaaagga cactatgtga taaagataag tttcctgctc agctggaggg gattaaaaac    960
gagataatcg agaaatgcga tggtttgcca ctggctattg ttactctagc tagcatgtta   1020
gctactaaac agagaacaag ggaagaatgg gagagggcac ttgattcaat ccattctacg   1080
cacaagaaag atagtagcct ggaagtgatg acaagatac tgtctctgag ttacagggat   1140
ctacctcaca acatgagaaa ttgcttgctg tatatcagta catttccaga ggaccacacg   1200
atttacaaag atgctctagt atggagatgg atggctgaag gtttatcgc tgaaacacaa   1260
ggctttactt tggagcaggt tgccgagggc tacttctacg agtttgtgaa caggagtttg   1320
gttcagccca taaccttgcg ttcaagatat gaaatgcgtg gagaaggagg ttgccgagtc   1380
catgacattg tactgaactt cctcatctct cgtgcagctg aagagaactt tttaactacg   1440
ctgtatggcg cccaggggt tccatcttca gaccgaagga ttcgccggct ctctgtctgg   1500
gacagtccag aacacgcact ggcagtctct agagcgacca tgaatctgtc ccatctccgg   1560
tcagttagaa tatgcaacgt tggagactgg cccgtgcctg ctgttctaga cttacctgtc   1620
cttcgagtgt tagatctaga gggatgccgt gatctgagga tcgtcgaccc tgactgcatt   1680
ctaagcttgt ttcatctgag gtacctgggt ttccgcagcg caagtggtgt cgtgctaccg   1740
gctcaaatag gaaatttaca ccatctgcag accatcgatt taagcgggac tggagtgaca   1800
cagctgccag aaagcattgt ccagctcaag cgactgatgc atcttgttgg gcaacggctc   1860
atcatgccag acgggtttgg tagcatggaa tcccttgagg agttaggtac tatcgactgc   1920
tgcaagtgcc ccgctgaggg tgctccgagt gaccgagtgg ctttcgtcgg ggtcgaaaca   1980
agtgacatgg aaaccagaag gaaatctttg atgtcatccc tctgcaaact cggaggagac   2040
aaccttcggc gtgtcactat tatcgacctc gctggcggtg gagattgctt tgtggagtcg   2100
tggcacctc ctcctcgtct cctccagaag ttcatccata tcagtcagca acagcacttc   2160
tccaggtttc cagaatggat cagttcctgc ctatgtgatc tcacccacct ggatataaag   2220
gccgaaaaga tggaaaggga gcatctaagt gttcttgaac acctgcccgc catccgttat   2280
ctatacctttt tcgtgaagcg agtctccgaa gacgggctcg tcatcagcca cagcgcgttc   2340
cgatgtctac ggcgtctcga gttctgtaac ttagatggac ctggttttgat gtttgcagga   2400
ggcgttccaa tgctggaatg gctgaggctc gggttcgacg cggatagagc gcaatcgaca   2460
tacggcggtc tggaggttgg catccagcgc ctctcgtctc tcaaacatgt cgtgctcatt   2520
gtctgtatgg tttctgaagg cggtgatgat ccagcggagc aagccgtctg gtctgccatc   2580
aatggccaag tagagatgct cccccaattct ccgacggttg atatccggtt tcgtagacgg   2640
agtcagctgc aggcaagctc agaataa                                        2667
```

<210> SEQ ID NO 58
<211> LENGTH: 888
<212> TYPE: PRT
<213> ORGANISM: Zea mays

<400> SEQUENCE: 58

Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

```
Phe Leu Arg Ile Ile Arg Lys Leu Lys Lys Leu His Tyr Arg His Arg
     50                  55                  60

Phe Ala Gln Glu Ile Lys Gln Leu His Asp Leu Ala Asn Glu Ser Tyr
 65                  70                  75                  80

Arg Arg Arg Lys Arg Tyr Arg Ile Glu Glu Gly Gly Ser Ser Leu Pro
                 85                  90                  95

His Ala Glu Ile Asp Pro Arg Leu Glu Ala Leu Tyr Val Glu Val Glu
             100                 105                 110

Lys Leu Val Gly Ile Gln Gly Pro Ser Gln Glu Ile Ile Gly Gln Leu
         115                 120                 125

Val Gly Glu Asn Ala Ala Glu Arg Arg Val Val Ala Val Val Gly
     130                 135                 140

Ser Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                 165                 170                 175

Pro Asn Met Asn Ser Leu Leu Trp Glu Leu Leu Ser Gln Ile Gly Asn
             180                 185                 190

His Gly Gly Asp Leu Gly Met Met Ala Val Gly Tyr Cys Ser Asp Lys
         195                 200                 205

Gln Leu Ile Asp Arg Leu Arg Ser His Leu Glu Lys Gln Arg Thr Asp
     210                 215                 220

Phe Ser Thr Ala Ser Gln Ser Ala Leu Arg Tyr Leu Val Val Ile Asp
225                 230                 235                 240

Asp Val Trp Thr Asn Ser Ala Trp Glu Thr Ile Gln Cys Ala Leu Pro
                 245                 250                 255

Lys Asn Ala His Ala Ser Lys Ile Ile Leu Thr Thr Arg Ile Asn Ser
             260                 265                 270

Val Gly Gln Phe Ser Cys Thr Pro Asp Glu Gly Phe Ile Tyr Gln Met
         275                 280                 285

Lys Pro Leu Cys Arg Asn Asp Ser Glu Asn Leu Phe Leu Lys Arg Thr
     290                 295                 300

Leu Cys Asp Lys Asp Lys Phe Pro Ala Gln Leu Glu Gly Ile Lys Asn
305                 310                 315                 320

Glu Ile Ile Glu Lys Cys Asp Gly Leu Pro Leu Ala Ile Val Thr Leu
                 325                 330                 335

Ala Ser Met Leu Ala Thr Lys Gln Arg Thr Arg Glu Glu Trp Glu Arg
             340                 345                 350

Ala Leu Asp Ser Ile His Ser Thr His Lys Lys Asp Ser Ser Leu Glu
         355                 360                 365

Val Met Asp Lys Ile Leu Ser Leu Ser Tyr Arg Asp Leu Pro His Asn
     370                 375                 380

Met Arg Asn Cys Leu Leu Tyr Ile Ser Thr Phe Pro Glu Asp His Thr
385                 390                 395                 400

Ile Tyr Lys Asp Ala Leu Val Trp Arg Trp Met Ala Glu Gly Phe Ile
                 405                 410                 415

Ala Glu Thr Gln Gly Phe Thr Leu Glu Gln Val Ala Glu Gly Tyr Phe
             420                 425                 430

Tyr Glu Phe Val Asn Arg Ser Leu Val Gln Pro Ile Thr Leu Arg Ser
         435                 440                 445

Arg Tyr Glu Met Arg Gly Glu Gly Gly Cys Arg Val His Asp Ile Val
     450                 455                 460
```

```
Leu Asn Phe Leu Ile Ser Arg Ala Ala Glu Glu Asn Phe Leu Thr Thr
465                 470                 475                 480

Leu Tyr Gly Ala Gln Gly Val Pro Ser Ser Asp Arg Arg Ile Arg Arg
                485                 490                 495

Leu Ser Val Trp Asp Ser Pro Glu His Ala Leu Ala Val Ser Arg Ala
                500                 505                 510

Thr Met Asn Leu Ser His Leu Arg Ser Val Arg Ile Cys Asn Val Gly
                515                 520                 525

Asp Trp Pro Val Pro Ala Val Leu Asp Leu Pro Val Leu Arg Val Leu
530                 535                 540

Asp Leu Glu Gly Cys Arg Asp Leu Arg Ile Val Asp Pro Asp Cys Ile
545                 550                 555                 560

Leu Ser Leu Phe His Leu Arg Tyr Leu Gly Phe Arg Ser Ala Ser Gly
                565                 570                 575

Val Val Leu Pro Ala Gln Ile Gly Asn Leu His His Leu Gln Thr Ile
                580                 585                 590

Asp Leu Ser Gly Thr Gly Val Thr Gln Leu Pro Glu Ser Ile Val Gln
                595                 600                 605

Leu Lys Arg Leu Met His Leu Val Gly Gln Arg Leu Ile Met Pro Asp
610                 615                 620

Gly Phe Gly Ser Met Glu Ser Leu Glu Glu Leu Gly Thr Ile Asp Cys
625                 630                 635                 640

Cys Lys Cys Pro Ala Glu Gly Ala Pro Ser Asp Arg Val Ala Phe Val
                645                 650                 655

Gly Val Glu Thr Ser Asp Met Glu Thr Arg Arg Lys Ser Leu Met Ser
                660                 665                 670

Ser Leu Cys Lys Leu Gly Gly Asp Asn Leu Arg Arg Val Thr Ile Ile
                675                 680                 685

Asp Leu Ala Gly Gly Gly Asp Cys Phe Val Glu Ser Trp His Pro Pro
690                 695                 700

Pro Arg Leu Leu Gln Lys Phe Ile His Ile Ser Gln Gln Gln His Phe
705                 710                 715                 720

Ser Arg Phe Pro Glu Trp Ile Ser Ser Cys Leu Cys Asp Leu Thr His
                725                 730                 735

Leu Asp Ile Lys Ala Glu Lys Met Glu Arg Glu His Leu Ser Val Leu
                740                 745                 750

Glu His Leu Pro Ala Ile Arg Tyr Leu Tyr Leu Phe Val Lys Arg Val
                755                 760                 765

Ser Glu Asp Gly Leu Val Ile Ser His Ser Ala Phe Arg Cys Leu Arg
                770                 775                 780

Arg Leu Glu Phe Cys Asn Leu Asp Gly Pro Gly Leu Met Phe Ala Gly
785                 790                 795                 800

Gly Val Pro Met Leu Glu Trp Leu Arg Leu Gly Phe Asp Ala Asp Arg
                805                 810                 815

Ala Gln Ser Thr Tyr Gly Gly Leu Glu Val Gly Ile Gln Arg Leu Ser
                820                 825                 830

Ser Leu Lys His Val Val Leu Ile Val Cys Met Val Ser Glu Gly Gly
                835                 840                 845

Asp Asp Pro Ala Glu Gln Ala Val Trp Ser Ala Ile Asn Gly Gln Val
850                 855                 860
```

Glu Met Leu Pro Asn Ser Pro Thr Val Asp Ile Arg Phe Arg Arg Arg
865                 870                 875                 880

Ser Gln Leu Gln Ala Ser Ser Glu
            885

<210> SEQ ID NO 59
<211> LENGTH: 2930
<212> TYPE: DNA
<213> ORGANISM: Zea mays

<400> SEQUENCE: 59

```
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg cgtcaagag gttcttcctc cggatcatcc ggaagcttaa gaaactccac     180
taccgccaca ggtttgttca ggagatcaaa caactccacg accttgccaa cgaatcgtac     240
cggcgtagga gaggtacag gattgaggag ggcggttcaa gcctctcgca cgcggagatc     300
gatcctcggt tagaggcgct ctacgtggag gtggagaaac tcgtgggcat ccagggccca     360
agccaggaga tcattggaca gctcgtcggc gagaacgcag cggagcgacg gagggttgtc     420
gccgttgttg gatctggagg ttcaggcaag accacacttg ccaaacaggt gtacgagaaa     480
atcaggtgcc aattctcttg tgcagccttt gtgtctgtgt cgcaaaagcc aacatgaat     540 agcctcctgt gggagttgct atctcaaatc gggaaccatg gtggagattt aggaatgatg     600
gcagtaggat attgcagtga caaacaactg atcgacagac taagatcaca tcttgaaaag     660
cagaggttag tttacctttt cattccggtt agcttaattc ggtacaccaa ctagagattt     720
gtgatttgct attaattaca ccaaatttct cctacacaac aataactggt ttagcatgat     780
ggcgatccaa agtcaaaact atcttctact actagtgtat gccatactca tatagatatt     840
ttcttttcat aaactctcgt agcatttta catgcattca tattcctatt gcctttatac     900
agaactgatt tttcactgct tcacaatctg ctcttaggta tctcgttgtg atagatgatg     960
tttggacaaa ctcagcgtgg gagaccatac aatgtgcgct ccctaaaaat gcccatgcaa    1020 gtaaataat tctgacaaca cgaatcaaca gtgtaggcca gttctcctgc actccagatg    1080
agggttttat ctatcagatg aagcctcttt gcagaaacga ttctgaaaat ctgtttctga    1140 aaggacact atgtgataaa gataagtttc ctgctcagct ggaggggatt aaaaacgaga    1200
taatcgagaa atgcgatggt ttgccactgg ctattgttac tctagctagc atgttagcta    1260
ctaaacagag aacaagggaa gaatgggaga gggcacttga ttcaatccat tctatgcaca    1320
agaaagatag tggcctggaa gtgatggaca agatactgtc tctgagttac agggatctac    1380
ctcacaacat gagaaattgc ttgctgtatc tcagtacatt tccagaggac cacacgattt    1440
acaaagatgc cctagtatgg agatggatgg ctgaagggtt tatcgctgaa acacaaggct    1500
ttactttgga gcaggttgcc gagggctact ctacgagtt tgtgaacagg agtttggttc    1560
agcccataac cttgcgttca agatatgaaa tgcgtggaga aggaggttgc cgagtccatg    1620
acattgtact gaacttcctc atctctcgtg cagctgaaga gaactttta actacgctgt    1680 atggcgccca gggggttcca tcttcagacc gaaggattcg ccggctctct gtctgggaca    1740
gtccagaaca cgcactggca gtctctagag cgaccatgaa tctgtcccat ctccggtcag    1800
ttagaatatg caacgttgga gactggcccg tgcctgctgt tctagactta cctgtccttc    1860
gagtgttaga tctagaggga tgccgtgatc tgaggatcga cgaacctgac tgcattctaa    1920
```

```
gcttgtttca tctgagatac ctgggtttcc gcagcgcaag tggtgtcgtg ctaccggctc    1980
aaatcggaaa tttacaccat ctgcagacca tcgatttaag cgggactgga gtgacacagc    2040
tgccagaaag cattgtccag ctcaagcgac tgatgcatct tgttgggcaa cggctcatca    2100
tgccagacgg gtttggtagc atggaatccc ttgaggagtt aggtactatc gactgctgca    2160
agtgccccgt cagttttggg aagacctag cacttctgag caggctgagg gtgctccgag    2220 tggcttttcat cggggtcgaa acaagtgaca tggaaaccag aaggaaatct ttgatgtcat    2280
ccctctgcaa actcggagga gacaaccttc ggcgtgtcac tattatcgac ctcgctggcg    2340
gtggagattg ctttgtggag tcgtggcacc ctcctcctcg tctcctccag aagttcatcc    2400
atatcagtca gcaacagcac ttctccaggt ttccagaatg gatcagttcc tgcctatgtg    2460
atctcaccca cctggatata aaggccgaaa agatggaaag ggagcatcta agtgttcttg    2520
aacacctgcc cgccatccgt tgcctatacc ttttcgtgaa gcgagtctcc gaagacgggc    2580
tcgccatcag ccacggcgcg ttccgatgtc tacggcgtct cgagttctgc aacgtagatg    2640
gacctggttt gatgtttgca ggaggcgttc caatgttgga atggctgagg ctcgggttcg    2700
acgcggatag agcgcaatcg acatacggcg gtctggaggt tggcatccag cgcctctcgt    2760
ctctcaaaca tgtcgtgctc attgtatgga tggtttctga aggcggtgat gatccagcgg    2820
agcaagccgt ctggtctgcc atcaatggcc aagtagagat gctccccaac tctccgacgg    2880
ttgatatccg gttcgtaga cggagtcagc tgcaggcaag ctcagaataa                2930
```

<210> SEQ ID NO 60
<211> LENGTH: 16
<212> TYPE: PRT
<213> ORGANISM: Zea mays

<400> SEQUENCE: 60

Val Ser Phe Gly Glu Asp Leu Ala Leu Leu Ser Arg Leu Arg Val Leu
1               5                   10                  15

<210> SEQ ID NO 61
<211> LENGTH: 2064
<212> TYPE: DNA
<213> ORGANISM: Zea mays

<400> SEQUENCE: 61

```
tccacctcgt ctaccacgtc ttctccccgc catggctgct caccagcctc acctctccgt      60
cctcctcctc gtcctcctcg ctgcccatgt cgtctccacc tccgcccatg gcgagcctcc     120
tcttccgagc ccttacaaca cctccgccca tggcgagcct cctcttccga gcacttacaa     180
cgcctccatg tgctcgtcgt tctggtgtgg cggcgtcgag atccgctacc gttctatct     240 tgccaacgca atcgccgact acagcggag ctactactcc tgcggctaca ccgacttgag     300
cgtttcctgc gaactcgagg tcgagggggtc gccgacgacc tggacccta ccatccgtct     360 cggcggcggc gactacaccg tcaagaacat ctcctacctc tacgaccagc agaccatctc     420
actggcggac agagatgtgc tcggaggcgg cggctgcccc gtcgtccgcc acaacgtcag     480
cttcgacgag acgtggctgc acctgcacaa cgccagcgcc ttcgacaacc tcaccttctt     540
cttcggatgc cactggggc cacgaatac accgcctgaa tttgccgact acaacatcag     600
ctgcgccggg ttcaatactc caactatcag cggtggaagg tccttcgtgt tcaagactgg     660
agatcttgac gaacaagagg agcaggagtt ggctttacac tgcgacgagg ttttctccgt     720
gccagtgaga agagatgctc tgcaggcgat cgtcagcaac ttcagcctca cacgggacgg     780
```

```
gtacggcgag gtgcttaggc aggggttcga gttggaatgg aatcggacat cggaggatca     840
gtgtggccgg tgcgagggat cgggctccgg cggatggtgc gcctacagcc agaagagaga     900
attcctgggc tgcttgtgca gcggagggaa ggtgggcagc ccgttctgca aaccatcgag     960
atcaaaaagg aaagaaggac ctattgttgg tgctgttgcc gttgcattcc tgtgtctagt    1020
cattctcaca tgcttcttgg cttgtagaca tggttcgctg cccttcaaat cggagaacaa    1080
accagggaca aggattgagt ccttcctaca gaagaacgag agtatacatc gaaaagata     1140 cacctacgcg gacgtgaaaa gaatgacaaa atccttcgct gtgaagctag gccaaggtgg    1200
gtttggtgct gtatacaaag gcagcctcca cgatggccga caggtagcag tcaagatgct    1260
gaaggacacc caaggtgacg gcgaggaatt catgaacgag gtggctagca tcagcaggac    1320
ttctcatgtc aacgtcgtga cacttctagg gttttgcttg caagggtcga aaagagcact    1380
gatctacgag tacatgccca atggttcgct cgaaaggtat gccttcaccg gtgacatgaa    1440
cagtgagaat ttgctaacct gggaaaggct atttgacata gcaattggca cggccagagg    1500
gctcgaatac ctacaccggg gatgcaacac tcggatcgtg cattttgaca tcaagccaca    1560
caacatcctg ttagaccagg atttctgtcc taagatctct gactttggac tggccaagct    1620
atgtctgaac aaagagagcg ctatctccat tgctggcgca agagggacga tagggtatat    1680
cgccccggag gtctactcaa agcaatttgg aataataagc agcaagtctg atgtctatag    1740
ctatgggatg atggtccttg agatggttgg agcaagggac aggaatacaa gcgcagatag    1800
tgaccatagc agccaatatt tccctcagtg gctttatgaa catttggacg actattgtgt    1860
tggtgcttcc gagattaatg gtgagaccac agagctcgtg aggaagatga tagttgtagg    1920
tctgtggtgc atacaagtga ttccgactga tcgaccaaca atgacgagag tcgtcgagat    1980
gttggaaggg agcacaagta atctagagtt gccacccaga gttctcttga gctgacaaag    2040
cgtagatatt tttcctatca aatg                                            2064
```

<210> SEQ ID NO 62
<211> LENGTH: 667
<212> TYPE: PRT
<213> ORGANISM: Zea mays

<400> SEQUENCE: 62

```
Met Ala Ala His Gln Pro His Leu Ser Val Leu Leu Val Leu Leu
1               5                   10                  15

Ala Ala His Val Val Ser Thr Ser Ala His Gly Glu Pro Pro Leu Pro
            20                  25                  30

Ser Pro Tyr Asn Thr Ser Ala His Gly Glu Pro Pro Leu Pro Ser Thr
        35                  40                  45

Tyr Asn Ala Ser Met Cys Ser Ser Phe Trp Cys Gly Gly Val Glu Ile
    50                  55                  60

Arg Tyr Pro Phe Tyr Leu Ala Asn Ala Ile Ala Asp Tyr Ser Gly Ser
65                  70                  75                  80

Tyr Tyr Ser Cys Gly Tyr Thr Asp Leu Ser Val Ser Cys Glu Leu Glu
                85                  90                  95

Val Glu Gly Ser Pro Thr Thr Trp Thr Pro Thr Ile Arg Leu Gly Gly
            100                 105                 110

Gly Asp Tyr Thr Val Lys Asn Ile Ser Tyr Leu Tyr Asp Gln Gln Thr
        115                 120                 125

Ile Ser Leu Ala Asp Arg Asp Val Leu Gly Gly Gly Cys Pro Val
    130                 135                 140
```

```
Val Arg His Asn Val Ser Phe Asp Glu Thr Trp Leu His Leu His Asn
145                 150                 155                 160

Ala Ser Ala Phe Asp Asn Leu Thr Phe Phe Gly Cys His Trp Gly
            165                 170                 175

Pro Arg Asn Thr Pro Pro Glu Phe Ala Asp Tyr Asn Ile Ser Cys Ala
                180                 185                 190

Gly Phe Asn Thr Pro Thr Ile Ser Gly Gly Arg Ser Phe Val Phe Lys
            195                 200                 205

Thr Gly Asp Leu Asp Glu Gln Glu Glu Gln Leu Ala Leu His Cys
210                 215                 220

Asp Glu Val Phe Ser Val Pro Val Arg Arg Asp Ala Leu Gln Ala Ile
225                 230                 235                 240

Val Ser Asn Phe Ser Leu Thr Arg Asp Gly Tyr Gly Glu Val Leu Arg
                245                 250                 255

Gln Gly Phe Glu Leu Glu Trp Asn Arg Thr Ser Glu Asp Gln Cys Gly
            260                 265                 270

Arg Cys Glu Gly Ser Gly Ser Gly Gly Trp Cys Ala Tyr Ser Gln Lys
        275                 280                 285

Arg Glu Phe Leu Gly Cys Leu Cys Ser Gly Gly Lys Val Gly Ser Pro
    290                 295                 300

Phe Cys Lys Pro Ser Arg Ser Lys Arg Lys Glu Gly Pro Ile Val Gly
305                 310                 315                 320

Ala Val Ala Val Ala Phe Leu Cys Leu Val Ile Leu Thr Cys Phe Leu
                325                 330                 335

Ala Cys Arg His Gly Ser Leu Pro Phe Lys Ser Glu Asn Lys Pro Gly
            340                 345                 350

Thr Arg Ile Glu Ser Phe Leu Gln Lys Asn Glu Ser Ile His Pro Lys
            355                 360                 365

Arg Tyr Thr Tyr Ala Asp Val Lys Arg Met Thr Lys Ser Phe Ala Val
370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
            405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
            435                 440                 445

Ala Leu Ile Tyr Glu Tyr Met Pro Asn Gly Ser Leu Glu Arg Tyr Ala
450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
            485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
            515                 520                 525

Lys Leu Cys Leu Asn Lys Glu Ser Ala Ile Ser Ile Ala Gly Ala Arg
            530                 535                 540

Gly Thr Ile Gly Tyr Ile Ala Pro Glu Val Tyr Ser Lys Gln Phe Gly
545                 550                 555                 560
```

```
Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
                660                 665

<210> SEQ ID NO 63
<211> LENGTH: 2061
<212> TYPE: DNA
<213> ORGANISM: Zea mays

<400> SEQUENCE: 63
tccacctcgt ctaccacgtc ttctcctcgc catggctgct cacctaccac gcctcccgt      60 cctcctcctc gtcctcctcg ctgctcatgt cgtctccacc tccgcccatg ccgagcctcc    120
tcttccgagc ccttacagca cctccgccca tggcgagcct cctcttccga gcacttacaa    180
cgtctccatg tgctcggaat cgttctggtg cggcggcgtc gaaatccgct acccgttcta    240
tcttgccaac gcaaccgccg actacagcgg gagctactac tcctgcggct acaccgactt    300 gagcgttttcc tgcaaactcg aggtcgaggg gccgacgacg acatgggaccc ctaccatccg    360 tctcggcggc gacaactaca ccgtcaagaa catcttgtac gactatcata ccatctcact    420
ggcggacagc gatgtgctcg gaggcggcga gtgccccgtc gtccaccaca cgtcagctt    480 cgacgagacg tggctgcaca ccccagcgc cttcgacaac ctcaccttct tcttcggatg    540
ccactggggg ccacgcgata cactgcctga atttgccggc aacaacatca gctgcgccgg    600
gttcagtact ccagctatca gcggtggagg ctccttcgtg ttcaagcctg aagatcttga    660
cgaacatgcg gagcaggagt tggcttcaca ctgcgacgag gttttctccg tgccagtgag    720
aagcgaggct ctgcagcagg cgatcgtcag caacctcagc ctcggggacg ggtacggcga    780
gctgcttagg cagggatcg agttggaatg gaaacggaca tcggaggatc agtgtggcca    840
gtgcgaggaa tcgggctccg gcggacggtg cgcctacagc cagaagagag aattccttgg    900
ctgcttgtgc agcggaggga aggcgggcaa cccgttctgc aaaccatcaa gatcaaaaag    960
gaaagaagca tctattgttg gtgctgttgc cgttgcattc ctgtgtctag tcattctcac   1020
atgcttcttg gcttgtagac atggttcgct gcccttcaaa tcggagaaca aaccagggac   1080
aaggattgag tccttcctac agaagaacga gagtatacat ccgaaaagat acacctacac   1140
ggacgtgaaa agaatgacaa aatccttcgc tgtgaagcta ggccaaggtg gtttggtgc   1200 tgtatacaaa gcagcctcc acgatggccg acaggtagca gtcaagatgc tcaaggacac   1260
ccaaggtgac ggcgaggaat tcatgaacga ggtggctagc atcagcagga cttctcatgt   1320
caacgtcgtg acacttctag ggttttgctt gcaagggtcg aaaagagcac tgatctacga   1380
gtacatgccc aatggttcgc tcgaaaggta tgccttcacc ggtgacatga acagtgagaa   1440
tttgctaacc tgggaaaggc tatttgacat agcaattggc acggccagag ggctcgaata   1500
```

```
cctacaccgg ggatgcaaca ctcggatcgt gcattttgac atcaagccac acaacatcct   1560
gttagaccag gatttctgtc ctaagatctc tgactttgga ctggccaagc tatgtctgaa   1620
caaagagagc gctatctcca ttgttggcgc aagagggacg atagggtata tcgccccgga   1680
ggtctactca aagcaatttg aacaatcag cagcaagtct gatgtctata gctatgggat    1740
gatggtcctt gagatggttg gagcaaggga aggaataca agcgcaagcg cagatagtga    1800
ccatagcagc caatatttcc ctcagtggat ttatgaacat ttggacgact attgtgttgg   1860
tgcttccgag attaatggtg agaccacaga gctcgtgagg aagatgatag ttgtaggtct   1920
gtggtgcata caagtgattc cgactgatcg accaacaatg acgagagtcg tcgagatgtt   1980
ggaagggagc acgagtaatc tagagttgcc acccagagtt ctcttgagct gacaaagcgt   2040
agatattttt cctatcaaat g                                             2061
```

<210> SEQ ID NO 64
<211> LENGTH: 666
<212> TYPE: PRT
<213> ORGANISM: Zea mays

<400> SEQUENCE: 64

```
Met Ala Ala His Leu Pro Arg Leu Pro Val Leu Leu Val Leu Leu
1               5                   10                  15

Ala Ala His Val Val Ser Thr Ser Ala His Ala Glu Pro Pro Leu Pro
                20                  25                  30

Ser Pro Tyr Ser Thr Ser Ala His Gly Glu Pro Pro Leu Pro Ser Thr
            35                  40                  45

Tyr Asn Val Ser Met Cys Ser Glu Ser Phe Trp Cys Gly Gly Val Glu
50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270
```

```
Glu Ser Gly Ser Gly Gly Arg Cys Ala Tyr Ser Gln Lys Arg Glu Phe
            275                 280                 285

Leu Gly Cys Leu Cys Ser Gly Gly Lys Ala Gly Asn Pro Phe Cys Lys
        290                 295                 300

Pro Ser Arg Ser Lys Arg Lys Glu Ala Ser Ile Val Gly Ala Val Ala
305                 310                 315                 320

Val Ala Phe Leu Cys Leu Val Ile Leu Thr Cys Phe Leu Ala Cys Arg
                325                 330                 335

His Gly Ser Leu Pro Phe Lys Ser Glu Asn Lys Pro Gly Thr Arg Ile
            340                 345                 350

Glu Ser Phe Leu Gln Lys Asn Glu Ser Ile His Pro Lys Arg Tyr Thr
        355                 360                 365

Tyr Thr Asp Val Lys Arg Met Thr Lys Ser Phe Ala Val Lys Leu Gly
    370                 375                 380

Gln Gly Gly Phe Gly Ala Val Tyr Lys Gly Ser Leu His Asp Gly Arg
385                 390                 395                 400

Gln Val Ala Val Lys Met Leu Lys Asp Thr Gln Gly Asp Gly Glu Glu
                405                 410                 415

Phe Met Asn Glu Val Ala Ser Ile Ser Arg Thr Ser His Val Asn Val
            420                 425                 430

Val Thr Leu Leu Gly Phe Cys Leu Gln Gly Ser Lys Arg Ala Leu Ile
        435                 440                 445

Tyr Glu Tyr Met Pro Asn Gly Ser Leu Glu Arg Tyr Ala Phe Thr Gly
    450                 455                 460

Asp Met Asn Ser Glu Asn Leu Leu Thr Trp Glu Arg Leu Phe Asp Ile
465                 470                 475                 480

Ala Ile Gly Thr Ala Arg Gly Leu Glu Tyr Leu His Arg Gly Cys Asn
                485                 490                 495

Thr Arg Ile Val His Phe Asp Ile Lys Pro His Asn Ile Leu Leu Asp
            500                 505                 510

Gln Asp Phe Cys Pro Lys Ile Ser Asp Phe Gly Leu Ala Lys Leu Cys
        515                 520                 525

Leu Asn Lys Glu Ser Ala Ile Ser Ile Val Gly Ala Arg Gly Thr Ile
    530                 535                 540

Gly Tyr Ile Ala Pro Glu Val Tyr Ser Lys Gln Phe Gly Thr Ile Ser
545                 550                 555                 560

Ser Lys Ser Asp Val Tyr Ser Tyr Gly Met Met Val Leu Glu Met Val
                565                 570                 575

Gly Ala Arg Glu Arg Asn Thr Ser Ala Ser Ala Asp Ser Asp His Ser
            580                 585                 590

Ser Gln Tyr Phe Pro Gln Trp Ile Tyr Glu His Leu Asp Asp Tyr Cys
        595                 600                 605

Val Gly Ala Ser Glu Ile Asn Gly Glu Thr Thr Glu Leu Val Arg Lys
    610                 615                 620

Met Ile Val Val Gly Leu Trp Cys Ile Gln Val Ile Pro Thr Asp Arg
625                 630                 635                 640

Pro Thr Met Thr Arg Val Val Glu Met Leu Glu Gly Ser Thr Ser Asn
                645                 650                 655

Leu Glu Leu Pro Pro Arg Val Leu Leu Ser
            660                 665

<210> SEQ ID NO 65
<211> LENGTH: 5930
```

```
<212> TYPE: DNA
<213> ORGANISM: Zea mays

<400> SEQUENCE: 65
gatattgaat ccaattcaat tctataacct ccaaaatcga tatcctaaca tagcatgata      60
gttttttga gaggtgtgat ttaacatatt agatgaattt tcttttttta atacgctatg     120
ttctagatgt ctgacgatga atggagccgc tctgcatata ccaaacgcta tctaagtttg    180
tgaacaaatg actaaattat ccacacgacc acaattgggc gctgataaga tccacacttg    240
ctggttttaa ttcatccggt ctttatcaac tgtcacatca gttatagatc attatcaact    300
tttatctaca attgatgttg taatacacgg tcacttaaga ccatgtttag gtacaatgtc    360
tctcaaaact atgattttac ttatgatgac aataccgtag ttttgaatag ctctaaaaat    420
atcatggttc taaaaatatt gtttggattc aacattataa atcgtggtat taagcaaaag    480
ctagtcatgt tataaaaact ttaggttgaa gtagagtttt caatactaaa aaaatatcat    540
ggtatttaga atatcatgat tttaaaaata tagttcttac gaatgcaacc aaacaccttta   600
tgatataaaa taatatggta ttgcctacaa actacaaaaa taaatcactc ccaagcatta    660
cataaacatc attttttataa acttttagt aaaataaagc gcaatgtttt tattaaatag    720
aaatttatac aagtatatat aattaagcaa ataaaaacta cgttattcat aaaaagctaa    780
taaaagtaa aaagtaaaaa ctatataatt cataaaaaa tcgttatctt tctcttccat       840
cttattatct attttagtt gttttgtcaa atttaaggct attttatggg ttctttttat     900
ctttgtacat gtcgtgagcc aataacttat tgaattggtc aatcaattta ggttgagttt    960
tacttttaac taacctagta tagtttgttc aacaccttt tttcataatc ggggactcat    1020
tccacttgtt gttgacccat ttttcttct actgagttct tgcccttttg caatcaatag    1080
gacgtggtga gcccatattt ttaggtgtta tggatttata atcaccgttc aaatttgaat   1140
gaatattttg ttttttattat tgaagtcttc gtcaatcgtt atcatgcctc gcataccact   1200
tagaccgacg aagtccaaca tatttctccc ccgacgagga gagattcttc gtaaaattgc   1260
tactggtatt actggtattg aatagaagat aagggtgcgt ttggttgcat gcatctacgc   1320
gtgcttgcat cacggaatgc gggttggtgc tgtttggttg ctataagcta gactatacat   1380
atgcaagttt tgtgtttggt tggctgcatg cagatttcga tccaaactcg cacgatccac   1440
acagcaccct gggccaggct taccagatac gagtagattg gtcgcatctt tggagccagg   1500
ctttagcggt ccgcggtcct ggctgacacg gccagattgc cgagagaaac caaccaaaca   1560
gggtctaaat gtccaatcgt ttgactgcta ctggatgaaa aaagaatgtc acaactttaa   1620
aatgtgtatt tatttatact cctacacatg aaataactac tatactcaga tttcttttac   1680
attcagattt tttctcagcc actgaaacat accagcccctt tactaccaaa acaggaact   1740
ccacggtcca atgattatgt gagtcggagg agagggagg aagaatcgcc tgtgaaggag    1800
ggagggaggg agggacgtcc gatccgaaga tggaaggagc tggggagggg agcgccttga   1860
cggggatgat gggtcctgcg ctcgacaagc tcgctagcct cgttgacaag tacaccgagc   1920
tcagaaacgt gaggaagaag atggagcagc tgaggaagga gctgattgcg atcaacctcg   1980
cgcttgagaa gcacgcggcc atggagaacc cagacgcgca ggcgaaggcg tgggcggcg   2040
agatgcgcga gctggcctac gacatggagg acagcatcga tctcttcacc caccacgtcg   2100
accacgaacc ggccgacacc gccaccaccg gcgtcaagag gttcttcctc cggatcatcc   2160
ggaagcttaa gaaactccac taccgccaca ggtttgttca ggagatcaaa caactccacg   2220
```

```
accttgccaa cgaatcgtac cggcgtagga agaggtacag gattgaggag ggcggttcaa    2280
gcctctcgca cgcggagatc gatcctcggt tagaggcgct ctacgtggag gtggagaaac    2340
tcgtgggcat ccagggccca agccaggaga tcattggaca gctcgtcggc gagaacgcag    2400
cggagcgacg gagggttgtc gccgttgttg gatctggagg ttcaggcaag accacacttg    2460
ccaaacaggt gtacgagaaa atcaggtgcc aattctcttg tgcagccttt gtgtctgtgt    2520
cgcaaaagcc aacatgaat agcctcctgt gggagttgct atctcaaatc gggaaccatg     2580
gtggagattt aggaatgatg gcagtaggat attgcagtga caaacaactg atcgacagac    2640
taagatcaca tcttgaaaag cagaggttag tttaccttt cattccggtt agcttaattc     2700
ggtacaccaa ctagagattt gtgatttgct attaattaca ccaaatttct cctacacaac    2760
aataactggt ttagcatgat ggcgatccaa agtcaaaact atcttctact actagtgtat    2820
gccatactca tatagatatt ttcttttcat aaactctcgt agcattttta catgcattca    2880
tattcctatt gcctttatac agaactgatt tttcactgct tcacaatctg ctcttaggta    2940
tctcgttgtg atagatgatg tttggacaaa ctcagcgtgg gagaccatac aatgtgcgct    3000
ccctaaaaat gcccatgcaa gtaaaataat tctgacaaca cgaatcaaca gtgtaggcca    3060
gttctcctgc actccagatg agggttttat ctatcagatg aagcctcttt gcagaaacga    3120
ttctgaaaat ctgttctga aaggacact atgtgataaa gataagtttc ctgctcagct      3180
ggaggggatt aaaaacgaga taatcgagaa atgcgatggt ttgccactgg ctattgttac    3240
tctagctagc atgttagcta ctaaacagag aacaagggaa gaatgggaga gggcacttga    3300
ttcaatccat tctatgcaca agaaagatag tggcctggaa gtgatggaca agatactgtc    3360
tctgagttac agggatctac ctcacaacat gagaaattgc ttgctgtatc tcagtacatt    3420
tccagaggac cacacgattt acaaagatgc cctagtatgg agatggatgg ctgaaggggtt   3480 tatcgctgaa acacaaggct ttactttgga gcaggttgcc gagggctact tctacgagtt    3540
tgtgaacagg agtttggttc agcccataac cttgcgttca agatatgaaa tgcgtggaga    3600
aggaggttgc cgagtccatg acattgtact gaacttcctc atctctcgtg cagctgaaga    3660
gaacttttta actacgctgt atggcgccca gggggttcca tcttcagacc gaaggattcg    3720
ccggctctct gtctgggaca gtccagaaca cgcactggca gtctctagag cgaccatgaa    3780
tctgtcccat ctccggtcag ttagaatatg caacgtggga gactggcccg tgcctgctgt    3840
tctagactta cctgtccttc gagtgttaga tctagaggga tgccgtgatc tgaggatcga    3900
cgaacctgac tgcattctaa gcttgtttca tctgagatac ctgggtttcc gcagcgcaag    3960
tggtgtcgtg ctaccggctc aaatcggaaa tttacaccat ctgcagacca tcgatttaag    4020
cgggactgga gtgacacagc tgccagaaag cattgtccag ctcaagcgac tgatgcatct    4080
tgttgggcaa cggctcatca tgccagacgg gtttggtagc atggaatccc ttgaggagtt    4140
aggtactatc gactgctgca agtgccccgt cagttttggg gaagacctag cacttctgag    4200
caggctgagg gtgctccgag tggctttcat cggggtcgaa acaagtgaca tggaaaccag    4260
aaggaaatct ttgatgtcat ccctctgcaa actcggagga gacaaccttc ggcgtgtcac    4320
tattatcgac ctcgctggcg gtggagattg ctttgtggag tcgtggcacc ctcctcctcg    4380
tctcctccag aagttcatcc atatcagtca gcaacagcac ttctccaggt ttccagaatg    4440
gatcagttcc tgcctatgtg atctcaccca cctggatata aaggccgaaa agatggaaag    4500
ggagcatcta agtgttcttg aacacctgcc cgcatccgt tgcctatacc ttttcgtgaa     4560
gcgagtctcc gaagacgggc tcgccatcag ccacggcgcg ttccgatgtc tacggcgtct    4620
```

```
cgagttctgc aacgtagatg gacctggttt gatgtttgca ggaggcgttc caatgttgga      4680
atggctgagg ctcgggttcg acgcggatag agcgcaatcg acatacggcg gtctggaggt      4740
tggcatccag cgcctctcgt ctctcaaaca tgtcgtgctc attgtatgga tggtttctga      4800
aggcggtgat gatccagcgg agcaagccgt ctggtctgcc atcaatggcc aagtagagat      4860
gctccccaac tctccgacgg ttgatatccg gtttcgtaga cggagtcagc tgcaggcaag      4920
ctcagaataa ggagcacgaa aaagacgatg atgttggatg tcgcctgcta gctgtagtat      4980
gttgctgctt ctgcttgttg ccaacacatt ttttttgggt tagggtgggg tacaaccata      5040
aaatgtgtgt ggatgtgctt gtaagcatta cttgtatgtt ttttttttgta aagcacaata      5100 tagatagatg catatatgtg tgcgtgcaaa gctatgatta tcgacactca cacttgtaca      5160
ttagctagat gaaggtctcg acagagcaga gcatagtaca catctctggg agttggactg      5220
gacactataa cggggatgct gcagccgaaa ctcaaaagct acatgcatgt cacttggctc      5280
atcggcgcag gaagcaacgc aggtccatca cgcgcagcac cttgaacccg tccaggctac      5340
accccagcag cagcctcggc ttcttcggcg ccggcgggca gcgcggggggg cgttcggttc      5400 cagcgccact cgccgtcgcc gacgacagcg gcgagagctt ccgtggacct tcttcgtcct      5460
cgtcgccgcc gcgggagtaa gaccgcttca gcttcagcgg ccgcagctcc accagctgcg      5520
gaatgctaac atcttcttca ggcacctgcc gggtggttct ctttcccaga atcttccgct      5580
ggagacccat ggcgagctcg gttcggttta acctgcaatt aatgcgcaat agcggagtag      5640
gaagcgagat tgttagctca ggcgagcaga gatgaaccgg ctaggaaagt ttagttgctc      5700
gtgcatgcta ccagctagct tgttggaggc tcttgctttg gacaccaagc aacggatatg      5760
acagcagaat gtgcgtgctt ataagcaagc aagcagagca gcagttgcaa agaagggaaa      5820
aggtggagtg gaaaaaggag ttgccattga agtgcacgag tgagcgagca tcatgtcaag      5880
gaaccaggag ggaagttgca acagatga aaagcggaga gctgtttccg                   5930

<210> SEQ ID NO 66
<211> LENGTH: 13125
<212> TYPE: DNA
<213> ORGANISM: Zea mays

<400> SEQUENCE: 66
tgaactcgtg ctatcgcaaa gtaagggcac ctgatgaaaa tacaagccaa aatcccataa        60
agtagccatc atccaaatca gctgcgagca atagttagcg gcaacgacat actcggctag       120
atagtggcaa caacaactag cgacttgatg ttgatctgcc cttttagatc tggtttggtg       180
ataggagaat tagagggaat ctatgggaaa ggaaatctct tggtactcaa ttttaaatag       240
taagggattt actctccata gtttccctct aaatcagttg tctcccaacc aacaagtccc       300
aaagatatgt agtgtccaac atcaactata agactgtatc cagcagttta cgcatatggt       360
cactcaaatt attgttttgt actgtaaatt gtactgttct gcacttttcg cagagtgagg       420
tttgaatgtg tgtatgtgga tgggcaagat gctagagcta ggccaaggcg catatcatac       480
tagtctccga cgttgacatc gttaacgagt aagcggtcgc aatcggctgc ccgcgcctcc       540
acgtgaacct caccttcgac atcgtctggc tacggcttgc accctccagc tccaacatca       600
cattcctcta caattgcaag aagaacatta gaccatctcc aacaggtcgt gtaaataccc       660
gtgcaaaata caattttgta ttatggatta cactgtttgc agagtaaagt ttaagataaa       720
gagttggata aggaatcagc tgaacatatt accctaccct ctgtcgtgga actgagtggg       780
```

```
tgcccacaac aacaagaaga tagaagtagg ccgtggatgg cgggatcatg ggtgctgagg   840
cgtacgtata catgtccaaa taggcaggtc gagccgacct ggcccgagcc tggctaggct   900
cggcacggat tgggatcatg ttggcctgac ccggattagt aagcgggtcg tgtcgtgcct   960
gtccacgggt ctcgaacgag gctcagacac aacatgctaa gatattaacc gtgtcgggtc  1020
ggcccacggc ccgacaggcc taacaagtct ataatagtat atggcattta aatgataaaa  1080
catatgttaa aatatacata tatgaaagtt taaaccatag ttattagctc taacaccctat 1140 ttacacccac ataaccaaca aaacaaatat ttttactgta ttttatacta tatattcaag  1200
tataatgtat gtatttgtat taaaaaatag gaaaaaaatt aaaaacgggt catgtctagc  1260
ctgtcgtgcc gcgtcttaga cccagacacg acttagtcac caggccgagc caaccagtgc  1320
ctgagtttcg gaccgcccga cccgcctgga catctattgg cgtacaagca cgggtgcgag  1380
ggcgtggtgg tggcgctgcc tgtgctggat gtacccaaga agggcttgtt cggttctacc  1440
ttccatatgg attgaggggg attgagggggt tcaactctca gtaagtcaaa aactcttcta  1500
atccatatca atctcctcta tctatatgga ttgaaaatag gcaccactgg cggtccgcct  1560
ccggaacggg tcgctccgtc ggttgctgca ggacgggttc gagctgaact acaacactca  1620
ctccgagcag tgcgaccgat gcgagggctc cgccggatgg tgtgtggcta ccagcgcgag  1680
gagacgcccg ccggcgggat gacattcgcc tgtttctgcg acggcggcca gaccacgggc  1740
cgatgcggtg ccggtatgtc tctgtttttt tttcttcgaa caaggtttgg catgtgttct  1800
accgtttcaa ctagtaaatg attacattga gctagccaca catttttcttg aatgattttc  1860 tttgattaaa ctgatgtttt ctttcatgac gtgaacaacg ggcctgcaag ctgccacata  1920
cctagggaga ctatttcgtg accttctttta cacgtcttct ctactcgcca ctgggagttg  1980
acgccgctcg gtcgtcccac tttgtgacgt tcaaccagag tctagagatg taattctctg  2040
cgaatacagg actagttgga gctaacaacg cagcttgacg agggtgaacc cagctccaca  2100
cctcgtctac cacgtcttct cctcgccatg gctgctcacc taccacgcct ccccgtcctc  2160
ctcctcgtcc tcctcgctgc ccatgtcgtc tccacctcca cccgtgccga gctcttcttc  2220
cccagcactt acaacgtctc catgtgctcg gaatcgttct ggtgcggcgg cgtcgagatc  2280
cgctacccgt tctatcttgc caacgcaacc gccgactaca gcgggagcta ctactcctgc  2340
ggctacaccg acttgagcgt ttcctgcgaa ctcgaggtcg aggggccgcc gacgacctgg  2400
acccctacca tccgtctcgg cggcgacaac tacaccgtca agaacatctt gtacgactat  2460
cataccatct cactggcgga cagcgatgtg ctcggaggcg gcgagtgccc cgtcgtccgc  2520
cacaacgtca gcttcgacga gacgtggctg cacaacgcca gcgccttcaa caacctcacc  2580
ttcttcttcg gatgccactg ggggccacgc gatacactgc ctgaatttgc cggctataac  2640
atcagctgcg acgggttcag tactccaact atcagcggtg gaggctcctt cgtgttcaag  2700
actgaagatc ttgacgaaca agaggagcag gatttcgctt cacactgcga cgaggttttc  2760
tccgtgccag tgggaagcga ggctctgcgg gcgaccgaca ccttcagcct ctcaaggtac  2820
gggtacggcg agctgcttag gcaggggttc gagttggaat ggaatcggac atcggaggat  2880
cagtgtggcc agtgcgaggg atcgagctcc ggcggacggt gcgcctacaa ccagaagaga  2940
gaattcctgg gctgcttgtg cagcggaggg aaggcgggca acccgttctg caaaccctca  3000
agtaaagtcc tgaaccgagc ctcccttatt ttttttcatt ttttgcaatc accagagagc  3060
acgcatcggt tgcgtcagta gcttgcaacc tcgtagctag ccccgcagtg tccccctgtgt 3120 gcgagtaccg cgctgctcca gcttgcctcc tgctaacgcc taacggtgaa tgcttcatgc  3180
```

```
ttgacatgat ctagctagtc tacactttgc ttggggtttg cctgggagct ggaaattctg    3240
tggctcctgt ttgcatcact cgacaaggac gctttcagac ttgcgagtct cgttctgctt    3300
ttgcaccaaa tccgtgtttt ttcatttcgt gatcgagatt aatccagcat agagatgaca    3360
ataggtatcc gaaactcaaa actcaatagg tttttactct attatggtac aagtttgagt    3420
caattttcat atcatagatt tgttaatagg cacaaatcta tatccaacag gttcatagat    3480
acgggtttgt tcctacaata atcaaatccg taaacccatg agttttttag acccgaccaa    3540
acctagtgca tattgtcatt ttattttata aacgaacaat attatctctc tatttacttt    3600 ctattttta tcggttggtg aatgtataag tagttggtga gagtgttgct tgcttgctat    3660
tataatattt agttatttac tagtgttata tatgtggtga tggataactt agtgcaaggt    3720
cacttgatta tacaacttat tatttgtatt cattctttct actaataatt tttataccaa    3780
atcatgaact cggtgtttat catataaatt ttggaccatg atctcattaa tcatcacgat    3840
agttattgat tatgagaaaa acaaacatat tggagataaa atcctcggct aacccgttaa    3900
cccgatgggt acgggtttga acagaatttc aaacccatta tgaatataag ttttttaaca    3960
aatatagata tgtttcacgg atagagtttg agatgacaaa atccaacgga tttgttgcca    4020
tctctatccg gcggccctta ccgtgctcca cgagcagagg tcgtatccct cttcccgtgt    4080
cgcctgcttc gcgttgccga acggagacgt ttggtagcgt tggccggctc tagcagtcgg    4140
gtcaattttt ttgttgttgt tttcgatgtt gttggatttt tgttccgtat aagccatgtt    4200
ttagtaattt atttagtcca gccgaatccg agacgtgttt gctgggttgg agacttggag    4260
ttgctagtca tgatatgctt tctactcggt ttgatttcaa cccagttagg ctatatttga    4320
tactccagta tttattccaa tataaatggt ttgaaaggga ttaaggtata aattagttta    4380
atttatatct ttaattcctc tcaacccata tgtattgggc tgaatactaa gtatccaaac    4440
aaacccttat ttaagatgca tttcctttag gtctcgtttg tttcgttgga attgaattct    4500
attttaataa ttataatata tttatatatg aaatatattt gaatattatc ctaaatcata    4560
tgagagagat agttatatac tacatttatg ttatatcgaa gcaagtaaaa gagtgtgata    4620
taagttgtgc atcggaaaaa tagtatgtaa atctataaaa tcaatttcca tctctcaccc    4680
aatgaatttg agataggata atatgataac tttgtaaagt ggtggaatat cacattctaa    4740
aaaaatagtc tattccatta gtaagattcc aattcctcaa aatgaaaggg aaacaaacgg    4800
gaccatagtt acacgtggcc actgttgtgt gggggtgggg gtgagggggg acaggccaat    4860
cctactcgtc agtgctcatt cgagagcaaa gataccgaag gagattagag agactaaaaa    4920
ctttttacta tttaaaatta gataataaga cgatttaatc ccgttccata tctttgctct    4980
aaacaaaccc tcaatgatca tatatctcga aagatccggc cggctgttct ttatttatca    5040
agtgatgact gctgaccgct tatagaatat atattttaaa gcaaaatttc ttctacagca    5100
gtaaaaggac tagacgaaac aatgatgcat ttctctaaca aaagaaagta gaattatcaa    5160
gcggagagcc aagaccaaaa gccttgcatc tatgggcgtc aaccaatgat accgcgacgg    5220
aaccacccca gctggtctat actgtctgtc acgacccagc gagtaaccgt gtggctacgc    5280
tgttagctta ggactcgacg aaatgctcga ttcattaaca aaccagctca cgagttaaat    5340
gatttattat ataacgaaat tatatgcata ttatttacca gtgtgacgac agagggcata    5400
ggtgggcaat attcagctcc tctaattcta tagggattgt taatttcttt agctaattat    5460
catgtaaacg atataaaaaa tgtttctaac agcacctcgg tccaccctaa tcttagaccc    5520
```

```
tagcttcgcc catgtcattt acgtaacaat tggtaaatat gttatacatg tgtagtgtct    5580
atgtcctatg aattaaacta atgattgatg aattgtgctt atatattaaa ttggtctatg    5640
cgaatataac tatgtgttaa actgatgaat atgtgtgtga attgtgaatt gataagtgac    5700
gagttgtgtc taatttagtg ttatattgat gtgttttatg aaactatgag tataattaat    5760
attttctata attaaatttg tttgaaatta actagaaatt gattattata tatatatatt    5820
gttttctgct ctaattcgca agctaaacaa gcaagctcaa gctcgtaaac gagccgaacc    5880
gagctgactc tgtggctcat taacttaaca acccgagccg ggccaacttg ttagcttaac    5940
gagccagctc gaatacggac gagttgagcc gagctggcat gatatccagc cttaattagg    6000
ctcgtaccag tgcaacatat ccctctcgcc tttgtcacgt ccagacatgt caatgggccc    6060
cgattcccgc aaggaattcc tctattaaga gatgaggatg agaaagtttc tccccacgga    6120
aaaattctct cctgacgcat aaacggggac aacactccac atccccattc ctcgtgggga    6180
cctattaaac ttacatatgg tgatgttttc atgtaaaagt taatgataaa aataaataat    6240
tacgttgtca agatatcact ttttgtacaa atgtgctcat tctgatgtag gcatattttt    6300
tcttacatct aacaatgtgt ataagtgaga atgttttgta ttaataacaa agtaagtatg    6360
tcctaattat aatttaagcg gggccgggta tccccgatgg ggatttatac ccttgggaaa    6420
cgaagatggg gaagaaatgt cctacacaag ttttcatggc gatcctcgcg gggaactttt    6480
tcgtcgtggg gatagggatg gggagctaaa acccgatgag gaattcctcg ttgccatccc    6540
cagtcacatc aactctcgac tccactattg tctatgctgc atagtctatg gtagactata    6600
gcctcagcct atagcacatc agcttttcta tttcagaatt aagtaattca tgcagtttta    6660
tttcaacgct cgaaaattac acaacataat attttttatt gaattaaaaa ttataaagtg    6720
catacaaatc aaaataaaaa aatattataa ttaaaacata tataaatcta atcggagacc    6780
tcgatcttat cctcgtcttc caccacctct ttccgttttg cttctggttc ctcttcttcg    6840
tcatcaacca gaccacgtcc ttttttcgaa catctttatg gccttggcat gggtttatct    6900
ttcggctagg tccatatccc tggttgaatg gctctttaga atattccgtt gctttaaaag    6960
cttggtcttc actaatccac cccacaagtt cttcatttta aatgcttcac ttgttgaccg    7020
ttgcttgtgg cttccttccc ttttccccttc accttcatct ttaacgcagc cgcctttgcc    7080
ctatcacgcc ctactgatcg gggcacttcc ttccttggtat ctttagtgcc tccagaacta    7140
tattcactag agactccgag tcgggttatc ttattcgtag tcccatttta tcctagaacc    7200
tcgtcattgc tgcctccatg accattgcct cgtctgctcc gctctgatgc aacttttctt    7260
ctcgaaggta gtatccatta aacttggtca cctcctggtt gtaggtgccc taatgatttt    7320
taagttgctt ggcggtttga ggatatcaag ggtcggaggt ggagttatat gttgtcgcta    7380
tttgactcca aaaacatgat ccaaacttat tattgacggg ggttgaatta ttagaatgca    7440
tattccaaga attaacctat aatataagta aactacaaat ataaatatta aataaatgag    7500
aaatgattca ctcaccaact tttcctcatc gtcattcatc cattctagcc tctttggacg    7560
cttttctttc ggcccaggat tttcctcagc ttggttttca aatccaacat attggacatg    7620
tatgtgaaat tggaggaggt ggtccataca gaggtggagc atatgcagga ggggcatacg    7680
gaggtactga gaaagaagtt tgacttccat ccgcagcagg tggagggcat acagacgtac    7740
cgaggaaaaa gcttgaattc tggcttggga agttggaggt tgaccatatg aaggcggcga    7800
gtatgaatac agatgatagg aaaaggttat ggtagtggtg gacgcgcaac tgaaaatagt    7860
gcatggggac tgaagctgaa gcatcagagc gacaatgtag tggagagact catcaaacgg    7920
```

-continued

```
aggggtttgt gacccatcgg actacaagag atctatgaag gtgttcaaat ctagggacca   7980
acccgacatt gtgtgaacag aggggagttt ggaagagaga aacgaaatga aatggtgtgt   8040
ggaatgagat caacccaagt agaggtactt acaaagggat tgggatgaaa tttgtgattt   8100
ttttgcaatt ttttattttt tggattccaa acgatcaaaa acaactagtt gcaatagcta   8160
gcacacgtga accaattgaa agcccccacc ttgctctcgt tcgcgccagc gcgtcaccca   8220
cccactgcgc cctctcatcc tccttgcccg agaacgtgct tcagagcagg cgagagtggg   8280
gcgatatcgc ccactctcat tgggcacggg cggtatcgcc cgagggatgc atctctccct   8340
cctctcaccc cgggccaggc tacaacagcc ccctactgcc caaccactcg ccctcgttgg   8400
caccaaccat actaccacaa cactccaatg cacagttttt aatgttagcc tatagtcacc   8460
ttagcatcac atcatatttc ttctacaaaa tcatatttag aacgaaacat gatgttttgc   8520
ttggaatttt ttcggtggag tagaaaaaat ataatccaaa aaaattacgt aaaatacgta   8580
aaataaaaaa tatagctcct aaaagttaaa attactcatc attatcaccc tcctcgtttt   8640
cttcctcgtc tagttttaat tgcgtgatca attttttcaga accaacctag accctcctca   8700
taccagtggt ggattgtttc agtaacttgg tgaactggtc gtacaatttt ttgattgatt   8760
tctcgtgtca ctaaccttga ataactgctt tgttatggtt ttcttctgga caagggactc   8820
attggtactc attcatggtc cctaaccctt gttttgtgct cttgcccaat cacgaccaat   8880
agggtgtggt ggtttggcac tatcagacga tgtagagtta taatcaccct ccacgttgag   8940
gcaagatcat ttgctctcat tgctagagtt tgaatcacca tgtcacgtgc accacttgaa   9000
ttgatgatga agagcacacc attagtttca tcgagcctgt tgtggaagag tagcatcaca   9060
ttatttgatc tgcttggtag gttatacgtg gtcgatattt ggcaccaaaa ggtcaaacat   9120
ttttgttgtt tccctcaaac cttttttggc ctcaaaaagg tcaaaccttt tttggctttc   9180
catccctgtc cccacgaaca gtcacgagta acttttttatc ccatccacgt tcgcgtgggg   9240
gaatttatcc ccatgggaaa tctatccctg ttagagaatg taatattttc gaggcaaggt   9300
caaattgata aaccaatata aattgaacaa ataagattta aaattacaag agaaatctac   9360
tttagagttg agcttgctat tttataaaag gctatgtgtt gaattttat tataacttta   9420
acatatcaat ggattgattt tagattaaga gaagttcgtg gggcggatat gcgaggaaca   9480
gggatgggga atggttcacc attctcgtcc cacgaacccg gcaaggacta aattttctc   9540
gtttcaatct ccgtggggac taaattacac ctattcccgt ccactaataa agggatacccc   9600
cgcgggaat tagggatcac gtccccattt cacattttta gacttctcac attgagcaac   9660
aacaaaacat tttatgaatt tgtagccatt ttacttatct aaaacaatta ctattgaatc   9720
ttaatcattt tgtgcaaaat aaagaatgaa ctaaattttg ggtcgggtgt gggtcacccg   9780
taggttgaaa taaaaactcg cacccacaac gtgaaacttt gggtcagatg cgggttacac   9840
ccgcggatta aaatctctac ccatacccac accccgtcaga tcgagtaccc aaagattttg   9900
ggtttgcggg ttaaattgtc atccctagac acgagcgtga tggaggattt ggaagtttcg   9960
caatgcgtac ttaccaagtg tttggttcta tggattaaac tttagcatgt gtcgcattag  10020
atgattgaat gcctattatg agtattaaat attgtctaat tattaatcaa attacacaag  10080
tgaaggctaa acaactagac aaatttatta agcctgatta atttatgatt agcaaatatt  10140
tatagtagca gcatccttagt gaatcatgaa ctaattaggt ttaataggtt cgtcttaacg  10200
tttagttctt atctatgtaa ttagtttttat aagtaaacta tatttaatat tcctaattag  10260
```

```
cctccaaaca tccgatataa catagactaa aatttagtgg tggtgctgct ggctccttttt  10320 catttcatcc gacataatgt tttcctccca atttattgtg ttgttttgtt tgtgctttaa  10380
aaatgacttg tcctctgctt gctgtatcaa ggtcgtgatg tgtgcttaac ttattcccttt  10440 ccttgctagc tgcccttagc atttatatag gggtatttgg ttacagggac taaagtttag  10500
tttagtccgt atccaattat aaaactaatt acataattaa atactaaaat accaaaatac  10560
gagaaaaatt attaaaccta attaatttat tatttggcaa atgtttattg taacatcaca  10620
taagaaaagc atagactaat ttagtttaat aggttcgtct tatcatttag tcttgatctg  10680
tataattagt tttgtaatta gactatattt actatttta actagtatcc aaacacatta  10740
aatgtgacat ggattaaaat ttagttagtg accttaggct tttagagttg agttagttgt  10800
agcttggttt agttacttgt ttgttctctt acgtttattt aggacctctc tataatgttt  10860
tatcaccttc ttaatacaaa ttaaaatacg cagctcttgc gtattgcagg cgtgtgtgtt  10920
cctatatttt ttagctcaat tatgaaggaa attattctca gcgagcatat aaccgttttc  10980
gaggtaaaat gaactaaaag catatgggcc tgcctgttcg cataagtaca ccctccgtct  11040
aaaaagaata aaaatctcat ttcttgatga gtcaaagaag ttcaaattta agaaaatata  11100
tgttacgaca cgaatattta taatgcgtaa taagtactgc tagattaatt ttaaaataaa  11160
attttcataa taaacctatt tgaagataca agtattggta ctatttctaa taaatctaat  11220
caaactggtg ttatatctttt tgtaacaaat ttgtgcttta tgtttctggt tgacgtgaat  11280
cagcttaatc ttgctgaaat ctaacattgt cttttgttcg ttggcataca ggatcaaaaa  11340
ggaatgaagg acctattgtt ggtaagagcc tatagccaat acccatgttc atttcgtcta  11400
aaagagcaga agaaaagcat atgatgaatt attgccatgt cttgtttaaa atacagaatt  11460
ctcaaaaaca aaaacaaaaa aaacttggaa tccactaacc actgatagca ttgtagaaaa  11520
tttcatcctc cctttgggca atacactgat gagtttacat gctgactagt ggtgcatttg  11580
ttctttgcca attgagtttt tagaatgctt tgcagctgaa ttcacttgtg gtgttttttt  11640
tttgtgtgat gcaggtgctg ttgttgccgt tgcattcctg tgtctagtca ttctcacatg  11700
cttcttggct tgtagacatg gttcgctgcc cttcaaatcg aagaacaaac cagggacaag  11760
gattgagtcc ttcctacaga agaacgagag tagtatacat ccgaaaagat acacctacgc  11820
ggacgtgaaa agaatgacaa aatccttcgc tgtgaagcta ggccaaggtg ggtttggtgc  11880
tgtatacaaa ggcagcctcc acggccgaca ggtagcagtc aagatgctga aggacaccca  11940
aggtgacggc gaggaattca tgaacgaggt ggctagcatc agcaggactt ctcatgtcaa  12000
cgtcgtgaca cttctagggt tttgcttgca agggtcgaaa agagcactga tctacgagta  12060
catgcccaat ggttcgctcg aaaggtatgc cttcaccgt gacatgaaca gtgagaattt  12120
gctaagctgg gaaagactat ttgacatagc gattggcacg gccagagggc tcgaatacct  12180
acaccgggga tgcaacactc ggatcgtgca ttttgacatc aagccacaca acatcctgtt  12240
agaccaggat ttctgcccta agatctctga ctttggactg gccaagctat gtctgaacaa  12300
agagagcgct atctccattg ttggcgcaag agggacgata gggtatatcg ccccggaggt  12360
ctactcaaag caatttggaa cgataagcag caagtctgat gtctatagct atgggatgat  12420
ggtccttgag atggttggag caagggacag gaatacaagc gcagatagtg accatagcag  12480
ccaatatttc cctcagtggc tttatgaaca tttggacgac tattgtgttg gtgcttccga  12540
gattaatggt gagaccacag agctcgtgag gaagatgata gttgtaggtc tgtggtgcat  12600
acaagtgatt ccgactgatc ggccaacaat gacgagagtc gtcgagatgt tggaagggag  12660
```

```
cacaagtaat ctagagttgc cacccagagt tctcttgagc tgacaaagcg tagatatttt    12720
tcctatcaaa tgctgcttcc aggtcacaca aatgcaaata tttgtggaga cgagtgccca    12780
gtaacctcat acactgtatc tgtatgacaa aagtcccacg actcactgga cacggaaatg    12840
tcgcttgact acgccaattt tctaaaaaga ttggcacaat taatgggct tatagcggta     12900 actttggttc gcattagtct aggattaggg ttgaatattg atcaaactcg acgcagcttg    12960
gtcgagctca agctagctcc gctcagctta ttaaagaatc cagctagaga atcaacccag    13020
gtcgtttacg agttaatttg ctggctcgtt taggtcgtaa atcacaacaa aaacaatata    13080
cacatatata caataatata attaatacta gttaattcta gacta                   13125
```

<210> SEQ ID NO 67
<211> LENGTH: 500
<212> TYPE: DNA
<213> ORGANISM: Zea mays

<400> SEQUENCE: 67

```
agtgtccaac atcaactata agactgtatc cagcagttta cgcatatggt cactcaaatt      60
attgttttgt actgtaaatt gtactgttct gcacttttcg cagagtgagg tttgaatgtg     120
tgtatgtgga tgggcaagat gctagagcta ggccaaggcg catatcatac tagtctccga     180
cgttgacatc gttaacgagt aagcggtcgc aatcggctgc ccgcgcctcc acgtgaacct     240
caccttcgac atcgtctggc tacggcttgc accctccagc tccaacatca cattcctcta     300
caattgcaag aagaacatta gaccatctcc aacaggtcgt gtaaataccc gtgcaaaata     360
caattttgta ttatggatta cactgtttgc agagtaaagt ttaagataaa gagttggata    420
aggaatcagc tgaacatatt accctaccct ctgtcgtgga actgagtggg tgcccacaac    480
aacaagaaga tagaagtagg                                                500
```

<210> SEQ ID NO 68
<211> LENGTH: 201
<212> TYPE: DNA
<213> ORGANISM: zea mays

<400> SEQUENCE: 68

```
ttagggttga atattgatca aactcgacgc agcttggtcg agctcaagct agctccgctc      60
agcttattaa agaatccagc tagagaatca acccaggtcg tttacgagtt aatttgctgg    120
ctcgtttagg tcgtaaatca caacaaaaac aatatacaca tatatacaat aatataatta    180
atactagtta attctagact a                                             201
```

<210> SEQ ID NO 69
<211> LENGTH: 492
<212> TYPE: DNA
<213> ORGANISM: Zea mays

<400> SEQUENCE: 69

```
tgaactcgtg ctatcgcaaa gtaagggcac ctgatgaaaa tacaagccaa atcccataa       60 agtagccatc atccaaatca gctgcgagca atagttagcg gcaacgacat actcggctag    120
atagtggcaa caacaactag cgacttgatg ttgatctgcc cttttagatc tggtttggtg    180
ataggagaat tagagggaat ctatgggaaa ggaaatctct tggtactcaa ttttaaatag    240
taagggattt actctccata gtttccctct aaatcagttg tctcccaacc aacaagtccc    300
aaagatatgt agtgtccaac atcaactata agactgtatc cagcagttta cgcatatggt    360
```

| | |
|---|---|
| cactcaaatt attgttttgt actgtaaatt gtactgttct gcacttttcg cagagtgagg | 420 |
| tttgaatgtg tgtatgtgga tgggcaagat gctagagcta ggccaaggcg catatcatac | 480 |
| tagtctccga cg | 492 |

<210> SEQ ID NO 70
<211> LENGTH: 13643
<212> TYPE: DNA
<213> ORGANISM: Zea mays

<400> SEQUENCE: 70

| | |
|---|---|
| tctaacgccg acaccgtcga cgagtaagag gtcgtggccg gctgcccaca cgtctgtgtg | 60 |
| aacctcacca tcgacaccac cgtccgcctg cggcctacgg cctcgaactc caacatcaca | 120 |
| ttcctctaca actgcatgaa gaacattacc ctaccctctg tcatggaact gagtgggttc | 180 |
| ccacaacaac aagaagatag atgtaggtcg tacgtgctgt gggatggcgg gatcacgggt | 240 |
| gctcaggcgt acgggtatgg gtgcgaggac ttggtggtag cgtcggagct ggatgtacac | 300 |
| aaaaagggag aaggcgatcc acctccggaa cggatcgctc catcggggttg ccgcatgacg | 360 |
| ggatcgagct gaactacgac actcactcta agcagtggga cctagggatg aaaacggtcg | 420 |
| gtaaacacta aagcaattac cgttttcata ttttttttat cgaaacaaa atcgaaaacg | 480 |
| gtaactccgg aaatggaaac gatatcggta tttcggaaac atcgcaaacg aaagttcggt | 540 |
| gcgaaaaata cacaagtaac ggtcgaaatc taaaatacga tcgataaaca tatcaaactt | 600 |
| cataatacaa caaagttgac aaaagatcac aaagaccaca agttcacaat tcatgatata | 660 |
| acaagtttaa aatataacaa gttcacaagg atcacaaatt tataatataa aaaaattaca | 720 |
| aagatcacaa gttcacaata taacaagttc acagtataac aagttcataa agatcacaag | 780 |
| ttcacaaact caaggttcac aattcacaat atccactcga tttagctgac atggcatgct | 840 |
| tactcatgaa atattttttc ctcaaataaa gagttttca cagactcgta ggaaaaccct | 900 |
| aaaatctagt atgtggaaaa gacagactgt cggctctatc attatatatt actaatacat | 960 |
| aacatgtgga cagaaaatgg tggattcgtt cgagagacca atcgttaat ctcaactgcc | 1020 |
| ttccaacacc atctatcaaa aaaaatctta aggcgtccaa aaaatacaaa aaataagtaa | 1080 |
| tccttatcta gagacgtaca ggcgatgcga aaaaaatcac atgctgaata attccgaaaa | 1140 |
| aaattccgga aaattctgag acataaatcc ggtaatttcc gacaaaaacc ggtaaccgaa | 1200 |
| ggaaacagtc ggtaaaacac cacgccgatt ccgataccga ctctaataga aatttccgaa | 1260 |
| aaccgatttc gttttcgaaa aatactgtta ccggtgaata caatcgaaaa atttcgaaat | 1320 |
| cggtttccgg aataccaaaa aattgtgaaa ctgttttcat cactagtggg accgatgtga | 1380 |
| tggctccgac ggatggtgtg gctaccagcg tgatgagacg cccaccggcg ggatgacatt | 1440 |
| cgcatgtttt tgcaaacgca gcccgatcac atgtgcacaa tcgttagtgg cgcgttttaa | 1500 |
| aaaagacgta actacgaaaa aaaatagcga catgttttta gccagtgtca caaacgtcat | 1560 |
| cttcgagcac ttttgatgta gtgtatacaa tctactagtc aaattaaaaa gaataacata | 1620 |
| cacgaaatgg ttcataactt ttatatagtt aaacaataat aaatttataa aaatccctaa | 1680 |
| acaaacaaca aaacgttgga cacctccccg ctatttatgg cggatggccc gcccaattga | 1740 |
| cgtaatttcc acatcgaagt cgaagaaccg gtcgctgtga ccagtcaccc caacctccgt | 1800 |
| cacttgtctc tcacgcgcgc gcaacatcgc cgagaaaacc agaacagacc tccggattgg | 1860 |
| tctctccccc gttcacacga gcacattgcg atggctcctc tgctcctgct gctcctcttc | 1920 |
| cccgtccagc tcccccctcgc agtagccgac gccgtctccg gtccctgcac cagagccaca | 1980 |

```
tgcgccggcc aggacgtcca ttacccgttc tggctcaagt cctccgcgcc cgactgcgtc    2040
tatcccggtg tcggccttgt ggcccttgtc tgcgagggca actcgacgct gatcctcccc    2100
ttcaagtccc acagatacgt agtgctcagc atcgactaca agacgcgtac cgtgctggtc    2160
tccgacgccg acatcgtcca cgagtacgac gcggccggct gcccgcgcgt ccgcgtgaac    2220
ctcaccatcg acaccgcctg gctgcggccc acggcctccg actccaacat caccttcctc    2280
tacaactgca agaagaacat caccctgccc tccgccgtgg aactgagcgg gtgccagcag    2340
cagcagcaac aagacggcag caggtcgtat tcgtacgtgc tgccggacgg cggggtcacg    2400
ggcgctgagg cgcaccagta cgggtgcgag gacttggtgg tggcgccggt gctggacgtc    2460
cacaggaggg cgatcttgag ggcgcctggc ggcccgactc tggagaacgg gtcgctccgt    2520
cggttgctgc agggcgggtt cgagctgaac tacgacactc actccgagca gtgcgaccga    2580
tgcgaggcct ccggcgggtg gtgtggctac cagcgcgacg agacgcccgc cggctggatg    2640
acgttcgcct gcttctgcga cggcgggccg acgaccacgg cccgatgcgg tgccggtatg    2700 tcttttttt ttcttcgaac aaggtgtggc atgtgttcta ccgtttcaac tagtaaatga    2760
ttacattgag ctaggcagct agccacacat tttcttgaat gattttcttt gatgaacctg    2820
ctgtttgctt ttatgacgtg aacaacgggg cctgcaagct gccacatacc tagggagact    2880
agttcgtgac cttctttaca cgtcttctct actcgccact gggagttgac gccgctcggt    2940
cgtcccactt tgtgacgttc aaccagagtc tagagatgta attctctgcg aatacaggac    3000
tagttggagc taacaacgca gcttgacgag ggtgaaccca gctccacctc gtctaccacg    3060
tcttctcctc gccatggctg ctcacctacc acgcctcccc gtcctcctcc tcgtcctcct    3120
cgctgctcat gtcgtctcca cctccgccca tgccgagcct cctcttccga gcccttacag    3180
cacctccgcc catggcgagc ctcctcttcc gagcacttac aacgtctcca tgtgctcgga    3240
atcgttctgg tgcggcggcg tcgaaatccg ctacccgttc tatcttgcca acgcaaccgc    3300
cgactacagc gggagctact actcctgcgg ctacaccgac ttgagcgttt cctgcaaact    3360
cgaggtcgag gggccgacga cgacatggac ccctaccatc cgtctcggcg gcgacaacta    3420
caccgtcaag aacatcttgt acgactatca taccatctca ctggcggaca gcgatgtgct    3480
cggaggcggc gagtgccccg tcgtccacca caacgtcagc ttcgacgaga cgtggctgca    3540
caaccccagc gccttcgaca acctcacctt cttcttcgga tgccactggg gccacgcga    3600 tacactgcct gaatttgccg gcaacaacat cagctgcgcc gggttcagta ctccagctat    3660
cagcggtgga ggctccttcg tgttcaagcc tgaagatctt gacgaacatg cggagcagga    3720
gttggcttca cactgcgacg aggttttctc cgtgccagtg agaagcgagg ctctgcagca    3780
ggcgatcgtc agcaacctca gcctcgggga cgggtacggc gagctgctta ggcagggga    3840 cgagttggaa tggaaacgga catcggagga tcagtgtggc cagtgcgagg aatcgggctc    3900
cggcggacgg tgcgcctaca gccagaagag agaattcctt ggctgcttgt gcagcggagg    3960
gaaggcgggc aacccgttct gcaaaccatc aagtaaagtc ctgaaccgag cctcccttat    4020
ttttttttca tttttttgcaa tccaccagag agcacgcatc ggttgcgtca gtatcttgca    4080
acctcgtagc tagccccgca gtgtcccctg tgtgcgagta ccgcgctgct ccagcttgcc    4140
tcctgctaac gcctaacggt gaatgcttca tgcttgacat gatctagcta gtctacactt    4200
tgcttggggt ttgcctggga gctggaaatt ctggctcctg tttgcatcac tcgacaagga    4260
cgctttcaga cttgcgactc tcgttctgct tttgcaccaa atccgtgttt ttttcatttc    4320
```

```
gtgatcgaga ttaatctagc ttagagatga caatgggtat ccgaaactcg aaacttgatg    4380
gattttttact ccattagggt ataggtttga atcaattttc atatttatgg atttgttaat    4440
aggcataaat atatatccaa caggtttata gatacgagtt tgtttctaca gtactcaaat    4500
ccgtgaacac atgaggtttt taaacccgac caaacctagt gcatattgtc attttatttt    4560
ataaacgaac aacaaaattg ttatctctat ttacttccta ttttttatcg attggtgaat    4620
gtataagtag ttggtgagaa tgtttcttgc ttgctattat agttttacta gcgttatata    4680
tgttgtgggt ggataactta gtgcaatgtc acttgattat acaacttatt atttgtattc    4740
attctctcta ctaataattt ttataccaaa tcatgaactc ggtgtttatt atataaattt    4800
tggaccataa tctcattaat catcacgata gttattgatt atgagaaaaa acaagcatat    4860
tggagataaa accctcggct aacccgttaa cccgatgggt acgggtttga acaaaatttc    4920
aaacctatta tgaatataag ttttttaaca agtatagata tatttcacgg atagagttta    4980
agatgacaaa atccaacgga tttgtatcca ttgccatctc tatccggcgg cccttacccg    5040
gcggccctta ccgtgctcca cgagcagagg tcgtatcgtc cctcttcccg tgtcgcctgc    5100
ttcgcgttgc cgaacggaga cgtttggtag cgttggccgg ctctagcagt cgggtcaact    5160
cttttttgttg ttgttttcga tgttgttgga ttttttgttcc gtataagcca tgttttagta    5220
atttatttag tccagccgaa tccgaagacg tgtttgctgg gttggagact ttggagttgc    5280
tagtcatgat atgctttcta ctcggtttga tttcaaccca gttaggctat atttaatact    5340
ctagtattta tttcaatata aatggtttga aacggattaa ggtataaatt agtttaattt    5400
atatatttaa ttcctctcaa tccatatgta ttgggctgaa tactgaggta gtgtttggtt    5460
gaagagccat atagaacgga gccgttctgt tccagttttg ttgttgtttg gttataaagt    5520
aactagaacg gaatgacttc aattaaggaa tattcttctc agatccagaa ccattccgct    5580
ctaaaaaatc aaccggacgg agccgctccg tttccatcct gctcttacag tcacgctccg    5640
ttccgttcac tctgcaacca aacaaaaaac agagccgctc cgttccaaat taccaaacac    5700
agaacagagc ggcttcattc ctagaattag gaatggaacg actctgttct acttgactcc    5760
tcaaccaaac actacctaag tatccaaaca agcccttatt taagatgcat ttcctttaca    5820
gttacacatg accactattg tgtggggca ggctgaacaa gcccttattt aagatgcatt    5880
tcctttagag ttacacgtgg ccactattgt gggggggggg ggggggggc aggccgatcc    5940
tactcgtcag tgctcattcg agagcaaaga taccgaagga gattagagag actaaaaact    6000
ttttactatt taaaattaga taataagacg atttaatccc gttccatatc tttgctctaa    6060
acaaaccctc aatgatcata tatctcggaa gatccggccg gctgttcttt atttatcaag    6120
tgatgactgc tgaccgctta tagaatatat attttaaagc aaaatttctt ctacagcagt    6180
aaaaggacta gacgaaacaa tgatgcattt ctctaacaaa agaaagtaga attatcaagc    6240
ggagagccaa gaccaaaagc cttacttcta tgggcgtcaa caaatgatac cgcgacggaa    6300
ccatcccagc aggtctatac tgtctgtcac gacccagcga gtaatcgtgt ggctacgcta    6360
ttagacttag gattggatga aatgctcggt ttattaatga ccagctcgt gagttaagag     6420
tgtttggttt gatgaatgaa gtaattcatc ttcttttcac tccccacttt tttatttggt    6480
ttgtgtaata gaatgagttg atccatcacc accacattca tcataagcta ataattagta    6540
tatacatgag tagtgagttg attccaccaa aattgatgaa atgaacttat gatgcatcat    6600
ctcatgaagc atagagtgac tccacaaacc aaacacacca taaatgatct attacataac    6660
gaaattatat gcatatcatt tatcagggcg acgacagggg gcataggag gcaatatccc       6720
```

```
cctaatgctc cccaaattct atagggattg ttagtttctt ttagctaatt ctcatgtaaa    6780
caatataaaa aatgcttcta acagtccctc ctaattataa tttggtccac cctaatctta    6840
gatcctggct tcgtccgtgc catttacgta acaattggta aatatgttat acatgtgtgg    6900
tatctatggc ctatgaattg aactaatgat tgatgaattg tgcttatgtg ttaaattggt    6960
ctatgcgaat ataactatgg gttaaacgga tgaacatgtg tgttcattgt taattcatga    7020
gtgatgaatt atgtataatt tggtgttata ttgatgtgtt ttgtgaaact atgtgtataa    7080
ttattatttt ctataattaa atttgtttga aattaactag aaattgatta ttatatatat    7140
atatatatat atattgtttt tctgctctag tctgcaagct aaacgagcaa gctcaagctc    7200
gtaaacgatc cgaaccgagc tgactttgtg gctcattaac ttaacaagcc gagttgggcc    7260
aacttgttag cttaacgagt cagctcgaat acggacaagt tgagccgagt tggcatgata    7320
tccagcccta attaggcttg taccagtgca acatatccct ctcgcctttg tcacgtccag    7380
acatgtcaat gggccccgat tcccgcaagg aatttctcta ttaagggatg aggatgggaa    7440
agtttctccc cccacagaaa aattctctcc cgacggataa gcgggacaa cactccccat      7500 ccccattccc cgtggggacc tattagactt acatatggtg atgttttcat gtaaaagtta    7560
atgataaaaa taaacaatta ccttgttgtc ggcgtttcga ccccggaggg tccctggacc    7620
gacgagtaaa ttgtcgctgc gtgtcccagc ccagatgggt cgacgcgaga cggaacacaa    7680 ggggaaaca ataaggggaa tcgcggcctc gtgttgtcct gcgcccaggg cggatgcgct      7740
tgcagtaagg ggttacaagc gttcgcgagg gagagagaga gagagcctgt gcgccagccc    7800
gtcctcccgc gcggccacct tctcgtacga gggccctgga cctttctttt atagatgtaa    7860
ggagagggtc caggtgtaca acagggagcg tagcaatgtg ctaacgtgtc tagcagaggg    7920
aagccagaat cctatgtaca ggccgacgtg actgtcgaag aggttttggc gccctgttca    7980
tgtgatgtcg tggccgtcgg aggagcgctt gagccctgta ggagcacagc tgtcggagct    8040
gtcgggtcct tgctgacgtc tcattgcttc catagggagc tgagaaccgc cgtcgtcatg    8100
gagcacgcgg ggtgccatca ttacttgttt taccgggacg agccagatgg gacgctggtc    8160
ttgttcccag tagcctgagg tagctagagg tagggtaatg atgtgccctc ctgcgacgtg    8220
gtcggtccga gcccaaggtc gggcgaggcg gaggctcctc cgaggtcgag gctgagtccg    8280
agacctgggg tcgggcgagg cggagaccgt cgtccgaggt cgaggttgag tccgagccct    8340
ggggtcgggc gaggcagagt ccatcgtccg aggtcgaggt tgagtccgag ccctgggtc      8400 gggcgaggcg gagacagtcg tccgaggtca aggttgagtc cgagcctgg ggtcgggcga      8460 ggcggagttc gtcttccgag gtcgaggtgg agtctgagcc ctagggtcag gcgaggcgga    8520
gaccgtcgtc cgaggtcgag gttgagtccg agctctgggg tcgggcgagg tggagcttcc    8580
tatggcgcct gaggccggac ttggcggctg tcagcctcaa cctgacgggt ggcacagcag    8640
tcgaagcagc gcaggcggcg ctgttttct atcaggtcag ccagtggagg ggcgaagtga      8700
ctgcggtcac ttcggctctg tcgactgaag agcgtgcgtc aggataaggt gtcaggcgat    8760
ccttgcattg aatgctcctg cgatccggtc ggctggcgag gcgatcttgg ctaaggttgc    8820
ttctccgcga agcctgcctg agctgggcct cgggcgagtc ggaggtgcgc ccgttgcttg    8880
aggaggccct cgggcgaggc gtgaacctgc ctgggcctgc tgtttctgcc cgaggctggg    8940
ctcgggtgag gcgagatcgt gtcccttgag cggacagagc tttgtcctgt gttgcgccca    9000
tcaggccttt gcagctttgt gctgatggtg tttaccagcc gagtttaaga gtcttggggg    9060
```

```
taccccctaat tatggtcccc gacacttgtc aagagatcac ttttttgtaca aatatattca   9120
ttctgatgta cacatatttt tttcttacat ctaacaatgt gtataagtga gaatgtttta   9180
tattaataac aaatgaagta tgtcctaatt agacttctca cattgagcag caacaaaaca   9240
tttttatgaat tagtaaccat tttacttact aaaataatta ctattgtatc ttaatcattt   9300
tgtgcaaaat aaagaatgaa ccaaattttg ggtcaggtgt gggtcactcg caggttgaaa   9360
taaaaacccg cacccacact cgtgaaactt tgggtcagat gcgggttaca cccgcggatt   9420
aaaatctcta cccataccca cactcatcag atcgagtacc caaagatttt aagtttgcgg   9480
gttaaattgt catccctcga caccaacgtg ttggaggatt tggaagtttc gcgatgcgta   9540
cttaccaagt gtttggttct atgataaaag tttagcctgt gtcgcattag atgattgaat   9600
gtctattatg agtattaaat attgtctaat tattaatcaa attacacaag tgaaggctaa   9660
acaacgagac aaatttatta agcctaatta atctatgatt agcaaatgtt tacagtagca   9720
ccatctagta gcaccatctg agcgaatcat gaactaatta ggtttaatag gttcgtctta   9780
acgtttaatt cttatctatg taattagttt tataagtaaa ttatatttaa tacttctaat   9840
tagcctccaa acattcgata taacatagac taaaatttag tcagtggtgc tgctgctggc   9900
tcttttcctt catccgacgt aatgttttcc tcccaattta ttgtgttgtt ttgtttgtgc   9960
tttaaaactg acttgctctc tgcttgctgt atcaaagtcg tgatgtgtgc ttagcttatt  10020
cccttccttg ctagctgccc ttagcatcta tagggata tttggttata gggactaaag  10080
tttagtttag tccgtgtcca attataaaac taattacata actgaatact aaaagacgag  10140
aaaatttat taaacttaat taattttatga ttagcaaatg tttattgtaa catcacataa  10200
gtaaattata gactaatttt gtttaatagg ttcatcttat catttagtct tcatctatgt  10260
aattagtttt gtaattagac tatatttact atttctaact agtatctaaa cattaaatgt  10320
gacatggatt aaaatttagt tagagcaact ccagtagttt tctaaaagac ttcctaaatc  10380
aataatttag gtagttaaca tgaaaactat tctccaacag ttctctaaat aaactttcta  10440
aatttaacaa cttgtcatct aacctcattt tctctctaca tttggcaacc atttaataac  10500
tccctaatca aaaatgttga ctgcattata tagttttttgt gacttatttt ttatgtggat  10560
aaatacaaaa taaaattaca acctatattt agagaactat tggagaaccc acttatttt  10620
atttcaaaag tcatttagca acttcttaaa tctgtaattt agaaagctaa aatttacata  10680
actattagag ttgctcttag tgacgttagg cttttagagt tgagttggtc gtagcttggt  10740
ttagttacgt gtttgttctc ttgcgtttat ttaggacctc tctataatgt tttatcaccct  10800
tcttaataca aattaaaata cgcagctctc ttgcgtattg gaggcgtgtg ttcctatatt  10860
tttttaggctc aattatgaat gaaattattc tcagcgagca tataaccgtt ttcgaggtaa  10920
aatgaactaa aagcatatgg gcctgcctgt tcgcataagt acaccctccg tctaaaaaag  10980
aataaaaata tcatttcttg atgagtcaaa aaagttcaaa tttaagaaaa tatatgttac  11040
gacaccaata tttataatgt gtaataagta ctgctgatta attttaaaat aaaatttttca  11100
taataaacct atttgaagat acaagtattg gtactatttc taataaatct aatcaaactg  11160
gtgttatatc ttttgtaaca aatttgtgct ttgtgtttct ggttgacgtg aatcagctta  11220
atcttgctga aatctaacat tgtctttttgt tcgttggcat acaggatcaa aaaggaaaga  11280
agcatctatt gttggtaaga gcctatagtc aatacccatg ttcattttcgt ctaaaagagc  11340
agaagaaaag catatgatga attattgcca tgtcatgttt aaaatacaga attctcaaaa  11400
acaaaaacaa aaaaaacttg gaatccacta accagtaacc actgatagca ttgtagaaaa  11460
```

```
tttcatcctc cctttgggca atacactgat gagtttacat gctgactagt ggtgcatttg    11520
ttctttgcca attgaatttt tagaatgctt tgcagctgaa ttcacttgtg attttttttt    11580
gtgatgcagg tgctgttgcc gttgcattcc tgtgtctagt cattctcaca tgcttcttgg    11640
cttgtagaca tggttcgctg cccttcaaat cggagaacaa accagggaca aggattgagt    11700
ccttcctaca gaagaacgag agtatacatc cgaaaagata cacctacacg gacgtgaaaa    11760
gaatgacaaa atccttcgct gtgaagctag gccaaggtgg gtttggtgct gtatacaaag    11820
gcagcctcca cgatggccga caggtagcag tcaagatgct caaggacacc caaggtgacg    11880
gcgaggaatt catgaacgag gtggctagca tcagcaggac ttctcatgtc aacgtcgtga    11940
cacttctagg gttttgcttg caagggtcga aaagagcact gatctacgag tacatgccca    12000
atggttcgct cgaaaggtat gccttcaccg gtgacatgaa cagtgagaat ttgctaacct    12060
gggaaaggct atttgacata gcaattggca cggccagagg gctcgaatac ctacaccggg    12120
gatgcaacac tcggatcgtg cattttgaca tcaagccaca caacatcctg ttagaccagg    12180
atttctgtcc taagatctct gactttggac tggccaagct atgtctgaac aaagagagcg    12240
ctatctccat tgttggcgca agagggacga tagggtatat cgccccggag gtctactcaa    12300
agcaatttgg aacaatcagc agcaagtctg atgtctatag ctatgggatg atggtccttg    12360
agatggttgg agcaagggaa aggaatacaa gcgcaagcgc agatagtgac catagcagcc    12420
aatatttccc tcagtggatt tatgaacatt tggacgacta ttgtgttggt gcttccgaga    12480
ttaatggtga gaccacagag ctcgtgagga agatgatagt tgtaggtctg tggtgcatac    12540
aagtgattcc gactgatcga ccaacaatga cgagagtcgt cgagatgttg gaagggagca    12600
cgagtaatct agagttgcca cccagagttc tcttgagctg acaaagcgta gatattttc    12660 ctatcaaatg ttgcttccag gtcacacaaa tgcaaaatat ttgtggagac gagtgcctat    12720
ttacctcata cactgtatct gtatgacaaa agtcccacga ctcactggac gcggaaatgt    12780
cgcttgacta cgccaatttt ctaaaaagat tggcagcaat taatggaggc ttatagcggt    12840
aactttggtt cgcattaatc ctaggactag ggttgaatat cgatctaact cgacgcggct    12900
tggtcaagct caagctagct ccactcatct cattaaagaa tccagctaga aaatcaaccc    12960
aagtcgttta cgaaacgagt ttgagctgac tcgtttagat cgtaaatcac aacaaaaaca    13020
atatgcacat atatacaata ataataatcaa tactagttaa ttctagacta gtttaacact    13080
agaaaagagt aatgatactc ataatttcac atacaatgtc aatccaacac caatttaaca    13140
cacttcatca cttattagtt catccaacca agtgtaggct ttgatttact aacaaatggt    13200
tgctcgttcg agctagcgag cttgcttgtt aacaaactga gttgagatgc tagcttaact    13260
tgtgacaaaa ttaaaacgag ccgagtcgag tcaagttgag ctcacgatga gtcgagcaag    13320
ctcacaatcc acgagtattt ttttagtcct atctaagact aaagtttaat cctaaaacta    13380
aattttaatc tctatttgtt tggttctata aactaaacag gttcagaaaa cataaaatac    13440
attatagaaa acctgaaata cccttctata cttaaggcat cactaagaga gagcaataaa    13500
taaagggtag agagaggaat aaatctgctt tattcccttt tagctaccct ttgagagagt    13560
aaacactaaa atgaaaggat ccttgaggat tttgatgttt tggatgacaa ctaacacaat    13620
taaaggtcta attaggatgt taa                                            13643
```

<210> SEQ ID NO 71
<211> LENGTH: 35391
<212> TYPE: DNA

<213> ORGANISM: Zea mays

<400> SEQUENCE: 71

```
tgttggatta atgtggcctt ggcctaaatt aatattcaat aatagtcaat gctaatggcc        60
cactttaatg ttatggtgta ctaattattt agtaccatat ttgaagttca aaggacaaat       120
caatcaactt aaataggtgg accattggtg catctattga gaagttgaga aaaggatgaa       180
ggactgccac acgcgcgcgc gcgccgcgtg ctgctgttct tcttcccggc gaccgttcga       240
gggactgcac agcgtatatc ttcctgcacc gacttcgtac ggctacatcg aacaaacaca       300
cgagatgtct cgtgtgaatg gttgtgcata tttcattgct gtttactact tatgcgagta       360
gttatacaca catgcacata catgtcatca catatatcgc actgttttc tggattaaat       420
taaaactaaa aatgcctaac tttctaacaa tccaaaaatc tgatattagg cattttctg        480
ttagtggttt tgctgctgcg ttaaaaccaa gtgaaccttt tgatgggacg ttttacaaga       540
gatggcgtag taagatgata ctgtggttga ccgcaatgaa ctgctatcac gccgcacagg       600
ggaaacccga acagttcact cctgaagagg agagaatgtt cgacgttgcc gataacctgt       660
ttcgaggcgc cgtgattggt gctcttgcca acaagtatgt tgattcttat ctaacgtgca       720
catctgcaaa agagttatgg gatgcattag atgagaagtt tggtgtttct gatgctgata       780
gcgagctgta catcatggag cagctatttg actataagat ggtggaaaac cgtcctgtag       840
ttgaacaggc tcatgaaata caggcactgg ctaaagaact cgaacaattc ccatgtgtct       900
tgcctgacaa gttcgtggcc ggcggtatta tcgctaaact gccaccttct tggacggact       960
tgctaccac tctaaaacat aagagacaag agtttagcgt ggctgagctt attggttctc      1020
ttgatgttga ggagagggcg agagcaaaag acactcgtgg aaaaggagtt gagacttcta      1080
gtgccaatat ggtacaaaag aagaactcca atgcatcaca taataataaa agaagaaca      1140
agcaacagaa tgccacgaag cccaagcagg cagcctcgtt caaaaagaag aacaaaggag      1200
ctggttgctt tgtttgcggg agtactgatc attgggcaag cgcttgtcca gactgcaaat      1260
taagcaaga gaaaaaacca gctcaagaga agaaaacagt aaacatggtt gttagcgaga      1320
ctgcagaagc aacatcgggg tatggtaatc ttttacctac tgttctttca gtgtgtcaat      1380
ccctgagtg gtgggctgat accggtgcta atattcatgt gtgtgctgat atttcttat       1440
tttcttctta tcagtgcaaa gggactggag ccttgctgat ggggaacgga tcacatgcgc      1500
gtgttcttgg tgttggtaca gtcattctga gtttacttc gggaaagacg gtgctattga      1560
agaacgtgca gcatgtcccc tccatcaaaa agaatctagt tagtggctct caattgtgtc      1620
gagatggcta caaaattgtc tttgagtcta ataaatgtat actgtctaag tatggaacgt      1680
ttgttggaaa aggctatgac agcggaggct tgttccgctt atctttgcat gatgcgtgta      1740
ataagtctgt gaacaatgtt gtttcgaatg agtcgtatat ttggcattca cgactttgtc      1800
atatcaattt tggttgtgtg tcgcggttag cagatttaaa tttaatcccg aaatttgatt      1860
tagtcaaagg ttctaagtgc caggtgtgcg tgcaatctaa gcaacctcgc aagcctcaca      1920
aggctgcaga ggcgaggaat ttggcaccac tagacttaat acattccgat ttatgtgaga      1980
tgaacggaat attgactaaa ggaggcaagc gatatttat tacttttatc gatgactcta      2040
ctagattttg ttatgtgtat ctcttaaaat caaaagatga agctttgcat tattttaaga      2100
cctacaaagc tgaagttgaa atcaactcg agaggaaaat taaacggtta aggtctgatc      2160
gtggtggaga atatttttcg ggtgattttt ctgattttg tgtggaacat ggtattattc      2220
atgagaggac accgccatac tcaccacaat ccaatggggt tactgaaaga aagaaccgta      2280
```

```
ctctaactaa tttggttaac gccatgttag agacttcagg gctatctaag gaatggtggg    2340
gtgaggcgat cttgacggcg tgtcatgtcc tgaataaagt tcccacaaag aacaaagaaa    2400
tcacaccatt cgaggaatga gaaaagaaga aattaaatat ctcctatttg cgcacctggg    2460
gttgtttgga taaagtgaat gtgccaatta acaagaagcg caaattagga ccgaaaactg    2520
ttgattgtgt tttccttggg tatgcttttcc acagcattgg atataggttt ttaattataa    2580
actctggagt accggacatg ttggttggta caattatgga gtccagagat gctacgtttt    2640
ttgaggacga atttcccatg aaagctacac atgatacgtc taatgatgaa ccaacgatac    2700
cccatgagca ttttattccg gtagaacaca ctgaggaatc ccatatacat aatcatgtgg    2760
aaaatgacaa tgtatcaact cgaaagagta agagaccaag gattgcaaag tcctttggtg    2820
atgattacat tgtatatctt gtggatgaca caccaagtac cattgaagag gcatattcct    2880
ctcctgatgc tgacttttgg aaggaagcaa taaggagtga gatggattct attatgtcta    2940
atgcaacttg ggaggtagtt gagcgtcctt atgggtgtaa gcccattgga agtaaatggg    3000
tgttcaagga aaaacttagg cctgatggta ctattgaaag gtacaaggcg aggcttgtaa    3060
ttaaaggcta ttcacagaag gaaggtgagg atttctttga tacttattca cctgtggctc    3120
gattgaccac aattcgtgtg ctactttctt tggctgcctc tcatggtcta ctcgtccatc    3180
aaatggatgt taagacagca ttcctaaatg gagagctaga tgaggaaatt tacatggagc    3240
agccagctgg gtttgtagca aacggtcaag aaggcatggt gtgtaaatta ttgaaatctt    3300
tatatggcct aaaacaagca cctaagcaat ggcatgaaaa gttcgataga actttgacat    3360
ctgccggttt tgttgtgaac gaagcagaca agtgtgtata ctatctgtcg gggaccataa    3420 ttagggggtac cctcaagacg cctaattctc agctggtaac ccccatcagc ataaagctgc    3480
aaaggcctga tgggtacgat taagtcaggg atcggtccac acgagtgact cgatcacgct    3540
tcacccgagc ctagcctcgg ccaagggcag ccgacctcga gagacttctg tctcgcccga    3600 ggccccttt ttacggcgga cacatcaccg gctcgcccga ggccttggct tcgctcagaa    3660
gtaaccctga ctaaatcgcc acaccgactg accaagttgc aggagcattt aacgcaaagg    3720
tggcctgaca cctttatcct gacacgcgcc cccccccccc ccggcagagc cgaagtgacc    3780
gccgtcactc caccgctcca ctgaccagtc tgacagaagg acagcgccgc ctgcgccact    3840
ccgactgcag tgccactcga cagagtgagt ctgacaagca gtcgggccct gccaaaggcg    3900
ccatgggaaa ctccactccg cccgacccca gggctcggac tcgggctaaa cccggaaga    3960 cggcgaactc cgctccgccc gaccccaggg ctcggactcg ggctaagacc cggaagacgg    4020
cgaactccgc tccgcccgac cccagggctc ggactcgggc taagacccgg aagacggcga    4080
actccgctcc gcccgacccc agggctcgga ctcgggctaa acccggaag acggcgaact    4140 ccgctccgcc cgaccccagg gctcggactc gggctaagac ccggaagacg gcgaactccg    4200
ctccgcccga cccagggct cggactcggg ctaagaccca agacgcgcg aatctccgcc    4260 tcgcccgacc ccagggctcg gactccgccc tggcctcggc caaacgatct ccgcctcgcc    4320
cgacccgggg gctcgggctc ggcctcggca acggaaggca aactcgacct cgacttcgga    4380
ggagccccca cgtcgccctg cctagggcac aggtccgcca cgtcaacagg aagcgccatc    4440
accaacctac cccgagccga cttgggacac gaaggacaag accggcgtcc catctggcca    4500
gctccgccga tgggcaatg atggcgcccc caagctctgt gacgacggcg gctcttagct    4560
ctcttacggc agcagagcga cgtcagcaag gactcgaccg ctccaacagc tgtccctccg    4620
```

```
ccaggctccg tcgctcctcc gacagccacg acatcacgcc agcaaggtgc caagacctct    4680
ccggctgcca cattggcatg tacccagggc gctagctctc tctctctctc cgctagacac    4740
gtagcactct gctaccccc attgtacacc tggatcctct ccttacgact ataaaaggaa    4800
ggaccagggc cttcttagag aaggttggcc gcgcggacc gaggacggga caggcgctct    4860
cttggggccg ctcgcttccc tcacccgcgt ggacgcttgt aaccccctac tgcaagcgca    4920
cctgacctgg gcgcgggacg aacacgaagg ccgcgggact ccacctctc tcacgctcga    4980 ctccggccac ctcgcctctc cccccttcgc gctcgcccac gcgctcgacc catctgggct    5040
ggggcacgca tcacactcac tcgtcggctt agggaccccc tgtctcgaaa cactgacagt    5100
tggcgcgcca ggtagggcct gctgcgtgct gacgaacagc tccccgtcaa gctccagatg    5160
ggcagtctcc agcaacctct ccggcccggg gcggtgcttc gtttcgggac tcttgagttc    5220
atgtccttcg acggcagcta cgacatgata cttcttccac cgccgcgcga cgacgacaat    5280
ggcggccgac agcccgcccg ccggcggcgg aatcgacgac atcttccccg cgtggtggaa    5340
gagcaacatt cgagctcact ccgttctctc ccccgccaac ggaggaggag gcggggccgt    5400
caaggccagg cggaggccg cgcttcgttg gccgtcgggc gaatcgacgc ccccgacgcc    5460
ccgacggaag gcacgccgga cgtcgacctc gcgttcaaga cggaggcaag cgccgtcccc    5520
ccgcgacacg ccgaccccaa acaagaagac gacgccagcg cgctcgcgga aagcctgcag    5580
gacgtcgccc tcgtacctga gatgacggtg caaccagtcc ccgatgtgac tacgtcgctc    5640
ctcgtcgacc aaaaggtacc aactaactcc catcttgcgt catttcgact cggcctcgac    5700
ccgccaaacg acctcgtttt ggcgggcgct ctcattgagg cgagtgcaac cccactgggg    5760
tttcgtatgc ggtcgccttg ggaccggctg acggacgtct cgacctacgg gccctctggg    5820
tccgaggaag atgacgatcc cagcatctgt tgggatttct ccggacttgg caaccccagt    5880
gccgtgcggg acttcatgac cgcatgtgac tactgcctct ccgactgttc cgacgaaagc    5940
cgcagccttg gcgacgagag ctgccggccca agccgcgaat gttccacat cgagctaggg    6000 gatccctccg aaggcaacca tctcggcatg ccggaggacg gtgatcttcc taggccggtg    6060
cctcgcgccg acatcccacg ggagctagct gtggtccccg ctccggcggg ggttacgacc    6120
cacaactcga gcaagtccgc gaggtgcagg ccaggctcaa cgagggaaca ggagcgcttg    6180
agccgatccg tcgggacgtc ggacaggcat gggcgggcca accctgcc ggagaaatat    6240 gccacctgcc ccaaggtctc cagcaccgcg tcgccaacga tgtcagggtc aggccgccgc    6300
ccgcatccag cggggttggt cagaacctgg cagccgcagc gatgctcctc cgcgcgatgc    6360
cggagccatc aaccaccgag ggtcagcgaa tccagggaga gctcaagaat cttctggaag    6420
gcgctgcggc ccgacgggcc gagagcactg cctcccgaag gcaaggatac cctcggaacc    6480
tcacgccgcg acttcccgat tcatgcggga agcctcggtc tacaccgagc gcacgcgcaa    6540
caccgcgcct gcggccccgg gccacctcgg caacgagcac catcgacgcg accgtcgggc    6600
tcacctcgac gaaagggtgc gccgaggcta ccacccagg cgtggggcg ctacgacagc    6660 ggggaggatc ggagtccctc gcccgaacca cccggtccgc aggccttcag tcgggccatc    6720
cgacgggcgc cattcccgac ccggttccga ccccggcta ctatcacgaa gtactcgggg    6780
gaaacgagac cggaactgtg gctcgcggac taccgccttg cctgccaact gggtgggacg    6840
gacgacgaca acctcatcat ccgtaacctc cccctgttcc tctccgacac tgcccgcgcc    6900
tggttggagc acctgcctcc ggggcagatc tccaactggg acgacttggt ctaggccttc    6960
gctggcaatt tccagggcac atacgtgcgc cccgggaatt cctgggacct tcgaagctgc    7020
```

```
cggcaacagc caggggagtc gctttgggac tacatccggc gattctcgaa gcagcgcacc    7080
gagctgccca acatcaccga ctcggatgtc atcggcgcgt tcctcgccgg acgccggcac    7140
cacttgccgc gacctggtga gcaagctggg tcgcaagacc cccaccaggg cgagcgagct    7200
gatggacatc gccaccaagt tcgcctctgg ccaggaggcg gtcgaggcta tcttccgaaa    7260
ggacaaccag ccccagggcc gcccatcgga agaggctccc gaggcgtctg ctccgcgcgg    7320
cgtcaagaag aaaggcaaga agaagtcgca atcgaaacgc gacgctgctg acgcggacct    7380
tgtcgccgcc gccgagtaca agaaccctcg gaagccccg gaggtgcaaa cctcttcgac    7440
aagatgctca aggagccgtg cccttaccat caggggcccg tcaagcacac cctcgaggag    7500
tgcgttatgc ttcggcgtca cttccacagg gccgggccac ccgccgaggg tggcagggcc    7560
cgcgacgacg acaagaacga agatcaccaa gcaggagagt tccccgaggt ccgcgactgc    7620
ttcctgatct atggagggca tgcgacgaat gcctcggctc ggcatcgcaa gcaagagcgc    7680
cgggaggtct gctcggtgaa ggtggcggcg ccagtctacc tagactggtc cgacaagtcc    7740
atcaccttcg accaggccga ccaccccgac catgtgccga gcccggggaa atacccgctc    7800
gtcgtcgacc ccgttgtcgg caatggcagg ctcaccaagg tcctgatgga tgggggcagc    7860
tgcctcaaca tcatctacgc cgagaccctc aagctcctgc gcgtcgatct atcctccgtc    7920
cgagctggcg ctgcgccctt ccacgggatc atccctggga agcgcgtcca gccctcgggc    7980
gactcgacct ccccgtctgc ttcggacgc cctccaactt ccgaagggag accctgacgt    8040
tcgaggtggt cgggttccga ggaacctacc acgccgtact agggaggcca tgctacgcga    8100
agttcatggc cgtccccagc tacacctacc tgaagctcaa gatgccgggc cccaacgggg    8160
tcatcaccgt cgaccccacg tacaaacacg cgttcgaatg cgacgtgggg tgcgtggagt    8220
acgccgaggc cctcgccgag tccaaggccc tcatcgccga cctggagaac ctctccaagg    8280
aggtgccaga cgtgaaacgc catgccggca acttcgagcc agcggagacg gtcaaggccg    8340
tccctcttga ccccggtggc gacaccacca agcagatccg gatcggttcc gggcccgacc    8400
ccaaatagga agcagtgctc gtcgactttc tccgcgcgaa cgccgacgtc tttgcgcgga    8460
gtccctcgga catgcccggc ataccgaggg atgtcgccaa acactcgctg gatatccggg    8520
ccggagcccg acccgtcagg cagcctctgc gccgatttga cgaggagaag cgcaaagtga    8580
ttggcgaaga gatccacaag ctaatggcag cagggttcat caaagaggta ttccatcccg    8640
aatggcttgc caaccctgtg cttgtgagga agaaggggg aaatggcgga tgtgtgtaga    8700
ctacactggt ctcaacaaag catgtccgaa ggttccctac cctctgcctc gcatcgatca    8760
aatcgtggat tccaccgctg ggtgcgaaac cctgtccttc ctcgatgcct actcagggta    8820
tcaccagatc cggatgaagg agtccgacca gcttgcgact tccttcatca cgccgttcgg    8880
catgtactgc tacgtcacca tgccgttcgg tttgaggaat gcgggcgcga cgtaccagcg    8940
gtgcatgaac catgtgttcg gcgaacacat cggtcgcaca gtcgaggcct acgtcgatga    9000
catcgtagtc aagacaagga aggcttccga cctcctctcc gaccttgaag tgacattccg    9060
atgtctcaag gcgaaaggag tcaagctcaa tcctgagaag tgtgtcttcg gggtgcccga    9120
ggcatgctcc tagggttcat cgtctccgag cgaggcatcg aagccaaccc ggagaagatc    9180
gcggccatca ccagcatggg acccatcaag gacttaaaag gtgtacagag ggtcatggga    9240
tgcctcgcgg ccctgagccg cttcatctcg cgcctcggcg aaagaggtct gcctctgtac    9300
cgcctcttaa ggaaggccga gtgtttcgct tggaccctg aggccgagga agccctcggc    9360
```

```
aacctgaagg cgctccttac aaaggcgcat gtcttggtgc ccccggcgga tggagaagcc    9420
ctcttggtct acgtcgccgc gaccactcag gtggttagcg ccgcgatcgt ggtcgagagg    9480
caagaggaag ggcatgcatt gcccgttcag aggccggttt acttcgtcag cgaagtgctg    9540
tccgagacca agatccgcta cccacaagtt caaaagctgc tgtatgcagt gatcctgaca    9600
aggtggaagc tgcgacacta cttcgagtct cacccggtaa ctgtggtgtc atccttcccc    9660
ctgggggaga tcatccagtg ccgagaagcc tcgggcagga tcgcaaagtg ggcggtggaa    9720
atcatgggcg aaacgatctc gttcgcccct cggaaggcca tcaagtccca ggtgttggcg    9780
gacttcgtgg ccgaatgggt cgacacccag ttgccgacgg ctccgatcca accggagctc    9840
tggaccatgt ttttcgacag gtcgctgatg aagacaggag ccggcgcggg cctgctcttc    9900
atctcgcccc tcgggaagca cttgcgctac gtgctgcgcc tccatttccc ggcgtccaac    9960
aatgtggccg agtacgaagc tcttgtcaac gggttgcgga tcgccatcga gctagggggtc   10020 agacgcctcg acgcccgcgg tgattcgcag ctcgtcatcg accaagtcat gaagaactcc   10080
cactgctgcg acccgaagat ggaggcctac tgcgacgagt tcggcgcct ggaagacaag    10140 ttcttcgggc tcgagctcaa ccacatcgct cggcgctaca cgaaaccgc agacgagctg    10200 gctaaaatag cctcggggcg aacgacggtc ccccggacgt cttctcccgg gatctgcatc   10260
aaccctctgt caagatcgac gacgcgcccg agcccgaggt accctcggct cagcccgagg   10320
cacccctcgg cagcccgag gtaccctcgg ccccgagggg cgaggcactg gacgtcgagg    10380
aagagcagag cggggccacg ccagatcgag attggcaggc cccgtacatg cagtatcttc   10440
gccgaggaga gctaccccg accaagtcga ggctcggcgg gtagcgcgac tgatagtcgc    10500 ctagagggg gtgaataggg cgaaactgaa atttacaaat ataaacacaa ctacaagccg     10560
ggttagcgtt agaaatataa acgagtccgc gagagagggc gcaaacaaa tcgcgagcaa     10620 atgatgaagt gtgacacacg gatttgtttt accgaggttc ggttctctca aacctactcc    10680
ccgttgagga ggccacaaag gccgggtctc tttcaaccct tccctctctc aaacggtccc    10740
tcggaccgag tgagcttctc ttctcaaatc aaagccggga acaaaacttc cccgcaaggg    10800
ccaccacaca attggtgcct cttgccttga ttacaatgga gttgtgatct caagaacaat    10860
tgagaaagaa aagaagcaat ccaagcgcaa gagctcaaat gaacacggca aatcactctc    10920
actagtcact agggctttgt gtggaattgg agaggatttg atctctttag tgtgtctaga    10980
attgaatgct agagctcttg tagtagttga gaagtggaaa acttggatgc aatgaatggt    11040
gggtggttgg ggtatttata gccccaacca ccaaacttga ccgttggctg gaggcgtctg    11100
ctcgatggcg caccggacag tccggtgcac accggacagt ccggtgcccc tgccacgtca    11160
tcactgccgt tggattctga ccgttggagc ttctgacttg tgggcccgcc tgggtgtccg    11220
gtgcacaccg gacatgtact gtttgatgtc cggtgcaccg gcatgggcga ttctgacttc   11280
tgcgcgcgct gagcgcgcat taaatgctcc gcagggagcc gttggcgccg aaaagagccg    11340
ttgctccgct gttacaccgg acagtccggt gcacaccgga cagtccggtg aattttagcg    11400
gagcggctgc cgcgcgaacc cgaggctggc gagttctgga accgcgcttc cttggagca     11460 ccggacatgt ccggtgcaca ccggacagtc cggtgaatta tagcgcgccg gctctcgaga    11520
attcccgagg gcgaagagtt tgagtctgag tcccctggtg caccggacag gtactgttca    11580
ctgtccggtg gcacaccgga cagtccggtg cgccagacca ggggtgcctt cggttccccc    11640
tttgctcctt tattgaatcc aaaacttggt cttttttattg gctgagggtg aacctttac     11700 acctgtaaaa tctatacact tgggcaaact agttagtcca attatttgtg ttgggcaatt    11760
```

```
caaccaccaa aattatttag gaactaggtg taagcctaat tccctttcaa tctccccctt    11820
tttggtgatt gatgccaaca caaaccaaag caaatagaga agtgcataat tgaactagtt    11880
tgcataatgt aagtgtaaag gttgcttgga attgagccaa tataactact ttacaagata    11940
tgcatggaat gtttctttct ttatttagca ttttggacca cgtttgcacc acgagatttg    12000
tttttgcaaa ttcttttgta aatccttttc aaagttcttt tgcaaatagt caaaggtaaa    12060
tgaataagag tttgcaaagc attttcaatt tcttttgact taacaaaact cccctaaaa     12120 gagatccacc tcttagtgtt caagagggtt ttgatatacc attttgaaa tactactttc     12180 tccccttttg aacacaatag tataccaaat gataaatact tttggaaagc actaagtttt    12240
tgaatttggt ggtggtggtg cggtcctttt gctttgggct catttctccc ccttttttggc  12300 atgaatcgcc aaaaacggaa tcattagagc cctcgaagta atttcttccc ctttggtcat   12360
aagtaaatga gttaagatta taccaaagac gaaatccggt cctttgtctt tgggctttta   12420
cttcctcccc caaagataag gtccgtttag tggagcgatg gcgaaggatg agttacggag   12480
tggaagcctt tgtctttgcc gaagactcca attcccttc aatacaccta tgacttggtt    12540
tgaaatagac tcgaaaaaca cattagtcat agcatatgaa agagatatga tcaaaggtat   12600
tcaatgagct atgtgtgcaa gctaacaaaa gaaatttcta gaatcaagaa tattgagctc   12660
atgcctaagt ctggtaaaag attgttcatc aagaggcttg gtaaagatat cggctaattg   12720
atctttagta ttaatgtaag aaatctcgat atccccttt gttggtgatc cctaagaaaa    12780
tgataccgaa tggctatgtg cttagtgcgg ctatgctcga cgggattgtc ggccatttg    12840 attgcactct cattatcaca tagcaaaggg actttggtta atttgtaacc atagtcccgc   12900
agggtttgcc tcatccaaag caattgcgcg caacaatgac ctgcggcaat gtactcggct   12960
tcggcggtgg aaagagcgac cgaattttgc ttctttgaag cccaagacac caaggatctt   13020
cccaagaact ggcaagtccc cgatgtgctc ttcctattga ttttgcaccc cgcccaatcg   13080
gcatccgaat aaccaatcaa atcaaatgtg atccccgag ggtaccaaag cccaaactta    13140
ggtgagtaag ccaaatatct caagattcgt tttacggccg taaggtggga ttccttaggg   13200
tcggattgga atcttgcaca catgcatacg gaaagcataa tgtccggtcg agatgcacat   13260
aaataaagca atgaaccaat catcgaccgg tataccttt gatccacgga cttacctcct    13320
gtgtcgaggt cgagatgccc attggttccc atgggagtct tgatgggctt ggcatccttc   13380
attccaaact tggttagaat gtcttgagtg tacttcgttt ggctaatgaa ggtgccctct   13440
tggagttgct tgacttggaa tcctagaaaa tacttcaact cccccatcat cgacatctcg   13500
aatttctgtg tcatgatcct actaaactct tcacatgtag actcgttagt agacccaaat   13560
ataatatcat caacataaat ttggcataca aataagtcat tttcaagagt tttagtgaag   13620
agtgtaggat cggccttgcc gactttgaag ccattagaaa taaggaaatc tcttaggcat   13680
tcataccatg ctcttggggc ttgcttgagc ccataaagcg ccttagagag cctatagaca   13740
tggttagggt actcactgtc ttcaaagccg ggaggttgct caacgtagac ctcttccttg   13800
attggtccgt tgaggaaggc acttttcacg tccatttgat agagcttaaa gccatggtaa   13860
gtagcatagg ccaataatat gcgaattgac tcaagcctag ctacgggtgc ataggtttca   13920
ccgaaatcca aaccttcgac ttgtgaatac cctttggcca cgagtcgagc tttgttcctt   13980
gtcaccacac catgctcatc ttgcttgttg cggaagaccc atttggttcc tacaacattt   14040
tggttaggac gtggaactaa atgccatacc tcattcctcg tgaaattgtt gagctcctct   14100
```

```
tgcattgcca tcacccaatc cgaatcttga agtgcttcct ctaccctgtg tggctcaata    14160
gaggaaacaa aagagtaatg ttcacaaaaa tgtgcaacac gagatcgagt ggttacccct    14220
tatggatgtc gccgaggatg gtgtcgacgg ggtgatctcg ttggattgct tggtggactc    14280
ttgggtgtgg cggccttggt tcttcctcat cctccttttc ttgatcattt gcatctcccc    14340
ttgatcattg ccattatctt gaggtggctc atcttcttga ttttgccctt catcaacttg    14400
agcctcatcc tcattttgag ttggtggaga tgcttgcatg gaggaggacg gttgatcttg    14460
tgcatttgga ggctcttcgg attccctagg acacacatcc ccaatggaca tgttccttag    14520
tgctatgcat ggagcctgtt cttcacctat ctcatcaaga tcaacttgct ctacttgaga    14580
gccgttagtt tcatcaaaca caacgtcaca tgagacttca actagtccag tggacttgtt    14640
aaagacccta tatgcccttg tgtttgagtc ataaccaagt aaaaagcctt ctacagtttt    14700
aggagcaaat ttagattttc tacctctttt aacaagaata aagcatttgc taccaaaaac    14760
tctaaagtat gaaatgttgg cttttttacc ggttaggagt tcatatgatg tcttcttgag    14820
gattcagtga agatataacc ggttgatggc gtagcaggcg gtgttgaccg cttcggccca    14880
aaaccggtcc ggtgtcttgt actcatcaag catggttctt gccatgtcca atagagttcg    14940
attcttcctc tccactacac cattttgttg tggcgtgtag ggagaggaga actcatgctt    15000
gatgccctcc tcctcaagga agctttcaat ttgagagttc ttgaactccg tcccgttgtc    15060
gcttcttatt ttcttgatct ttaagccgaa ctcattttga gcccgtctca agaacccctt    15120
taaggtctct tgggtttgag attttttctg taaaaagaat acccaagtga agcgagaata    15180
atcatccact attacaagac aatacttact cccgccgatg cttatgtaag caatcgggct    15240
gaaaaggtcc atgtggagta gctcaagtgg cctgtcggtc gtcatgatgt tcttgtgtgg    15300
atgatggact ccaacttgct tccctgcctg gcatgcgcta caaatcctgt ctttctcaaa    15360
atgaacattt gttaatccta aaatgtgttc tccctttaga agcttgtgaa gattcttcat    15420
cccaacatgg gctagtcggc ggtgccagag ccaacccatg ttagtcttag caattaagca    15480
tgtgtcgagc tcagctctat caaaatctac taagtatagc tgaccctcta acacacccct    15540
aaatgctatt gaatcatcac ttcttctaaa gacagtgaca cctacatcag taaagagaca    15600
gttgtagccc atttgacata attgtgaaac agaaagcaag ttgtaatcta aggaatcaac    15660
aagaaaaaca ttggaaatag aatggtcagg agatatagca attttaccaa gtcctttgac    15720
caaaccttga tttccatccc cgaatgtgat agctcgttgg ggatcttggt ttttctcata    15780
tgaggagaac atccttttct ccccggtcat gtggtttgtg cacccgctgt cgagtatcca    15840
acttgagccc ccggatgcat aaacctacaa acaattttta gttcttgact ttaggtaccc    15900
aaacggtttt gggtccttttg gcattagaca caagaacttt gggaacccaa acacaagtct    15960 tggaacccctt gtgtttgccc ccaacaaact tggcaacgac cttgccggat tgttagtca    16020 aaacatatga tgcatcaaaa gtcttaaatg aaatgctatg ttcatttgat gcattagaaa    16080
ttttctttct aggcaacttg gcacggggttg gttgcctaga gttagatgtc tcacccttat    16140
acataaaagc atgattaggg ccagagtgag acttcctgga atgaattttc ctaattttgc    16200
tctcgggata accggcaggg tacaaaatgt aaccctcgtt atcctgaggc atgggagcct    16260
tgcccttaac aaagttagac aaattttag gagggggcatt aagtttgaca ttgtctcccc    16320 tttgaagcc aatgccatcc ttaatgccag ggcgtctccc attataaagc atgctacgag    16380
caaatttaaa tttctcattt tctaggttgt gctcggcaat tttagcatct agttttgcta    16440
tatgatcatt ttgttgttta attaaagcca tatgatcatg aatagcatca atatcaacat    16500
```

```
ttctacatct agtacaaata gatacatgct caacaataga tgtagatggt ttgcaagaat   16560
caagttcaac aatcttagca tgaagaatat catttttatc tctaagattg caatggtaa    16620 ctttgcaaac gtcaaaatct ttagccttag caatcaaact ttcattctct aatctaaggc   16680
tagcaagaga aatgtttaat tcttcaatcc tagcaagcaa atcatcatta ttatttctag   16740
gattgggaat tgaaacatta caaacatgag aatcaacctt agcatttaaa ctagcatttt   16800
catttctaag gttgtcaatc atctcacggc aagtgcttag ctcactagat aattttcac    16860 attttctac ttctagagca taagcctttt taaccttaac atgtttcttg ttttctttaa    16920
ttagacaatc ctcttgggag tccaaaaggt catccttttc atgaatagca ctaactaatt   16980
catttaattt ttcttttga gctatgttaa ggttggcaaa aagggaacgc aaattatcct    17040
cctcatcact agcattatca tcactagaag attcatattt agtggaggag ttagatttaa   17100
cctttttccg tttgccgtcc tttgccatga ggcacttgtg gccgacgttg gggaagagga   17160
gtcccttggt gacggcgatg ttggcggcgt cctcgtcgtc ggaggagtcg cttgagcttt   17220
cgtcggaatc ccattcccga caaacatggg catcgccgcc cttcttcttg tagtaccttt   17280
tcttctcctt tcttctcccc ttcttgtcgt cgcctcggtc actgtcacta gatataggac   17340
atttagcaat aaaatgaccg ggcttaccac acttgtagca aaccttcttg gagcgggact   17400
tgtaatcctt ccccctcctt tgcttgagga tttggcggaa actcttgatg acgagcgcca   17460
tttcctcatt gtcgagtttg gaggcgtcta ttggttgtcg acttggtgta gactcctcct   17520
ccttctcctc cgttgccttg aatgcaacgg gttgggcttc ggatgggtcg ccaagctcgt   17580
tgattttcct cgagccttct atcatgcact caaaacttac aaaatgcccg ataacttcct   17640 cggggggtcat tttagtatat ctaggattgc catgaatcaa ttgaacttga gtgggattaa   17700
gaaaaatgag agatcttaaa ataacattta ccacttcgtg gtcgtccac ttcttgctcc     17760 cgaggttgcg cacttggttc accaaagtct tgagccggtt gtacatgtgt gtggctcct    17820 cccctttgtg aagccggaac cgaccgagct cccccctcgat cgtttcccgc ttggtgatct   17880
tggtgagctc atctccctcg tgcgcagttt tgagcacatc ccaaatctcc ttggcgctct   17940
tcaacccttg cactttgtta tactcttctc tacttaaaga ggcgagaaat atcgttgtcg   18000
cttgagagtt gaagtgctcg atttgggcca cctcatcctc atcatagttc tcatcccta    18060 tggatggtac ctgcgcacca aactcaacaa catcccatat gcttttgtgg agcgaggtta   18120
gatgaaatcg cattaaatcg ctccacctag cgtaatcttc accatcaaaa gttggtggtt   18180
tgcctaatgg gacggaaagt aaaggtgtat gtttggaaat gcgagggtag cgtaggggga   18240
tcttactata cttcttgcgc tcttggcgct taaaagtgac ggagggcgca tcggagtcgg   18300
aggtcgatgt tgatgaagtg tcggtctcgt agtagaccac cttcctcatc ctcttgtgct   18360
tgtcgccttt ccgatgcggc ttgtgggaag aagattttc cttcttctct ttgtggtgag    18420
aagaagattt cttctccttc cctttgtggg aggagctctt cttcttctcc ctccttttgg   18480
tgcgggactc ttccgatgaa gtgctcccgt ggcttgtagt gggcttttcg ccggtctcca   18540
tctccttctt ggcgtgatct cccgacatca cttcgagcgg ttaggctcta atgaagcacc   18600
gtgctccgat accaattgat agtcgcctag aggggggtga ataggcgaa actgaaattt    18660 acaaatataa acacaactac aagccggggtt agcgttagaa atataaacga gtccgcgaga   18720
gagggcgcaa aacaaatcgc gagcaaatga tgaagtgtga cacacggatt tgttttaccg   18780
aggttcggtt ctctcaaacc tactccccgt tgaggaggcc acaaaggccg ggtctctttc   18840
```

```
aacccttccc tctctcaaac ggtccctcgg accgagtgag cttctcttct caaatcaaag   18900
ccgggaacaa aacttccccg caagggccac cacacaattg gtgcctcttg ccttgattac   18960
aatggagttg tgatctcaag aacaagtgag aaagaaaaga agcaatccaa gcgcaagagc   19020
tcaaatgaac acggcaaatc actctcacta gtcactaggg ctttgtgtgg aattggagag   19080
gatttgatct ctttagtgtg tctagaattg aatgctagag ctcttgtagt agttgagaag   19140
tggaaaactt ggatgcaatg aatggtgggg tggttggggt atttatagcc ccaaccacca   19200
aacttgaccg ttggctggag gcgtctgctc gatgcgcac cggacagtcc ggtgcacacc   19260
ggacagtccg gtgcccctgc cacgtcatca ctgccgttgg attctgaccg ttggagcttc   19320
tgacttgtgg gcccgcctgg gtgtccggtg caccggac atgtactgtt tgatgtccgg   19380
tgcaccggca tgggcgattc tgacttctgc gcgcgctgag cgcgcattaa atgctccgca   19440
gggagccgtt ggcgccgaaa agagccgttg gcgccgaaaa gagccgttgc tccgctgtta   19500
caccggacag tccggtgcac accgacagt ccggtgaatt ttagcggagc ggctgccgcg   19560
cgaacccgag gctggcgagt tctggagacc gcgcttcctt ggagcaccgg acatgtccgg   19620
tgcacaccgg acagtccggt gaattatagc gcgccggctc tcgagaattc ccgagggcga   19680
agagtttgag tctgagtccc ttggtgcacc ggacaggtac tgttcactgt ccggtggcac   19740
accggacagt ccggtgcgcc agaccagggg tgccttcggt tccccctttg ctcctttatt   19800
gaatccaaaa cttggtcttt gatagtcgcc tagagggggg tgaataggc gaaactgaaa   19860 tttacaaaaa ataatcacaa ctacaagccg gggttagcgt tagtaataat aaatgagtcc   19920
tcaagagagg gcgcaaaaca aatcgcaagc aaataaagag agtgacacgt ggatttgttt   19980
taccgaggtt cggttcttgc aaacctactc cccgttgagg aggccacaaa ggccgggtct   20040
ctttcaaccc ttccctctct caaacggtcc ctcggaccga gtgagctttc cttcttctca   20100
atcaaccggg aacaaagctt ccccgcaagg gccaccacac aatcggtgcc tcttgccttg   20160
gttacaattg agtgttgatc acaagagcat aagagaaaga aagaatgcga tccaagcgca   20220
agagctcaaa agaacacggc aaatcactct cactagtcac tagggttttg tgtggaattg   20280
gagaggattt gatctctttg aatgtgtcta gaattgaatg cctagctctt gtaagtggtt   20340
gagaagtgga aaacttggat ggctatgaat gtggggtggt tggggtattt atagccccaa   20400
ccaccaaaca tgaccgttgg ctggaggctt ctgttcgatg gcgcaccgga cagtccggtg   20460
cacaccggac agtccggtgc ccctgccacg tcatcgttgc cgttggattc tgaccgttgg   20520
agcttctgac ttgtgggccc gcctgggtgt ccggtgcaca ccggacatgc actgtttgat   20580
gtccggtgca ccggtatggg cagccctgac gtctgcgcgc gctgcgcgcg catttaatgc   20640
accgcaggga gccgttggcg ccgcaggag ccgttgctcc gctggcacac cggacagtcc   20700
ggtgcacacc ggacagtccg gtgaattata gcggagcggc tgccgcgcga acccgaggct   20760
ggcgagttca ggaggccgag cttccttgga gcaccgaca tgtccggtgc acaccggaca   20820
gtccggtgaa ttatagcgcg ccggcctcca cgaattcccg agggcgaagg gttggagtct   20880
gagtcccctg gtgcaccgga caggtactgt tcactgtccg gtggcacacc ggacagtccg   20940
gtgcgccaga ccaggggtgc cctcggttgc ccttttgctc ctttattgaa tccaaacttg   21000 gtcttttat tggctgagtg tgaaccttt acacctgtat aatctataca cttgggcaaa   21060
ctagttagtc caaagatttg tgttggacaa ttcaaccacc aaaattatat aggaactagg   21120
tgtaagccta attcccttc aatctccccc ttttggtga ttgatgccaa cacaaaccaa   21180
agcaaatata gaagtgcata attgaactag tttgcataat gtaagtgtaa aggttgcttg   21240
```

```
gaattgagcc aataaaacta cttacaagat atgcatggaa tgtttctttc ttatataaca   21300
ttttggacca cgtttgcacc acttgttttg tttttgcaaa accttttgta aatccttttc   21360
atagatcttt tgcaaatagt caaaggtaaa taaatgagag tttgcaaaag cattttcaag   21420
atttgaaatt tcctcccctt gtttcaaatg cttttccctt tgactaaaca aaactccccc   21480
taaaagagat ccacctctta gtgttcaaga gggttttgat atactacttt ctcccctttt   21540
tgagcaaaat aggataccaa atgataaata ttttagaaa gcactaagtt tttaaatttg    21600
gtggtggtgg tgcggtcctt ttgctttggg ctcatttctc cccctttttg gcatgaatcg   21660
ccaaaaacgg aatcattaga gcccttgaag tgcaatcttc ccctttggtc ataaataagt   21720
gagttaggat taccaaaag acgaagtcct tttgcgtttg agcttttact ctctccccca    21780
aggatgaagt cctttcctt gatgctcatt tctcccccaa agacgagaga gttgctcgga    21840
gtgatggcga agtatgagtt acggagtgga agcctttgtc ttcgccgaag actccaattc   21900
cctttcaata tacctatgac ttggtttgaa ataaacttga aaacacatta gtcatagcat   21960
ataaaagaga tatgatcaaa ggtattcaaa tgagctatgt gtgcaagctt agcaaaagaa   22020
atttctagaa tcaagaatat tgagctcatg cctaagtctg gtaaaagatt gttcatcaag   22080
tggcttggta aagatatcgg ctaattgatc tttagtgtta atgtaagaaa tctcgatatc   22140
cccttttgtt ggtgatccct aagaaaatga taccgaatgg ctatgtgctt agtgcggcta   22200
tgctcgacgg gattgtcggc catttaatt gcactctcat tatcacatag caaagggact    22260
ttggttaatt tgtaaccgta gtcccgcagg gtttgcctca tccaaagcaa ttgcgcgcaa   22320
caatgtcctg cggcaatgta ctcggcttcg gcggtggaaa gagcgaccga attttgcttc   22380
tttgaagccc aagacaccaa ggatcttccc aagaactggc aagtcccga tgtgctcttc    22440 ctattgattt tgcaccccgc ccaatcggca tccgaataac caattaaatc aaatgtggat   22500
cccctagggt accaaagccc aaacttagga gtgtaagcca aatatctcaa gattcgtttt   22560
acggccgtaa ggtgggattc cttagggtcg gattggaatc ttgcacacat gcaaacggaa   22620
agcataatgt ccggtcgaga tgcacataaa taaagcaatg aaccaatcat cgaccggtat   22680 acctttgat ccacggactt acctcccgtg ttgaggtcga gatgcccatt agttcccatg    22740
ggtgtcttga tgggtttggc atccttcatc ccaaacttag caagaatgtc ttgagtgtac   22800
ttcgtttggc taatgaaggt gccctctcgg agttgcttga cttggaatcc cagaaaatat   22860
ttcaactccc ccatcatcga catctcgaat ttctgtgtca tgatcctact aaactcttca   22920
catgtagact cgttagtaga cccaaatata atatcatcaa cataaatttg gcatacaaac   22980
aagtcatttt caagagtttt agtaaagagt gtaggatcgg ccttgccaac tttgaagcca   23040
ttagcaataa ggaaatctct taggcattca taccatgctc ttggggcttg cttgagccca   23100
taaagcgcct tagagagcct atagacatgg ttaggatact tactgtcttc aaagccggga   23160
ggttgctcaa catagacctc ttccttgatt ggtccattga ggaaggcact tttcacgtcc   23220
atttgataaa gcttaaagcc atggtaagta gcataggcta ataatatgcg aattgactca   23280
agcctagcta cgggtgcata ggtttcaccg aaatccaaac cttcgacttg tgaataccct   23340
ttggccacga gtcgagcttt gttccttgtc accacaccat gctcatcttg cttgttgcgg   23400
aagacccatt tggttcctac aacatttgg ttaggacgtg gaactaaatg ccatacctcg    23460
ttcctcgtga aattgttgag ctcctcttgc atcgccacca cccaatccga atcttggaga   23520
gcttcctcta ccctgtgtgg ctcaatggag gaaacaaaag agtaatgttc acaaaaatga   23580
```

```
gcaacccgag atcgagtagt tacccccttn tgaatgtcgc cgaggatggt gtcgacgggg   23640
tgatctcgtt ggattgcttg gtggactctt gggtgtggcg gtcttggttc ttcctcatcc   23700
tccttttctt gatcatttgt atctccccct tgatcattgc tatcatcttg aggtggctcg   23760
tcttcttgat tttgctcttc atcattttga gcctcatcct cattttgagt tggtggagat   23820
gcttgcatgg aggaggatgg ttgatcttgt gtacttggag gctcttcgga ttccttagga   23880
cacacatccc cgatggacat gttccttagc gcgatgcatg gagcctgttc ttcacctatc   23940
tcgtcaagat caacttgctc tacttgagag ccgttagttt catcaaacac aacgtcacaa   24000
gagacttcaa ctagtccagt ggacttgtta aagaccctat atgcccttgt gtttgagtca   24060
taaccaagta aaaaaccttc tacagttttta ggagcaaatt ttgattttct acctctttta   24120
ataagaatga agcatttgct accaaaaact ctaaaatatg aaatattggg cttttttaccg   24180
gttaggagtt catatgatgt cttcttgagg atttggtgaa gatataaccg gttgatggcg   24240
tagcaggcgg tgttgactgc ttcggcccaa aaccggttcg gtgtcttgta ctcatcaagc   24300
atggttcttg ccatgtccaa tagagttcga ttcttcctct ccactacacc attttgttgt   24360
gacgtgtagg gagaagagaa ctcatgcttg atgccctcct cctcaaggaa gctttcaatt   24420
tgagagttct tgaactccgt cccattgtcg cttcttatttt tcttgatcct taagccgaac   24480
tcatttttgag ctcgtctcca gaatcccttt aaggtctctt gggtttgaga ttttttcctgt   24540
aaaaagaata cccaagtgaa gcgagaataa tcatccacaa taactagaca gtacttactc   24600
ccgccgatgc ttatgtaagc gatcgggccg aatagatcca tgtgtaggag ctccagtggc   24660
ctgtcagtcg tcattatgtt cttgtgtgga tgatgagtgc caacttgctt ccctgcttgg   24720
catgcgctac aaatcctgtc tttctcaaaa tgaacattgg ttagtcctaa aatgtgctct   24780
ccttttagaa gcttatgaag attcttcatc ccaacatggg ctagtcggcg gtgccagagc   24840
caacccatgt tagtcttagc aattaaacat gtgtcgagct cagctctatc aaaatctact   24900
aagtatagct gaccctctaa cacacccttta aatgctattg aatcatcact tcttctaaag   24960
acagtgacac ctatatcagt aaaaagatag ttgtagccca tttgacataa ttgggaaaca   25020
gaaagcaagt tgtaatctaa tgaatcaaca agaaaaacat tggaaatgga atggtcaggt   25080
gaaatagcaa ttttacccaa acctttgacc aacccttgat ttccatcccc aaatgtgata   25140
gctcgttggg gtctttgttt ttctcatatg aggagaacat cctttttctcc ccggtcatgt   25200
ggtttgtgca cccgctgtcg agtatccaac ttgagccccc ggatgcataa acctacaaaa   25260
caaatttagt tcttttgtttt aggtacccaa acggttttgg gtcctttagc attagataca   25320
agaactttgg gtacccaaac acaagtcttg gagcctttgt gtttgccccc aacaattttg   25380
gcaactacct tgccagattt gctagtcaat acataagatg catcaaaagt tttaaatgaa   25440
atggcatgat catttgatgc attaggagtt ttctttctag gcaacttggc acgggttggt   25500
tgcctagagc tagatgtctc acccttatac ataaaagcat ggttagggcc agagtgagac   25560
ttcctagagt gaattctcct aatttttgctc tcgggataac cggcagggta caaaatgtaa   25620
ccctcgttat cctgaggcat gggagccttg cccttaacaa aattagacaa atttttaggt   25680
ggggcattaa ttttgacatt gtctcccctt tgaaagccaa tgccgtcctt aatgcccggg   25740
cgtctcccat tatagagcat gcttctagcc aatttaaatt tttcattttc taagtcatgc   25800
tctctaattt tagcattaag ttgtgctatg tgatcatttt gttttttaat taaggcaagg   25860
tgatcatgga tagcatcaac attaatatct ctacatctag tgcaaatgga cacatgctca   25920
atagtagatg tagagggttt gcaagacttt aattcaataa ccttagcatg caacaaatca   25980
```

```
ttcttagttc taaggtcaga aatagtagta ttgcaaacat caaaatcctt agccttagca   26040
attaatttct cattctcatt tctaaggcta gcgatggaag cattcaattc atcaatccta   26100
gcaagcaaat caacatcatc atttctagga tcaatgcaaa catgagaatc aaccttagcc   26160
aacaaattag cattttcatt tctaaggttg tctagaatct catggcaagt gcttagctca   26220
ctagataatt tttcacattt ttctctttct agagcataag cattttaac cttaacatgt    26280 ttcttatttt ccttgattag gaaatcctct tgggagtcca agagatcatc cttttcatgg   26340
atagcactaa ttagctcatt taatttttcc ttttgttcca tgttaaggtt ggcaaaaaga   26400
atacgcaagt tatcctcctc attttatca tcctcatcac tagatgttc atatttagtg    26460 gaggactttg attttacctt cttttttgccg tccttggcca tgaggcactt gtggccgacg   26520
ttggggaaga ggaggccttt ggtgacggcg atgttggcgg cgtcctcgtc gtcggaggag   26580
tcgcttgagc tttcgtcgga gtcccactcc cgacaaacat gggcatcgcc gcccttcttc   26640
ttgtagtact tcttcttctc cttcctcttg cccttcttgt cgttgtccct gtcactgtca   26700
cttgataatg gacatttagc aataaagtga ccgggcttac cacacttgta gcaaaccttc   26760
ttggaacggg atttgtagtc cttccccttc cgttgcttga ggatttgccg gaagcttttg   26820
atgattaggg ccatctcctc gttgtcgagc ttggaggcgt caattggttg tctacttggt   26880
gtagactcct cctccgttgc cttgaaggcc acggggttgcg cctcggatgt ggaaggctca   26940
tcaagctcgt tgatcttctt ggagcccta atcatgcatt caaaactaac aaaattcccg    27000
atgacttcct cgggggtcat ttgtgtatat ctaggattgc cacgaattaa ttgtacttga   27060
gtagggttaa ggaaaataag ggctctcaga ataaccttaa ccacttcgtg gtcatcccat   27120
tttgtgctcc cgaggttgcg cacttggttc accaaggtct tgagccggtt gtacatgtct   27180
tgtggctcct cccccttggcg aagacggaag cgaccgagct cccctcgat cgtttcccgc   27240 ttggtgatct tggtgagttc atcaccttca tgcgccgtct tgagtaggtc ccaaatctcc   27300
ttggcgttct tcaacccttg tactttgttg tattcctcct tgcttaaaga ggcaaggaga   27360
atggttgtgg cttgagagtt gaagtgctcg atttgggcca cttcgtccgt gtcgtagtcc   27420
tcatccccta cggatggtac ctgtacacca tactcaacaa catcccataa tcttttgtgg   27480
agagaggtta gatgaaatcg catcaaatta ctccacatag cataatcttc accattaaaa   27540
gttggtggtt tgcctaatgg gacggaaagt aaaggtgtat gtttaggaac gcgagggtag   27600
cgtaggggat cttactatac ttcttacgct cttggcgttt agaagtgacg gacgccgcgt   27660
cggagccgga ggtggagatc gatgaagtgt cggtctcgta gaagaccacc ttcctcatcc   27720
ttttgtgctt gtccccactc cgatgcggct tgtgagaaga ttttccttc ttctccttat    27780 ggtgagaaga ggaagatctt ttctccttcc gcttggagga tttcttcttc ttctctcttc   27840
tcttggtgcg ggattcttcc gatgaagatg aagtgctccc ttggcttgta gtaggcttgt   27900
cgtcgccggt ctccatctcc ttcttggcgt gatctcccga catcacttcg agcggttagg   27960
ctctaatgaa gcaccgggct ccgataccaa ttgatagtcg cctagagggg ggtgaatagg   28020
gcgaaactga aatttacaaa aaataatcac aactacaagc cggggttagc gttagtaata   28080
ataaatgagt cctcaagaga gggcgcaaaa caaatcgcaa gcaaataaag agagtgacac   28140
gtggatttgt tttaccgagg ttcggttctt gcaaacctac tccccgttga ggaggccaca   28200
aaggccgggt ctctttcaac ccttccctct ctcaaacggt ccctcggacc gagtgagctt   28260
tccttcttct caatcaaccg ggaacaaagc ttccccgcaa gggccaccac acaatcggtg   28320
```

```
cctcttgcct tggttacaat tgagtgttga tcacaagagc ataagagaaa gaaagaatgc   28380
gatccaagcg caagagctca aaagaacacg gcaaatcact ctcactagtc actagggttt   28440
tgtgtggaat tggagaggat ttgatctctt tgaatgtgtc tagaattgaa tgcctagctc   28500
ttgtaagtgg ttgagaagtg gaaaacttgg atggctatga atgtggggtg gttggggtat   28560
ttatagcccc aaccaccaaa catgaccgtt ggctggaggc ttctgttcga tggcgcaccg   28620
gacagtccgg tgcacaccgg acagtccggt gcccctgcca cgtcatcgtt gccgttggat   28680
tctgaccgtt ggagcttctg acttgtgggc ccgcctgggt gtccggtgca caccggacat   28740
gcactgtttg atgtccggtg caccggtatg ggcagccctg acgtctgcgc gcgctgcgcg   28800
cgcatttaat gcaccgcagg gagccgttgg cgccgcaggg agccgttgct ccgctggcac   28860
accggacagt ccggtgcaca ccggacagtc cggtgaatta tagcggagcg gctgccgcgc   28920
gaacccgagg ctggcgagtt caggaggccg agcttccttg gagcaccgga catgtccggt   28980
gcacaccgga cagtccggtg aattatagcg cgccggcctc cacgaattcc cgagggcgaa   29040
gggttggagt ctgagtcccc tggtgcaccg gacaggtact gttcactgtc cggtggcaca   29100
ccggacagtc cggtgcgcca gaccaggggt gccctcggtt gccctttgc tcctttattg   29160 aatccaaact tggtcttttt attggctgag tgtgaacctt ttacacctgt ataatctata   29220
cacttgggca aactagttag tccaaagatt tgtgttggac aattcaacca ccaaaattat   29280
ataggaacta ggtgtaagcc taattccctt tcagtctttt tattggctga gggtgaacct   29340
tttacacctg taaatctat acacttgggc aaactagtta gtccaattat ttgtgttggg   29400
caattcaacc accaaaatta tttaggaact aggtgtaagc ctaattccct ttcagcgacg   29460
cgccaagtcg ttcgtcttgc tgggcgatga agaggagctc taccatcgca gcccctcggg   29520
catcctccag cgatgcatct ccatcgccga aggtcgggaa ctgctgcaag aaatacactc   29580
gggggcttgc ggccatcacg cagcaccccg agcccttgtc gggaatgctt tccgacaagg   29640
cttctactgg ccaacggcgg tggatgacgc cactagaatt ttccgcacct gcgaagggtg   29700
ccaattctat gcgaagcaga cccacctgcc cgctcaggct ctgcagacaa tacccatcac   29760
ctggcccttc gctgtatggg gtctggacct cgtcggtccc ttgcagaagg cgcccggggc   29820
tacacgcacc tgctggtcgc catcgacaaa ttctccaagt ggatcgaggt ccgacctctg   29880
aacagcatca ggtccgagca ggcggtggcg ttcttcacca acatcatcca tcgcttcggg   29940
gtcccgaact ccatcatcac cgacaacggt acccagttca ccccgtcgca ttaactctgc   30000
ggcgggacac gcggcgcctc tggcgggaga agcgcgcgac gcttcgcctt cgccgtaata   30060
accgcgtcaa aaagaggtac gccacgtcgt tcggtttcgt atcctcttcc ttttcctct   30120 ttctctatct cttgcaacag ggaccgggaa aggggatacc ccgaaaagga cccttctccg   30180
cgaaggaacc gggctccgag ccccctact gatcaggggt tcgaagactg gccctccgaa   30240
gggttcaaca gtcgccttag atcgcgtggg cccgacaccc actactggtc aggggttcga   30300
aggccagccc ccaaagggtt ctatggccgc ctcaggctac tcgggctccg cgcccattac   30360
tgatcagggg ttcgaaggct ggccccgaa gggttcacag tcgcctcaga caccgagcga   30420
gggatgacca ggggtacgtt cgatacataa ccgaggctcg ggctgcgctc ccgaggtacc   30480
ctaggacatt tccgagacca gcgggaacga tcttgtaacg gaatcccatc ggagggaggc   30540
atcgagccct cggaccccgt cgccagggga ccgggtccgg caaatcaccc gcaggtactt   30600
ttgggcgtgc ctctgggccc ctagccgacc cccaacgaac ggggcacgga cgtccactcg   30660
gattacccgc ttgcagctca ccggagacac catgttcgat gcccatcgag ggtaacatgg   30720
```

```
cgcactcccc cctcctcctt gcggaaaggc gacgtagggg cgtatgtaaa aagccgagtc   30780
tgtccctgat cgtcctctcg ccctgtgcag aggctcgggg gctgctctcg cgaaaaccgg   30840
ctccggccga accgttgaca gcgtcaacat accagcccga gagcttgggc cccgaccgtg   30900
cacccgggct acggccagtt cgcatgaggg aacgaccaga ccagccgaag cgttacgcaa   30960
ggtattaaga cctcgaagga gtgtaaccac tcctccgagg cctcggggct acacccggcg   31020
ggtgcgctcg cgcgcaccca ccggaacgaa atgcaaccga gaaaggctgg tcccttgca   31080 aaaaagtgcg acgaaagcct ccaagcgagt gctaacactc ccttcgaggc tcgggggcta   31140
ctgtcgggga ccataattag gggtaccctc aagacgccta attctcagct ggtaacccc   31200 atcatcataa agctgcaaag gcctgatggg tacgattaag tcagggatcg gtccacacga   31260
gtaactcgat cacgcttcac ccgagcctag cctcggccaa gggcagccga cctcgagaga   31320
cttccgtctc gcccgaggcc cccttttta cggcggacac atcaccggct cgcccaaggc   31380
cttggcttcg ctcagaagta accctgacta aatcgccaca ccgactgacc aagttgcagg   31440
agcatttaac gcaaaggtgg cctgacacct ttatcctgac acgcgccccc ggcagagcc   31500 gaagtgaccg ccgtcactcc accgctccac tgaccagtct gacagaagga cagcgccgcc   31560
tgcgccactc cgactgcagt gccactcgac agagtgagtc tgacaagcag tcgggccctg   31620
ccaaaggcgc catgggaaac tccgctccgc ccgaccccag ggctcggact cgggctaaaa   31680
cccggaagac ggcgaactcc gctccgcccg accccagggc tcggactcgg gctaagagcc   31740
ggaagacggc gaactccgct ccgcccgacc cagggctcg gactcgggct aagacccgga   31800
agacggcgaa ctccgctccg cccgacccca gggctcggac tcgggctaag acccggaaga   31860
cggcgaactc cgctccgccc gaccccaggg ctcggactcg gctaagacc cggaagacgg   31920 cgaactccgc tccgcccgac cccagggctc ggactcgggc taagacccgg aagacggcga   31980
actccgctcc gcccgacccc agggctcgga ctcgggctaa gacccggaag acggcgaatc   32040
tccgcctcgc ccgaccccag ggctcggact ccgcctggc ctcggccaaa cgatctccgc   32100
ctcgcccgac ccggggctcg ggctcggcct cggcaacgga aggcaaactc gacctcgact   32160
tcggaggagc ccccacgtcg ccctgcctag ggcacaggtc cgccacgtca acaggaagcg   32220
ccatcaccaa tctaccccga gccgacttgg gacacgaagg acaagaccgg cgtcccatct   32280
ggccagctcc gccggatggg caatgatggc gcccccaag ctctgtgacg acggcggctc   32340
ttagctctct tacggcagca gagcgacgtc agcaaggact cgaccgctcc aacagctgtc   32400
cctccgccag gctccgtcgc tcctccgaca gccacgacat cacgccagca aggtgccaag   32460
acctctccgg ctgccacatt ggcatgtacg cagggcgcta gctctctctc tctctctctc   32520
cgctagacac gtagcactct gctacccca ttgtacacct ggatcctctc cttacgacta   32580
taaaaggaag gaccagggcc ttcttagaga aggttggccg cgcgggaccg aggacgggac   32640
aggcgctctc ttggggccgc tcgcttccct caccgcgtg gacgcttgta accccctact   32700
gcaagcgcac ctgacctggg cgcgggacga acacgaaggc cgcgggactt ccacctctct   32760
cacgctcgac tccggccacc tcgcctctcc cccttcgcg ctcgcccacg cgctcgaccc   32820
atctgggctg gggcacgtag cacactcact cgtcggctta ggaccccct gtctcgaaac   32880 gccgacacta tcggtatggt ggggcgaggg agtaatttta tgcctatatg ttgatgacat   32940
tctaatcttg gggacgagtc ttgatgtgat taaagagaca aaagactttc tgtctaataa   33000
ttttgaaatg aaagatttgg gagaagctga tgttattctt aacattaagc tactgagaga   33060
```

```
aggcattggt gggatcacac ttgtgcaatc ccattatgtg gaaaaggttt tgagtcgctt   33120
tggtttagc gaatgtgaac ctgctccaac gccttatgat cctagtaagc tattaaagaa    33180
aaatcgaagg atagttaggg atcaattgag atattcccaa ataattggtt cactcatgta   33240
tttagctagc gctacgaggc ctaacatctc atttgctgtg agcaaactta gtcgatttgt   33300
ttcaaatccg ggagatgatc actggcgtgc tcttgagaga gttttgcgct atctaaaggg   33360
tactatgagt ttaggcatcc attataccgg gtacccaaca gttctggagg gttattgtga   33420
tgcaaactgg atatctgatg ctgatgagat atatgccaca agtggatatg tgttttcact   33480
tggaggtggt gctgtttcat ggaagtcttg caagcagacc atcttaacga ggtcgactat   33540
ggaagcagaa ctcacagcat tagataccgc ttcagttgag gctgagtggc ttcgtgaact   33600
ccttatggat ttaccggtgg ttgaaaaacc tgtgccggct atttccatga actgtgataa   33660
tcagactgtg ataattaaga taaacagttc taaggataat atgaagtcga caaggcacat   33720
aaagaggcgt ttgaaatctg tcaggaaatt gagaaactcc ggagtaatag cgttggatta   33780
tgtccatacg tctaaaaatc tggcagatca atttactaag gggctatcac gtagtgtgat   33840
agatagtgca tcaagtgaga tgggcatgag acccacctaa agtttatcat agtggtaacc   33900
tgttctatgt gatcggagat cccgtgaatt agaatggtga aacaagctag tggtagactg   33960
agaggaaaga cccttaataa ggctcatttc agatgcatat ctttccttac tgtaaggtag   34020
gttggtgttt acaccttaat atgttccaag tggctttgtg aagcaaagat gttgtcctac   34080
agaacatctt tagaggaaca tacctatatg ggttaactgc tagtcacagt ttatgagatc   34140
tgggtggttt ctagataccc atgaaaggct atggagtttg acttatatgc tccaaccaga   34200
ggggatgcgt tcaacaatct agtactggta aagagtttag atgaaactca ttccacgcaa   34260
aactgccaat tcaaggccta gtccattgtg cagttgtggt caagtgtagt ctaagttcta   34320
ggtggatgtt caacttaaca gtctccatct aaacaccagt atatcaaacg tttgagatga   34380
tgagagcttt tttgtgtgac ttagcatttg gtggggattg ttggattaat gtgggcttgg   34440
cccaaattaa tattcaataa tagtcaatgc taatggccca ctttaatgct atggtgtact   34500
aattatttag taccatattg gaagttcaaa ggacaaatca atcaacttaa ataggtggac   34560
cattggtgca tctattgaga agttgagaaa aggacgaagg actgccacac gcgcgcgccg   34620
ccgccgccgc cgccggccgg gccaggccgg gccgtgtccg tgttcgaata ttcctttcaa   34680
acggttgcgc attttgcctg gagcgatgac cgtcatgata accgccgtt tcttgtctta    34740
tggctagtaa cggacgtcag ttactgtcgt cagtttccag ttctaatgcg cgaccgtttc   34800
tgtccgttgt tcttctccct ccttctgacc gcctataaga atggagaggg agggctcttc   34860
cagttatgcg aattatctca cacgaattgc aaacaacaca ttcccgtccc atcttctgcg   34920
agcacagaga gagtgggaga gcaggcctcc gaaatcaccg accgcagaga tacacttgca   34980
cgggtgtgcg ggcgatcaga ttttttgggga gcgtcttcgc gactgctcgc gtgatctgtt   35040
tgtccagctg cttcgttcac agcttgttgt tcgtcgcctt cccgagttga cgcgtgctgc   35100
tgttcttctt cccggcgacc gttcgaggga ctgcacagcg tacatcttcc tgcaccgact   35160
tcgtacggct acatcgaaca aacacacgag atgtctcgtg tgaatggagc cactgatgcc   35220
ttgagcatcg gtccctccgc tgggtacact ctgttcttcg tatttgtaca tgtttcattg   35280
ctgtttacta cttatgcgag tagttataca cacatgcaca tacatgtcat cacatatatc   35340
gcactgtttt tctggattaa attaaaacta aaatgcctaa actttctaac a            35391
```

<210> SEQ ID NO 72
<211> LENGTH: 5966
<212> TYPE: DNA
<213> ORGANISM: Artificial
<220> FEATURE:
<223> OTHER INFORMATION: Cas9 expression construct

<400> SEQUENCE: 72

| | | | | | |
|---|---|---|---|---|---|
| gtgcagcgtg | acccggtcgt | gcccctctct | agagataatg | agcattgcat gtctaagtta | 60 |
| taaaaaatta | ccacatattt | ttttttgtcac | acttgtttga | agtgcagttt atctatcttt | 120 |
| atacatatat | ttaaacttta | ctctacgaat | aatataatct | atagtactac aataatatca | 180 |
| gtgttttaga | gaatcatata | aatgaacagt | tagacatggc | ctaaaggaca attgagtatt | 240 |
| ttgacaacag | gactctacag | ttttatcttt | ttagtgtgca | tgtgttctcc ttttttttg | 300 |
| caaatagctt | cacctatata | atacttcatc | cattttatta | gtacatccat ttagggttta | 360 |
| gggttaatgg | ttttttataga | ctaatttttt | tagtacatct | attttattct attttagcct | 420 |
| ctaaattaag | aaaactaaaa | ctctatttta | gtttttttat | taataatttt agatataaaa | 480 |
| tagaataaaa | taaagtgact | aaaaattaaa | caaatacccct | ttaagaaatt aaaaaaacta | 540 |
| aggaaacatt | tttcttgttt | cgagtagata | atgccagcct | gttaaacgcc gtcgacgagt | 600 |
| ctaacggaca | ccaaccagcg | aaccagcagc | gtcgcgtcgg | gccaagcgaa gcagacggca | 660 |
| cggcatctct | gtcgctgcct | ctggaccccct | tcgagagtt | ccgctccacc gttggacttg | 720 |
| ctccgctgtc | ggcatccaga | aattgcgtgg | cggagcggca | gacgtgagcc ggcacggcag | 780 |
| gcggcctcct | cctcctctca | cggcaccggc | agctacgggg | gattcctttc ccaccgctcc | 840 |
| ttcgctttcc | cttcctcgcc | cgccgtaata | aatagacacc | ccctccacac cctctttccc | 900 |
| caacctcgtg | ttgttcggag | cgcacacaca | cacaaccaga | tctcccccaa atccacccgt | 960 |
| cggcacctcc | gcttcaaggt | acgccgctcg | tcctccccccc | cccccctctc taccttctct | 1020 |
| agatcggcgt | tccggtccat | gcatggttag | ggcccggtag | ttctacttct gttcatgttt | 1080 |
| gtgttagatc | cgtgtttgtg | ttagatccgt | gctgctagcg | ttcgtacacg gatgcgacct | 1140 |
| gtacgtcaga | cacgttctga | ttgctaactt | gccagtgttt | ctctttgggg aatcctggga | 1200 |
| tggctctagc | cgttccgcag | acgggatcga | tttcatgatt | ttttttgttt cgttgcatag | 1260 |
| ggtttggttt | gcccttttcc | tttatttcaa | tatatgccgt | gcacttgttt gtcgggtcat | 1320 |
| cttttcatgc | ttttttttgt | cttggttgtg | atgatgtggt | ctggttgggc ggtcgttcta | 1380 |
| gatcggagta | gaattctgtt | tcaaactacc | tggtggattt | attaattttg gatctgtatg | 1440 |
| tgtgtgccat | acatattcat | agttacgaat | tgaagatgat | ggatggaaat atcgatctag | 1500 |
| gataggtata | catgttgatg | cgggttttac | tgatgcatat | acagagatgc tttttgttcg | 1560 |
| cttggttgtg | atgatgtggt | gtggttgggc | ggtcgttcat | tcgttctaga tcggagtaga | 1620 |
| atactgtttc | aaactacctg | gtgtatttat | taattttgga | actgtatgtg tgtgtcatac | 1680 |
| atcttcatag | ttacgagttt | aagatggatg | gaaatatcga | tctaggatag gtatacatgt | 1740 |
| tgatgtgggt | tttactgatg | catatacatg | atggcatatg | cagcatctat tcatatgctc | 1800 |
| taaccttgag | tacctatcta | ttataataaa | caagtatgtt | ttataattat tttgatcttg | 1860 |
| atatacttgg | atgatggcat | atgcagcagc | tatatgtgga | ttttttttagc cctgccttca | 1920 |
| tacgctattt | atttgcttgg | tactgtttct | tttgtcgatg | ctcaccctgt tgtttggtgt | 1980 |
| tacttctgca | ggtcgactct | agaggatcca | tggcaccgaa | gaagaagcgc aaggtgatga | 2040 |
| gcgacctcgt | cctcggactc | gacatcggaa | taggcagcgt | cggagtcggt atcctgaaca | 2100 |

-continued

```
aggtcaccgg cgagatcatc cataaaaaca gcaggatcgt aagtttctgc ttctaccttt    2160
gatatatata taataattat cattaattag tagtaatata atatttcaaa tattttttc     2220
aaaataaaag aatgtagtat atagcaattg cttttctgta gtttataagt gtgtatattt    2280
taatttataa cttttctaat atatgaccaa aacatggtga tgtgcagttc ccagcagcac    2340
aagctgaaaa taacctcgtc agaaggacca accgccaagg caggaggctt gcacgcagga    2400
agaagcacag aagggtgagg ctcaaccgcc tcttcgaaga gagcggatta atcacagact    2460
tcaccaagat ctcaattaat ctcaaccccct accagctcag agtcaaggg ctcacagacg     2520
agctcagcaa cgaggagctc ttcatcgccc tcaaaaatat ggtcaagcac aggggcatca    2580
gctacctcga cgacgcatca gacgacggaa acagcagcgt cggcgactac gcccagatcg    2640
tcaaggaaaa tagtaagcag ctcgagacca agacccagg acagatccag ctcgaacgct     2700
accagacata cggccagctc agaggcgact tcaccgtcga aaaggacggc aagaagcacc    2760
gcctcattaa tgtcttcccc acaagcgcct acaggagcga agcactgcgg attctccaga    2820
cccagcagga gttcaacccc cagatcaccg acgagttcat taatcgctac ctagagatcc    2880
tcaccggcaa gcgcaaatac tatcacggac cagggaatga aaagagccgc acagactacg    2940
gacgctacag aaccagcggc gagaccctcg acaacatatt cggcatcctc atcggcaagt    3000
gcaccttcta ccccgacgag ttcagagccg ccaaggcatc ctataccgcc caagagttca    3060
acctactaaa cgaccttaac aacctcacag tccccaccga aaccaaaaag ctcagcaagg    3120
agcagaagaa tcaaatcatt aattacgtca agaatgaaaa ggcgatgggc ccagccaagc    3180
tcttcaagta catcgccaag ctcctcagct gcgatgtcgc cgacatcaag ggataccgca    3240
tcgacaaaag cggcaaggcc gaaatccaca ccttcgaagc ctaccgcaag atgaaaaccc    3300
tcgagaccct cgacatcgag caaatggacc gcgagaccct cgacaagctc gcctacgtcc    3360
tcacattaaa cacagagcgc gaaggcatcc aggaggcact cgaacacgag ttcgcagacg    3420
gctccttcag ccaaaagcag gtcgacgaac tcgtccaatt ccgcaaggcc aacagcagca    3480
tcttcggaaa aggctggcac aacttcagcg tcaagctcat gatggaactc atccccgagc    3540
tctacgaaac cagcgaggag caaatgacca tcctcacaag gctcggcaag cagaagacca    3600
ccagcagcag caataaaaca aaatatatcg atgaaaaact cctcacagag gaaatctaca    3660
accccgtcgt cgcaaagagc gtcaggcagg ccataaaaat cgtcaacgcc gccattaaag    3720
agtacggcga cttcgacaac atcgtcatcg agatggcaag ggagaccaac gaggacgatg    3780
aaaagaaagc catccagaag atacagaagg ccaacaagga tgaaaaagac gcagccatgc    3840
tcaaggcagc caaccaatat aatggcaagg ccgagctccc cactcagtc ttccacggcc      3900
acaagcaact agccaccaag atacgcctgt ggcaccaaca aggcgaacgc tgcctctaca    3960
caggcaagac catcagcatc cacgacctca tcaataatag caaccagttc gaggtcgacc    4020
acatcctccc actcagcatc accttcgacg acagcctcgc caacaaggtc ctcgtctacg    4080
caaccgcaaa ccaagagaag ggacaaagaa ccccgtacca agccctcgac agcatggacg    4140
acgcctggag cttccgcgaa ttaaaagcct tcgtcaggga gagcaagacc ctcagcaaca    4200
agaagaaaga gtacctcctc accgaggagg acatcagcaa attcgacgtc cgcaagaagt    4260
tcatcgaacg caacctcgtc gacacaaggt acgccagcag agtcgtcctc aacgcactcc    4320
aggagcactt cagagcccac aagatcgaca ccaaggtcag cgtcgtcaga ggacagttca    4380
ccagccaact cagacgccac tgggggatcg agaagacacg cgacacctac caccaccacg    4440
ccgtcgacgc cctcatcatc gcagcaagca gccaactcaa cctctggaaa aagcagaaga    4500
```

```
acaccctcgt cagctacagc gaagaccagc tcctcgacat agagaccggc gagctcatca    4560
gcgacgacga atacaaggag agcgtcttca aggcccccta ccagcacttc gtcgatacat    4620
tgaagagcaa agagttcgag gacagcatac tcttcagcta ccaggtcgac agcaaattca    4680
accgcaaaat aagcgacgcc accatctacg ccaccagaca ggccaaggtc ggaaaggaca    4740
aggccgatga aacttacgtc ctcggcaaaa tcaagacat atacacccag gacggatacg     4800
acgcattcat gaagatctac aagaaggaca agagcaagtt cctcatgtac agacacgacc    4860
cacagacatt cgagaaggtc atcgagccca tcctcgaaaa ctaccccaac aagcaaataa    4920
atgaaaaagg aaaggaggtc ccatgcaacc ccttcctaaa atataaagag gagcacggct    4980
acatcaggaa gtacagcaag aaaggaaacg gccccgaaat caagagcctc aaatactatg    5040
acagcaagct cggcaaccac atcgacatca cccccaagga cagcaacaat aaagtcgtcc    5100
tccaaagcgt cagcccctgg agagccgacg tctacttcaa caagaccacc ggaaaatacg    5160
agatcctcgg cctaaagtac gccgacctcc aattcgaaaa aggcaccggc acatataaga    5220
tcagccagga aaaatacaat gacatcaaga agaaggaagg agtcgacagc gacagcgaat    5280
tcaagttcac cctctataaa aatgacctcc tcctcgtcaa ggacaccgag accaaggagc    5340
agcagctctt ccgcttcctc agcagaacca tgcccaagca gaagcattac gtcgaattaa    5400
aaccctacga caagcagaag ttcgaaggcg gcgaagcctt aattaaagtc ctcggcaacg    5460
tcgccaacag cggacagtgc aaaaagggcc tcggcaaatc aaatatcagc atatacaagg    5520
tccgcacaga cgtcctcgga aaccaacaca tcatcaagaa cgaaggagac aagcccaagc    5580
tcgacttcaa gagaccacgg gaccgccacg atggcgagct gggaggccgc aagcgggcaa    5640
ggtaggtacc gttaacctag acttgtccat cttctggatt ggccaactta attaatgtat    5700
gaaataaaag gatgcacaca tagtgacatg ctaatcacta taatgtgggc atcaaagttg    5760
tgtgttatgt gtaattacta gttatctgaa taaagagaa agagatcatc catatttctt    5820
atcctaaatg aatgtcacgt gtcttttataa ttctttgatg aaccagatgc atttcattaa    5880
ccaaatccat atacatataa atattaatca tatataatta atatcaattg ggttagcaaa    5940
acaaatctag tctaggtgtg ttttgc                                         5966
```

<210> SEQ ID NO 73
<211> LENGTH: 4377
<212> TYPE: DNA
<213> ORGANISM: Artificial
<220> FEATURE:
<223> OTHER INFORMATION: Sp Cas9 used in Example 4

<400> SEQUENCE: 73

```
atggcaccga agaagaagcg caaggtgatg gacaagaagt acagcatcgg cctcgacatc     60
ggcaccaact cggtgggctg gccgtcatc acggacgaat ataaggtccc gtcgaagaag     120
ttcaaggtcc tcggcaatac agaccgccac agcatcaaga aaaacttgat cggcgccctc    180
ctgttcgata gcggcgagac cgcggaggcg accaggctca gaggaccgc caggagacgg     240 tacactaggc gcaagaacag gatctgctac ctgcaggaga tcttcagcaa cgagatggcg    300
aaggtggacg actccttctt ccaccgcctg gaggaatcat tcctggtgga ggaggacaag    360
aagcatgagc ggcacccaat cttcggcaac atcgtcgacg aggtaagttt ctgcttctac    420
ctttgatata tatataataa ttatcattaa ttagtagtaa tataatattt caaatatttt    480
tttcaaaata aagaatgta gtatatagca attgcttttc tgtagtttat aagtgtgtat    540
```

```
atttttaattt ataactttttc taatatatga ccaaaacatg gtgatgtgca ggtggcctac    600
cacgagaagt acccgacaat ctaccacctc cggaagaaac tggtggacag cacagacaag    660
gcggacctcc ggctcatcta ccttgccctc gcgcatatga tcaagttccg cggccacttc    720
ctcatcgagg gcgacctgaa cccggacaac tccgacgtgg acaagctgtt catccagctc    780
gtgcagacgt acaatcaact gttcgaggag aaccccataa acgctagcgg cgtggacgcc    840
aaggccatcc tctcggccag gctctcgaaa tcaagaaggc tggagaacct tatcgcgcag    900
ttgccaggcg aaaagaagaa cggcctcttc ggcaacctta ttgcgctcag cctcggcctg    960
acgccgaact tcaaatcaaa cttcgacctc gcggaggacg ccaagctcca gctctcaaag   1020
gacacctacg acgacgacct cgacaacctc ctggcccaga taggagacca gtacgcggac   1080
ctcttcctcg ccgccaagaa cctctccgac gctatcctgc tcagcgacat ccttcgggtc   1140
aacaccgaaa ttaccaaggc accgctgtcc gccagcatga ttaaacgcta cgacgagcac   1200
catcaggacc tcacgctgct caaggcactc gtccgccagc agctccccga gaagtacaag   1260
gagatcttct tcgaccaatc aaaaaacggc tacgcgggat atatcgacgg cggtgccagc   1320
caggaagagt tctacaagtt catcaaacca atcctggaga agatggacgg caccgaggag   1380
ttgctggtca agctcaacag ggaggacctc ctcaggaagc agaggacctt cgacaacggc   1440
tccatcccgc atcagatcca cctgggcgaa ctgcatgcca tcctgcggcg ccaggaggac   1500
ttctacccgt tcctgaagga taaccgggag aagatcgaga gatcttgac gttccgcatc   1560 ccatactacg tgggcccgct ggctcgcggc aactcccggt tcgcctggat gacccggaag   1620
tcggaggaga ccatcacacc ctggaacttt gaggaggtgg tcgataaggg cgctagcgct   1680
cagagcttca tcgagcgcat gaccaacttc gataaaaacc tgcccaatga aaaagtcctc   1740
cccaagcact cgctgctcta cgagtacttc accgtgtaca acgagctcac caaggtcaaa   1800
tacgtcaccg agggcatgcg gaagccggcg ttcctgagcg gcgagcagaa gaaggcgata   1860
gtggacctcc tcttcaagac caacaggaag gtgaccgtga gcaattaaa agaggactac   1920 ttcaagaaaa tagagtgctt cgactccgtg gagatctcgg gcgtggagga tcggttcaac   1980
gcctcactcg gcacgtatca cgacctcctc aagatcatta aagacaagga cttcctcgac   2040
aacgaggaga acgaggacat cctcgaggac atcgtcctca ccctgaccct gttcgaggac   2100
cgcgaaatga tcgaggagag gctgaagacc tacgcgcacc tgttcgacga caaggtcatg   2160
aaacagctca agaggcgccg ctacactggt tggggaaggc tgtcccgcaa gctcattaat   2220
ggcatcaggg acaagcagag cggcaagacc atcctggact tcctcaagtc cgacgggttc   2280
gccaaccgca acttcatgca gctcattcac gacgactcgc tcacgttcaa ggaagacatc   2340
cagaaggcac aggtgagcgg gcagggtgac tccctccacg aacacatcgc caacctggcc   2400
ggctcgccgg ccattaaaaa gggcatcctg cagacggtca aggtcgtcga cgagctcgtg   2460
aaggtgatgg gccggcacaa gcccgaaaat atcgtcatag atgggccag ggagaaccag   2520 accacccaaa aagggcagaa gaactcgcgc gagcggatga acggatcga ggagggcatt   2580 aaagagctcg ggtccagat cctgaaggag caccccgtgg aaaatacca gctccagaat   2640 gaaaagctct acctctacta cctgcagaac ggccgcgaca tgtacgtgga ccaggagctg   2700
gacattaatc ggctatcgga ctacgacgtc gaccacatcg tgccgcagtc gttcctcaag   2760
gacgatagca tcgacaacaa ggtgctcacc cggtcggata aaaatcgggg caagagcgac   2820 aacgtgcccta gcgaggagt cgtgaagaag atgaaaaact actggcgcca gctcctcaac   2880
gcgaaactga tcacccagcg caagttcgac aacctgacga aggcggaacg cggtggcttg   2940
```

```
agcgaactcg ataaggcggg cttcataaaa aggcagctgg tcgagacgcg ccagatcacg    3000
aagcatgtcg cccagatcct ggacagccgc atgaatacta agtacgatga aaacgacaag    3060
ctgatccggg aggtgaaggt gatcacgctg aagtccaagc tcgtgtcgga cttccgcaag    3120
gacttccagt tctacaaggt ccgcgagatc aacaactacc accacgccca cgacgcctac    3180
ctgaatgcgg tggtcgggac cgccctgatc aagaagtacc cgaagctgga gtcggagttc    3240
gtgtacggcg actacaaggt ctacgacgtg cgcaaaatga tcgccaagtc cgagcaggag    3300
atcggcaagg ccacggcaaa atacttcttc tactcgaaca tcatgaactt cttcaagacc    3360
gagatcaccc tcgcgaacgg cgagatccgc aagcgcccgc tcatcgaaac caacggcgag    3420
acgggcgaga tcgtctggga taagggccgg gatttcgcga cggtccgcaa ggtgctctcc    3480
atgccgcaag tcaatatcgt gaaaaagacg gaggtccaga cgggcgggtt cagcaaggag    3540
tccatcctcc cgaagcgcaa ctccgacaag ctcatcgcga ggaagaagga ttgggacccg    3600
aaaaaatatg gcggcttcga cagcccgacc gtcgcataca gcgtcctcgt cgtggcgaag    3660
gtggagaagg gcaagtcaaa gaagctcaag tccgtgaagg agctgctcgg gatcacgatt    3720
atggagcggt cctccttcga gaagaacccg atcgacttcc tagaggccaa gggatataag    3780
gaggtcaaga aggacctgat tattaaactg ccgaagtact cgctcttcga gctggaaaac    3840
ggccgcaaga ggatgctcgc ctccgcaggc gagttgcaga agggcaacga gctcgccctc    3900
ccgagcaaat acgtcaattt cctgtacctc gctagccact atgaaaagct caagggcagc    3960
ccggaggaca cgagcagaa gcagctcttc gtggagcagc acaagcatta cctggacgag    4020
atcatcgagc agatcagcga gttctcgaag cgggtgatcc tcgccgacgc gaacctggac    4080
aaggtgctgt cggcatataa caagcaccgc gacaaaccaa tacgcgagca ggccgaaaat    4140
atcatccacc tcttcaccct caccaacctc ggcgctccgg cagccttcaa gtacttcgac    4200
accacgattg accggaagcg gtacacgagc acgaaggagg tgctcgatgc gacgctgatc    4260
caccagagca tcacagggct ctatgaaaca cgcatcgacc tgagccagct gggcggagac    4320
aagagaccac gggaccgcca cgatggcgag ctgggaggcc gcaagcgggc aaggtag      4377
```

<210> SEQ ID NO 74
<211> LENGTH: 18
<212> TYPE: DNA
<213> ORGANISM: Artificial
<220> FEATURE:
<223> OTHER INFORMATION: ZM-U6:08CR1

<400> SEQUENCE: 74

```
gtacgtaacg tgcagtac                                                     18
```

<210> SEQ ID NO 75
<211> LENGTH: 21
<212> TYPE: DNA
<213> ORGANISM: Artificial
<220> FEATURE:
<223> OTHER INFORMATION: ZM-U6:45CR1

<400> SEQUENCE: 75

```
gcataatgag gatcgaggat g                                                 21
```

<210> SEQ ID NO 76
<211> LENGTH: 18
<212> TYPE: DNA
<213> ORGANISM: Artificial
<220> FEATURE:

<223> OTHER INFORMATION: ZM-U6:10CR3

<400> SEQUENCE: 76
gctcgtgttg gagataca                                                18

<210> SEQ ID NO 77
<211> LENGTH: 14124
<212> TYPE: DNA
<213> ORGANISM: Artificial
<220> FEATURE:
<223> OTHER INFORMATION: CTL1-TS8 DNA repair template

<400> SEQUENCE: 77

| | | | | | |
|---|---|---|---|---|---|
| cagaatttac | ggtccagcac | gggcatgccg | cgcgggctga | ctttgctcca | ctgactcgat | 60 |
| catgtgcgga | ttccatcgcg | gcgtagcgta | gccaaccgca | acgcaaaccg | acttcatctt | 120 |
| ttttttttat | tatgaacaaa | aggagatcga | gagaaacgtg | aacggtaaat | aatatatctg | 180 |
| atcccatgca | tgcacgctgc | ctgggtcgat | ctcgctctcg | ctccgcccag | acgaacatgc | 240 |
| atgctggtca | ggctcaacgc | tcaggcgggc | aagctgtggg | aggacatggg | atgggagagg | 300 |
| aggacacatg | catgctggcc | agtcaggcac | tgtgctggca | catgaggtag | gatagggg | 360 |
| gccctcggcc | agtgtccagg | ccgcatgcat | gcatgccccc | cctgctgctc | gaccgaacaa | 420 |
| cgttggatgc | ctggattgat | gcaacagttt | ggacggacgg | accatacgtt | atgtaccagt | 480 |
| atctaacgcc | gacaccgtcg | acgagtaaga | ggtcgtggcc | ggctgcccac | acgtctgtgt | 540 |
| gaacctcacc | atcgacacca | ccgtccgcct | gcggcctacg | gcctcgaact | ccaacatcac | 600 |
| attcctctac | aactgcatga | agaacattac | cctaccctct | gtcatggaac | tgagtgggtt | 660 |
| cccacaacaa | caagaagata | gatgtaggtc | gtacgtgctg | tgggatggcg | ggatcacggg | 720 |
| tgctcaggcg | tacgggtatg | ggtgcgagga | cttggtggta | gcgtcggagc | tggatgtaca | 780 |
| caaaaggga | gaaggcgatc | cacctccgga | acggatcgct | ccatcgggtt | gccgcatgac | 840 |
| gggatcgagc | tgaactacga | cactcactct | aagcagtggg | acctagggat | gaaaacggtc | 900 |
| ggtaaacact | aaagcaatta | ccgttttcat | attttttta | tcgaaaacaa | aatcgaaaac | 960 |
| ggtaactccg | gaaatggaaa | cgatatcggt | atttcggaaa | catcgcaaac | gaaagttcgg | 1020 |
| tgcgaaaaat | acacaagtaa | cggtcgaaat | ctaaatacg | atcgataaac | atatcaaact | 1080 |
| tcataataca | acaagttga | caaaagatca | caaagaccac | aagttcacaa | ttcatgatat | 1140 |
| aacaagttta | aaatataaca | agttcacaag | gatcacaaat | ttataatata | aaaaaattac | 1200 |
| aaagatcaca | agttcacaat | ataacaagtt | cacagtataa | caagttcata | agatcacaa | 1260 |
| gttcacaaac | tcaaggttca | caattcacaa | tatccactcg | atttagctga | catggcatgc | 1320 |
| ttactcatga | aatattttt | cctcaaataa | agagttttc | acagactcgt | aggaaaaccc | 1380 |
| taaaatctag | tatgtggaaa | agacagactg | tcggctctat | cattatatat | tactaataca | 1440 |
| taacatgtgg | acagaaaatg | gtggattcgt | tcgagagacc | aaatcgttaa | tctcaactgc | 1500 |
| cttccaacac | catctatcaa | aaaaaatctt | aaggcgtcca | aaaatacaa | aaataagta | 1560 |
| atccttatct | agagacgtac | aggcgatgcg | aaaaaaatca | catgctgaat | aattccgaaa | 1620 |
| aaaattccgg | aaaattctga | gacataaatc | cggtaatttc | cgacaaaaac | cggtaaccga | 1680 |
| aggaaacagt | cggtaaaaca | ccacgccgat | tccgataccg | actctaatag | aaatttccga | 1740 |
| aaaccgattt | cgttttcgaa | aaatactgtt | accggtgaat | acaatcgaaa | aatttcgaaa | 1800 |
| tcggtttccg | gaataccaaa | aaattgtgaa | actgttttca | tcactagtgg | gaccgatgtg | 1860 |
| atggctccga | cggatggtgt | ggctaccagc | gtgatgagac | gcccaccggc | gggatgacat | 1920 |

```
tcgcatgttt ttgcaaacgc agcccgatca catgtgcaca atcgttagtg gcgcgtttta    1980
aaaaagacgt aactacgaaa aaaaatagcg acatgttttt agccagtgtc acaaacgtca    2040
tcttcgagca cttttgatgt agtgtataca atctactagt caaattaaaa agaataacat    2100
acacgaaatg gttcataact tttatatagt taaacaataa taaatttata aaaatcccta    2160
aacaaacaac aaaacgttgg acacctcccc gctatttatg gcggatggcc cgcccaattg    2220
acgtaatttc cacatcgaag tcgaagaacc ggtcgctgtg accagtcacc caacctccg     2280 tcacttgtct ctcacgcgcg cgcaacatcg ccgagaaaac cagaacagac ctccggattg    2340
gtctctcccc cgttcacacg agcacattgc gatggctcct ctgctcctgc tgctcctctt    2400
ccccgtccag ctcccccctcg cagtagccga cgccgtctcc ggtccctgca ccagagccac    2460
atgcgccggc caggacgtcc attacccgtt ctggctcaag tcctccgcgc ccgactgcgt    2520
ctatcccggt gtcggccttg tggcccttgt ctgcgagggc aactcgacgc tgatcctccc    2580
cttcaagtcc cacagatacg tagtgctcag catcgactac aagacgcgta ccgtgctggt    2640
ctccgacgcc gacatcgtcc acgagtacga cgcggccggc tgcccgcgcg tccgcgtgaa    2700
cctcaccatc gacaccgcct ggctgcggcc cacggcctcc gactccaaca tcaccttcct    2760
ctacaactgc aagaagaaca tcaccctgcc ctccgccgtg gaactgagcg ggtgccagca    2820
gcagcagcaa caagacggca gcaggtcgta ttcgtacgtg ctgccggacg gcggggtcac    2880
gggcgctgag gcgcaccagt acgggtgcga ggacttggtg gtgcgccgg tgctggacgt     2940 ccacaggagg gcgatcttga gggcgcctgg cggcccgact ctggagaacg ggtcgctccg    3000
tcggttgctg cagggcgggt tcgagctgaa ctacgacact cactccgagc agtgcgaccg    3060
atgcgaggcc tccggcgggt ggtgtggcta ccagcgcgac gagacgcccg ccggctggat    3120
gacgttcgcc tgcttctgcg acggcgggcc gacgaccacg gcccgatgcg gtgccggtat    3180 gtctttttt tttcttcgaa caaggtgtgg catgtgttct accgtttcaa ctagtaaatg     3240
attacattga gctaggcagc tagccacaca ttttcttgaa tgattttctt tgatgaacct    3300
gctgtttgct tttatgacgt gaacaacggg gcctgcaagc tgccacatac ctagggagac    3360
tagttcgtga ccttctttac acgtcttctc tactcgccac tgggagttga cgccgctcgg    3420
tcgtcccact ttgtgacgtt caaccagagt ctagagatgt aattctctgc gaatacagga    3480
ctagttggag ctaacaacgc agcttgacga gggtgaaccc agctccacct cgtctaccac    3540
gtcttctcct cgccatggct gctcacctac cacgcctccc cgtcctcctc ctcgtcctcc    3600
tcgctgctca tgtcgtctcc acctccgccc atgccgagcc tcctcttccg agcccttaca    3660
gcacctccgc ccatggcgag cctcctcttc cgagcactta caacgtctcc atgtgctcgg    3720
aatcgttctg gtgcggcggc gtcgaaatcc gctacccgtt ctatcttgcc aacgcaaccg    3780
ccgactacag cgggagctac tactcctgcg gctacaccga cttgagcgtt tcctgcaaac    3840
tcgaggtcga ggggccgacg acgacatgga cccctaccat ccgtctcggc ggcgacaact    3900
acaccgtcaa gaacatcttg tacgactatc ataccatctc actggcggac agcgatgtgc    3960
tcggaggcgg cgagtgcccc gtcgtccacc acaacgtcag cttcgacgag acgtggctgc    4020 acaacccag cgccttcgac aacctcacct tcttcttcgg atgccactgg gggccacgcg    4080
atacactgcc tgaatttgcc ggcaacaaca tcagctgcgc cgggttcagt actccagcta    4140
tcagcggtgg aggctccttc gtgttcaagc ctgaagatct tgacgaacat gcggagcagg    4200
agttggcttc acactgcgac gaggttttct ccgtgccagt gagaagcgag gctctgcagc    4260
```

-continued

```
aggcgatcgt cagcaacctc agcctcgggg acgggtacgg cgagctgctt aggcagggga    4320
tcgagttgga atggaaacgg acatcggagg atcagtgtgg ccagtgcgag gaatcgggct    4380
ccggcggacg gtgcgcctac agccagaaga gagaattcct tggctgcttg tgcagcggag    4440
ggaaggcgga caacccgttc tgcaaaccat caagtaaagt cctgaaccga gcctccctta    4500 ttttttttc attttttgca atccaccaga gagcacgcat cggttgcgtc agtatcttgc     4560
aacctcgtag ctagccccgc agtgtcccct gtgtgcgagt accgcgctgc tccagcttgc    4620
ctcctgctaa cgcctaacgg tgaatgcttc atgcttgaca tgatctagct agtctacact    4680
ttgcttgggg tttgcctggg agctggaaat tctggctcct gtttgcatca ctcgacaagg    4740
acgctttcag acttgcgact ctcgttctgc ttttgcacca aatccgtgtt tttttcattt    4800
cgtgatcgag attaatctag cttagagatg acaatgggta tccgaaactc gaaacttgat    4860
ggatttttac tccattaggg tataggtttg aatcaatttt catatttatg gatttgttaa    4920
taggcataaa tatatatcca acaggtttat agatacgagt ttgtttctac agtactcaaa    4980
tccgtgaaca catgaggttt ttaaacccga ccaaacctag tgcatattgt cattttattt    5040
tataaacgaa caacaaaatt gttatctcta tttacttcct atttttttatc gattggtgaa    5100 tgtataagta gttggtgaga atgtttcttg cttgctatta tagtttttact agcgttatat    5160 atgttgtggg tggataactt agtgcaatgt cacttgatta taaacttat tatttgtatt    5220 cattctctct actaataatt tttataccaa atcatgaact cggtgtttat tatataaatt    5280
ttggaccata atctcattaa tcatcacgat agttattgat tatgagaaaa aacaagcata    5340
ttggagataa aaccctcggc taacccgtta acccgatggg tacgggtttg aacaaaattt    5400
caaacctatt atgaatataa gttttttaac aagtatagat atatttcacg gatagagttt    5460
aagatgacaa aatccaacgg atttgtatcc attgccatct ctatccggcg gcccttaccc    5520
ggcggcccct accgtgctcc acgagcagag gtcgtatcgt ccctcttccc gtgtcgcctg    5580
cttcgcgttg ccgaacggag acgtttggta gcgttggccg gctctagcag tcgggtcaac    5640 tcttttttgtt gttgtttttcg atgttgttgg atttttgttc cgtataagcc atgttttagt    5700
aatttattta gtccagccga atccgaagac gtgtttgctg ggttggagac tttggagttg    5760
ctagtcatga tatgctttct actcggtttg atttcaaccc agttaggcta tatttaatac    5820 tctagtattta atttcaatat aaatggtttg aaacggatta aggtataaat tagtttaatt    5880
tatatattta attcctctca atccatatgt attgggctga atactgaggt agtgtttggt    5940
tgaagagcca tatagaacgg agccgttctg ttccagtttt gttgttgttt ggttataaag    6000
taactagaac ggaatgactt caattaagga atattcttct cagatccaga accattccgc    6060
tctaaaaaat caaccggacg gagccgctcc gtttccatcc tgctcttaca gtcacgctcc    6120
gttccgttca ctctgcaacc aaacaaaaaa cagagccgct ccgttccaaa ttaccaaaca    6180
cagaacagag cggcttcatt cctagaatta ggaatggaac gactctgttc tacttgactc    6240
ctcaaccaaa cactacctaa gtatccaaac aagcccttat ttaagatgca tttcctttac    6300
agttacacat gaccactatt gtgtgggggc aggctgaaca agcccttatt taagatgcat    6360
ttcctttaga gttacgcgtg gccactattg tgggggggg ggggggggggg caggccgatc    6420 ctactcgtca gtgctcattc gagagcaaag ataccgaagg agattagaga gactaaaaac    6480
tttttactat ttaaaattag ataataagac gatttaatcc cgttccatat ctttgctcta    6540
aacaaaccct caatgatcat atatctcgga agatccggcc ggctgttctt tatttatcaa    6600
gtgatgactg ctgaccgctt atagaatata tattttaaag caaaatttct tctacagcag    6660
```

```
taaaaggact agacgaaaca atgatgcatt tctctaacaa agaaagtag aattatcaag    6720 cggagagcca agaccaaaag ccttacttct atgggcgtca acaaatgata ccgcgacgga    6780
accatcccag caggtctata ctgtctgtca cgacccagcg agtaatcgtg tggctacgct    6840
attagactta ggattggatg aaatgctcgg tttattaatg agccagctcg tgagttaaga    6900
gtgtttggtt tgatgaatga agtaattcat cttcttttca ctccccactt ttttatttgg    6960
tttgtgtaat agaatgagtt gatccatcac caccacattc atcataagct aataattagt    7020
atatacatga gtagtgagtt gattccacca aaattgatga aatgaactta tgatgcatca    7080
tctcatgaag catagagtga ctccacaaac caaacacacc ataaatgatc tattacataa    7140
cgaaattata tgcatatcat ttatcagggc gacgacaggg ggcataggga ggcaatatcc    7200
ccctaatgct ccccaaattc tatagggatt gttagtttct tttagctaat tctcatgtaa    7260
acaatataaa aaatgcttct aacagtccct cctaattata atttggtcca ccctaatctt    7320
agatcctggc ttcgtccgtg ccatttacgt aacaattggt aaatatgtta tacatgtgtg    7380
gtatctatgg cctatgaatt gaactaatga ttgatgaatt gtgcttatgt gttaaattgg    7440
tctatgcgaa ataactatg ggttaaacgg atgaacatgt gtgttcattg ttaattcatg    7500
agtgatgaat tatgtataat ttggtgttat attgatgtgt tttgtgaaac tatgtgtata    7560
attattattt tctataatta aatttgtttg aaattaacta gaaattgatt attatatata    7620
tatatatata tatattgttt ttctgctcta gtctgcaagc taaacgagca agctcaagct    7680
cgtaaacgat ccgaaccgag ctgactttgt ggctcattaa cttaacaagc cgagttgggc    7740
caacttgtta gcttaacgag tcagctcgaa tacggacaag ttgagccgag ttggcatgat    7800
atccagccct aattaggctt gtaccagtgc aacatatccc tctcgccttt gtcacgtcca    7860
gacatgtcaa tgggccccga ttcccgcaag gaatttctct attaagggat gaggatggga    7920
aagtttctcc ccccacagaa aaattctctc ccgacggata gcggggaca acactccca    7980 tccccattcc ccgtggggac ctattagact tacatatggt gatgttttca tgtaaaagtt    8040
aatgataaaa ataaacaatt accttgttgt cggcgtttcg accccggagg gtccctggac    8100
cgacgagtaa attgtcgctg cgtgtcccag cccagatggg tcgacgcgag acggaacaca    8160
aggggaaaac aataagggga atcgcggcct cgtgttgtcc tgcgcccagg gcggatgcgc    8220
ttgcagtaag gggttacaag cgttcgcgag ggagagagag agagagcctg tgcgccagcc    8280
cgtcctcccg cgcggccacc ttctcgtacg agggccctgg acctttcttt tatagatgta    8340
aggagagggt ccaggtgtac aacagggagc gtagcaatgt gctaacgtgt ctagcagagg    8400
gaagccagaa tcctatgtac aggccgacgt gactgtcgaa gaggttttgg cgccctgttc    8460
atgtgatgtc gtggccgtcg gagagcgct tgagccctgt aggagcacag ctgtcggagc    8520
tgtcgggtcc ttgctgacgt ctcattgctt ccatagggag ctgagaaccg ccgtcgtcat    8580
ggagcacgcg gggtgccatc attacttgtt ttaccgggac gagccagatg ggacgctggt    8640
cttgttccca gtagcctgag gtagctagag gtagggtaat gatgtgccct cctgcgacgt    8700
ggtcggtccg agcccaaggt cgggcgaggc ggaggctcct ccgaggtcga ggctgagtcc    8760
gagacctggg gtcgggcgag gcggagaccg tcgtccgagg tcgaggttga gtccgagccc    8820
tggggtcggg cgaggcagag tccatcgtcc gaggtcgagg ttgagtccga gccctgggt    8880 cgggcgaggc ggagacagtc gtccgaggtc aaggttgagt ccgagccctg ggtcgggcg    8940 aggcggagtt cgtcttccga ggtcgaggtg gagtctgagc cctagggtca ggcgaggcgg    9000
```

| | |
|---|---|
| agaccgtcgt ccgaggtcga ggttgagtcc gagctctggg gtcgggcgag gtggagcttc | 9060 |
| ctatggcgcc tgaggccgga cttggcggct gtcagcctca acctgacggg tggcacagca | 9120 |
| gtcgaagcag cgcaggcggc gctgtttttc tatcaggtca gccagtggag gggcgaagtg | 9180 |
| actgcggtca cttcggctct gtcgactgaa gagcgtgcgt caggataagg tgtcaggcga | 9240 |
| tccttgcatt gaatgctcct gcgatccggt cggctggcga ggcgatcttg gctaaggttg | 9300 |
| cttctccgcg aagcctgcct gagctgggcc tcgggcgagt cggaggtgcg cccgttgctt | 9360 |
| gaggaggccc tcgggcgagg cgtgaacctg cctgggcctg ctgtttctgc ccgaggctgg | 9420 |
| gctcgggtga ggcgagatcg tgtcccttga gcggacagag ctttgtcctg tgttgcgccc | 9480 |
| atcaggcctt tgcagctttg tgctgatggt gtttaccagc cgagtttaag agtcttgggg | 9540 |
| gtacccctaa ttatggtccc cgacacttgt caagagatca cttttgtac aaatatattc | 9600 |
| attctgatgt acacatattt ttttcttaca tctaacaatg tgtataagtg agaatgtttt | 9660 |
| atattaataa caaatgaagt atgtcctaat tagacttctc acattgagca gcaacaaaac | 9720 |
| attttatgaa ttagtaacca ttttacttac taaaataatt actattgtat cttaatcatt | 9780 |
| ttgtgcaaaa taaagaatga accaaatttt gggtcaggtg tgggtcactc gcaggttgaa | 9840 |
| ataaaaccc gcacccacac tcgtgaaact ttgggtcaga tgcgggttac acccgcggat | 9900 |
| taaaatctct acccataccc acactcatca gatcgagtac ccaaagattt taagtttgcg | 9960 |
| ggttaaattg tcatccctcg acaccaacgt gttggaggat ttggaagttt cgcgatgcgt | 10020 |
| acttaccaag tgtttggttc tatgataaaa gtttagcctg tgtcgcatta gatgattgaa | 10080 |
| tgtctattat gagtattaaa tattgtctaa ttattaatca aattcacaa gtgaaggcta | 10140 |
| aacaacgaga caaatttatt aagcctaatt aatctatgat tagcaaatgt ttacagtagc | 10200 |
| accatcagt agcaccatct gagcgaatca tgaactaatt aggtttaata ggttcgtctt | 10260 |
| aacgtttaat tcttatctat gtaattagtt ttataagtaa attatattta atacttctaa | 10320 |
| ttagcctcca acattcgat ataacataga ctaaaattta gtcagtggtg ctgctgctgg | 10380 |
| ctcttttcct tcatccgacg taatgttttc ctcccaattt attgtgttgt tttgtttgtg | 10440 |
| ctttaaaact gacttgctct ctgcttgctg tatcaaagtc gtgatgtgtg cttagcttat | 10500 |
| tcccttcctt gctagctgcc cttagcatct atatagggat atttggttat agggactaaa | 10560 |
| gtttagttta gtccgtgtcc aattataaaa ctaattacat aactgaatac taaaagacga | 10620 |
| gaaaatttta ttaaacttaa ttaatttatg attagcaaat gtttattgta acatcacata | 10680 |
| agtaaaattat agactaattt tgtttaatag gttcatctta tcatttagtc ttcatctatg | 10740 |
| taattagttt tgtaattaga ctatatttac tatttctaac tagtatctaa acattaaatg | 10800 |
| tgacatggat taaaatttag ttagagcaac tccagtagtt ttctaaaaga cttcctaaat | 10860 |
| caataatttta ggtagttaac atgaaaacta ttctccaaca gttctctaaa taaactttct | 10920 |
| aaatttaaca acttgtcatc taacctcatt ttctctctac atttggcaac catttaataa | 10980 |
| ctccctaatc aaaaatgttg actgcattat atagttttg tgacttattt tttatgtgga | 11040 |
| taaatacaaa ataaaattac aacctatatt tagagaacta ttggagaacc cacttatttt | 11100 |
| tatttcaaaa gtcatttagc aacttcttaa atctgtaatt tagaaagcta aaatttacat | 11160 |
| aactattaga gttgctctta gtgacgttag gcttttagag ttgagttggt cgtagcttgg | 11220 |
| tttagttacg tgtttgttct cttgcgttta tttaggacct ctctataatg ttttatcacc | 11280 |
| ttcttaatac aaattaaaat acgcagctct cttgcgtatt ggaggcgtgt gttcctatat | 11340 |
| ttttttaggct caattatgaa tgaaattatt ctcagcgagc atataaccgt tttcgaggta | 11400 |

```
aaatgaacta aaagcatatg ggcctgcctg ttcgcataag tacaccctcc gtctaaaaaa   11460
gaataaaaat atcatttctt gatgagtcaa aaaagttcaa atttaagaaa atatatgtta   11520
cgacaccaat atttataatg tgtaataagt actgctgatt aattttaaaa taaaattttc   11580
ataataaacc tatttgaaga tacaagtatt ggtactattt ctaataaatc taatcaaact   11640
ggtgttatat cttttgtaac aaatttgtgc tttgtgtttc tggttgacgt gaatcagctt   11700
aatcttgctg aaatctaaca ttgtcttttg ttcgttggca tacaggatca aaaaggaaag   11760
aagcatctat tgttggtaag agcctatagt caatacccat gttcatttcg tctaaaagag   11820
cagaagaaaa gcatatgatg aattattgcc atgtcatgtt taaaatacag aattctcaaa   11880
aacaaaaaca aaaaaaactt ggaatccact aaccagtaac cactgatagc attgtagaaa   11940
atttcatcct cccctttgggc aatacactga tgagtttaca tgctgactag tggtgcattt   12000
gttctttgcc aattgaattt ttagaatgct ttgcagctga attcacttgt gattttttt   12060 tgtgatgcag gtgctgttgc cgttgcattc ctgtgtctag tcattctcac atgcttcttg   12120
gcttgtagac atggttcgct gcccttcaaa tcggagaaca accagggac aaggattgag   12180 tccttcctac agaagaacga gagtatacat ccgaaaagat acacctacac ggacgtgaaa   12240
agaatgacaa aatccttcgc tgtgaagcta ggccaaggtg ggttttggtgc tgtatacaaa   12300 ggcagcctcc acgatggccg acaggtagca gtcaagatgc tcaaggacac ccaaggtgac   12360
ggcgaggaat tcatgaacga ggtggctagc atcagcagga cttctcatgt caacgtcgtg   12420
acacttctag ggttttgctt gcaagggtcg aaaagagcac tgatctacga gtacatgccc   12480
aatggttcgc tcgaaaggta tgccttcacc ggtgacatga acagtgagaa tttgctaacc   12540
tgggaaaggc tatttgacat agcaattggc acggccagag ggctcgaata cctacaccgg   12600
ggatgcaaca ctcggatcgt gcattttgac atcaagccac acaacatcct gttagaccag   12660
gatttctgtc ctaagatctc tgactttgga ctggccaagc tatgtctgaa caaagagagc   12720
gctatctcca ttgttggcgc aagagggacg atagggtata tcgccccgga ggtctactca   12780
aagcaatttg gaacaatcag cagcaagtct gatgtctata gctatgggat gatggtcctt   12840
gagatggttg gagcaaggga aaggaataca agcgcaagcg cagatagtga ccatagcagc   12900
caatatttcc ctcagtggat ttatgaacat ttggacgact attgtgttgg tgcttccgag   12960
attaatggtg agaccacaga gctcgtgagg aagatgatag ttgtaggtct gtggtgcata   13020
caagtgattc cgactgatcg accaacaatg acgagagtcg tcgagatgtt ggaagggagc   13080
acgagtaatc tagagttgcc acccagagtt ctcttgagct gacaaagcgt agatattttt   13140
cctatcaaat gttgcttcca ggtcacacaa atgcaaaata tttgtggaga cgagtgccta   13200
tttacctcat acactgtatc tgtatgacaa aagtcccacg actcactgga cgcggaaatg   13260
tcgcttgact acgccaattt tctaaaaaga ttggcagcaa ttaatggagg cttatagcgg   13320
taactttggt tcgcattaat cctaggacta gggttgaata tcgatctaac tcgacgcggc   13380
ttggtcaagc tcaagctagc tccactcatc tcattaaaga atccagctag aaaatcaacc   13440
caagtcgttt acgaaacgag tttgagctga ctcgtttaga tcgtaaatca caacaaaaac   13500
aatatgcaca tatatacaat aatataatca atactagtta attctagact agtttaacac   13560
tagaaaagag taatgatact cataatttca catacaatgt caatccaaca ccaatttaac   13620
acacttcatc acttattagt tcatccaacc aagtgtaggc tttgatttac taacaaatgg   13680
ttgctcgttc gagctagcga gcttgcttgt taacaaactg agttgagatg ctagcttaac   13740
```

| | | |
|---|---|---|
| ttgtgacaaa attaaaacga gccgagtcga gtcaagttga gctcacgatg agtcgagcaa | 13800 |
| gctcacaatc cacgagtatt tttttagtcc tatctaagac taaagtttaa tcctaaaact | 13860 |
| aaattttaat ctctatttgt ttggttctat aaactaaaca ggttcagaaa acataaaata | 13920 |
| cattatagaa aacctgaaat acccttctat acttaaggca tcactaagag agagcaataa | 13980 |
| ataaagggta gagagaggaa taaatctgct ttattcccctt ttagctaccc tttgagagag | 14040 |
| taaacactaa aatgaaagga tccttgagga ttttgatgtt ttggatgaca actaacacaa | 14100 |
| ttaaaggtct aattaggatg ttaa | 14124 |

<210> SEQ ID NO 78
<211> LENGTH: 14471
<212> TYPE: DNA
<213> ORGANISM: Artificial
<220> FEATURE:
<223> OTHER INFORMATION: CTL1-TS45 DNA repair template

<400> SEQUENCE: 78

| | | |
|---|---|---|
| cggatagatg gcgtctagca tatcgatagg acatgacaag tggtacgatc cccgtcacat | 60 |
| gtccatggag gcatctgata tggacacggc gtgtatctat cgcggctgga acagaaccag | 120 |
| cgctcgcgcg gcggtcggcg ggagggacag accttggctc cgtgcgttca ggttgtgctt | 180 |
| gtgccgcgcg ccacgcacgg tctccgccgc ctgcagctga aatttttagat ttacatccta | 240 |
| tcccttttatt ttttttattt gtcacaattc agttcaaaaa tgaagaacgg aggtagtgca | 300 |
| tcctttgtga gactaatgaa aatcacatct ggatcctgaa atcggcgtcg taacctacaa | 360 |
| ggccacggac tggattagat agtggtccat ggtgcataat gaggatcgag gtctaacgcc | 420 |
| gacaccgtcg acgagtaaga ggtcgtggcc ggctgcccac acgtctgtgt gaacctcacc | 480 |
| atcgacacca ccgtccgcct gcggcctacg gcctcgaact ccaacatcac attcctctac | 540 |
| aactgcatga agaacattac cctaccctct gtcatggaac tgagtgggtt cccacaacaa | 600 |
| caagaagata gatgtaggtc gtacgtgctg tgggatggcg ggatcacggg tgctcaggcg | 660 |
| tacgggtatg ggtgcgagga cttggtggta gcgtcggagc tggatgtaca caaaaaggga | 720 |
| gaaggcgatc cacctccgga acggatcgct ccatcgggtt gccgcatgac gggatcgagc | 780 |
| tgaactacga cactcactct aagcagtggg acctagggat gaaaacggtc ggtaaacact | 840 |
| aaagcaatta ccgttttcat attttttttta tcgaaaacaa aatcgaaaac ggtaactccg | 900 |
| gaaatggaaa cgatatcggt atttcggaaa catcgcaaac gaaagttcgg tgcgaaaaat | 960 |
| acacaagtaa cggtcgaaat ctaaaatacg atcgataaac atatcaaact tcataataca | 1020 |
| acaaagttga caaaagatca caaagaccac aagttcacaa ttcatgatat aacaagttta | 1080 |
| aaatataaca agttcacaag gatcacaaat ttataatata aaaaaattac aaagatcaca | 1140 |
| agttcacaat ataacaagtt cacagtataa caagttcata aagatcacaa gttcacaaac | 1200 |
| tcaaggttca caattcacaa tatccactcg atttagctga catggcatgc ttactcatga | 1260 |
| aatatttttt cctcaaataa agagttttttc acagactcgt aggaaaaccc taaaatctag | 1320 |
| tatgtggaaa agacagactg tcggctctat cattatatat tactaataca taacatgtgg | 1380 |
| acagaaaatg gtggattcgt tcgagagacc aaatcgttaa tctcaactgc cttccaacac | 1440 |
| catctatcaa aaaaaatctt aaggcgtcca aaaaatacaa aaaataagta atccttatct | 1500 |
| agagacgtac aggcgatgcg aaaaaaatca catgctgaat aattccgaaa aaaattccgg | 1560 |
| aaaattctga gacataaatc cggtaatttc cgacaaaaac cggtaaccga aggaaacagt | 1620 |
| cggtaaaaca ccacgccgat tccgataccg actctaatag aaatttccga aaaccgattt | 1680 |

```
cgttttcgaa aaatactgtt accggtgaat acaatcgaaa aatttcgaaa tcggtttccg    1740
gaataccaaa aaattgtgaa actgttttca tcactagtgg gaccgatgtg atggctccga    1800
cggatggtgt ggctaccagc gtgatgagac gcccaccggc gggatgacat tcgcatgttt    1860
ttgcaaacgc agcccgatca catgtgcaca atcgttagtg gcgcgtttta aaaagacgt     1920
aactacgaaa aaaatagcg acatgttttt agccagtgtc acaaacgtca tcttcgagca    1980
cttttgatgt agtgtataca atctactagt caaattaaaa agaataacat acacgaaatg    2040
gttcataact tttatatagt taaacaataa taaatttata aaaatcccta acaaacaac     2100
aaaacgttgg acacctcccc gctatttatg gcggatggcc cgcccaattg acgtaatttc    2160
cacatcgaag tcgaagaacc ggtcgctgtg accagtcacc ccaacctccg tcacttgtct    2220
ctcacgcgcg cgcaacatcg ccgagaaaac cagaacagac ctccggattg gtctctcccc    2280
cgttcacacg agcacattgc gatggctcct ctgctcctgc tgctcctctt ccccgtccag    2340
ctcccccctcg cagtagccga cgccgtctcc ggtcccctgca ccagagccac atgcgccggc   2400
caggacgtcc attacccgtt ctggctcaag tcctccgcgc ccgactgcgt ctatcccggt    2460
gtcggccttg tggcccttgt ctgcgagggc aactcgacgc tgatcctccc cttcaagtcc    2520
cacagatacg tagtgctcag catcgactac aagacgcgta ccgtgctggt ctccgacgcc    2580
gacatcgtcc acgagtacga gcggccggc tgcccgcgcg tccgcgtgaa cctcaccatc      2640
gacaccgcct ggctgcggcc cacggcctcc gactccaaca tcaccttcct ctacaactgc    2700
aagaagaaca tcaccctgcc ctccgccgtg gaactgagcg ggtgccagca gcagcagcaa    2760
caagacggca gcaggtcgta ttcgtacgtg ctgccggacg gcggggtcac gggcgctgag    2820
gcgcaccagt acgggtgcga ggacttggtg gtggcgccgg tgctggacgt ccacaggagg    2880
gcgatcttga gggcgcctgg cggcccgact ctggagaacg ggtcgctccg tcggttgctg    2940
cagggcgggt tcgagctgaa ctacgacact cactccgagc agtgcgaccg atgcgaggcc    3000
tccggcgggt ggtgtggcta ccagcgcgac gagacgcccg ccggctggat gacgttcgcc    3060
tgcttctgcg acggcgggcc gacgaccacg gcccgatgcg gtgccggtat gtctttttt     3120
tttcttcgaa caaggtgtgg catgtgttct accgtttcaa ctagtaaatg attacattga    3180
gctaggcagc tagccacaca ttttcttgaa tgatttttctt tgatgaacct gctgtttgct   3240
tttatgacgt gaacaacggg gcctgcaagc tgccacatac ctaggagac tagttcgtga     3300
ccttctttac acgtcttctc tactcgccac tgggagttga cgccgctcgg tcgtcccact    3360
ttgtgacgtt caaccagagt ctagagatgt aattctctgc gaatacagga ctagttggag    3420
ctaacaacgc agcttgacga gggtgaaccc agctccacct cgtctaccac gtcttctcct    3480
cgccatggct gctcacctac cacgcctccc cgtcctcctc ctcgtcctcc tcgctgctca    3540
tgtcgtctcc acctccgccc atgccgagcc tcctcttccg agcccttaca gcacctccgc    3600
ccatggcgag cctcctcttc cgagcactta caacgtctcc atgtgctcgg aatcgttctg    3660
gtgcggcggc gtcgaaatcc gctacccgtt ctatcttgcc aacgcaaccg ccgactacag    3720
cgggagctac tactcctgcg gctacaccga cttgagcgtt tcctgcaaac tcgaggtcga    3780
ggggccgacg acgacatgga cccctaccat ccgtctcggc ggcgacaact acaccgtcaa    3840
gaacatcttg tacgactatc ataccatctc actggcggac agcgatgtgc tcggaggcgg    3900
cgagtgcccc gtcgtccacc acaacgtcag cttcgacgag acgtggctgc acaacccag     3960
cgccttcgac aacctcacct tcttcttcgg atgccactgg gggccacgcg atacactgcc    4020
```

```
tgaatttgcc ggcaacaaca tcagctgcgc cgggttcagt actccagcta tcagcggtgg    4080
aggctccttc gtgttcaagc ctgaagatct tgacgaacat gcggagcagg agttggcttc    4140
acactgcgac gaggttttct ccgtgccagt gagaagcgag gctctgcagc aggcgatcgt    4200
cagcaacctc agcctcgggg acgggtacgg cgagctgctt aggcagggga tcagttggga    4260
atggaaacgg acatcggagg atcagtgtgg ccagtgcgag gaatcgggct ccggcggacg    4320
gtgcgcctac agccagaaga gagaattcct tggctgcttg tgcagcggag ggaaggcggg    4380
caacccgttc tgcaaaccat caagtaaagt cctgaaccga gcctccctta ttttttttc    4440 attttttgca atccaccaga gagcacgcat cggttgcgtc agtatcttgc aacctcgtag    4500
ctagccccgc agtgtcccct gtgtgcgagt accgcgctgc tccagcttgc ctcctgctaa    4560
cgcctaacgg tgaatgcttc atgcttgaca tgatctagct agtctacact ttgcttgggg    4620
tttgcctggg agctggaaat tctggctcct gtttgcatca ctcgacaagg acgctttcag    4680
acttgcgact ctcgttctgc ttttgcacca aatccgtgtt tttttcattt cgtgatcgag    4740
attaatctag cttagagatg acaatgggta tccgaaactc gaaacttgat ggattttac    4800 tccattaggg tataggtttg aatcaatttt catatttatg gatttgttaa taggcataaa    4860
tatatatcca acaggtttat agatacgagt ttgtttctac agtactcaaa tccgtgaaca    4920
catgaggttt ttaaacccga ccaaacctag tgcatattgt cattttattt tataaacgaa    4980
caacaaaatt gttatctcta tttacttcct atttttatc gattggtgaa tgtataagta    5040
gttggtgaga atgtttcttg cttgctatta tagtttact agcgttatat atgttgtggg    5100
tggataactt agtgcaatgt cacttgatta tacaacttat tatttgtatt cattctctct    5160
actaataatt tttataccaa atcatgaact cggtgtttat tatataaatt ttggaccata    5220
atctcattaa tcatcacgat agttattgat tatgagaaaa acaagcata ttggagataa    5280 aaccctcggc taaccgtta acccgatggg tacgggtttg aacaaaattt caaacctatt    5340
atgaatataa gttttttaac aagtatagat atatttcacg gatagagttt aagatgacaa    5400
aatccaacgg atttgtatcc attgccatct ctatccggcg gcccttaccc ggcggccctt    5460
accgtgctcc acgagcagag gtcgtatcgt ccctcttccc gtgtcgcctg cttcgcgttg    5520
ccgaacggag acgtttggta gcgttggccg gctctagcag tcgggtcaac tcttttttgtt    5580 gttgttttcg atgttgttgg attttttgttc cgtataagcc atgttttagt aatttattta    5640
gtccagccga atccgaagac gtgtttgctg ggttggagac tttggagttg ctagtcatga    5700 tatgcttct actcggtttg atttcaaccc agttaggcta tatttaatac tctagtattt    5760
atttcaatat aaatggtttg aaacggatta aggtataaat tagtttaatt tatatattta    5820
attcctctca atccatatgt attgggctga atactgaggt agtgtttggt tgaagagcca    5880
tatagaacgg agccgttctg ttccagtttt gttgttgttt ggttataaag taactagaac    5940
ggaatgactt caattaagga atattcttct cagatccaga accattccgc tctaaaaaat    6000
caaccggacg gagccgctcc gtttccatcc tgctcttaca gtcacgctcc gttccgttca    6060
ctctgcaacc aaacaaaaaa cagagccgct ccgttccaaa ttaccaaaca cagaacagag    6120
cggcttcatt cctagaatta ggaatggaac gactctgttc tacttgactc ctcaaccaaa    6180
cactacctaa gtatccaaac aagcccttat ttaagatgca tttcctttac agttacacat    6240
gaccactatt gtgtgggggc aggctgaaca agcccttatt taagatgcat ttcctttaga    6300
gttacacgtg gccactattg tggggggggg ggggggggg caggccgatc ctactcgtca    6360
gtgctcattc gagagcaaag ataccgaagg agattagaga gactaaaaac tttttactat    6420
```

```
ttaaaattag ataataagac gatttaatcc cgttccatat ctttgctcta aacaaaccct    6480
caatgatcat atatctcgga agatccggcc ggctgttctt tatttatcaa gtgatgactg    6540
ctgaccgctt atagaatata tattttaaag caaaatttct tctacagcag taaaaggact    6600
agacgaaaca atgatgcatt tctctaacaa agaaagtag aattatcaag cggagagcca     6660
agaccaaaag ccttacttct atgggcgtca acaaatgata ccgcgacgga accatcccag    6720
caggtctata ctgtctgtca cgacccagcg agtaatcgtg tggctacgct attagactta    6780
ggattggatg aaatgctcgg tttattaatg agccagctcg tgagttaaga gtgtttggtt    6840
tgatgaatga agtaattcat cttcttttca ctccccactt ttttatttgg tttgtgtaat    6900
agaatgagtt gatccatcac caccacattc atcataagct aataattagt atatacatga    6960
gtagtgagtt gattccacca aaattgatga aatgaactta tgatgcatca tctcatgaag    7020
catagagtga ctccacaaac caaacacacc ataaatgatc tattacataa cgaaattata    7080
tgcatatcat ttatcagggc gacgacaggg ggcataggga ggcaatatcc ccctaatgct    7140
ccccaaattc tatagggatt gttagtttct tttagctaat tctcatgtaa acaatataaa    7200
aaatgcttct aacagtccct cctaattata atttggtcca ccctaatctt agatcctggc    7260
ttcgtccgtg ccatttacgt aacaattggt aaatatgtta tacatgtgtg gtatctatgg    7320
cctatgaatt gaactaatga ttatgaatt gtgcttatgt gttaaattgg tctatgcgaa     7380
tataactatg ggttaaacgg atgaacatgt gtgttcattg ttaattcatg agtgatgaat    7440
tatgtataat ttggtgttat attgatgtgt tttgtgaaac tatgtgtata attattattt    7500
tctataatta aatttgtttg aaattaacta gaaattgatt attatatata tatatatata    7560
tatattgttt ttctgctcta gtctgcaagc taaacgagca agctcaagct cgtaaacgat    7620
ccgaaccgag ctgactttgt ggctcattaa cttaacaagc cgagttgggc caacttgtta    7680
gcttaacgag tcagctcgaa tacgacaag ttgagccgag ttggcatgat atccagccct     7740
aattaggctt gtaccagtgc aacatatccc tctcgccttt gtcacgtcca gacatgtcaa    7800
tgggccccga ttcccgcaag gaatttctct attaagggat gaggatggga aagtttctcc    7860
ccccacagaa aaattctctc ccgacggata agcgggaca acactcccca tccccattcc     7920
ccgtggggac ctattagact tacatatggt gatgttttca tgtaaaagtt aatgataaaa    7980
ataaacaatt accttgttgt cggcgtttcg acccccgagg gtccctggac cgacgagtaa    8040
attgtcgctg cgtgtcccag cccagatggg tcgacgcgag acggaacaca agggggaaac    8100
aataagggga atcgcggcct cgtgttgtcc tgcgcccagg gcggatgcgc ttgcagtaag    8160
gggttacaag cgttcgcgag ggagagagag agagagcctg tgcgccagcc cgtcctcccg    8220
cgcggccacc ttctcgtacg agggccctgg acctttcttt tatagatgta aggagagggt    8280
ccaggtgtac aacagggagc gtagcaatgt gctaacgtgt ctagcagagg gaagccagaa    8340
tcctatgtac aggccgacgt gactgtcgaa gaggttttgg cgccctgttc atgtgatgtc    8400
gtggccgtcg gaggagcgct tgagccctgt aggagcacag ctgtcggagc tgtcgggtcc    8460
ttgctgacgt ctcattgctt ccataggag ctgagaaccg ccgtcgtcat ggagcacgcg     8520
gggtgccatc attacttgtt ttaccgggac gagccagatg gacgctggt cttgttccca     8580 gtagcctgag gtagctagag gtagggtaat gatgtgccct cctgcgacgt ggtcggtccg    8640
agcccaaggt cgggcgaggc ggaggctcct ccgaggtcga ggctgagtcc gagacctggg    8700
gtcgggcgag gcggagaccg tcgtccgagg tcgaggttga gtccgagccc tggggtcggg    8760
```

```
cgaggcagag tccatcgtcc gaggtcgagg ttgagtccga gccctggggt cgggcgaggc    8820
ggagacagtc gtccgaggtc aaggttgagt ccgagccctg gggtcgggcg aggcggagtt    8880
cgtcttccga ggtcgaggtg gagtctgagc cctagggtca ggcgaggcgg agaccgtcgt    8940
ccgaggtcga ggttgagtcc gagctctggg gtcgggcgag gtggagcttc ctatggcgcc    9000
tgaggccgga cttggcggct gtcagcctca acctgacggg tggcacagca gtcgaagcag    9060
cgcaggcggc gctgtttttc tatcaggtca gccagtggag gggcgaagtg actgcggtca    9120
cttcggctct gtcgactgaa gagcgtgcgt caggataagg tgtcaggcga tccttgcatt    9180
gaatgctcct gcgatccggt cggctggcga ggcgatcttg gctaaggttg cttctccgcg    9240
aagcctgcct gagctgggcc tcgggcgagt cggaggtgcg cccgttgctt gaggaggccc    9300
tcgggcgagg cgtgaacctg cctgggcctg ctgtttctgc ccgaggctgg gctcgggtga    9360
ggcgagatcg tgtcccttga gcggacagag ctttgtcctg tgttgcgccc atcaggcctt    9420
tgcagctttg tgctgatggt gtttaccagc cgagtttaag agtcttgggg gtaccccttaa   9480 ttatggtccc cgacacttgt caagagatca cttttttgtac aaatatattc attctgatgt    9540
acacatattt ttttcttaca tctaacaatg tgtataagtg agaatgtttt atattaataa    9600
caaatgaagt atgtcctaat tagacttctc acattgagca gcaacaaaac attttatgaa    9660
ttagtaacca ttttacttac taaaataatt actattgtat cttaatcatt ttgtgcaaaa    9720
taaagaatga accaaatttt gggtcaggtg tgggtcactc gcaggttgaa ataaaaaccc    9780
gcacccacac tcgtgaaact ttgggtcaga tgcgggttac accgcggat taaaatctct    9840 acccataccc acactcatca gatcgagtac ccaaagattt taagtttgcg ggttaaattg    9900
tcatccctcg acaccaacgt gttggaggat ttggaagttt cgcgatgcgt acttaccaag    9960
tgtttggttc tatgataaaa gtttagcctg tgtcgcatta gatgattgaa tgtctattat    10020
gagtattaaa tattgtctaa ttattaatca aattacacaa gtgaaggcta acaacgaga    10080 caaatttatt aagcctaatt aatctatgat tagcaaatgt ttacagtagc accatctagt    10140
agcaccatct gagcgaatca tgaactaatt aggtttaata ggttcgtctt aacgtttaat    10200
tcttatctat gtaattagtt ttataagtaa attatatttta atacttctaa ttagcctcca    10260
aacattcgat ataacataga ctaaaattta gtcagtggtg ctgctgctgg ctcttttcct    10320
tcatccgacg taatgttttc ctcccaattt attgtgttgt tttgtttgtg ctttaaaact    10380
gacttgctct ctgcttgctg tatcaaagtc gtgatgtgtg cttagcttat tcccttcctt    10440
gctagctgcc cttagcatct atatagggat atttggttat agggactaaa gtttagttta    10500
gtccgtgtcc aattataaaa ctaattacat aactgaatac taaaagacga gaaaattta    10560 ttaaacttaa ttaatttatg attagcaaat gtttattgta acatcacata agtaaaattat   10620 agactaattt tgtttaatag gttcatctta tcatttagtc ttcatctatg taattagttt    10680
tgtaattaga ctatatttac tatttctaac tagtatctaa acattaaatg tgacatggat    10740
taaaatttag ttagagcaac tccagtagtt ttctaaaaga cttcctaaat caataattta    10800
ggtagttaac atgaaaacta ttctccaaca gttctctaaa taaactttct aaatttaaca    10860
acttgtcatc taacctcatt ttctctctac atttggcaac catttaataa ctccctaatc    10920
aaaaatgttg actgcattat atagttttg tgacttattt tttatgtgga taaatacaaa     10980
ataaaattac aacctatatt tagagaacta ttggagaacc cacttatttt tatttcaaaa    11040
gtcatttagc aacttcttaa atctgtaatt tagaaagcta aaatttacat aactattaga    11100
gttgctctta gtgacgttag gcttttagag ttgagttggt cgtagcttgg tttagttacg    11160
```

```
tgtttgttct cttgcgttta tttaggacct ctctataatg tttatcacc ttcttaatac   11220 aaattaaaat acgcagctct cttgcgtatt ggaggcgtgt gttcctatat tttttaggct   11280
caattatgaa tgaaattatt ctcagcgagc atataaccgt tttcgaggta aaatgaacta   11340
aaagcatatg ggcctgcctg ttcgcataag tacaccctcc gtctaaaaaa gaataaaaat   11400
atcatttctt gatgagtcaa aaaagttcaa atttaagaaa atatatgtta cgacaccaat   11460
atttataatg tgtaataagt actgctgatt aattttaaaa taaaattttc ataataaacc   11520
tatttgaaga tacaagtatt ggtactattt ctaataaatc taatcaaact ggtgttatat   11580
cttttgtaac aaatttgtgc tttgtgtttc tggttgacgt gaatcagctt aatcttgctg   11640
aaatctaaca ttgtcttttg ttcgttggca tacaggatca aaaggaaag aagcatctat    11700 tgttggtaag agcctatagt caatacccat gttcatttcg tctaaaagag cagaagaaaa   11760
gcatatgatg aattattgcc atgtcatgtt taaaatacag aattctcaaa aacaaaaaca   11820
aaaaaaactt ggaatccact aaccagtaac cactgatagc attgtagaaa atttcatcct   11880
ccctttgggc aatacactga tgagtttaca tgctgactag tggtgcattt gttctttgcc   11940
aattgaattt ttagaatgct ttgcagctga attcacttgt gattttttt tgtgatgcag    12000 gtgctgttgc cgttgcattc ctgtgtctag tcattctcac atgcttcttg gcttgtagac   12060
atggttcgct gcccttcaaa tcggagaaca aaccagggac aaggattgag tccttcctac   12120
agaagaacga gagtatacat ccgaaaagat acacctacac ggacgtgaaa agaatgacaa   12180
aatccttcgc tgtgaagcta ggccaaggtg ggtttggtgc tgtatacaaa ggcagcctcc   12240
acgatggccg acaggtagca gtcaagatgc tcaaggacac ccaaggtgac ggcgaggaat   12300
tcatgaacga ggtggctagc atcagcagga cttctcatgt caacgtcgtg acacttctag   12360
ggttttgctt gcaagggtcg aaaagagcac tgatctacga gtacatgccc aatggttcgc   12420
tcgaaaggta tgccttcacc ggtgacatga acagtgagaa tttgctaacc tgggaaaggc   12480
tatttgacat agcaattggc acggccagag ggctcgaata cctacaccgg ggatgcaaca   12540
ctcggatcgt gcattttgac atcaagccac acaacatcct gttagaccag gatttctgtc   12600
ctaagatctc tgactttgga ctggccaagc tatgtctgaa caaagagagc gctatctcca   12660
ttgttggcgc aagagggacg atagggtata tcgccccgga ggtctactca aagcaatttg   12720
gaacaatcag cagcaagtct gatgtctata gctatgggat gatggtcctt gagatggttg   12780
gagcaaggga aaggaataca agcgcaagcg cagatagtga ccatagcagc caatatttcc   12840
ctcagtggat ttatgaacat ttggacgact attgtgttgg tgcttccgag attaatggtg   12900
agaccacaga gctcgtgagg aagatgatag ttgtaggtct gtggtgcata caagtgattc   12960
cgactgatcg accaacaatg acgagagtcg tcgagatgtt ggaagggagc acgagtaatc   13020
tagagttgcc acccagagtt ctcttgagct gacaaagcgt agatattttt cctatcaaat   13080
gttgcttcca ggtcacacaa atgcaaaata tttgtggaga cgagtgccta tttacctcat   13140
acactgtatc tgtatgacaa aagtcccacg actcactgga cgcggaaatg tcgcttgact   13200
acgccaattt tctaaaaaga ttggcagcaa ttaatggagg cttatagcgg taactttggt   13260
tcgcattaat cctaggacta gggttgaata tcgatctaac tcgacgcggc ttggtcaagc   13320
tcaagctagc tccactcatc tcattaaaga atccagctag aaaatcaacc caagtcgttt   13380
acgaaacgag tttgagctga ctcgtttaga tcgtaaatca caacaaaaac aatatgcaca   13440
tatatacaat aatataatca atactagtta attctagact agtttaacac tagaaaagag   13500
```

| | | | | | |
|---|---|---|---|---|---|
| taatgatact | cataatttca | catacaatgt | caatccaaca | ccaatttaac | acacttcatc | 13560 |
| acttattagt | tcatccaacc | aagtgtaggc | tttgatttac | taacaaatgg | ttgctcgttc | 13620 |
| gagctagcga | gcttgcttgt | taacaaactg | agttgagatg | ctagcttaac | ttgtgacaaa | 13680 |
| attaaaacga | gccgagtcga | gtcaagttga | gctcacgatg | agtcgagcaa | gctcacaatc | 13740 |
| cacgagtatt | ttttagtcc | tatctaagac | taaagtttaa | tcctaaaact | aaattttaat | 13800 |
| ctctatttgt | ttggttctat | aaactaaaca | ggttcagaaa | acataaaata | cattatagaa | 13860 |
| aacctgaaat | acccttctat | acttaaggca | tcactaagag | agagcaataa | ataaagggta | 13920 |
| gagagaggaa | taaatctgct | ttattcccctt | ttagctaccc | tttgagagag | taaacactaa | 13980 |
| aatgaaagga | tccttgagga | ttttgatgtt | ttggatgaca | actaacacaa | ttaaaggtct | 14040 |
| aattaggatg | ttaaatgagg | agcaatcatt | gttcaagaca | tgatgcaaag | ctagaaaact | 14100 |
| ttgattgtgg | ccgtcctaat | tgtgaagttt | aggccggggg | gaacttcatg | aaccctatcg | 14160 |
| aagcttaatt | agttctttttt | tgttgttagc | catgtttgta | ttgtagttta | ggtgaacaac | 14220 |
| atgacgccgc | acccgcgatc | tcagggctcg | tccccacaca | ggagggcacg | tcgtcgtctt | 14280 |
| cgccgccgag | catcagagat | tcagagcacg | tacacgcaca | tctcaagcaa | acggagtagt | 14340 |
| acgtcctact | cctacgtaca | tacctagccg | acgaccttta | tgtgcacacc | accactgctc | 14400 |
| tgctgcccgg | cctctccgtc | gtccgttcat | caccagctgg | tctggtcctt | caatttccat | 14460 |
| gcgtcggtcc | g | | | | | 14471 |

<210> SEQ ID NO 79
<211> LENGTH: 7154
<212> TYPE: DNA
<213> ORGANISM: Artificial
<220> FEATURE:
<223> OTHER INFORMATION: CTL1-TS10 DNA repair template

<400> SEQUENCE: 79

| | | | | | |
|---|---|---|---|---|---|
| aaatagtaaa | cgggagggga | ggtcgctagt | agtaaacgct | aggtagctag | gataatccgt | 60 |
| ctcgtgttgg | acggaaggtt | ttggacgcat | ctgcgtgcac | agcccgctga | tacagatctg | 120 |
| atcgactagc | tagctagatg | ccgaggcccc | agagcaaggc | ccggatactc | ctgcacagtc | 180 |
| cctgagattt | cagcacagca | ggtgctgttg | catcaatata | taaatccctg | ctttattaat | 240 |
| ttaatctctg | tgcatgtatc | catacatcgt | cagcggctca | gcgctatcac | actgcagtgc | 300 |
| acgcagctag | ttgagcgcct | gggtcagtat | atatatagct | agtagggaca | aaggggggca | 360 |
| ctgtacgttg | gtttggtttg | gcacgcacgc | gatcgagagt | ggtggaatgg | actgcagatc | 420 |
| atcgatcgct | gcactgtacg | cacgcgcacc | ggactgcatt | tgcatgcccc | tgaaggagga | 480 |
| aaggggaagg | aaagaaaaga | aataggagaa | agaagaagaa | gcagagaaat | acgtcacagt | 540 |
| ccaagaagag | tgagccgccc | tagctagctt | caaccctgac | gaacccggca | gccacacttc | 600 |
| cggccatgta | tgcatgcatg | catggcttag | cttcagatgt | ccaatcgaat | ccatcaagac | 660 |
| ctggccggtt | ttccatggcc | gcctcgcctt | cgctagttaa | gggccaagta | cttgctgtcc | 720 |
| ctgtgatatt | gaatccaatt | caattctata | acctccaaaa | tcgatatcct | aacatagcat | 780 |
| gatagttttt | ttgagaggtg | tgatttaaca | tattagtga | attttctttt | tttaatacgc | 840 |
| tatgttctag | atgtctgacg | atgaatggag | ccgctctgca | tataccaaac | gctatctaag | 900 |
| tttgtgaaca | aatgactaaa | ttatccacac | gaccacaatt | gggcgctgat | aagatccaca | 960 |
| cttgctggtt | ttaattcatc | cggtctttat | caactgtcac | atcagttata | gatcattatc | 1020 |
| aactttatc | tacaattgat | gttgtaatac | acggtcactt | aagaccatgt | ttaggtacaa | 1080 |

```
tgtctctcaa aactatgatt ttacttatga tgacaatacc gtagttttga atagctctaa    1140
aaatatcatg gttctaaaaa tattgtttgg attcaacatt ataaatcgtg gtattaagca    1200
aaagctagtc atgttataaa aactttaggt tgaagtagag ttttcaatac taaaaaaata    1260
tcatggtatt tagaatatca tgattttaaa aatatagttc ttacgaatgc aaccaaacac    1320
cttatgatat aaaataatat ggtattgcct acaaactaca aaaataaatc actcccaagc    1380
attacataaa catcattttt ataaactttt tagtaaaata aagcgcaatg ttttttattaa    1440 atagaaattt atacaagtat atataattaa gcaaataaaa actacgttat tcataaaaag    1500
ctaataaaaa gtaaaagta aaaactatat aattcataaa aaaatcgtta tctttctctt    1560
ccatcttatt atctatttt agttgtttg tcaaatttaa ggctattta tgggttcttt    1620 ttatctttgt acatgtcgtg agccaataac ttattgaatt ggtcaatcaa tttaggttga    1680
gttttacttt taactaacct agtatagttt gttcaacacc ttttttttcat aatcggggac    1740 tcattccact tgttgttgac ccatttttc ttctactgag ttcttgccct tttgcaatca    1800
ataggacgtg gtgagcccat attttaggt gttatggatt tataatcacc gttcaaattt    1860
gaatgaatat tttgttttta ttattgaagt cttcgtcaat cgttatcatg cctcgcatac    1920
cacttagacc gacgaagtcc aacatatttc tcccccgacg aggagagatt cttcgtaaaa    1980
ttgctactgg tattactggt attgaataga agataagggt gcgtttggtt gcatgcatct    2040
acgcgtgctt gcatcacgga atgcgggttg gtgctgtttg gttgctataa gctagactat    2100
acatatgcaa gttttgtgtt tggttggctg catgcagatt tcgatccaaa ctcgcacgat    2160
ccacacagca ccctgggcca ggcttaccag atacgagtag attggtcgca tctttggagc    2220
caggctttag cggtccgcgg tcctggctga cacggccaga ttgccgagag aaaccaacca    2280
aacagggtct aaatgtccaa tcgtttgact gctactggat gaaaaagaa tgtcacaact    2340 ttaaaatgtg tatttattta tactcctaca catgaaataa ctactatact cagatttctt    2400
ttacattcag attttttctc agccactgaa acataccagc cctttactac caaaaacagg    2460
aactccacgg tccaatgatt atgtgagtcg gaggagaggg gaggaagaat cgcctgtgaa    2520
ggagggaggg agggagggac gtccgatccg aagatggaag gagctgggga ggggagcgcc    2580
ttgacgggga tgatgggtcc tgcgctcgac aagctcgcta gcctcgttga caagtacacc    2640
gagctcagaa acgtgaggaa gaagatggag cagctgagga aggagctgat tgcgatcaac    2700
ctcgcgcttg agaagcacgc ggccatggag aacccagacg cgcaggcgaa ggcgtgggcg    2760
gcggagatgc gcgagctggc ctacgacatg gaggacagca tcgatctctt cacccaccac    2820
gtcgaccacg aaccggccga caccgccacc accggcgtca agaggttctt cctccggatc    2880
atccggaagc ttaagaaact ccactaccgc cacaggtttg ttcaggagat caaacaactc    2940
cacgaccttg ccaacgaatc gtaccggcgt aggaagaggt acaggattga ggagggcggt    3000
tcaagcctct cgcacgcgga gatcgatcct cggttagagg cgctctacgt ggaggtggag    3060
aaactcgtgg gcatccaggg cccaagccag gagatcattg gacagctcgt cggcgagaac    3120
gcagcggagc gacggagggt tgtcgccgtt gttggatctg gaggttcagg caagaccaca    3180
cttgccaaac aggtgtacga gaaaatcagg tgccaattct cttgtgcagc ctttgtgtct    3240
gtgtcgcaaa agcccaacat gaatagcctc ctgtgggagt tgctatctca aatcggggac    3300
catggtggag atttaggaat gatggcagta ggatattgca gtgacaaaca actgatcgac    3360
agactaagat cacatcttga aaagcagagg ttagtttacc ttttcattcc ggttagctta    3420
```

```
attcggtaca ccaactagag atttgtgatt tgctattaat tacaccaaat ttctcctaca   3480
caacaataac tggtttagca tgatggcgat ccaaagtcaa aactatcttc tactactagt   3540
gtatgccata ctcatataga tatttctttt tcataaactc tcgtagcatt tttacatgca   3600
ttcatattcc tattgccttt atacagaact gatttttcac tgcttcacaa tctgctctta   3660
ggtatctcgt tgtgatagat gatgtttgga caaactcagc gtgggagacc atacaatgtg   3720
cgctccctaa aaatgcccat gcaagtaaaa taattctgac aacacgaatc aacagtgtag   3780
gccagttctc ctgcactcca gatgagggtt ttatctatca gatgaagcct ctttgcagaa   3840
acgattctga aaatctgttt ctgaaaagga cactatgtga taaagataag tttcctgctc   3900
agctggaggg gattaaaaac gagataatcg agaaatgcga tggtttgcca ctggctattg   3960
ttactctagc tagcatgtta gctactaaac agagaacaag ggaagaatgg gagagggcac   4020
ttgattcaat ccattctatg cacaagaaag atagtggcct ggaagtgatg gacaagatac   4080
tgtctctgag ttacagggat ctacctcaca acatgagaaa ttgcttgctg tatctcagta   4140
catttccaga ggaccacacg atttacaaag atgccctagt atggagatgg atggctgaag   4200
ggtttatcgc tgaaacacaa ggctttactt tggagcaggt tgccgagggc tacttctacg   4260
agtttgtgaa caggagtttg gttcagccca taaccttgcg ttcaagatat gaaatgcgtg   4320
gagaaggagg ttgccgagtc catgacattg tactgaactt cctcatctct cgtgcagctg   4380
aagagaactt tttaactacg ctgtatggcg cccagggggt tccatcttca gaccgaagga   4440
ttcgccggct ctctgtctgg gacagtccag aacacgcact ggcagtctct agagcgacca   4500
tgaatctgtc ccatctccgg tcagttagaa tatgcaacgt tggagactgg cccgtgcctg   4560
ctgttctaga cttacctgtc cttcgagtgt tagatctaga gggatgccgt gatctgagga   4620
tcgacgaacc tgactgcatt ctaagcttgt ttcatctgag atacctgggt ttccgcagcg   4680
caagtggtgt cgtgctaccg gctcaaatcg gaaatttaca ccatctgcag accatcgatt   4740
taagcgggac tggagtgaca cagctgccag aaagcattgt ccagctcaag cgactgatgc   4800
atcttgttgg gcaacggctc atcatgccag acgggtttgg tagcatggaa tcccttgagg   4860
agttaggtac tatcgactgc tgcaagtgcc ccgtcagttt tggggaagac ctagcacttc   4920
tgagcaggct gagggtgctc cgagtggctt tcatcggggt cgaaacaagt gacatggaaa   4980
ccagaaggaa atctttgatg tcatccctct gcaaactcgg aggagacaac cttcggcgtg   5040
tcactattat cgacctcgct ggcggtggag attgctttgt ggagtcgtgg caccctcctc   5100
ctcgtctcct ccagaagttc atccatatca gtcagcaaca gcacttctcc aggttttccag   5160 aatggatcag ttcctgccta tgtgatctca cccacctgga tataaaggcc gaaaagatgg   5220
aaagggagca tctaagtgtt cttgaacacc tgcccgccat ccgttgccta tacctttttcg   5280 tgaagcgagt ctccgaagac gggctcgcca tcagccacgg cgcgttccga tgtctacggc   5340
gtctcgagtt ctgcaacgta gatggacctg gtttgatgtt tgcaggaggc gttccaatgt   5400
tggaatggct gaggctcggg ttcgacgcgg atagagcgca atcgacatac ggcggtctgg   5460
aggttggcat ccagcgcctc tcgtctctca acatgtcgt gctcattgta tggatggttt   5520
ctgaaggcgg tgatgatcca gcggagcaag ccgtctggtc tgccatcaat ggccaagtag   5580
agatgctccc caactctccg acggttgata tccggtttcg tagacggagt cagctgcagg   5640
caagctcaga ataaggagca cgaaaaagac gatgatgttg gatgtcgcct gctagctgta   5700
gtatgttgct gcttctgctt gttgccaaca catttttttt gggttagggt ggggtacaac   5760
cataaaatgt gtgtggatgt gcttgtaagc attacttgta tgttttttttt tgtaaagcac   5820
```

```
aatatagata gatgcatata tgtgtgcgtg caaagctatg attatcgaca ctcacacttg    5880
tacattagct agatgaaggt ctcgacagag cagagcatag tacacatctc tgggagttgg    5940
actggacact ataacgggga tgctgcagcc gaaactcaaa agctacatgc atgtcacttg    6000
gctcatcggc gcaggaagca acgcaggtcc atcacgcgca gcaccttgaa cccgtccagg    6060
ctacacccca gcagcagcct cggcttcttc ggcgccggcg ggcagcgcgg ggggcgttcg    6120
gttccagcgc cactcgccgt cgccgacgac agcggcgaga gctgccgtgg accttcttcg    6180
tcctcgtcgc cgccgcggga gtaagaccgc ttcagcttca gcggccgcag ctccaccagc    6240
tgcggaatgc taacatcttc ttcaggcacc tgccgggtgg ttctctttcc cagaatcttc    6300
cgctggagac ccatggcgag ctcggttcgg tttaacctgc aattaatgcg caatagcgga    6360
gtaggaagcg agattgttag ctcaggcgag cagagatgaa ccggctagga aagtttagtt    6420
gctcgtgcat gctaccagct agcttgttgg aggctcttgc tttggacacc aagcaacgga    6480
tatgacagca gaatgtgcgt gcttataagc aagcaagcag agcagcagtt gcaaagaagg    6540
gaaaaggtgg agtggaaaaa ggagttgcca ttgaagtgca cgagtgagcg agcatcatgt    6600
caaggaacca ggagggaagt tgcacaacag atgaaaagcg gagagctgtt tccgatctcc    6660
aacacgagcc ttgattcctg ccggccggtg atggcaatgg ccgctagtag tctccgctag    6720
ctagggagcg gcgatccgac gcgacgccac catgtgtcta gaaagaagt ttcttgcttt    6780 gcatgcagac ttattagcgc ggtcgacacc tgtggggacc ccgtgtcttg agacaatgag    6840
actgcctgtc cgcccaagac actacttgta gccatgaagc catcgactcc tctccttgct    6900
ctccagtaat ccagtggatg gatccatcat cgatagttta gtttatcagt cttcttgagg    6960
ccggtgtccc ccatgcataa tgatgacaga aagcctgggc caggtaaaag ccaaaaagtt    7020
tgaccctcta ggtactgggg ccagccctgg cgtttgaaca aaaaaaaaat ctgagcgtgt    7080
cgccccggcc tgttttcgaa ctcctaaacg acgtcgcaac tttttttata cacacactac    7140
cggtacatgg cttt                                                     7154
```

<210> SEQ ID NO 80
<211> LENGTH: 18
<212> TYPE: PRT
<213> ORGANISM: Agrobacterium tumefaciens

<400> SEQUENCE: 80

Lys Arg Pro Arg Asp Arg His Asp Gly Glu Leu Gly Gly Arg Lys Arg
1               5                   10                  15

Ala Arg

<210> SEQ ID NO 81
<211> LENGTH: 341
<212> TYPE: DNA
<213> ORGANISM: Zea mays

<400> SEQUENCE: 81

```
ttgtgaggtc tattaaggca tgtttggttt tggaccctag ttgtatagaa tggcttcgtt      60
cgaggcctcc aacttatgag aatgaaatga ctcgtttgaa agatagaatg actttggtcc     120
attgtgagcc aaaaggtttg ataacccgtt tggatgtaga tattggagca ctaaattgga     180
aatttgaatc aattttttctg aattctattg tttggttgca catggaattg agattagaaa     240
ttagatattc aatttcaggg aattggtaaa ttctctctca atatatagca tcatccctttt    300 gaattgcgtt taactagacc acataattct aaactccaat c                         341
```

<210> SEQ ID NO 82
<211> LENGTH: 276
<212> TYPE: DNA
<213> ORGANISM: Zea mays

<400> SEQUENCE: 82

```
ctgatcacgt gagcagcagc tagccaaagt gaaggtgaaa gaggaataaa ggaaaaagag      60
gacgacgaga aaagcacagc tttgtctttg ttgaaaagga acaataaaa aaacacaaag     120
aaaaacacgg ggaatgtgca aaaggaagcc ttatttggct ggatgcgttc ttgagtgcac    180
tgttttggag ggaatgagaa taccaagggc ttgttcggtt aggggtggat tgaggaggac    240
aaaccccttc aaaccgaaca aaccctaata ggggtg                              276
```

<210> SEQ ID NO 83
<211> LENGTH: 403
<212> TYPE: DNA
<213> ORGANISM: Zea mays

<400> SEQUENCE: 83

```
gaagactggg ttgtgaggtc tattaaggca tgtttggttt tggaccctag ttgtatagaa     60
tggcttcgtt cgaggcctcc aacttatgag aatgaaatga ctcgtttgaa agatagaatg    120
actttggtcc attgtgagcc aaaaggtttg ataaccgtt tggatgtaga tattggagca    180
ctaaattgga aatttgaatc aattttttctg aattctattg tttggttgca catggaattg   240
agattagaaa ttagatattc aatttcaggg aattggtaaa ttctctctca atatatagca    300
tcatcccttt gaattgcgtt taactagacc acataattct aaactccaat catgtgacat    360
ccaaacaata taattaaaat gtctgacgat gaatgagccg ctc                      403
```

<210> SEQ ID NO 84
<211> LENGTH: 368
<212> TYPE: DNA
<213> ORGANISM: Zea mays

<400> SEQUENCE: 84

```
actaggcgat cttctttccg taacacagca tatgatgaaa acggaacgat gaaagcgcca     60
tttgagaggg gaggggaggg aaaatgcctt ggctgatcac gtgagcagca gctagccaaa    120
gtgaaggtga agaggaata aggaaaaag aggacgacga gaaaagcaca gctttgtctt     180
tgttgaaaag gaacaataa aaaaacacaca agaaaaacac ggggaatgtg caaaaggaag    240
ccttatttgg ctggatgcgt tcttgagtgc actgttttgg agggaatgag aataccaagg    300
gcttgttcgg ttagggtgg attgaggagg acaaaccccct tcaaaccgaa caaaccctaa    360
tagggtg                                                              368
```

<210> SEQ ID NO 85
<211> LENGTH: 481
<212> TYPE: DNA
<213> ORGANISM: Zea mays

<400> SEQUENCE: 85

```
cagaatttac ggtccagcac gggcatgccg cgcgggctga ctttgctcca ctgactcgat     60
catgtgcgga ttccatcgcg gcgtagcgta gccaaccgca acgcaaaccg acttcatctt    120
ttttttttat tatgaacaaa aggagatcga gagaaacgtg aacggtaaat aatatatctg    180
atcccatgca tgcacgctgc ctgggtcgat ctcgctctcg ctccgcccag acgaacatgc    240
```

```
atgctggtca ggctcaacgc tcaggcgggc aagctgtggg aggacatggg atgggagagg      300
aggacacatg catgctggcc agtcaggcac tgtgctggca catgaggtag ggataggggg      360
gccctcggcc agtgtccagg ccgcatgcat gcatgccccc cctgctgctc gaccgaacaa      420
cgttggatgc ctggattgat gcaacagttt ggacggacgg accatacgtt atgtaccagt      480
a                                                                     481
```

```
<210> SEQ ID NO 86
<211> LENGTH: 486
<212> TYPE: DNA
<213> ORGANISM: Zea mays

<400> SEQUENCE: 86
ctgcacgtta cgtacgtacg aactaatata ctccaccagc tgatcactga tgagccgagc       60
cgccatgcat tgtaatttat aacatgtgcg gctgtacgct tccatctcaa ataccttttt      120
atatatatat tgtactttat agtctacgac ataatctgcc atggtaattt ataagatgtg      180
ctttattgct cgttgttctg ttctcatctg tgtccatggc atggcatgga tacaaaatgt      240
atgtatggcc acgcatccaa tctgtgacgt tgtcaaggca gaggtccaac cgtccaagac      300
cctcttgtgc cgccctgtac ttgcagtcag tgacgttgtg agaaaaagct gtgggtggtc      360
tccgcagagc gcgcgggcca cgagagggag ccccatctct cggccagggg gtacgggggc      420
tccagacacg gtcctttggt ttcttctgcc tgtagcgagc ggccccgccc ccaccgcgc      480 tgctag                                                                486
```

```
<210> SEQ ID NO 87
<211> LENGTH: 411
<212> TYPE: DNA
<213> ORGANISM: Zea mays

<400> SEQUENCE: 87
cggatagatg gcgtctagca tatcgatagg acatgacaag tggtacgatc cccgtcacat       60
gtccatggag gcatctgata tggacacggc gtgtatctat cgcggctgga acagaaccag      120
cgctcgcgcg gcgtcggcg ggagggacag accttggctc cgtgcgttca ggttgtgctt      180
gtgccgcgcg ccacgcacgg tctccgccgc ctgcagctga aattttagat ttacatccta      240 tcccttatt tttttattt gtcacaattc agttcaaaaa tgaagaacgg aggtagtgca      300
tcctttgtga gactaatgaa atcacatct ggatcctgaa atcggcgtcg taacctacaa      360
ggccacggac tggattagat agtggtccat ggtgcataat gaggatcgag g              411
```

```
<210> SEQ ID NO 88
<211> LENGTH: 417
<212> TYPE: DNA
<213> ORGANISM: Zea mays

<400> SEQUENCE: 88
atgaggagca atcattgttc aagacatgat gcaaagctag aaaactttga ttgtggccgt       60
cctaattgtg aagtttaggc cggggggaac ttcatgaacc ctatcgaagc ttaattagtt      120
cttttttgtt gttagccatg tttgtattgt agtttaggtg aacaacatga cgccgcaccc      180
gcgatctcag ggctcgtccc cacacaggag ggcacgtcgt cgtcttcgcc gccgagcatc      240
agagattcag agcacgtaca cgcacatctc aagcaaacgg agtagtacgt cctactccta      300
cgtacatacc tagccgacga cctttatgtg cacaccacca ctgctctgct gcccggcctc      360
tccgtcgtcc gttcatcacc agctggtctg gtccttcaat ttccatgcgt cggtccg        417
```

```
<210> SEQ ID NO 89
<211> LENGTH: 724
<212> TYPE: DNA
<213> ORGANISM: Zea mays

<400> SEQUENCE: 89
aaatagtaaa cgggagggga ggtcgctagt agtaaacgct aggtagctag gataatccgt      60
ctcgtgttgg acggaaggtt ttggacgcat ctgcgtgcac agcccgctga tacagatctg     120
atcgactagc tagctagatg ccgaggcccc agagcaaggc ccggatactc ctgcacagtc     180
cctgagattt cagcacagca ggtgctgttg catcaatata taaatccctg ctttattaat     240
ttaatctctg tgcatgtatc catacatcgt cagcggctca gcgctatcac actgcagtgc     300
acgcagctag ttgagcgcct gggtcagtat atatatagct agtagggaca aaggggggca     360
ctgtacgttg gtttggtttg gcacgcacgc gatcgagagt ggtggaatgg actgcagatc     420
atcgatcgct gcactgtacg cacgcgcacc ggactgcatt tgcatgcccc tgaaggagga     480
aaggggaagg aaagaaaaga aataggagaa agaagaagaa gcagagaaat acgtcacagt     540
ccaagaagag tgagccgccc tagctagctt caaccctgac gaacccggca gccacacttc     600
cggccatgta tgcatgcatg catggcttag cttcagatgt ccaatcgaat ccatcaagac     660
ctggccggtt ttccatggcc gcctcgcctt cgctagttaa gggccaagta cttgctgtcc     720
ctgt                                                                   724

<210> SEQ ID NO 90
<211> LENGTH: 500
<212> TYPE: DNA
<213> ORGANISM: Zea mays

<400> SEQUENCE: 90
atctccaaca cgagccttga ttcctgccgg ccggtgatgg caatggccgc tagtagtctc      60
cgctagctag ggagcggcga tccgacgcga cgccaccatg tgtctagaaa agaagtttct     120
tgctttgcat gcagacttat tagcgcggtc gacacctgtg gggacccgt gtcttgagac      180 aatgagactg cctgtccgcc caagacacta cttgtagcca tgaagccatc gactcctctc     240
cttgctctcc agtaatccag tggatggatc catcatcgat agtttagttt atcagtcttc     300
ttgaggccgg tgtcccccat gcataatgat gacagaaagc ctgggccagg taaaagccaa     360
aaagtttgac cctctaggta ctggggccag ccctggcgtt tgaacaaaaa aaaaatctga     420
gcgtgtcgcc ccggcctgtt ttcgaactcc taaacgacgt cgcaacttt tttatacaca      480 cactaccggt acatggcttt                                                  500

<210> SEQ ID NO 91
<211> LENGTH: 35
<212> TYPE: DNA
<213> ORGANISM: Artificial
<220> FEATURE:
<223> OTHER INFORMATION: HT1-TS2 Sequence

<400> SEQUENCE: 91
acggggatga tgggtcctgc gctcgatgtt ggatt                                  35

<210> SEQ ID NO 92
<211> LENGTH: 32
<212> TYPE: DNA
<213> ORGANISM: Artificial
<220> FEATURE:
```

```
<223> OTHER INFORMATION: HT1-TS4 Sequence

<400> SEQUENCE: 92
gcctcgttga caagtacacc gagctcagaa ac                                    32

<210> SEQ ID NO 93
<211> LENGTH: 51
<212> TYPE: DNA
<213> ORGANISM: Artificial
<220> FEATURE:
<223> OTHER INFORMATION: Junction Sequence with CR2/CR4

<400> SEQUENCE: 93
acggggatga tgggtcctgc gctcgatgac aagtacaccg agctcagaaa c               51

<210> SEQ ID NO 94
<211> LENGTH: 42
<212> TYPE: DNA
<213> ORGANISM: Artificial
<220> FEATURE:
<223> OTHER INFORMATION: HT1-ST1-TS1 Sequence

<400> SEQUENCE: 94
ctaactttct aacactcgac aagctcgcta gcctcgttga ca                         42

<210> SEQ ID NO 95
<211> LENGTH: 53
<212> TYPE: DNA
<213> ORGANISM: Artificial
<220> FEATURE:
<223> OTHER INFORMATION: Junction Sequence with CR2/ST1-CR1

<400> SEQUENCE: 95
acggggatga tgggtcctgc gctcgatcga caagctcgct agcctcgttg aca             53
```

GENERATING NORTHERN LEAF BLIGHT RESISTANT MAIZE

CROSS-REFERENCE TO RELATED APPLICATIONS

This application claims priority to International Patent Application PCT/US2017/55835 filed on Oct. 10, 2017, which claims priority to U.S. Provisional Application No. 62/407,867, filed Oct. 13, 2016, the contents of which are herein incorporated by reference in their entirety.

FIELD

The field is molecular biology, and more specifically, methods for editing the genome of a plant cell to produce northern leaf blight resistant corn.

REFERENCE TO SEQUENCE LISTING SUBMITTED ELECTRONICALLY

The official copy of the sequence listing is submitted electronically via EFS-Web as an ASCII formatted sequence listing with a file named 7156-US-PCT_ST25.txt created on May 3, 2022 and having a size of 241,817 bytes and is filed concurrently with the specification. The sequence listing contained in this ASCII formatted document is part of the specification and is herein incorporated by reference in its entirety.

BACKGROUND

Northern leaf blight (NLB), induced by the fungal pathogen *Exserohilum turcicum* (previously called *Helminthosporium turcicum*), is a serious foliar wilt disease of maize in many tropical and temperate environments. Symptoms can range from cigar-shaped lesions on the lower leaves to complete destruction of the foliage, thereby reducing the amount of leaf surface area available for photosynthesis. A reduction in photosynthetic capability leads to a lack of carbohydrates needed for grain fill, which impacts grain yield. Mid-altitude regions of the tropics, about 900-1600 m above sea level, have a particularly favorable climate for northern leaf blight, as dew periods are long and temperatures moderate. However, northern leaf blight can also yield losses of 30-50% in temperate environments, such as in the United States, during wet seasons, particularly if the infection is established on the upper leaves of the plant by the silking stage.

The most effective and most preferred method of control for northern leaf blight is the planting of resistant hybrids. Resistance to specific races of the pathogen can be controlled by certain native disease resistance maize genes, such as Ht1, Ht2, Ht3, Htm1, Htn1, HtN, HtP, ht4 and rt (Welz and Geiger 2000. *Plant Breeding.* 119(1):1-14; Ogliari et al. 2005. *Genet Mol Biol* 28:435-439; Hurni et al. 2015 *PNAS* 112(28):8780-5). However, introgressing the resistance genes into other inbreds is an arduous task, which may or may not come with a yield penalty due to linkage drag. There is a need to produce northern leaf blight resistant maize plants more efficiently and in a way that will reduce linkage drag associated with the introgression of multiple resistance loci into elite maize lines via conventional means.

SUMMARY

The limitations of conventional breeding for introgressing northern leaf blight resistance into maize lines can be overcome through the editing of genes that confer enhanced resistance to northern leaf blight, such as, for example, Ht1 and NLB18, or by the movement of resistant alleles of Ht1 and NLB18 to another site in the genome such that enhanced resistance to northern leaf blight can be obtained by introgressing a single genomic locus comprising multiple nucleotide sequences, each conferring enhanced resistance to northern leaf blight, into maize plants.

Methods for obtaining a maize plant cell with a modified Ht1 nucleotide sequence are provided herein. The methods include: introducing a double-strand break or site-specific modification at one or more target sites in an endogenous HT1 encoding sequence in a maize plant cell and obtaining a maize plant cell having a modified Ht1 nucleotide sequence. The method may further comprise introducing an Ht1 substitution template in the maize plant cell, wherein said Ht1 substitution template comprises at least one nucleic acid alteration compared to the endogenous HT1 encoding sequence and wherein said Ht1 substitution template is incorporated into the endogenous HT1 encoding sequence. The double-strand break may be induced by a nuclease such as, but not limited to, a TALEN, a meganuclease, a zinc finger nuclease, or a CRISPR-associated nuclease. The method may further comprise growing a maize plant from the maize plant cell having the modified Ht1 nucleotide sequence, and the maize plant may exhibit enhanced resistance to northern leaf blight.

In some aspects, the modified Ht1 nucleotide sequence comprises a deletion in the promoter of the endogenous HT1 encoding sequence. The methods may involve the use of Cas9 endonuclease and one or more guide RNAs. In one embodiment, at least two guide RNAs are used, wherein a first guide RNA comprises a variable targeting domain that is complementary to SEQ ID NO:1 [Ht1-T52], and a second guide RNA comprises a variable targeting domain complementary to SEQ ID NO:2 [Ht1-TS4]. In another embodiment, a first guide RNA comprises a variable targeting domain that is complementary to SEQ ID NO:1 [Ht1-TS2], and a second guide RNA comprises a variable targeting domain complementary to SEQ ID NO:3 [Ht1-ST1-TS1].

In other aspects, an Ht1 subsitution template is used, which comprises an Ht1 nucleotide sequence from PH4GP (Ht1-PH4GP). The Ht1-PH4GP nucleotide sequence may comprise SEQ ID NO:59. In another embodiment, the Ht1-PH4GP nucleotide sequence may comprise a nucleotide sequence that encodes a polypeptide having an amino acid sequence that is at least 90%, 91%, 92%, 93%, 94%, 95%, 96%, 97%, 98%, or 99% to SEQ ID NO:52, wherein the polypeptide confers resistance to northern leaf blight. The Ht1-PH4GP nucleotide sequence may also comprise SEQ ID NO:65. The methods may involve the use of Cas9 endonuclease and one or more guide RNAs. In an embodiment, at least two guide RNAs are used, wherein a first guide RNA comprises a variable targeting domain that is complementary to SEQ ID NO:14 [Ht1-TS6], and a second guide RNA comprises a variable targeting domain complementary to SEQ ID NO:16 [Ht1-TS9]. In another embodiment, a first guide RNA comprises a variable targeting domain complementary to SEQ ID NO:15 [Ht1-TS7], and a second guide RNA comprises a variable targeting domain that is complementary to SEQ ID NO:17 [Ht1-TS10].

Methods for obtaining a maize plant cell with a modified NLB18 nucleotide sequence are provided herein. The methods include: introducing a double-strand break or site-specific modification at one or more target sites in an endogenous NLB18 encoding sequence in a maize plant cell and obtaining a maize plant cell having a modified NLB18 nucleotide sequence. The methods may further comprise introducing an NLB18 substitution template in the maize plant cell, wherein said NLB18 substitution template comprises at least one nucleic acid alteration compared to the endogenous NLB18 encoding sequence and wherein said NLB18 substitution template is incorporated into the endogenous NLB18 encoding sequence. The double-strand break may be induced by a nuclease such as but not limited to a TALEN, a meganuclease, a zinc finger nuclease, or a CRISPR-associated nuclease. The method may further comprise growing a maize plant from the maize plant cell having the modified NLB18 nucleotide sequence, and the maize plant may exhibit enhanced resistance to northern leaf blight.

In some aspects, the modified NLB18 nucleotide sequence comprises a modification in the promoter of the endogenous NLB18 encoding sequence. In some embodiments, the modification in the promoter of an endogenous Ht1 encoding sequence comprises a deletion of a region of repetitive sequences in the Ht1 promoter. In one embodiment, the modification in the promoter of an endogenous Ht1 encoding sequence comprises a deletion of SEQ ID NO: 71 from the Ht1 promoter.

In other aspects, an NLB18 subsitution template is used, which comprises an NLB18 nucleotide sequence from PH26N or PH99N (NLB18-PH26N or NLB18-PH99N). In one embodiment, an NLB18-PH26N nucleotide sequence comprises any nucleotide sequence that encodes a polypeptide having an amino acid sequence that is at least 90%, 91%, 92%, 93%, 94%, 95%, 96%, 97%, 98%, or 99% to SEQ ID NO:64, wherein the polypeptide confers resistance to norhtern leaf blight. In some aspects, the NLB18-PH26N nucleotide sequence comprises SEQ ID NO:70. The NLB18-PH99N nucleotide sequence may comprise any nucleotide sequence that encodes a polypeptide having an amino acid sequence that is at least 90%, 91%, 92%, 93%, 94%, 95%, 96%, 97%, 98%, or 99% to SEQ ID NO:62, wherein the polypeptide confers resistance to norhtern leaf blight. The methods may involve the use of Cas9 endonuclease and one or more guide RNAs. In one embodiment, at least two guide RNAs are used, wherein a first guide RNA comprises a variable targeting domain that is complementary to SEQ ID NO:30 [NLB18-TS1], and a second guide RNA comprises a variable targeting domain complementary to SEQ ID NO:32 [NLB18-TS4]. In another embodiment, a first guide RNA comprises a variable targeting domain complementary to SEQ ID NO:31 [NLB18-TS8], and a second guide RNA comprises a variable targeting domain complementary to SEQ ID NO:32 [NLB18-TS4].

Methods for obtaining a maize plant cell with an edited genomic locus comprising at least one nucleotide sequence that confers enhanced resistance to northern leaf blight are provided herein. The methods include 1) introducing a double-strand break or site-specific modificaiton at one or more target sites in a genomic locus in a maize plant cell; 2) introducing one or more nucleotide sequences encoding a polypeptide that confers enhanced resistance to northern leaf blight, wherein each nucleotide sequence is flanked by 300-500 contiguous nucleotides of nucleotide sequences 5' or 3' of the corresponding target sites; and 3) obtaining a maize plant cell having a genomic locus comprising one or more nucleotide sequences that confer enhanced resistance to northern leaf blight. The double-strand break or site-specific modification may be induced by a nuclease such as but not limited to a TALEN, a meganuclease, a zinc finger nuclease, or a CRISPR-associated nuclease. The method may further comprise growing a maize plant from the maize plant cell having the edited genomic locus comprising the at least one nucleotide sequence that confers enhanced resistance to northern leaf blight, and the maize plant may exhibit enhanced resistance to northern leaf blight.

In some aspects, an edited plant cell comprises the one or more nucleotide sequences include any of the following: Ht1-PH4GP (SEQ ID NO: 51), NLB18-PH26N (SEQ ID NO: 63), and NLB18-PH99N (SEQ ID NO: 61). In other aspects, the genomic locus is CTL1. The Ht1-PH4GP nucleotide sequence may comprise SEQ ID NO:59 or any nucleotide sequence that encodes a polypeptide having an amino acid sequence that is at least 90%, 91%, 92%, 93%, 94%, 95%, 96%, 97%, 98%, or 99% to SEQ ID NO:52, wherein said polypeptide confers enhanced resistance to northern leaf blight in a maize plant. In some aspects, the Ht1-PH4GP nucleotide sequence comprises SEQ ID NO:65. The NLB18-PH26N nucleotide sequence may comprise any nucleotide sequence that encodes a polypeptide having an amino acid sequence that is at least 90%, 91%, 92%, 93%, 94%, 95%, 96%, 97%, 98%, or 99% to SEQ ID NO:64, wherein said polypeptide confers enhanced resistance to northern leaf blight in a maize plant. In some aspects, the NLB18-PH26N nucleotide sequence comprises SEQ ID NO:70. The NLB18-PH99N nucleotide sequence may comprise any nucleotide sequence that encodes a polypeptide having an amino acid sequence that is at least 90%, 91%, 92%, 93%, 94%, 95%, 96%, 97%, 98%, or 99% to SEQ ID NO:62, wherein said polypeptide confers enhanced resistance to northern leaf blight in a maize plant.

In still other aspects, a nucleotide sequence encoding NLB18-PH26N is targeted to TS8 of CTL1; a nucleotide sequence encoding NLB18-PH4GP is targeted to TS10 of CTL1; and/or a nucleotide sequence encoding NLB18-PH26N is targeted to TS45 of CTL1.

In one aspect, a method to edit a plant cell comprises using a Cas9 endonuclease as the DSB-inducing agent, and one or more guide RNAs to target the Cas9 to sites in the CTL1 locus. One guide RNA may comprise a variable targeting domain that is complementary to SEQ ID NO:36 [CTL1-TS8]; one guide RNA may comprise a variable targeting domain that is complementarty to SEQ ID NO:37 [CTL1-TS10], and one guide RNA may comprise a variable targeting domain that is complementary to SEQ ID NO:38 [CTL1-TS45].

Maize plant cells produced by the methods presented herein are also provided as are maize plants produced the maize plant cells and seeds produced by the maize plants.

The guide polynucleotides comprising variable targeting domains complementary to target sites in the endogenous Ht1 encoding sequence, the endogenous NLB18 encoding sequence, or the CTL1 genomic locus are also provided herein. The guide polynucleotides may be RNA sequences, DNA sequences, or RNA-DNA combination sequences. For Ht1, the guide polynucleotides may have a variable targeting domain complementarty to SEQ ID NO:1, SEQ ID NO:2, or SEQ ID NO:3. For NLB18, the guide polynucleotides may have a variable targeting domain complementary to SEQ ID NO:30, SEQ ID NO:31, or SEQ ID NO:32. For CTL1, the guide polynucleotides may have a variable targeting domain complementary to SEQ ID NO:36, SEQ ID NO:37, or SEQ ID NO:38.

BRIEF DESCRIPTION OF THE DRAWINGS AND SEQUENCE LISTINGS

FIG. 1 shows a schematic drawing of the Ht1 locus; the location of each target site in the Ht1 genomic sequence for deletion of repetitive sequence in the promoter region; and the locations of the primers used for validation. The introns between exons are in white, and the target sites are indicated with up triangles. E1 represents exon1; e2 represents exon 2; and pro represents the promoter region.

FIGS. 2A and 2B show the expected junction sequences after removal of repetitive sequences in the promoter region of the Ht1 gene. FIG. 2A shows the expected junction sequence (SEQ ID NO:93) with CR2/CR4 (sequences in italics are the TS2 sequences in SEQ ID NO:91, and sequences that are underlined are the TS4 sequences in SEQ ID NO:92). FIG. 2B shows the expected junction sequence SEQ ID NO:95 with CR2/ST1-CR1 (sequences in italics are the TS2 sequences in SEQ ID NO:91, and sequences that are underlined are the ST1-TS1 sequences in SEQ ID NO:94). The boxed regions indicate junctions.

Figure 1:
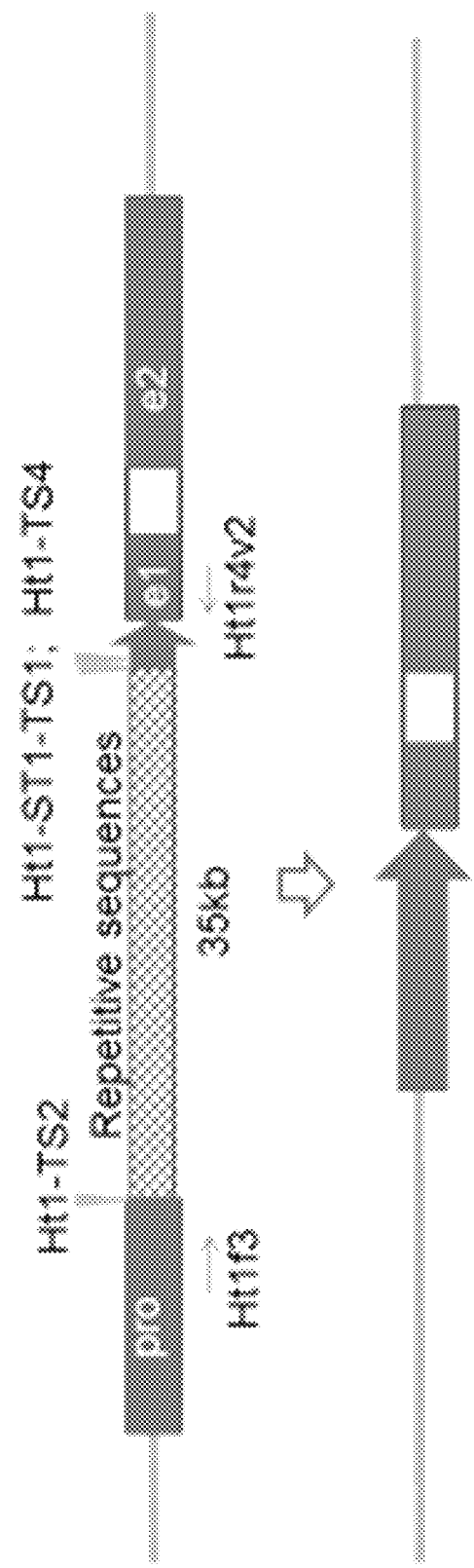

SEQ ID NO:1 is the nucleotide sequence of the Ht1-TS2 target site.

SEQ ID NO:2 is the nucleotide sequence of the Ht2-TS4 target site.

SEQ ID NO:3 is the nucleotide sequence of the Ht1-ST1-TS1 target site.

SEQ ID NO:4 is the nucleotide sequence of the Cas9 gene.

SEQ ID NO:5 is the amino acid sequence of the SV40 monopartite amino terminal nuclear localization signal.

SEQ ID NO:6 is the nucleotide sequence of the U6 polymerase III promoter.

SEQ ID NO:7 is the nucleotide sequence of the DNA capable of expressing the Ht1-CR2 guide RNA.

SEQ ID NO:8 is the nucleotide sequence of the DNA capable of expressing the Ht1-CR4 guide RNA.

SEQ ID NO:9 is the nucleotide sequence of the DNA capable of expressing the Ht1-ST1-CR1 guide RNA.

SEQ ID NO:10 is the nucleotide sequence of the Ht1f3 forward primer.

SEQ ID NO:11 is the nucleotide sequence of the Ht1r4v2 Reverse primer.

SEQ ID NO:12 is the nucleotide sequence of the secondary PCR reaction forward primer.

SEQ ID NO:13 is the nucleotide sequence of the secondary PCR reaction reverse primer.

SEQ ID NO:14 is the nucleotide sequence of the Ht1-TS6 target site.

SEQ ID NO:15 is the nucleotide sequence of the HT1-TS7 target site.

SEQ ID NO:16 is the nucleotide sequence of the HT1-TS9 target site.

SEQ ID NO:17 is the nucleotide sequence of the HT1-TS10 target site.

SEQ ID NO:18 is the nucleotide sequence of the DNA capable of expressing the HT1-CR6 guide RNA.

SEQ ID NO:19 is the nucleotide sequence of the DNA capable of expressing the HT1-CR9 guide RNA.

SEQ ID NO:20 is the nucleotide sequence of the DNA capable of expressing the HT1-CR7 guide RNA.

SEQ ID NO:21 is the nucleotide sequence of the DNA capable of expressing the HT1-CR10 guide RNA.

SEQ ID NO:22 is the nucleotide sequence of the Ht1HR1f1 forward primer.

SEQ ID NO:23 is the nucleotide sequence of the Ht1HR1r1 reverse primer.

SEQ ID NO:24 is the nucleotide sequence of the Ht1HR2f1 forward primer.

SEQ ID NO:25 is the nucleotide sequence of the Ht1HR2r1 reverse primer.

SEQ ID NO:26 is the nucleotide sequence of the hdr2b_f forward primer.

SEQ ID NO:27 is the nucleotide sequence of the hdr2b_r reverse primer.

SEQ ID NO:28 is the nucleotide sequence of the hdr2b_PV probe.

SEQ ID NO:29 is the nucleotide sequence of the hdr2b_PG probe.

SEQ ID NO:30 is the nucleotide sequence of the NLB18-TS1 target site.

SEQ ID NO:31 is the nucleotide sequence of the NLB18-TS8 target site.

SEQ ID NO:32 is the nucleotide sequence of the NLB18-TS4 target site.

SEQ ID NO:33 is the nucleotide sequence of the DNA capable of expressing the NLB18-CR1 guide RNA.

SEQ ID NO:34 is the nucleotide sequence of the DNA capable of expressing the NLB18-CR8 guide RNA.

SEQ ID NO:35 is the nucleotide sequence of the DNA capable of expressing the NLB18-CR4 guide RNA.

SEQ ID NO:36 is the nucleotide sequence of the CTL1-TS8 target site.

SEQ ID NO:37 is the nucleotide sequence of the CTL1-TS45 target site.

SEQ ID NO:38 is the nucleotide sequence of the CTL1-TS10 target site.

SEQ ID NO:39 is the nucleotide sequence of the 8HR1f1 forward primer.

SEQ ID NO:40 is the nucleotide sequence of the PH26NPr reverse primer.

SEQ ID NO:41 is the nucleotide sequence of the PH26NTf forward primer.

SEQ ID NO:42 is the nucleotide sequence of the 8HR2r1 reverse primer.

SEQ ID NO:43 is the nucleotide sequence of the 10HR1f forward primer.

SEQ ID NO:44 is the nucleotide sequence of the Ht1Pr reverse primer.

SEQ ID NO:45 is the nucleotide sequence of the Ht1Tf forward primer.

SEQ ID NO:46 is the nucleotide sequence of the 10HR2r reverse primer.

SEQ ID NO:47 is the nucleotide sequence of the 45hr1f1 forward primer.

SEQ ID NO:48 is the nucleotide sequence of the PH26NPr reverse primer.

SEQ ID NO:49 is the nucleotide sequence of the PH26NTf forward primer.

SEQ ID NO:50 is the nucleotide sequence of the 45hr2r1 reverse primer.

SEQ ID NO:51 is the nucleotide sequence of the Ht1 cDNA found in inbred line PH4GP.

SEQ ID NO:52 is the amino acid sequence of the polypeptide encoded by SEQ ID NO:51.

SEQ ID NO:53 is the nucleotide sequence of the Ht1 cDNA found in inbred line PH1W2.

SEQ ID NO:54 is the amino acid sequence of the polypeptide encoded by SEQ ID NO:53.

SEQ ID NO:55 is the nucleotide sequence of the Ht1 cDNA found in inbred line B73 and herein referred to as the "B73-high allele".

SEQ ID NO:56 is the amino acid sequence of the polypeptide encoded by SEQ ID NO:55.

SEQ ID NO:57 is the nucleotide sequence of the Ht1 cDNA found in inbred line B73 and herein referred to as the "B73-low allele".

SEQ ID NO:58 is the amino acid sequence of the polypeptide encoded by SEQ ID NO:57.

SEQ ID NO:59 is the nucleotide sequence of the Ht1 genomic DNA found in inbred line PH4GP.

SEQ ID NO:60 is the amino acid sequence of a region found in the Ht1 polypeptides of resistant alleles.

SEQ ID NO:61 is the NLB18 cDNA sequence from PH99N.

SEQ ID NO:62 is the amino acid sequence of the protein encoded by SEQ ID NO:61.

SEQ ID NO:63 is the NLB18 cDNA sequence from PH26N.

SEQ ID NO:64 is the amino acid sequence of the protein encoded by SEQ ID NO:63.

SEQ ID NO:65 is the nucleotide sequence of the ZM-HT1-PH4GP including the ZM-HT1-PH4GP promoter, exon 1, intron 1, and terminator.

SEQ ID NO:66 is the NLB18 nucleotide sequence from PH184C, including the 5' of NLB18-CR8 through the 3' of NLB18-CR4.

SEQ ID NO:67 is the homology arm sequence flanking the 5' of NLB18-TS1 in PH184C.

SEQ ID NO:68 is the homology arm sequence flanking the 3' of NLB18-TS4 in PH184C.

SEQ ID NO:69 is the homology arm sequence flanking the 5' of NLB18-TS8 in PH184C.

SEQ ID NO:70 is the NLB18 nucleotide sequence from PH26N, including the PH26N NLB18 promoter, exon 1, intron 1, exon 2, intron 2, exon 3, and terminator.

SEQ ID NO:71 is the nucleotide sequence of a region of repetitive sequences in the Ht1 promoter of PH184C.

SEQ ID NO:72 is the nucleotide sequence of an expression cassette including the Zea mays ubiquitin promoter, the 5' UTR of the ZM-ubiquitin gene, intron 1 of the ZM-ubiquitin gene, the SV40 nuclear localization signal, Cas9 exon 1 (ST1), the potato-LS1 intron, Cas9 exon 2 (ST1), the VirD2 endonuclease nuclear localization signal, and the pinII terminator.

SEQ ID NO:73 is the nucleotide sequence containing the Cas9 used in Example 4; SEQ ID NO:73 contains the cas9 exon 1 (SP), the ST-LS1 intron 2, the Cas9 exon 2 (SP), and the VirD2 nuclear localization signal.

SEQ ID NO:74 is the nucleotide sequence of the DNA capable of expressing the ZM-U6:08CR1 guide RNA.

SEQ ID NO:75 is the nucleotide sequence of the DNA capable of expressing the ZM-U6:45CR1 guide RNA.

SEQ ID NO:76 is the nucleotide sequence of the DNA capable of expressing the ZM-U6:10CR3 guide RNA.

SEQ ID NO:77 is the nucleotide sequence of the 08CR1HR1-NLB18(PH26N) genomic sequence-8CR1HR2 repair template targeted to TS8 of CTL1.

SEQ ID NO:78 is the nucleotide sequence of the 45CR1HR1-NLB18(PH26N) genomic sequence-45CR1HR2 repair template targeted to TS45 of CTL1.

SEQ ID NO:79 is the nucleotide sequence of the 10CR3HR1-HT1 (PH4GP) genomic sequence-10CR3HR2 repair template targeted to TS10 of CTL1.

SEQ ID NO:80 is the amino acid sequence of the Agrobacterium tumefaciens bipartite VirD2 T-DNA border endonuclease carboxyl terminal nuclear localization signal.

SEQ ID NO:81 is the nucleotide sequence of the homology arm flanking the 5' of HT1-TS6 in PH184C (Example 2).

SEQ ID NO:82 is the nucleotide sequence of the homology arm flanking the 3' of HT1-TS9 in PH184C (Example 2).

SEQ ID NO:83 is the nucleotide sequence of the homology arm flanking the 5' of HT1-TS7 in PH184C (Example 2).

SEQ ID NO:84 is the nucleotide sequence of the homology arm flanking the 5' of HT1-TS10 in PH184C (Example 2).

SEQ ID NO:85 is the nucleotide sequence of the homology arm flanking the 5' of CTL1-TS8 in PH184C (Example 4).

SEQ ID NO:86 is the nucleotide sequence of the homology arm flanking the 3' of CTL1-TS8 in PH184C (Example 4).

SEQ ID NO:87 is the nucleotide sequence of the homology arm flanking the 5' of CTL1-TS45 in PH184C (Example 4).

SEQ ID NO:88 is the nucleotide sequence of the homology arm flanking the 3' of CTL1-TS45 in PH184C (Example 4).

SEQ ID NO:89 is the nucleotide sequence of the homology arm flanking the 5' of CTL1-TS10 in PH184C (Example 4).

SEQ ID NO:90 is the nucleotide sequence of the homology arm flanking the 3' of CTL1-TS10 in PH184C (Example 4).

DETAILED DESCRIPTION

It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules. Unless defined otherwise, all technical and scientific terms used herein have the same meaning as commonly understood by one of ordinary skill in the art to which this disclosure belongs unless clearly indicated otherwise.

Compositions and methods are presented herein to edit the maize genome to produce maize plants that have enhanced resistance to northern leaf blight.

The term "allele" refers to one of two or more different nucleotide sequences that occur at a specific locus.

"*Exserohilum turcicum*", previously referred to as *Helminthosporium turcicum*, is the fungal pathogen that induces northern leaf blight infection. The fungal pathogen is also referred to herein as *Exserohilum* or Et.

"Disease resistance" (such as, for example, northern leaf blight resistance) is a characteristic of a plant, wherein the plant avoids, miminimzes, or reduces the disease symptoms that are the outcome of plant-pathogen interactions, such as maize-*Exserohilum turcicum* interactions. That is, pathogens are prevented from causing plant diseases and the associated disease symptoms, or alternatively, the disease symptoms caused by the pathogen are minimized or lessened.

A "locus" is a position on a chromosome where a gene or marker is located.

"Resistance" is a relative term, indicating that the infected plant produces better plant health or yield of maize than another, similarly treated, more susceptible plant. That is, the conditions cause a reduced decrease in maize survival, growth, and/or yield in a tolerant maize plant, as compared to a susceptible maize plant. One of skill will appreciate that maize plant resistance to northern leaf blight, or the pathogen causing such, can represent a spectrum of more resistant or less resistant phenotypes, and can vary depending on the severity of the infection. However, by simple observation, one of skill can determine the relative resistance or susceptibility of different plants, plant lines or plant families to northern leaf blight, and furthermore, will also recognize the phenotypic gradations of "resistant". For example, a 1 to 9 visual rating indicating the level of resistance to northern leaf blight can be used. A higher score indicates a higher resistance. Data should be collected only when sufficient selection pressure exists in the experiment measured. The terms "tolerance" and "resistance" are used interchangeably herein.

The resistance may be "newly conferred" or "enhanced". "Newly conferred" or "enhanced" resistance refers to an increased level of resistance against a particular pathogen, a wide spectrum of pathogens, or an infection caused by the pathogen(s). An increased level of resistance against a particular fungal pathogen, such as Et, for example, constitutes "enhanced" or improved fungal resistance. The embodiments may enhance or improve fungal plant pathogen resistance.

I. Gene Editing

In some embodiments, gene editing may be facilitated through the induction of a double-stranded break (a "DSB") in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

A polynucleotide modification template may be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template may be introduced into a cell as a single stranded polynucleotide molecule, a double stranded polynucleotide molecule, or as part of a circular DNA (vector DNA). The polynucleotide modification template may also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous homologous recombination HR machinery is expected to be highly diminished (Mali et al. 2013 *Nature Methods* Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii). An "edited cell" or an "edited plant cell" refers to a cell containing at least one alteration in the genomic sequnce when compared to a control cell or plant cell that does not include such alteration in the genomic sequence.

The term "polynucleotide modification template" or "modification template" as used herein refers to a polynucleotide that comprises at least one nucleotide modification when compared to the target nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSBs and modification templates generally comprises: providing to a host cell a DSB-inducing agent, or a nucleic acid encoding a DSB-inducing agent, that recognizes a target sequence in the chromosomal sequence, and wherein the DSB-inducing agent is able to induce a DSB in the genomic sequence; and providing at least one polynucleotide modification template comprising at least one nucleotide alteration when compared to the nucleotide sequence to be edited. The endonuclease may be provided to a cell by any method known in the art, for example, but not limited to transient introduction methods, transfection, microinjection, and/or topical application or indirectly via recombination constructs. The endonuclease may be provided as a protein or as a guided polynucleotide complex directly to a cell or indirectly via recombination constructs. The endonuclease may be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433.

As used herein, a "genomic region" refers to a segment of a chromosome in the genome of a cell. In one embodiment, a genomic region includes a segment of a chromosome in the genome of a cell that is present on either side of the target site or, alternatively, also comprises a portion of the target site. The genomic region may comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (See Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLI-DADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, WO2015/026886 A1, WO2016007347, and WO201625131, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein, or complex of proteins, encoded by a Cas gene. A Cas endonuclease as disclosed herein, when in complex with a suitable polynucleotide component, is capable of recognizing, binding to, and optionally nicking or cleaving all or part of a specific DNA target sequence. A Cas endonuclease as described herein comprises one or more nuclease domains. Cas endonucleases of the disclosure includes those having a HNH or HNH-like nuclease domain and/or a RuvC or RuvC-like nuclease domain. A Cas endonuclease of the disclosure may include a Cas9 protein, a Cpf1 protein, a C2c1 protein, a C2c2 protein, a C2c3 protein, Cas3, Cas5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, and US 2015-0059010 A1, both hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of a Cas endonuclease that can cleave both strands of a DNA target sequence. A Cas9 protein comprising functional RuvC and HNH nuclease domains is an example of a Cas protein that can cleave both strands of a DNA target sequence. A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. Non-limiting examples of Cas9 nickases suitable for use herein are disclosed in U.S. Patent Appl. Publ. No. 2014/0189896, which is incorporated herein by reference.

A pair of Cas9 nickases may be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a double strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair. For example, a Cas9 nickase with a mutant RuvC domain, but functioning HNH domain (i.e., Cas9 HNH+/RuvC−), could be used (e.g., *Streptococcus pyogenes* Cas9 HNH+/RuvC−). Each Cas9 nickase (e.g., Cas9 HNH+/RuvC−) would be directed to specific DNA sites nearby each other (up to 100 base pairs apart) by using suitable RNA components herein with guide RNA sequences targeting each nickase to each specific DNA site.

A Cas protein may be part of a fusion protein comprising one or more heterologous protein domains (e.g., 1, 2, 3, or more domains in addition to the Cas protein). Such a fusion protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein can also be in fusion with a protein that binds DNA molecules or other molecules, such as maltose binding protein (MBP), S-tag, Lex A DNA binding domain (DBD), GAL4 A DNA binding domain, and herpes simplex virus (HSV) VP16. See PCT patent applications PCT/US16/32073, filed May 12, 2016 and PCT/US16/32028 filed May 12, 2016 (both applications incorporated herein by reference) for more examples of Cas proteins.

A guide polynucleotide/Cas endonuclease complex in certain embodiments may bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). In other aspects, an inactivated Cas protein may be fused with another protein having endonuclease activity, such as a Fok I endonuclease.

The Cas endonuclease gene herein may encode a Type II Cas9 endonuclease, such as but not limited to, Cas9 genes listed in SEQ ID NOs: 462, 474, 489, 494, 499, 505, and 518 of WO2007/025097, and incorporated herein by reference. In another embodiment, the Cas endonuclease gene is a microbe or optimized Cas9 endonuclease gene. The Cas endonuclease gene can be operably linked to a SV40 nuclear targeting signal upstream of the Cas codon region and a bipartite VirD2 nuclear localization signal (Tinland et al. (1992) *Proc. Natl. Acad. Sci. USA* 89:7442-6) downstream of the Cas codon region.

Other Cas endonuclease systems have been described in PCT patent applications PCT/US16/32073, and PCT/US16/32028, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

A Cas protein herein such as a Cas9 can comprise a heterologous nuclear localization sequence (NLS). A heterologous NLS amino acid sequence herein may be of sufficient strength to drive accumulation of a Cas protein in a detectable amount in the nucleus of a yeast cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. Non-limiting examples of suitable NLS sequences herein include those disclosed in U.S. Pat. No. 7,309,576, which is incorporated herein by reference.

The Cas endonuclease can comprise a modified form of the Cas9 polypeptide. The modified form of the Cas9 polypeptide can include an amino acid change (e.g., deletion, insertion, or substitution) that reduces the naturally-occurring nuclease activity of the Cas9 protein. For example, in some instances, the modified form of the Cas9 protein has less than 50%, less than 40%, less than 30%, less than 20%, less than 10%, less than 5%, or less than 1% of the nuclease activity of the corresponding wild-type Cas9 polypeptide (US patent application US20140068797 A1). In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA.

A catalytically inactive Cas9 can be fused to a heterologous sequence (US patent application US20140068797 A1). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 can also be fused to a FokI nuclease to generate double strand breaks (Guilinger et al. *Nature Biotechnology*, volume 32, number 6, June 2014).

The terms "functional fragment", "fragment that is functionally equivalent" and "functionally equivalent fragment" of a Cas endonuclease are used interchangeably herein, and refer to a portion or subsequence of the Cas endonuclease sequence of the present disclosure in which the ability to recognize, bind to, and optionally nick or cleave (introduce a single or double strand break in) the target site is retained. The terms "functional variant", "Variant that is functionally equivalent" and "functionally equivalent variant" of a Cas endonuclease are used interchangeably herein, and refer to a variant of the Cas endonuclease of the present disclosure in which the ability to recognize, bind to, and optionally nick or cleave (introduce a single or double strand break in) the target site is retained. Fragments and variants can be obtained via methods such as site-directed mutagenesis and synthetic construction.

Any guided endonuclease can be used in the methods disclosed herein. Such endonucleases include, but are not limited to Cas9 and Cpf1 endonucleases. Many endonucleases have been described to date that can recognize specific PAM sequences (see for example—Jinek et al. (2012) *Science* 337 p 816-821, PCT patent applications PCT/US16/32073, and PCT/US16/32028and Zetsche B et al. 2015. *Cell* 163, 1013) and cleave the target DNA at a specific positions. It is understood that based on the methods and embodiments described herein utilizing a guided Cas system one can now tailor these methods such that they can utilize any guided endonuclease system.

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also U.S. Patent Application US 2015-0082478 A1, and US 2015-0059010 A1, both hereby incorporated in its entirety by reference).

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA- combination sequences. In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. The size of the fragment of the cRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex is a duplexed RNA comprising a duplex crRNA-tracrRNA.

The tracrRNA (trans-activating CRISPR RNA) contains, in the 5'-to-3' direction, (i) a sequence that anneals with the repeat region of CRISPR type II crRNA and (ii) a stem loop-containing portion (Deltcheva et al., Nature 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) into the target site. (See also U.S. Patent Application US 2015-0082478 A1, published on Mar. 19, 2015 and US 2015-0059010 A1 both hereby incorporated in its entirety by reference.)

The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, and US 2015-0059010 A1, both hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, incorporated in its entirety by reference herein), or any combination thereof.

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "Variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, *Science* 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, and US 2015-0059010 A1, both hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., *Nucleic Acids Res*. 41: 4336-4343; Ma et al., *Mol. Ther. Nucleic Acids* 3: e161) as described in WO2016025131, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence including, but not limited to, a nucleotide sequence within a chromosome, an episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long. The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting may be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein may be performed in such a way that two or more DNA target sites are targeted in the method, for example. Such a method can optionally be characterized as a multiplex method. Two, three, four, five, six, seven, eight, nine, ten, or more target sites may be targeted at the same time in certain embodiments. A multiplex method is typically performed by a targeting method herein in which multiple different RNA components are provided, each designed to guide an guidepolynucleotide/Cas endonuclease complex to a unique DNA target site.

The terms "knock-out", "gene knock-out" and "genetic knock-out" are used interchangeably herein. A knock-out as used herein represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, and WO2015/026886 A1, both hereby incorporated in its entirety by reference.)

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins include, but are not limited to, a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct may further comprise a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. To determine the percent identity of two amino acid sequences or of two nucleic acid sequences, the sequences are aligned for optimal comparison purposes. The percent identity between the two sequences is a function of the number of identical positions shared by the sequences (e.g., percent identity of query sequence=number of identical positions between query and subject sequences/total number of positions of query sequence (e.g., overlapping positions)×100).

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) *Cell* 31:25-33; Shen and Huang, (1986) *Genetics* 112:441-57; Watt et al., (1985) *Proc. Natl. Acad. Sci. USA* 82:4768-72, Sugawara and Haber, (1992) *Mol Cell Biol* 12:563-75, Rubnitz and Subramani, (1984) *Mol Cell Biol* 4:2253-8; Ayares et al., (1986) *Proc. Natl. Acad. Sci.* USA 83:5199-203; Liskay et al., (1987) *Genetics* 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 *Annu. Rev. Biochem.* 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. (2014) PNAS (0027-8424), 111 (10), p. E924-E932).

Alteration of the genome of a plant cell, for example, through homologous recombination (HR), is a powerful tool for genetic engineering. Homologous recombination has been demonstrated in plants (Halfter et al., (1992) *Mol Gen Genet* 231:186-93) and insects (Dray and Gloor, 1997, *Genetics* 147:689-99). Homologous recombination has also been accomplished in other organisms. For example, at least 150-200 bp of homology was required for homologous recombination in the parasitic protozoan Leishmania (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche et al., (2000) *Nucleic Acids Res* 28: e97). Targeted gene replacement has also been demonstrated in the ciliate *Tetrahymena thermophila* (Gaertig et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo (Watson et al., 1992, Recombinant DNA, 2nd Ed., (Scientific American Books distributed by WH Freeman & Co.). Error-prone DNA repair mechanisms can produce mutations at double-strand break sites. The Non-Homologous-End-Joining (NHEJ) pathways are the most common repair mechanism to bring the broken ends together (Bleuyard et al., (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al., (2000) *EMBO J* 19:5562-6), however if two different double-strand breaks occur, the free ends from different breaks can be ligated and result in chromosomal deletions (Siebert and Puchta, (2002) *Plant Cell* 14:1121-31), or chromosomal translocations between different chromosomes (Pacher et al., (2007) Genetics 175:21-9).

The donor DNA may be introduced by any means known in the art. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome. (see guide language)

Further uses for guide RNA/Cas endonuclease systems have been described (See U.S. Patent Application US 2015-0082478 A1, WO2015/026886 A1, US 2015-0059010 A1, U.S. application 62/023,246, and U.S. application 62/036,652, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

II. Methods of Generating Maize Plants with Modified Ht1 and/or NLB18 Nucleotide Sequences A. Ht1

Mapping of a QTL associated with northern leaf blight resistance on chromosome 2 was described in U.S. Patent Application US2010095395. The Ht1 gene was cloned and identified as a putative CC-NB-LRR (coiled-coil, nucleotide-binding, leucine-rich repeat) gene (U.S. 62/242,691). Ht1 cDNA sequences from PH4GP and from PH1W2 (another source of a resistant allele of Ht1; U.S. Patent Application US2010095395) are represented by SEQ ID NOs:51 and 53, respectively, while the amino acid sequences of the encoded polypeptides are represented by SEQ ID NO:52 and 54 and are 99.6% identical. B73 (which has the susceptible allele) has two splicing variants, and the novel variant expresses at a much higher level (referred to herein as B73-high) than the known variant (referred to herein as B73-low). SEQ ID NO:55 is the cDNA sequence of the B73-high allele, while the amino acid sequence of the encoded polypeptide is represented by SEQ ID NO:56. SEQ ID NO:57 is the cDNA sequence of the B73-low allele, while the amino acid sequence of the encoded polypeptide is represented by SEQ ID NO:58. The genomic sequence of the PH4GP (resistant) allele is provided herein as SEQ ID NO:59. The CC and NB domains are highly similar between the susceptible allele (B73) and resistant alleles (from PH4GP and PH1W2), as shown in U.S. 62/242,691. However, B73 has a deletion in the LRR. The amino acid sequence of this region in the Ht1 resistant alleles is represented by SEQ ID NO:60.

The methods for obtaining a maize plant cell with a modified Ht1 nucleotide sequence include: introducing a double-strand break at one or more target sites in an endogenous HT1 encoding sequence in a maize plant cell and obtaining a maize plant cell having a modified Ht1 nucleotide sequence. In other aspects, the methods include: introducing a double-strand break at one or more target sites in an endogenous Ht1 encoding sequence in a maize plant cell and obtaining a maize plant cell having a modified Ht1 nucleotide sequence. The method may further comprise introducing an NLB18 substitution template in the maize plant cell, wherein said Ht1 substitution template comprises at least one nucleic acid alteration compared to the endogenous Ht1 encoding sequence and wherein said Ht1 substitution template is incorporated into the endogenous Ht1 encoding sequence. The method may further comprise introducing an Ht1 substitution template in the maize plant cell, wherein said Ht1 substitution template comprises at least one nucleic acid alteration compared to the endogenous HT1 encoding sequence and wherein said Ht1 substitution template is incorporated into the endogenous HT1 encoding sequence. The double-strand break may be induced by a nuclease, including, but not limited to, a TALEN, a meganuclease, a zinc finger nuclease, or a CRISPR-associated nuclease. The method may further comprise growing a maize plant from the maize plant cell having the modified Ht1 nucleotide sequence, and the maize plant may exhibit enhanced resistance to northern leaf blight.

An "Ht1 nucleotide sequence" as presented herein can refer to the Ht1 promoter, exons, introns, and/or terminator sequences as a whole or in fragments.

The "endogenous HT1 encoding sequence" refers to the nucleotide sequence that is present in the unmodified maize plant cell and encodes the HT1 polypeptide.

An "Ht1 substitution template" is a polynucleotide modification template containing a favorable version of the Ht1 nucleotide sequence (i.e. one that confers enhanced resistance to northern leaf blight).

The maize plants exhibit enhanced resistance to northern leaf blight when compared to equivalent maize plants lacking the modified Ht1 nucleotide sequence. "Equivalent" means that the maize plants are genetically similar with the exception of the Ht1 sequence.

In some aspects, the modified Ht1 nucleotide sequence comprises a deletion in the promoter of the endogenous HT1 encoding sequence. This may involve the use of Cas9 endonuclease and one or more guide RNAs. If two guide RNAs are used, a first guide RNA may comprise a variable targeting domain that is complementary to SEQ ID NO:1 [Ht1-TS2] and a second guide RNA may comprise a variable targeting domain that is complementary to SEQ ID NO:2 [Ht1-TS4]; or a first guide RNA may comprise a variable targeting domain that is complementary to SEQ ID NO:1 [Ht1-TS2] and a second guide RNA may comprise a variable targeting domain that is complementary toSEQ ID NO:3 [Ht1-ST1-TS1].

In other aspects, an Ht1 subsitution template is used, which comprises an Ht1 nucleotide sequence from PH4GP or fragment thereof, or an Ht1 nucleotide sequence that when introduced into the maize plant cell encodes a polypeptide with an amino acid sequence that is at least 90%, 91%, 92%, 93%, 94%, 95%, 96%, 97%, 98%, or 99% identical to SEQ ID NO:52. This may involve the use of Cas9 endonuclease and one or more guide RNAs. If two guide RNAs are used, a first guide RNA may comprise a variable targeting domain that is complementary to SEQ ID NO:14 [Ht1-TS6] and a second guide RNA may comprise a variable targeting domain that is complementary to SEQ ID NO:16 [Ht1-TS9]; or a first guide RNA may comprise a variable targeting domain that is complementary to SEQ ID NO:15 [Ht1-TS7] and a second guide RNA may comprise a variable targeting domain that is complementary to SEQ ID NO:17 [Ht1-TS10].

B. NLB18

Mapping of a QTL associated with northern leaf blight resistance on chromosome 8 was described in international patent application WO2011163590. Two protein kinase (PK)-like genes with highly conserved kinase catalytic domains were identified in close proximity and were referred to in international patent application WO2011163590 as NLB17 and NLB18. NLB18 was validated as the gene conferring enhanced resistance to northern leaf blight (unpublished). NLB18 cDNA sequences from PH26N and PH99N, the two resistant sources described in WO2011163590, are represented by SEQ ID NOs:61 and 63, respectively, while the amino acid sequences of the encoded polypeptides are represented by SEQ ID NO:62 and 64. SEQ ID NO:62 and SEQ ID NO:64 are 92.4% identical.

Methods for obtaining a maize plant cell with a modified NLB18 nucleotide sequence are provided herein. The methods include: introducing a double-strand break at one or more target sites in an endogenous NLB18 encoding sequence in a maize plant cell and obtaining a maize plant cell having a modified NLB18 nucleotide sequence. The method may further comprise introducing an NLB18 substitution template in the maize plant cell, wherein said NLB18 substitution template comprises at least one nucleic acid alteration compared to the endogenous NLB18 encoding sequence and wherein said NLB18 substitution template is incorporated into the endogenous NLB18 encoding sequence. The double- strand break may be induced by a nuclease such as but not limited to a TALEN, a meganuclease, a zinc finger nuclease, or a CRISPR-associated nuclease. The method may further comprise growing a maize plant from the maize plant cell having the modified NLB18 nucleotide sequence, and the maize plant may exhibit enhanced resistance to northern leaf blight.

An "NLB18 nucleotide sequence" as presented herein can refer to the NLB18 promoter, exons, introns, terminator sequences, and/or any other genomic nucleotide sequence located within the NLB18 genomic locus as a whole or in fragments.

An "endogenous NLB18 encoding sequence" refers to a nucleotide sequence that is present in the unmodified maize plant cell and encodes a NLB18 polypeptide.

An "NLB18 substitution template" is a polynucleotide modification template containing a favorable version of the NLB18 nucleotide sequence (i.e. one that confers enhanced resistance to northern leaf blight).

The maize plants exhibit enhanced resistance to northern leaf blight when compared to equivalent maize plants lacking the modified NLB18 nucleotide sequence. "Equivalent" means that the maize plants are genetically similar with the exception of the NLB18 sequence.

In some aspects, a modified NLB18 nucleotide sequence comprises a modification in the promoter of the endogenous NLB18 encoding sequence.

In other aspects, an NLB18 subsitution template is used, which comprises an NLB18 nucleotide sequence from PH26N or PH99N, or an NLB18 nucleotide sequence that when introduced into the maize plant cell encodes a polypeptide with an amino acid sequence that is at least 90%, 91%, 92%, 93%, 94%, 95%, 96%, 97%, 98%, or 99% identical to SEQ ID NO:62 or SEQ ID NO:64. In some aspects, the NLB18 substitution template comprises SEQ ID NO:70. In some embodiments, the use of a NLB substitution template may involve the use of Cas9 endonuclease and one or more guide RNAs. If two guide RNAs are used, a first guide RNA may comprise a variable targeting domain that is complementary to SEQ ID NO:30 [NLB18-TS1] and a second guide RNA may comprise a variable targeting domain that is complementary to SEQ ID NO:32 [NLB18-TS4]; or a first guide RNA may comprise a variable targeting domain that is complementary to SEQ ID NO:31 [NLB18-TS8] and a second guide RNA may comprise a variable targeting domain that is complementary toSEQ ID NO:32 [NLB18-TS4].

III. Methods for Obtaining Maize Plant Cells with a Genomic Locus Comprising Nucleotide Sequences that Confer Enhanced Resistance to Northern Leaf Blight Polynucleotides of interest and/or traits can be stacked together in a complex trait locus as described in US 2013/0263324-A1 and in PCT/US13/22891, both applications hereby incorporated by reference.

Methods for obtaining a maize plant cell with a genomic locus comprising at least one nucleotide sequence that confers enhanced resistance to northern leaf blight are provided herein. The disclosed methods include introducing a double-strand break at one or more target sites in a genomic locus in a maize plant cell; introducing one or more nucleotide sequences that confer enhanced resistance to northern leaf blight, wherein each is flanked by 300-500 bp of nucleotide sequences 5' or 3' of the corresponding target sites; and obtaining a maize plant cell having a genomic locus comprising one or more nucleotide sequences that confer enhanced resistance to northern leaf blight. The double-strand break may be induced by a nuclease such as but not limited to a TALEN, a meganuclease, a zinc finger nuclease, or a CRISPR-associated nuclease. The method may further comprise growing a maize plant from the maize plant cell having the genomic locus comprising the at least one nucleotide sequence that confers enhanced resistance to northern leaf blight, and the maize plant may exhibit enhanced resistance to northern leaf blight.

The maize plants exhibit enhanced resistance to northern leaf blight when compared to equivalent maize plants lacking the nucleotide sequences conferring enhanced resistance to northern leaf blight at the genomic locus of interest. "Equivalent" means that the maize plants are genetically similar with the exception of the genomic locus of interest.

In some aspects, the one or more nucleotide sequences that confers enhanced resistance to northern leaf blight include any of the following: Ht1-PH4GP, NLB18-PH26N, and NLB18-PH99N. The Ht1-PH4GP nucleotide sequence may comprise SEQ ID NO:59 or any nucleotide sequence that encodes a polypeptide having an amino acid sequence that is at least 90%, 91%, 92%, 93%, 94%, 95%, 96%, 97%, 98%, or 99% to SEQ ID NO:52, wherein said polypeptide confers enhanced resistance to northern leaf blight in a maize plant. In some aspects, the Ht1-PH4GP nucleotide sequence is SEQ ID NO:65. The NLB18-PH26N nucleotide sequence may comprise any nucleotide sequence that encodes a polypeptide having an amino acid sequence that is at least 90%, 91%, 92%, 93%, 94%, 95%, 96%, 97%, 98%, or 99% to SEQ ID NO:64, wherein said polypeptide confers enhanced resistance to northern leaf blight in a maize plant. In some aspects, the NLB18-PH26N nucleotide sequence is SEQ ID NO:70. The NLB18-PH99N nucleotide sequence may comprise any nucleotide sequence that encodes a polypeptide having an amino acid sequence that is at least 90%, 91%, 92%, 93%, 94%, 95%, 96%, 97%, 98%, or 99% to SEQ ID NO:62, wherein said polypeptide confers enhanced resistance to northern leaf blight in a maize plant.

In other aspects, the genomic locus that confers enhanced resistance to northern leaf blight comprises CTL1. In still other aspects, a nucleotide sequence encoding NLB18-PH26N is targeted to TS8 of CTL1; a nucleotide sequence encoding NLB18-PH4GP is targeted to TS10 of CTL1; and/or a nucleotide sequence encoding NLB18-PH26N is targeted to TS45 of CTL1.

The guide polynucleotide/Cas9 endonuclease system as described herein provides for an efficient system to generate double strand breaks and allows for traits to be stacked in a complex trait locus. Thus, in one aspect, Cas9 endonuclease is used as the DSB-inducing agent, and one or more guide RNAs are used to target the Cas9 to sites in the CTL1 locus. One guide RNA may comprise a variable targeting domain that is complementary to SEQ ID NO:36 [CTL1-TS8]; one guide RNA may comprise a variable targeting domain that is complementarty to SEQ ID NO:37 [CTL1-TS10], and one guide RNA may comprise a variable targeting domain that is complementary to SEQ ID NO:38 [CTL1-TS45].

The maize plants generated by the methods described herein may provide durable and broad spectrum resistance to northern leaf blight and may assist in breeding of northern leaf blight resistant maize plants. For instance, because the nucleotide sequences that confer enhanced resistance to northern leaf blight are in tight linkage with one another (at one locus), this reduces the number of specific loci that require trait introgression through backcrossing and minimizes linkage drag from non-elite resistant donors.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

IV. Maize Plant Cells, Plants, and Seeds

"Maize" refers to a plant of the *Zea mays* L. ssp. mays and is also known as "corn". The use of "ZM" preceding an object described herein refers to the fact that the object is from *Zea mays*.

Maize plants, maize plant cells, maize plant parts and seeds, and maize grain having the modified Ht1 or NLB18 sequences disclosed herein are also provided.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, kernels, ears, cobs, husks, stalks, roots, root tips, anthers, and the like. Grain is intended to mean the mature seed produced by commercial growers for purposes other than growing or reproducing the species.

V. Guide Polynucleotides

The guide polynucleotides comprising variable targeting domains complementary to target sites in the endogenous Ht1 encoding sequence, the endogenous NLB18 encoding sequence, or the CTL1 genomic locus are also provided herein. These guide polynucleotides may be RNA sequences, DNA sequences, or RNA-DNA combination sequences. For Ht1, the guide polynucleotides may have a variable targeting domain to complementarity to SEQ ID NO:1, SEQ ID NO:2, or SEQ ID NO:3. For NLB18, the guide polynucleotides may have a variable targeting domain complementary to SEQ ID NO:30, SEQ ID NO:31, or SEQ ID NO:32. For CTL1, the guide polynucleotides may have a variable targeting domain complementary to SEQ ID NO:36, SEQ ID NO:37, or SEQ ID NO:38.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Editing of the Ht1 Gene Via Deletion of Repetitive Sequences in the Promoter Region

Target Site Selection

The gRNA/Cas9 site directed nuclease system, described in WO2015026885, WO20158026887, WO2015026883, and WO2015026886, was used to edit the Ht1 gene in maize (WO2017066597, which is incorporated by reference herein). The following pairs of target sites were used for deletion of the repetitive sequence in the Ht1 promoter region of PH184C (represented by SEQ ID NO:71): HT1-TS2 with HT1-TS4 and HT1-TS2 with HT1-ST1-TS1. The location of each target site in the Ht1 genomic sequence and the deletion result schematic drawing are shown in FIG. 1, and target sequences are listed in Table 1.

TABLE 1

Ht1 Promoter Region Genomic Target Site Sequences

| Target Site Designation | Maize Genomic Target Site Sequence | PAM Sequence |
| --- | --- | --- |
| Ht1-TS2 | SEQ ID NO: 1 | TGG |
| Ht1-TS4 | SEQ ID NO: 2 | AGG |
| Ht1-ST1-TS1 | SEQ ID NO: 3 | TTAGAAA |

Cas9 Vector Construction

A Cas9 gene from *Streptococcus pyogenes* M1 GAS (SF370) (SEQ ID NO:4) was maize codon optimized per standard techniques known in the art, and the potato ST-LS1 intron was introduced in order to eliminate its expression in *E.coli* and *Agrobacterium*. To facilitate nuclear localization of the Cas9 protein in maize cells, the Simian virus 40 (SV40) monopartite amino terminal nuclear localization signal (SEQ ID NO:5) was incorporated at the amino terminus of the Cas9 open reading frame. The maize optimized Cas9 gene was operably linked to a maize Ubiquitin promoter using standard molecular biological techniques. In addition to the amino terminal nuclear localization signal SV40, a C-terminal bipartitite nuclear localization signal from *Agrobacterium tumefaciens* VirD2 endonuclease was fused at the end of exon 2. The resulting sequence is SEQ ID NO:72, which includes the *Zea mays* ubiquitin promoter, the 5' UTR of the ZM-ubiquitin gene, intron 1 of the ZM-ubiquitin gene, the SV40 nuclear localization signal, Cas9 exon 1 (ST1), the potato-LS1 intron, Cas9 exon 2 (ST1), the VirD2 endonuclease nuclear localization signal, and the pinII terminator.

Guide RNA Vector Construction

To direct the Cas9 nuclease to the designated genomic target sites (in Table 1), a maize U6 polymerase III promoter (SEQ ID NO:6; see WO2015026885, WO20158026887, WO2015026883, and WO2015026886) and its cognate U6 polymerase III termination sequences (TTTTTTTT) were used to direct initiation and termination of gRNA expression. Guide RNA variable targeting domains for HT1 gene editing are identified as HT1-CR2 and HT1-CR4 which correspond to the genomic target sites HT1-TS2, HT1-TS4, and HT1-ST1-CR1 correspond to HT1-ST1-TS, respectively. DNA encoding each of the variable nucleotide targeting domains was cloned into a gRNA expression cassette through BsbI sites using double strand oligos. Each guide RNA expression cassette consists of the U6 polymerase III maize promoter operably linked to one of the DNA versions of the guide RNA (Table 2), and then the cognate U6 polymerase III termination sequence. The DNA version of guide RNA consists of the respective nucleotide variable targeting domain followed by a polynucleotide sequence capable of interacting with the double strand break inducing endonuclease. The guide RNA expression cassette for HT1-ST1-CR1 was constructed into the ST1 Cas9 expression cassette via standard procedures.

TABLE 2

Guide RNA Expression Cassettes

| Name | DNA version of guide RNA |
| --- | --- |
| Ht1-CR2 | SEQ ID NO: 7 |
| Ht1-CR4 | SEQ ID NO: 8 |
| Ht1-ST1-CR1 | SEQ ID NO: 9 |

Delivery of the Guide RNA/Cas9 Endonuclease System DNA to Maize

Plasmids containing the Cas9 and guide RNA expression cassettes described above were co-bombarded with plasmids containing the transformation selectable marker NPTII and the transformation enhancing developmental genes ODP2 (AP2 domain transcription factor ODP2 (Ovule development protein 2)) and Wuschel (20151030-6752 USPSP) into elite maize lines' genomes. Transformation of maize immature embryos can be performed using any method known in the art or the method described below.

In one transformation method, ears are husked and surface sterilized in 30-50% Clorox bleach plus 0.5% Micro detergent for 10 minutes and then rinsed two times with sterile water. The immature embryos are isolated and placed embryo axis side down (scutellum side up), with 25 embryos per plate, on 13224E medium for 2-4 hours and then aligned within the 2.5-cm target zone in preparation for bombardment.

DNA of plasmids is adhered to 0.6 μm (average diameter) gold pellets using a proprietary lipid-polymer mixture of TransIT®-2020 (Cat # MIR 5404, Mirus Bio LLC, Madison, WI 5371). A DNA solution was prepared using 1 μg of plasmid DNA and optionally, other constructs were prepared for co-bombardment using 10 ng (0.5 μl) of each plasmid. To the pre-mixed DNA, 50 μl of prepared gold particles (30 mg/ml) and 1 μl TransIT®-2020 are added and mixed carefully. The final mixture is allowed to incubate under constant vortexing at low speed for 10 minutes. After the precipitation period, the tubes are centrifuged briefly, and liquid is removed. Gold particles are pelleted in a microfuge at 10,000 rpm for 1 min, and aqueous supernatant is removed. 120 μl of 100% EtOH is added, and the particles are resuspended by brief sonication. Then, 10 μl is spotted on to the center of each macrocarrier and allowed to dry about 2 minutes before bombardment, with a total of ten aliquots taken from each tube of prepared particles/DNA.

The sample plates are bombarded with a Biolistic PDA-1000/He (Bio-Rad). Embryos are 6 cm from the macrocarrier, with a gap of ⅛th of an inch between the 200 psi rupture disc and the macrocarrier. All samples receive a single shot.

Following bombardment, the embryos are incubated on the bombardment plate for ~20 hours then transferred to 13266L (rest/induction medium) for 7-9 days at temperatures ranging from 26-30° C. Embryos are then transferred to the maturation media 289H for ~21 days. Mature somatic embryos are then transferred to germination media 272G and moved to the light. In about 1 to 2 weeks plantlets containing viable shoots and roots are sampled for analysis and sent to the greenhouse where they are transferred to flats (equivalent to a 2.5" pot) containing potting soil. After 1-2 weeks, the plants are transferred to Classic 600 pots (1.6 gallon) and grown to maturity.

Media

Bombardment medium (13224E) comprises 4.0 g/l N6 basal salts (SIGMA C-1416), 1.0 ml/l Eriksson's Vitamin Mix (1000X SIGMA-1511), 0.5 mg/l thiamine HCl, 190.0 g/l sucrose, 1.0 mg/l 2,4-D, and 2.88 g/l L-proline (brought to volume with D-I H2O following adjustment to pH 5.8 with KOH); 6.3 g/l Sigma agar (added after bringing to volume with D-I H2O); and 8.5 mg/l silver nitrate (added after sterilizing the medium and cooling to room temperature).

Selection medium (13266L) comprises 1650 mg/l ammonium Nitrate, 277.8 mg/l ammonium Sulfate, 5278 mg/l potassium nitrate, calcium chloride, anhydrous 407.4 mg/l calcium chloride, anhydrous, 234.92 mg/l magnesium sulfate, anhydrous, 410 mg/l potassium phosphate, monobasic, 8 mg/l boric acid, 8.6 mg/l, zinc sulfate·7h2o, 1.28 mg/l potassium iodide, 44.54 mg/l ferrous sulfate·7h2o, 59.46 mg/l na2edta·2h2o, 0.025 mg/l cobalt chloride·6h2o, 0.4 mg/l molybdic acid (sodium salt)·2h2o, 0.025 mg/l cupric sulfate·5h2o, 6 mg/l manganese sulfate monohydrate, 2 mg/l thiamine, 0.6 ml/l b5h minor salts 1000x, 0.4 ml/l eriksson's vitamins 1000x, 6 ml/l s&h vitamin stock 100x, 1.98 g/l l-proline, 3.4 mg/l silver nitrate, 0.3 g/l casein hydrolysate (acid), 20 g/l sucrose, 0.6 g/l glucose, 0.8 mg/l 2,4-d, 1.2 mg/l dicamba, 6 g/l tc agar, 100 mg/l agribio carbenicillin, 25 mg/l cefotaxime, and 150 mg/l geneticin (g418)

Plant regeneration medium (289H) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 8.0 g/l Sigma agar (added after bringing to volume with D-I H2O); and 1.0 mg/l indoleacetic acid and 150 mg/l Geneticin (G418) (added after sterilizing the medium and cooling to 60° C.).

Hormone-free medium (272G) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 0.5 mg/l IBA and 150 mg/l Geneticin (G418) and 6 g/l bacto-agar (added after bringing to volume with polished D-I H2O), sterilized and cooled to 60° C.

Screening of T0 Plants and Event Characterization

To identify repetitive sequence deletion positive events, genomic DNA was extracted from leaf tissue of T0 plants, and PCR was performed using Phusion master mix (Thermo Scientific F-581) and the primers listed in Table 3. Primer locations are shown in FIG. 1. Amplicons were obtained when the TS2/TS4 or TS2/ST1-TS1 were cleaved; sequence (~35 kb) between the two sites was removed, and the remaining sequences were joined together. Deletion variants with the expected size product were obtained.

Figures 2A, 2B:
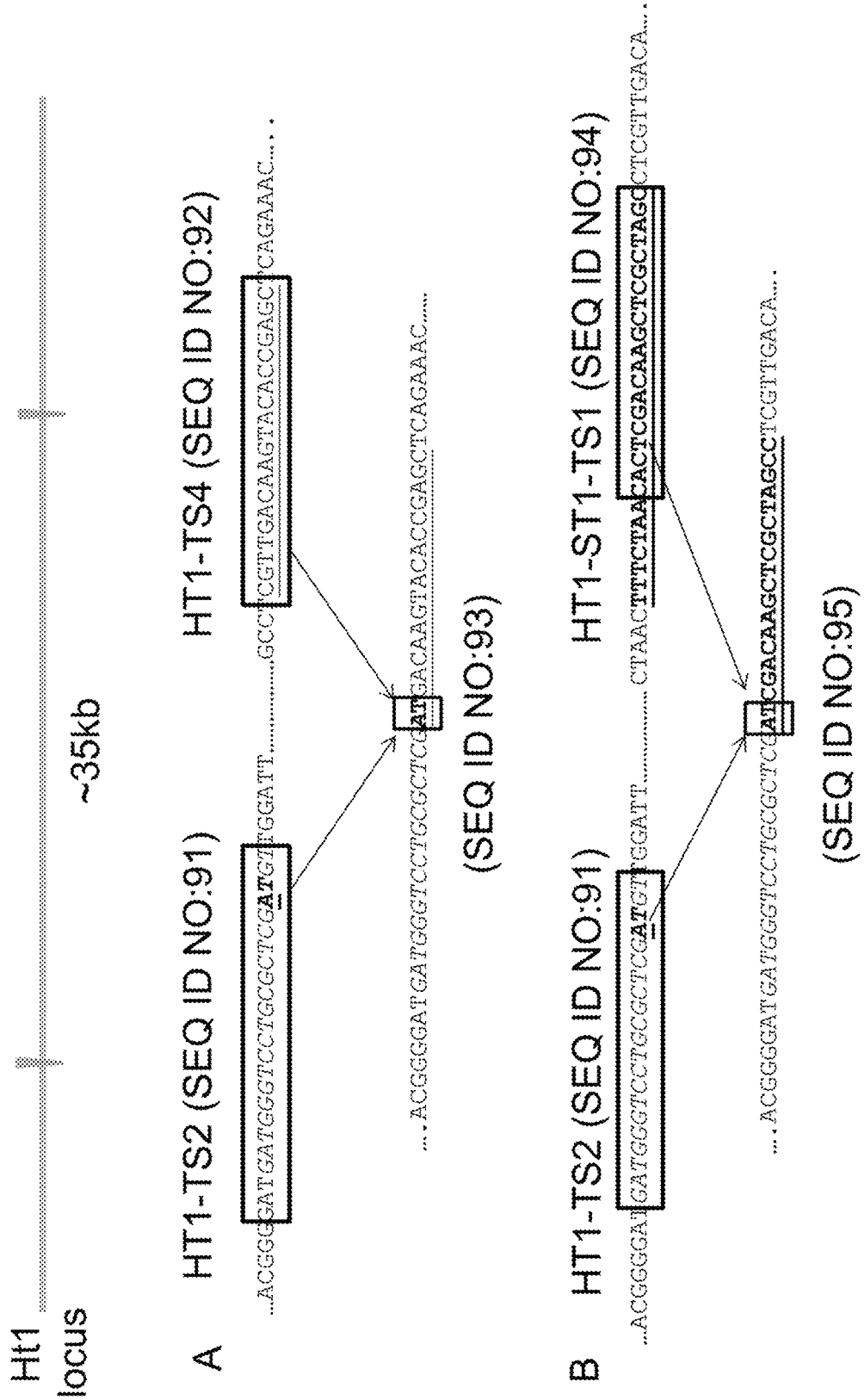
Figure 3:
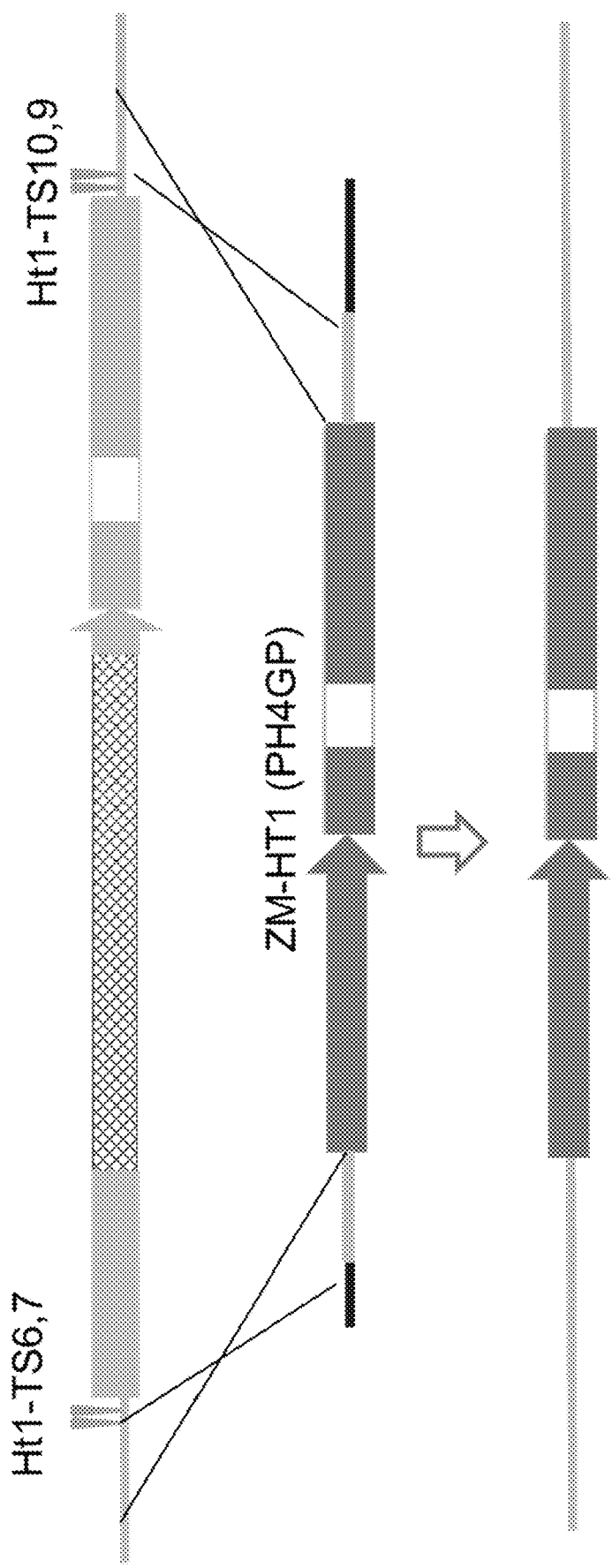
FIG. 3 shows the location of each target site and the schematic drawing of the Ht1 allele swap. The PH4GP Ht1 allele is shown in darker gray and the allele it is replacing is shown in light gray.
Figure 4:
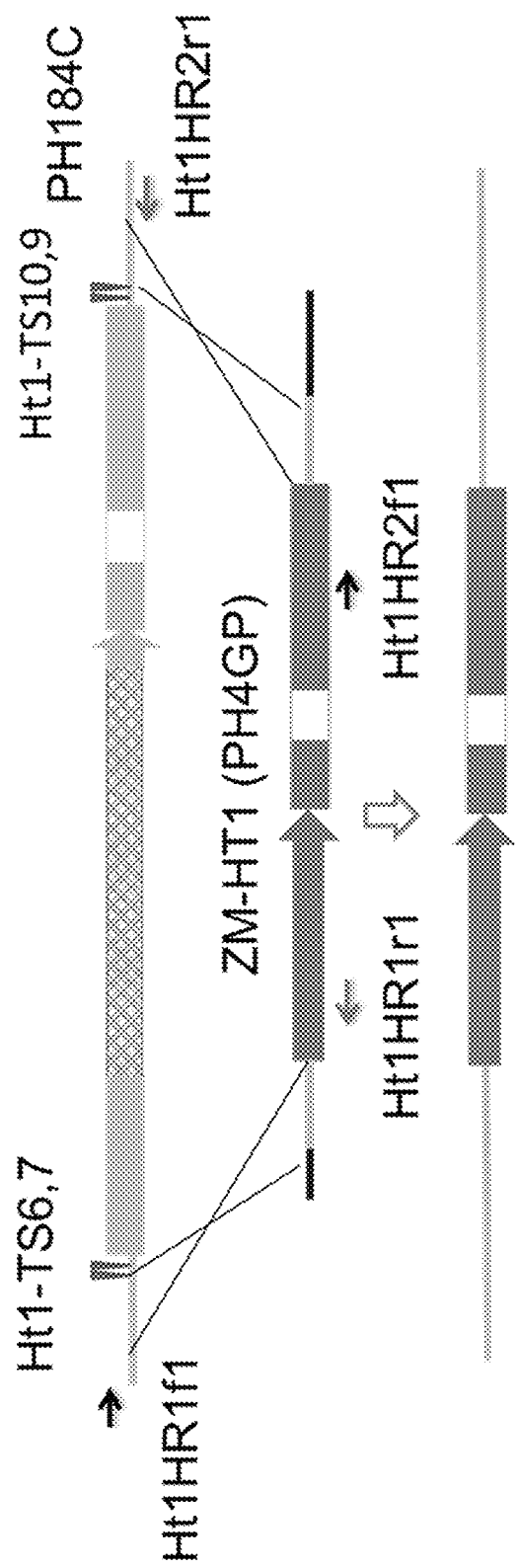
FIG. 4 shows the locations of the primers used to evaluate the Ht1 allele swap.

Next Generation Sequencing (NGS) was used to evaluate the junction sequences in the deletion positive events. The junction was PCR amplified with PHUSION® Flash High Fidelity PCR Master Mix (Termo Scientific, F-531). The same primers can be used for both the CR2/CR4 and CR2/ST1-CR1 deletions. The primers used in the primary PCR reaction are shown in Table 3 and the primers used in the secondary PCR reaction are provided in SEQ ID NO:12 and SEQ ID NO:13. "NNNNNNNN" in the reverse primer is the barcode sequence corresponding to a sample location on a plate. FIG. 2A shows the junction sequence generated at the TS2/TSS4 deletion; and FIG. 2B shows the junction sequences generated at the TS2/ST1-TS1 deletion. A summary of the T0 deletion events that were obtained is shown in Table 4.

TABLE 3

Primers Used to Screen for Repetitive Sequence Deletions

| Name of deletion | Primer name | Primer Orientation | Primer SEQ ID NO: |
|---|---|---|---|
| Ht1-CR2-CR4 de | Ht1f3 | Forward | SEQ ID NO: 10 |
| | Ht1r4v2 | Reverse | SEQ ID NO: 11 |

TABLE 4

Summary of T0 Deletion Events

| guide | # embryos bombarded | # T0 plants screened | # plants with deletion |
|---|---|---|---|
| CR2/CR4 | 2000 | 178 | 59 |
| CR2/ST1 | 1000 | 108 | 29 |

T1 Analysis

The Ht1 repetitive sequence deletion T0 plants were transferred to a controlled environment. Pollen from T0 plants was carried to recurrent parent plants to produce seed. T1 plants went through more comprehensive molecular characterization to not only confirm that mutations observed in T0 plant were stably inherited but also to verify that the T1 or later generation plants were free from any foreign DNA elements used during the transformation process. First, qPCR was performed on all helper genes including Cas9, the guide RNAs, the transformation selection marker (NPTII), and the transformation enhancing genes ODP2 and WUS2 to make sure the genes segregated away from the generated mutant alleles. The T1 plants will be sampled using Southern by Sequencing (SbS) analysis to further demonstrate that the plants are free of any foreign DNA.

Example 2

Editing HT1 Genes via Allele Substitution Target Site Selection

The gRNA/Cas9 Site directed nuclease system, described in WO2015026885, WO20158026887, WO2015026883, and WO2015026886, was used to edit the Ht1 gene by replacing a native allele with a resistant allele of Ht1 from PH4GP (US2010095395; SEQ ID NO:65). The following pairs of target sites were used for removing the entire Ht1 allele from line PH184C (U.S. Pat. No. 8,445,763), including the predicated promoter, the coding sequence, and 1 kb of 3' UTR: HT1-TS6 with HT1-TS9 and HT1-TS7 with HT1-TS10. The location of each target site and the schematic drawing of the allele swap are shown in FIG. 3. The target sequences are listed in Table 5. The DNA repair template was co-delivered with Cas9 and guide RNA plasmids.

TABLE 5

HT1 Allele Substitution Target Site Sequences

| Target Site Designation | Maize Genomic Target Site Sequence | PAM Sequence |
|---|---|---|
| HT1-TS6 | SEQ ID NO: 14 | TGG |
| HT1-TS7 | SEQ ID NO: 15 | CGG |
| HT1-TS9 | SEQ ID NO: 16 | AGG |
| HT1-TS10 | SEQ ID NO: 17 | AGG |

Cas9 Vector Construction

See Example 1.

Guide RNA Vector Construction

To direct Cas9 nuclease to the designated genomic target sites (Table 4), a maize U6 polymerase III promoter (SEQ ID NO:6; see WO2015026885, WO20158026887, WO2015026883, and WO2015026886) and its cognate U6 polymerase III termination sequences (TTTTTTTT) were used to direct initiation and termination of gRNA expression. Guide RNA variable targeting domains for HT1 gene editing are identified as HT1-CR6, HT1-CR7, HT1-CR9, and HT1-CR10, which correspond to the genomic target sites HT1-TS6, HT1-TS7, HT1-TS9, and HT1-TS10, respectively. Oligos containing the DNA encoding each of the variable nucleotide targeting domains were synthesized and cloned into a gRNA expression cassette as described in Example 1. Each guide RNA expression cassette consists of the U6 polymerase III maize promoter operably linked to one of the the DNA versions of the guide RNA (Table 6) followed by the cognate U6 polymerase III termination sequence. The DNA version of the guide RNA consists of the respective nucleotide variable targeting domain followed by a polynucleotide sequence capable of interacting with the double strand break inducing endonuclease.

TABLE 6

Ht1 allele swap guide RNA Expression Cassettes

| Name | DNA version of guide RNA SEQ ID NO: |
|---|---|
| HT1-CR6 | SEQ ID NO: 18 |
| HT1-CR9 | SEQ ID NO: 19 |
| HT1-CR7 | SEQ ID NO: 20 |
| HT1-CR10 | SEQ I D NO: 21 |

Repair Template Vector Construction

The substitution/replacement template for CR6/CR9 contains the resistant allele of ZM-HT1-(PH4GP) and the homology sequences flanking the 5' of HT1-TS6 and 3' of HT1-TS9; the substitution template for CR7/CR10 contains the same resistant allele of ZM-HT1-(PH4GP) and the homology sequences flanking the 5' of HT1-TS7 and 3' of HT1-TS11 in line PH184C. The homology arm sequences (SEQ ID NOs:81-84) were synthesized and then cloned with substitutive ZM-HT1-(PH4GP) genomic sequences via a standard seamlessness Gibson cloning method.

Delivery of the Guide RNA/Cas9 Endonuclease System DNA to Maize

Plasmids containing the Cas9, guide RNA expression cassettes, and substitution template described above were co-bombarded with plasmids containing the transformation selectable marker NPTII and the transformation enhancing developmental genes ODP2 (AP2 domain transcription factor ODP2 (Ovule development protein 2)) and Wuschel (20151030-6752 USPSP) into elite maize lines' genomes. Transformation of maize immature embryos can be performed using any method known in the art or the method described in Example 1.

Screening of T0 Plants and Event Characterization

The T0 plant leaf tissue DNA extraction protocol is the same as described in Example 1. To identify swap positive events, PCR was performed using Sigma Extract-N-Amp PCR ready mix. PCR was performed to assay the HR1 Junction using the primer pair of Ht1HR1f1/Ht1HR1r1, while primary PCR with primer pair Ht1HR2 f1 and Ht1HR2r1 was combined with secondary allele differentiation qPCR to screen the HR2 junction due to high homology of the intended edited variants and the unmodified genomic sequence. The primers for primary PCR and the primers and probes for 2nd qPCR are listed in Table 7. The same assay described previously for CR6/CR9 swap is also used for CR7/CR10 allele swap event screening.

TABLE 7

Primers Used to Screen for Ht1 Allele Swap Variants

| | Primer name | Primer orientation | Primary PCR primer sequence |
|---|---|---|---|
| HR1 junction | Ht1HR1f1 | Forward | SEQ ID NO: 22 |
| | Ht1HR1r1 | Reverse | SEQ ID NO: 23 |
| HR2 junction | Ht1HR2f1 | Forward | SEQ ID NO: 24 |
| | Ht1HR2r1 | Reverse | SEQ ID NO: 25 |
| HR2 junction 2nd qPCR | hdr2b_f | Forward | SEQ ID NO: 26 |
| | hdr2b_r | Reverse | SEQ ID NO: 27 |
| | hdr2b_PV | Probe | 6FAM-SEQ ID NO: 28 |
| | hdr2b_PG | Probe | VIC-SEQ ID NO: 29 |

The identified allele swap variants will be further molecularly characterized, and qPCR will be used to screen T1(BC0) plants for null segregants, which are expected to be free of the plasmid DNA used during transformation initiation. Southern by sequencing will also be performed to confirm null segregant plants. Table 8 shows a summary of the T0 results obtained from the allele swap experiments. Three T0 plants have been identified as potential allele swap variants among 300 screened T0 plants.

TABLE 8

Summary of T0 allele swap screening results

| # T0 screened | # T0 HR1 only | # T0 HR2 only | # T0 with HR1 + HR2 |
|---|---|---|---|
| 100 | 2 | 2 | 1 |
| 150 | 13 | 3 | 1 |
| 50 | 4 | 3 | 1 |

Example 3

Editing the NLB18 Gene Via Allele Substitution

Target Site Selection

A wall-associated kinase (WAK) gene, NLB18, was identified and validated as a northern leaf blight resistance gene (WO2011163590). The NLB18 gene is clustered with NLB17 on the long arm of chromosome 8. The NLB18 and NLB17 genes are 6.9 kb apart and share a high degree of homology; thus, identifying a unique target site for the NLB18 allele swap is challenging. Multiple sites were identified and guide RNAs were tested. Guides that only cut the NLB18 gene region, and not the NLB17 gene region, were selected for NLB18 allele swap.

Figure 5:
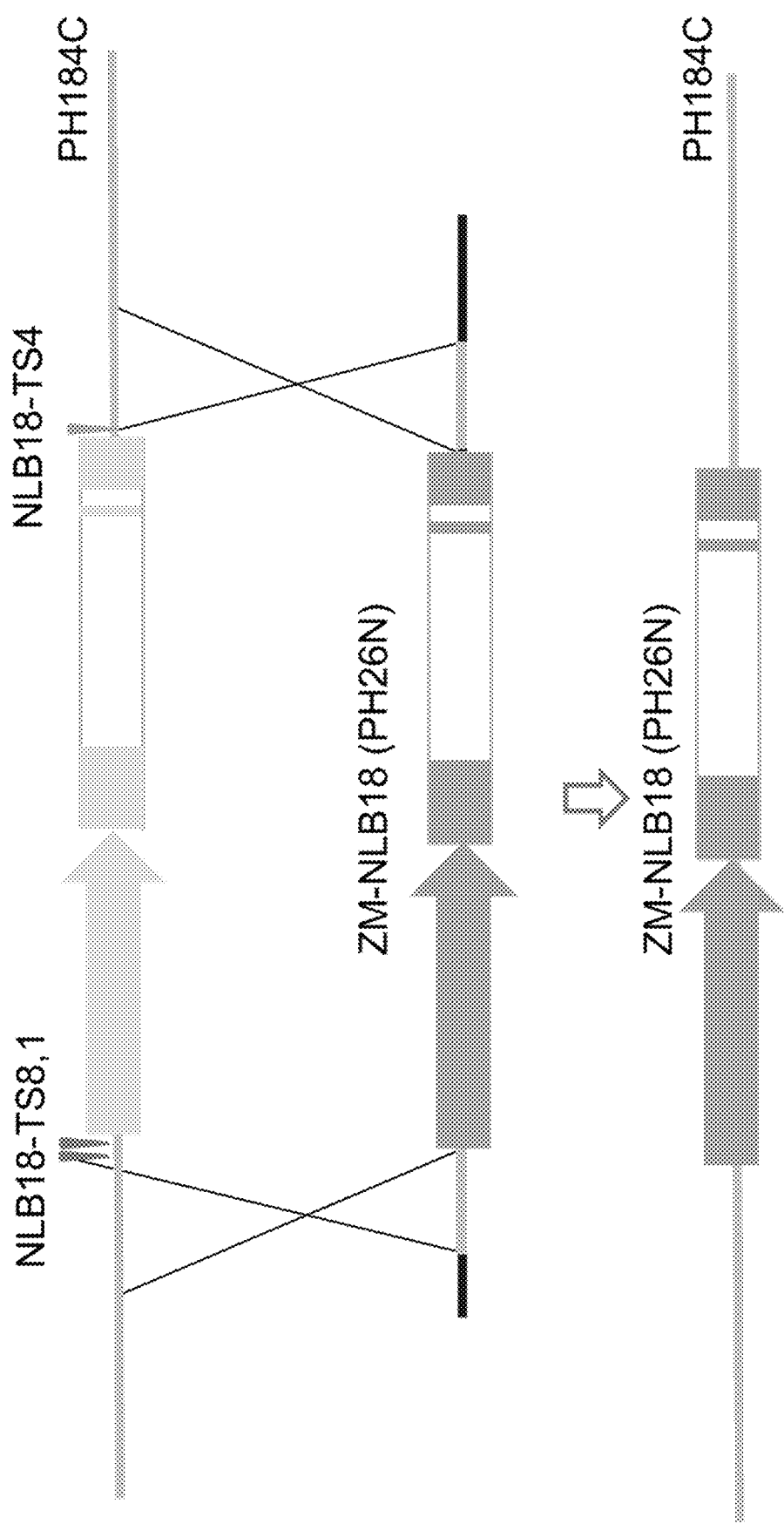
FIG. 5 shows the location of each target site and the schematic drawing of the NLB18 allele swap.

The gRNA/Cas9 Site directed nuclease system, described in WO2015026885, WO20158026887, WO2015026883, and WO2015026886, was used to edit the NLB18 gene. The following pairs of target sites were used for removing the entire NLB18 allele from line PH184C, including the potential promoter, the coding sequence, and 3' UTR: NLB18-TS1 with NLB18-TS4 and NLB18-TS8 with NLB18-TS4. The location of each target site at the NLB18 locus and the schematic drawing of the allele swap are shown in FIG. 5. The target sequences are listed in Table 9. The removed allele is substituted with a resistant allele of NLB18 from PH26N (U.S. Pat. No. 6,765,132; SEQ ID NO:70); the DNA repair template was co-delivered with Cas9 and guide RNA plasmids.

TABLE 9

NLB18 allele substitution target site sequences

| Target Site Designation | Maize Genomic Target Site Sequence | PAM Sequence |
|---|---|---|
| NLB18-TS1 | SEQ ID NO: 30 | TGG |
| NLB18-TS8 | SEQ ID NO: 31 | CGG |
| NLB18-TS4 | SEQ ID NO: 32 | GGG |

Cas9 Vector Construction

See Example 1

Guide RNA Vector Construction

To direct Cas9 nuclease to the designated genomic target sites (Table 9), a maize U6 polymerase III promoter (SEQ ID NO:6; see WO2015026885, WO20158026887, WO2015026883, and WO2015026886) and its cognate U6 polymerase III termination sequences (TTTTTTTT) were used to direct initiation and termination of gRNA expression. Guide RNA variable targeting domains for the NLB18 gene are identified as NLB18-CR1, NLB18-CR8, and NLB18-CR4, which correspond to the genomic target sites NLB18-TS1, NLB18-TS8, and NLB18-TS4, respectively. Oligos containing the DNA encoding each of the variable nucleotide targeting domains were synthesized and cloned into a gRNA expression cassette as described in above Example 1. Each guide RNA expression cassette consists of the U6 polymerase III maize promoter operably linked to one of the DNA version of the guide RNA (Table 10), and then the cognate U6 polymerase III termination sequence. The DNA version of the guide RNA consists of the respective nucleotide variable targeting domain followed by a polynucleotide sequence capable of interacting with the double strand break inducing endonuclease.

TABLE 10

NLB18 allele swap guide RNA expression cassettes

| Name | DNA version of guide RNA SEQ ID NO: |
|---|---|
| NLB18-CR1 | SEQ ID NO: 33 |
| NLB18-CR8 | SEQ ID NO: 34 |
| NLB18-CR4 | SEQ ID NO: 35 |

Substitution Template Vector Construction

The substitution/replacement templates for NLB18-CR1/CR4 contain the resistant allele of ZM-NLB18 (from PH26N) and the homology sequences flanking the 5' of NLB18-TS1 (SEQ ID NO:67) and the 3' of NLB18-TS4 (SEQ ID NO:68) in PH184C; the substitution templates for NLB18-CR1/CR4 contain the resistant allele of ZM-NLB18 (from PH26N) and the homology sequences flanking the 5' of NLB18-TS8 (SEQ ID NO:69) and 3' of NLB18-TS4 (SEQ ID NO:68) in PH184C. SEQ ID NO:66 is the NLB18 nucleotide sequence from PH184C, including the 5' of NLB18-CR8 through the 3' of NLB18-CR4. The homology arm sequences were synthesized with additional sequence containing restriction sites; after restriction digestion, they were assembled together with the desired resistant allele of NLB18 (from PH26N) into a yeast backbone using standard yeast in vivo assembly protocols. The plasmids from pooled yeast transformants of the assembly reaction were recovered in E. coli, and the plasmids that passed quality control were used as templates for co-bombardment.

Delivery of the Guide RNA/Cas9 Endonuclease System DNA to Maize

Plasmids containing the Cas9, guide RNA expression cassettes, and substitution templates described above were co-bombarded with plasmids containing the transformation selectable marker NPTII and the transformation enhancing developmental genes ODP2 (AP2 domain transcription factor ODP2 (Ovule development protein 2)) and Wuschel (20151030-6752 USPSP) into elite maize lines' genomes. Transformation of maize immature embryos can be performed using any method known in the art or using the method described in Example 1.

Screening of T0 Plants and Event Characterization

Screening will be performed similar to the experiments described previously.

Example 4

Relocating HT1 and NLB18 Resistant Alleles to a Complex Trait Locus

Target Sites Selection

Figure 6:
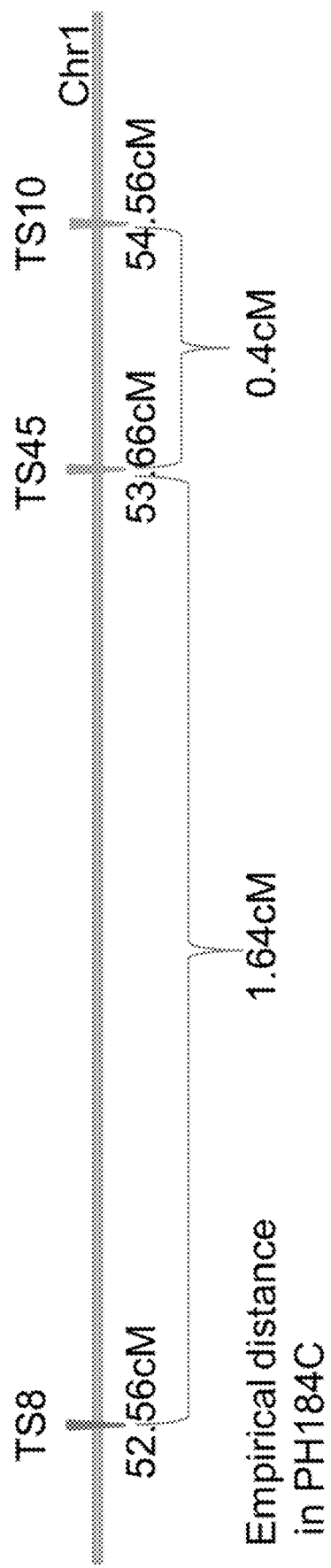
FIG. 6 shows the location of three loci comprising target sites (TS8, TS45, and TS10) for the guide RNA/Cas endonuclease system at CTL1 on chromosome 1 of maize.

A maize genomic window spanning from ZM01:13.7MM to ZM01:16.4MM on chromosome 1 was identified and developed to become Complex Trait Locus (CTL) 1 (WO2016040030). Three sites on CTL1, TS8, TS10, and TS45, were selected for relocating the NLB resistant genes NLB18-PH26N (SEQ ID NO:70), Ht1-PH4GP (SEQ ID NO:65), and NLB18-PH26N (SEQ ID NO:70), respectively. Table 11 shows the genetic map positions for Cas endonuclease target sites (TS8, TS45, TS10), and FIG. 6 shows the schematic drawing of the sites locations.

TABLE 11

Cas endonuclease target sites at Complex Trait Locus (CTL1) on chromosome 1 of maize

| Target site | Target site sequence | PAM sequence | Genetic Position PH B73v2 (cM) |
|---|---|---|---|
| CTL1-TS8 | SEQ ID NO: 36 | TGG | 52.56 |
| CTL1-TS45 | SEQ ID NO: 37 | AGG | 53.66 |
| CTL1-TS10 | SEQ ID NO: 38 | GGG | 54.56 |

Cas9, Guide RNA, and Donor Template Vector Construction

The Cas9 gene from *Streptococcus pyogenes* M1 GAS (SF370) was maize codon optimized per standard techniques known in the art and the potato ST-LS1 intron was introduced in order to eliminate its expression in *E.coli* and *Agrobacterium*. To facilitate nuclear localization of the Cas9 protein in maize cells, Simian virus 40 (SV40) monopartite amino terminal nuclear localization signal (SEQ ID NO:5) and *Agrobacterium tumefaciens* bipartite VirD2 T-DNA border endonuclease carboxyl terminal nuclear localization signal (SEQ ID NO:80) were incorporated at the amino and carboxyl-termini of the Cas9 open reading frame respectively. SEQ ID NO:73 is the nucleotide sequence containing the Cas9 used in Example 4; SEQ ID NO:73 contains the cas9 exon 1 (SP), the ST-LS1 intron 2, the Cas9 exon 2 (SP), and the VirD2 nuclear localization signal. (The SP version of Cas9 differs from the ST version used in the previous examples with respect to codon usage; however, the SP version and the ST version encoded by SEQ ID NO:4 are identical) The maize optimized Cas9 gene was operably linked to a maize ubiquitin promoter by standard molecular biology techniques.

The maize U6 polymerase III promoter (SEQ ID NO:6; see WO2015026885, WO20158026887, WO2015026883, and WO2015026886) was used to express guide RNAs which direct Cas9 nuclease to designated genomic sites. The guide RNA coding sequence was 77 bp long and comprised a 12-30 bp variable targeting domain from a chosen maize genomic target site on the 5' end maize U6 polymerase III terminator.

In order for the Cas9 endonuclease and the guide RNA to form a protein/RNA complex to mediate site-specific DNA double strand cleavage, the Cas9 endonuclease and guide RNA have to be present in simultaneously. To improve their co-expression and presence, the Cas9 endonuclease and guide RNA expression cassettes were linked into a single DNA construct. A 480-490 bp sequence containing the guide RNA coding sequence, the 12-30 bp variable targeting domain from the chosen maize genomic target site, and part of the U6 promoter were synthesized. The sequence was then cloned to the backbone already have the cas9 cassette and the rest of the gRNA expression cassette through restrict sites of BstBI/HindIII.

The relocating template for CTL1-8CR1 contains the resistant allele of ZM-NLB18 (from PH26N) (SEQ ID NO:70) and the homology sequences flanking the 5' of CTL1-TS8 (SEQ ID NO:85) and the 3' of CTL1-TS8 (SEQ ID NO:86) in PH184C. The relocating template for CTL1-45CR1 contains the resistant allele of ZM-NLB18 (from PH26N) (SEQ ID NO:70) and the homology sequences flanking the 5' of CTL1-TS45 (SEQ ID NO:87) and the 3' of CTL1-TS45 (SEQ ID NO:88) in PH184C. The relocating template for CTL1-10CR3 contains the resistant allele of ZM-HT1 (from PH4GP) (SEQ ID NO:65) and the homology sequences flanking the 5' of CTL1-TS10 (SEQ ID NO:89) and the 3' of CTL1-TS10 (SEQ ID NO:90) in PH184C. The 300-500 bp homology arm sequences were synthesized and then cloned with desired resistant allele sequence via a standard seamlessness Gibson cloning method.

A plasmid comprising the maize codon optimized Cas9 endonuclease expression cassette and guide RNA expression cassettes were co-delivered with a plasmid comprising a DNA template containing NLB18-PH26N (FIG. 7 or FIG. 8) or ZM-HT1 (PH4GP) (FIG. 9), which upon gene integration by homologous recombination (homology directed repair) will be integrated at the designated site when the sites are cleaved by Cas9.

The guide RNA-DNA constructs targeting various maize genomic sites and the template DNA constructs that were constructed for introduction of the resistant genes into Cas endonuclease target sites through homologous recombination (homology directed repair) are provided in Table 12. These guide RNA, Cas9 DNA constructs, and repair template DNAs were co-delivered into an elite maize genome (e.g. PH184C) by the stable transformation procedure described in Example 1.

TABLE 12

Guide RNA/Cas9 and repair template DNA used in maize stable transformation for Ht1-PH4GP or NLB18-PH26N insertion at ZM01_CTL1

| Experiment | guide RNA | SEQ ID NO: | relocating template DNA | SEQ ID NO: |
|---|---|---|---|---|
| CTL1-TS8 | ZM-U6:08CR1 | 74 | 08CR1HR1-NLB18(PH26N) genomic sequence-8CR1HR2 | 77 |
| CTL1-TS45 | ZM-U6:45CR1 | 75 | 45CR1HR1-NLB18(PH26N) genomic sequence-45CR1HR2 | 78 |
| CTL1-TS10 | ZM-U6:10CR3 | 76 | 10CR3HR1-HT1 (PH4GP) genomic sequence-10CR3HR2 | 79 |

Delivery of the Guide RNA/Cas9 Endonuclease System DNA to Maize

See Example 1.

Screening of T0 Plants and Event Characterization

Figure 7:
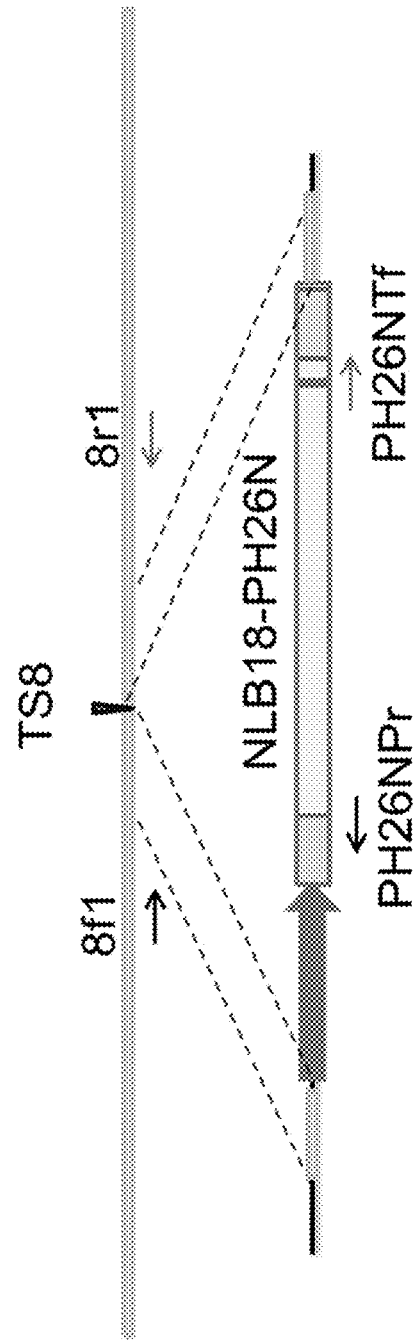
FIG. 7 shows a schematic drawing of the NLB18-PH26N insertion at TS8.
Figure 8:
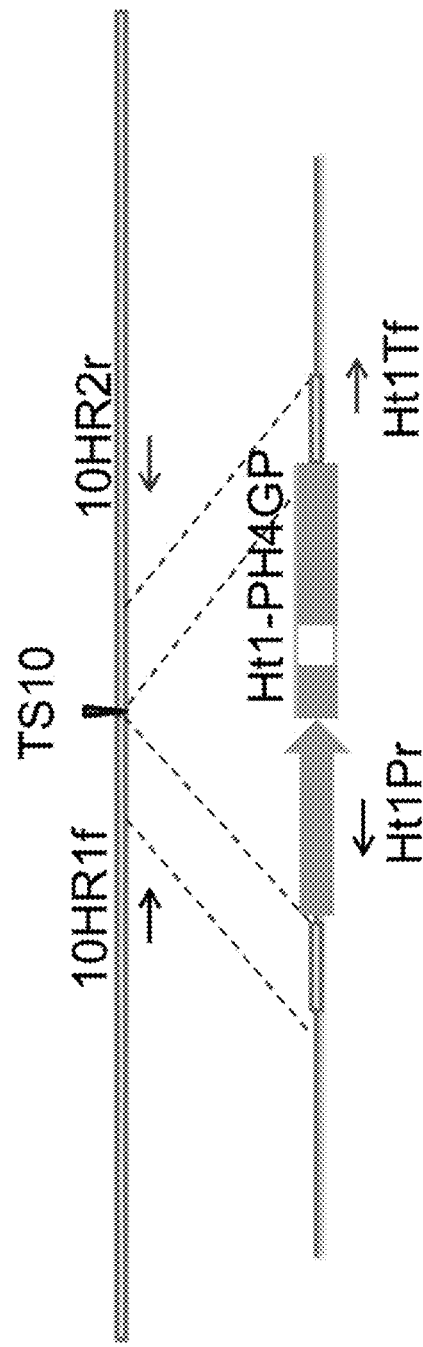
FIG. 8 shows a schematic drawing of the Ht1-PH4GP insertion at TS10.
Figure 9:
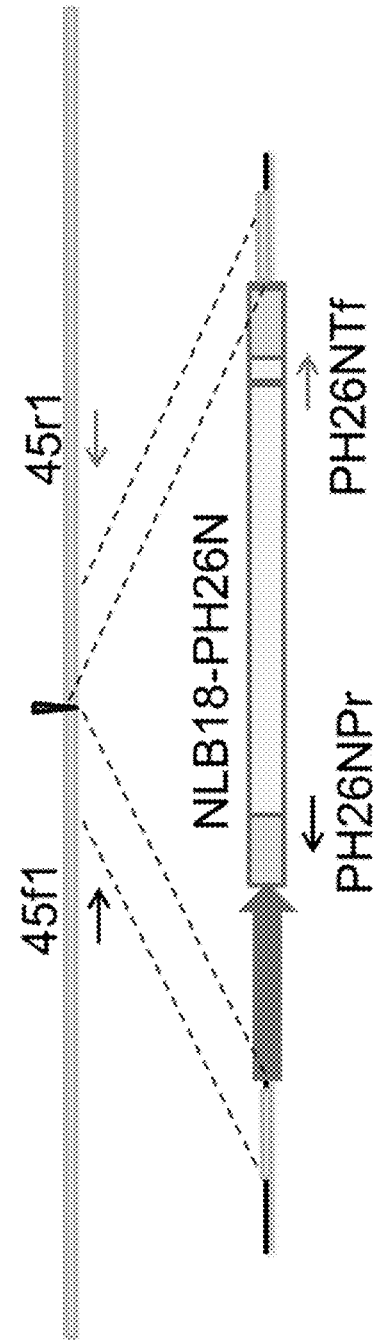
FIG. 9 shows a schematic drawing of the NLB18-PH26N insertion at TS45.
Figure 10:
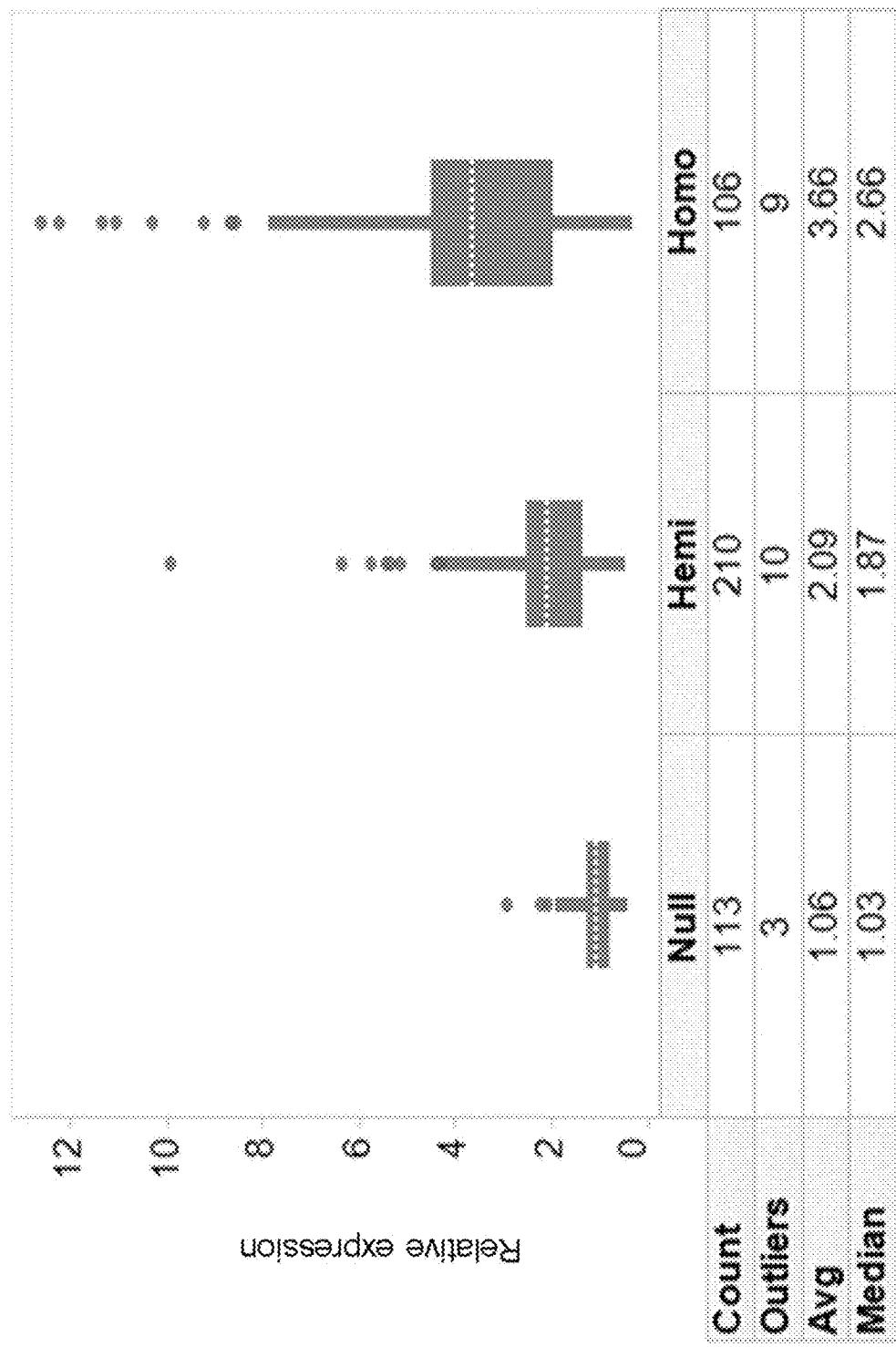
FIG. 10 shows NLB18 Expression using qRT-PCR in T2 TS45 NLB18-BC26N maize plants.
Figure 11:
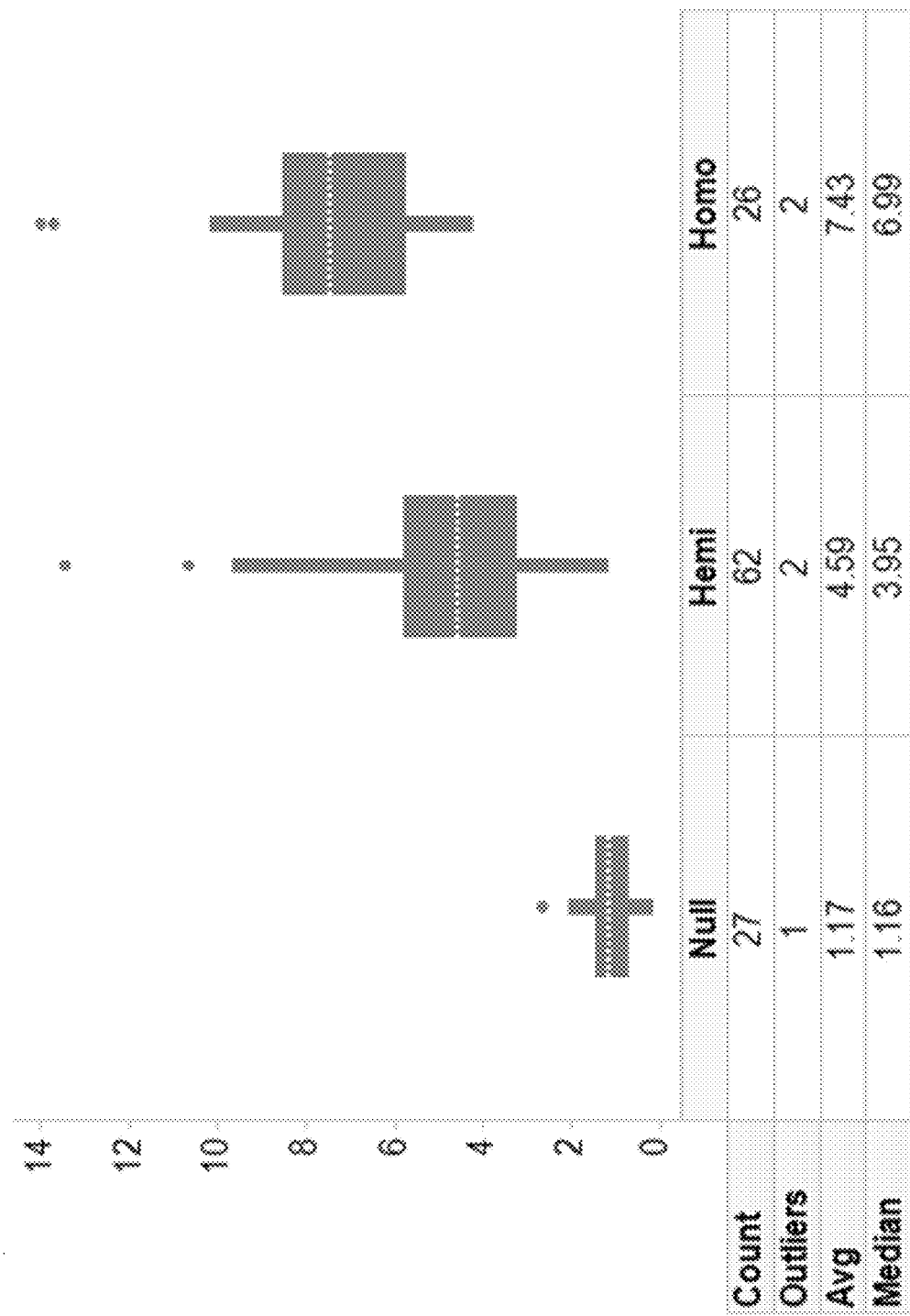
FIG. 11 shows Ht1 Expression using qRT-PCR in T2 TS10 Ht1-ED4GP maize plants.

To identify relocation events(insertion positive events), genomic DNA was extracted from leaf tissue of T0 plants, and junction PCR was performed using Sigma Extract-N-Amp PCR ready mix. Primer locations are shown in FIGS. 7, 8, and 9, and the primer sequences are listed in Table 13. Junction PCR screening for insertion events showed three T0 plants with both HR1 and HR2 junctions for the CTL1-TS8 experiment, four T0 plants with both HR1 and HR2 junctions for the CTL1-TS10 experiment, and four T0 plants with both HR1 and HR2 junctions for the CTL1-TS45 experiment. The identified T0 plants will be further characterized in the next generation.

TABLE 13

| Primers used to screen for insertion (relocating) event screening | | | |
|---|---|---|---|
| Experiments | Primer name | Primer Orientation | Primer Sequence |
| NLB18- | 8HR1f1 | Forward | SEQ ID NO: 39 |
| PH26N to | PH26NPr | Reverse | SEQ ID NO: 40 |
| CTL1 TS8 | PH26NTf | Forward | SEQ ID NO: 41 |
| | 8HR2r1 | Reverse | SEQ ID NO: 42 |
| Ht1-PH4GP | 10HR1f | Forward | SEQ ID NO: 43 |
| to CTL1 | Ht1Pr | Reverse | SEQ ID NO: 44 |
| TS10 | Ht1Tf | Forward | SEQ ID NO: 45 |
| | 10HR2r | Reverse | SEQ ID NO: 46 |
| NLB18- | 45hr1f1 | Forward | SEQ ID NO: 47 |
| PH26N to | PH26NPr | Reverse | SEQ ID NO: 48 |
| CTL1 TS45 | PH26NTf | Forward | SEQ ID NO: 49 |
| | 45hr2r1 | Reverse | SEQ ID NO: 50 |

Screening of T2 Plants and Event Characterization

T0 plants containing relocation of the NLB18(BC26N) and HT1(ED4GP) were backcrossed with wild type recurring parents to make BC0 (T1) seeds. BC0 seedlings were molecular characterized for junction PCR to confirm the insertion at the CTL1-TS45 with NLB18 (BC26) and insertion at CTL1-TS10 with HT1 (ED4GP) inherited to the next generation. qPCR on the helper genes used during transformation process were also performed to make sure they were segregated away from the relocating plants, null segregants were also confirmed by SbS (Southern by Sequencing). The seeds from self-plants (BC0F2) were planted in field, zygosity analysis were done on the leaf samples, 1:2:1 of homozygous: hemizygous: null insertion ratio observed for both CTL1-TS45 with BC26N and CTL1-TS10 with HT1 (ED4GP) insertion. The plants were also analyzed for RNA expression using qRT-PCR after inoculation with NLB. Comparing to null, both hem izygous and homozygous showed resistance to infection, and both NLB18 and HT1 expression were elevated (FIGS. 10 and 11).

Events were tested in field experiments for efficacy against the northern leaf blight pathogen (*Exserohilum turcicum*). First, events were challenged with the pathogen for which Ht1 and NLB18 genes are known to provide resistance. All positive events, as determined by qPCR, were resistant to the pathogen. The results are shown in Tables 14 and 15. The number of plants for each event is indicated in column "N", representing the number of plants tested. The resistance score for NLNB ranges from 1 to 9, with 9 being the most resistant.

TABLE 14

| TS10 Ht1-ED4GP | | | |
|---|---|---|---|
| Zygosity | Mean NLFBLT | Std. Error of NLFBLT | N |
| Homozygous | 7.3 | 0.1 | 16 |
| Hemizygous | 6.3 | 0.1 | 28 |
| Null | 4.9 | 0.1 | 12 |

TABLE 15

| TS45 NLB18-BC26N | | | |
|---|---|---|---|
| Zygosity | Mean NLFBLT | Std. Error of NLFBLT | N |
| Homozygous | 8.5 | 0.1 | 53.0 |
| Hemizygous | 6.2 | 0.1 | 91.0 |
| Null | 4.7 | 0.1 | 55.0 |

What is claimed is:

1. A method for obtaining a maize plant cell with a modified Ht1 nucleotide sequence, the method comprising:
   a) introducing a site-specific modification at at least one target site in an endogenous genomic locus encoding Ht1 in a plant cell;
   b) obtaining the maize plant cell having a modified Ht1 nucleotide sequence; and
   c) introducing an Ht1 substitution template in the maize plant cell, wherein said Ht1 substitution template comprises at least one nucleic acid alteration compared to the endogenous Ht1 encoding sequence, allele, or genomic locus and wherein said Ht1 substitution template is incorporated into the endogenous genomic locus encoding Ht1,
   wherein said Ht1 substitution template comprises SEQ ID NO:59, SEQ ID NO: 65, or a nucleotide sequence that encodes a polypeptide comprising the amino acid sequence of SEQ ID NO:52.

2. The method of claim 1, wherein the site-specific modification is induced by a nuclease selected from the group consisting of: a TALEN, a meganuclease, a zinc finger nuclease, and a CRISPR-associated nuclease.

3. The method of claim 1, wherein said method further comprises growing a plant from the maize plant cell having the modified Ht1 nucleotide sequence.

4. The method of claim 3, wherein said plant exhibits enhanced resistance to northern leaf blight.

5. The method of claim 1, wherein said modified Ht1 nucleotide sequence comprises a deletion in the promoter of the endogenous HT1 encoding sequence.

6. The method of claim 5, wherein the site-specific modification comprises double-strand breaks at the at least one target site which are introduced by a Cas9 endonuclease.

7. The method of claim 6, wherein the Cas9 endonuclease is guided by at least one guide RNA.

8. The method of claim 7, wherein two guide RNAs are used, a first guide RNA comprising a variable targeting domain that is complementary to a targeting region of SEQ ID NO:1 [Ht1-TS2] and a second guide RNA comprising a variable targeting domain that is complementary to SEQ ID NO:2 [Ht1-TS4].

9. The method of claim 7, wherein two guide RNAs are used, a first guide RNA comprising a variable targeting domain that is complementary to SEQ ID NO:1 [Ht1-TS2] and a second guide RNA comprising a variable targeting domain that is complementary to SEQ ID NO:3 [Ht1-ST1-TS1].

10. The method of claim 1, wherein said site-specific modification is induced by a Cas9 endonuclease.

11. The method of claim 10, wherein Cas9 endonuclease is guided by at least one guide RNA.

12. The method of claim 11, wherein two guide RNAs are used, a first guide RNA comprising a variable targeting domain that is complementary to SEQ ID NO:14 [Ht1-TS6] and a second guide RNA comprising a variable targeting domain that is complementary to SEQ ID NO:16 [Ht1-TS9].

13. The method of claim 11, wherein two guide RNAs are used, a first guide RNA comprising a variable targeting domain that is complementary to SEQ ID NO:15 [Ht1-TS7]

and a second guide RNA comprising a variable targeting domain that is complementary to SEQ ID NO:17 [Ht1-TS10].

14. A method for obtaining a maize plant cell with a genomic locus comprising at least one nucleotide sequence that confers enhanced resistance to northern leaf blight, wherein said at least one nucleotide sequence is heterologous to the genomic locus, the method comprising:

a) introducing a site-specific modification at at least one target site in a genomic locus in a maize plant cell;

b) introducing at least one nucleotide sequence that confers enhanced resistance to northern leaf blight, wherein said at least one nucleotide sequence is flanked by 300-500 bp of nucleotide sequences 5' or 3' of the corresponding target sites; and c) obtaining a maize plant cell having a genomic locus comprising at least one nucleotide sequence that confers enhanced resistance to northern leaf blight, wherein the at least one nucleotide sequence comprises SEQ ID NO:59, SEQ ID NO: 65, or a nucleotide sequence that encodes a polypeptide comprising the amino acid sequence of SEQ ID NO:52.

15. The method of claim 14, wherein said site-specific modification is induced by a nuclease selected from the group consisting of: a TALEN, a meganuclease, a zinc finger nuclease, and a CRISPR-associated nuclease.

16. The method of claim 14, wherein said method further comprises growing a plant from the maize plant cell having the genomic locus comprising the at least one nucleotide sequence that confers enhanced resistance to northern leaf blight.

17. A method for obtaining a maize plant cell with a modified Ht1 nucleotide sequence, the method comprising:

a. introducing a site-specific modification at one or more target sites in a Ht1 genomic locus in a maize plant cell;

b. introducing one or more nucleotide sequences encoding a Ht1 polypeptide as set forth in SEQ ID NO: 52, 54, or 60 that confers enhanced resistance to northern leaf blight, wherein each nucleotide sequence is flanked by 300-500 contiguous nucleotides of nucleotide sequences 5' or 3' of the corresponding target sites; and c. obtaining a maize plant cell having a genomic locus comprising one or more nucleotide sequences that confer enhanced resistance to northern leaf blight.

18. The method of claim 17, wherein the one or more nucleotide seqeunces comprises the nucleotide sequence set forth in SEQ ID NO: 59 or 65.

* * * * *